United States Patent
Levi et al.

(10) Patent No.: US 12,364,736 B2
(45) Date of Patent: Jul. 22, 2025

(54) METHODS FOR TREATING HETEROTOPIC OSSIFICATION

(71) Applicants: Acceleron Pharma Inc., Cambridge, MA (US); The Regents of the University of Michigan, Ann Arbor, MI (US)

(72) Inventors: Benjamin Levi, Ann Arbor, MI (US); Ravindra Kumar, Acton, MA (US); Shailesh Agarwal, Ann Arbor, MI (US)

(73) Assignees: Acceleron Pharma Inc., Rahway, NJ (US); The Regents of the University of Michigan, Ann Arbor, MI (US)

( * ) Notice: Subject to any disclaimer, the term of this patent is extended or adjusted under 35 U.S.C. 154(b) by 689 days.

(21) Appl. No.: 16/967,922

(22) PCT Filed: Feb. 8, 2019

(86) PCT No.: PCT/US2019/017297
§ 371 (c)(1),
(2) Date: Aug. 6, 2020

(87) PCT Pub. No.: WO2019/157342
PCT Pub. Date: Aug. 15, 2019

(65) Prior Publication Data
US 2022/0211805 A1 Jul. 7, 2022

Related U.S. Application Data

(60) Provisional application No. 62/666,235, filed on May 3, 2018, provisional application No. 62/628,649, filed on Feb. 9, 2018.

(51) Int. Cl.
*A61K 38/17* (2006.01)
*A61K 45/06* (2006.01)
*A61K 47/68* (2017.01)
*A61P 19/08* (2006.01)
*C07K 14/71* (2006.01)

(52) U.S. Cl.
CPC ............ *A61K 38/179* (2013.01); *A61K 45/06* (2013.01); *A61K 47/68* (2017.08); *A61P 19/08* (2018.01); *C07K 14/71* (2013.01)

(58) Field of Classification Search
CPC ..... A61K 38/179; C07K 14/495; C07K 14/71
See application file for complete search history.

(56) References Cited

U.S. PATENT DOCUMENTS

| | | | | |
|---|---|---|---|---|
| 2008/0118512 A1* | 5/2008 | Auf Der Maur | ...... | A61K 39/00 424/139.1 |
| 2015/0056199 A1 | 2/2015 | Kumar et al. | | |
| 2016/0376341 A1* | 12/2016 | Kumar | ................... | C07K 16/22 424/134.1 |

FOREIGN PATENT DOCUMENTS

| | | |
|---|---|---|
| WO | WO-2016/164089 A2 | 10/2016 |
| WO | WO-2016/164501 A1 | 10/2016 |
| WO | WO-2016/165808 A1 | 10/2016 |
| WO | WO-2017/070194 A1 | 4/2017 |
| WO | WO-2019/089506 A1 | 5/2019 |

OTHER PUBLICATIONS

Wang et al., Nat. Commun., Feb. 7, 2018, vol. 9(1):551.*
Shehab et al., J. Nucl. Med., 2002, vol. 43(3):346-353.*
Supplementary EP Search Report, EP 19 75 1135, dated Oct. 4, 2021 (3 pages).
ISR and Written Opinion PCT/US2019/017297, dated Apr. 18, 2019 (10 pages).
Wang et al., "Inhibition of overactive TGF-beta attenuates progression of heterotopic ossification in mice," Nature Communications, vol. 9, Article No. 551; 1-13 (2018).
Ranganathan, Kavitha et al., Current Concepts Review, Heterotopic Ossification: Basic-Science Principles and Clinical Correlates, J Bone Joint Surg Am, 2011, 1101-1111, 97.
Fujimoto, Mai et al., Molecular mechanisms for activation of mutant activin receptor-like kinase 2 in fibrodysplasia ossificans progressiva, Journal of Oral Biosciences, 69, 121-126, 2017.
Silacci, Michela et al., Linker Length Matters, Fynomer-Fc Fusion with an Optimized Linker Displaying Picomolar IL-17A Inhibition Potency, J Biol Chem, 289(20), 14392-14398, 2014.
Yang, G.G. et al., Linker length affects expression and bioactivity of the onconase fusion protein in Pichia pastoris, Genetics and Molecular Research, 14(4), 19360-19370, 2015.

* cited by examiner

*Primary Examiner* — Xiaozhen Xie
(74) *Attorney, Agent, or Firm* — Tamaria Dewdney; Andrew W. Custer

(57) ABSTRACT

In part, the present disclosure relates methods for treating heterotopic ossification or one or more complications of heterotopic ossification. In particular, the disclosure provided methods for treating heterotopic ossification by administering to a patient in need thereof one or more TGFβ antagonists, optionally in combination with one or more additional active agents or supportive therapies for treating heterotopic ossification. For example, in some embodiments, the disclosure provided methods for treating heterotopic ossifications by administering to a patient in need thereof an effective amount of a TβRII polypeptide.

20 Claims, 13 Drawing Sheets
Specification includes a Sequence Listing.

```
  1  mgrqllrglw plhivlwtri astipphvgk synndmivtd nngavkfpql
 51  ckfcdvrfst cdngkscmsn csitsicekp qevcvavwrk ndenitletv
101  chdpklpyhd filedaaspk cimkekkkpg etffmcscss decndniifs
151  eeyntsnpdl llvifqvtgi sllpplgvai sviiifycyr vnrqqklsst
201  wetgktrklm efsehcaiil eddrsdisst canninhnte llpieldtlv
251  gkgrfaevyk aklkqntseq fetvavkifp yeeyaswkte kdifsdinlk
301  henilqflta eerktelgkq ywlitafhak gnlqeyltrh viswedlrkl
351  gsslargiah lhsdhtpcgr pkmpivhrdl kssnilvknd ltcclcdfgl
401  slrldptlsv ddlansgqvg tarymapevl esrmnlenve sfkqtdvysm
451  alvlwemtsr cnavgevkdy eppfgskvre hpcvesmkdn vlrdrgrpei
501  psfwlnhqgi qmvcetltec wdhdpearlt aqcvaerfse lehldrlsgr
551  scseekiped gslnttk                    (SEQ ID NO: 1)
```

FIGURE 1

```
  1  mgrgllrglw plhivlwtri astipphvqk sdvemeaqkd eiicpscnrt
 51  ahplrhinnd mivtdnngav kfpqlckfcd vrfstcdnqk scmsncsits
101  icekpqevcv avwrkndeni tletvchdpk lpyhdfiled aaspkcimke
151  kkkpqetffm cscssdecnd niifseeynt snpdlllvif qvtgisllpp
201  lgvaisviii fycyrvnrqq klsstwetgk trklmefseh cailleddrs
251  disstcanni nhntellpie ldtlvgkqrf aevykaklkq ntseqfetva
301  vkifpyeeya swktekdifs dinlkhenil qfltaeerkt elgkqywlit
351  afhakgnlqe yltrhviswe dlrklgssla rglahlhsdh tpcgrpkmpi
401  vhrdlkssni lvkndltccl cdfglslrld ptlsvddlan sqqvgtarym
451  apevlesrmn lenvesfkqt dvysmalvlw emtsrcnavg evkdyeppfg
501  skvrehpcve smkdnvlrdr grpeipsfwl nhqgiqmvce tltecwdhdp
551  earltaqcva erfselehld rlsgrscsee kipedgslnt tk
     (SEQ ID NO: 2)
```

FIGURE 2

| Fusion Protein | | $k_a$ (1/Ms) | $k_d$ (1/s) | $K_D$ (pM) |
|---|---|---|---|---|
| TGFβ1 | hTβRII-hFc | 2.01 × 10⁶ | 4.16 × 10⁻⁴ | 207.0 |
| | hTβRII (G4S)2-hFc | 2.91 × 10⁶ | 4.83 × 10⁻⁴ | 165.8 |
| | hTβRII (G4S)3-hFc | 3.89 × 10⁶ | 5.10 × 10⁻⁴ | 92.4 |
| | hTβRII (G4S)4-hFc | 6.69 × 10⁶ | 4.57 × 10⁻⁴ | 68.4 |
| | hTβRII-extended hinge-hFc | 2.38 × 10⁶ | 4.64 × 10⁻⁴ | 195.5 |
| TGFβ3 | hTβRII-hFc | 1.99 × 10⁷ | 1.57 × 10⁻³ | 79.1 |
| | hTβRII (G4S)2-hFc | 1.74 × 10⁷ | 1.81 × 10⁻³ | 104.1 |
| | hTβRII (G4S)3-hFc | 2.09 × 10⁷ | 8.32 × 10⁻⁴ | 39.9 |
| | hTβRII (G4S)4-hFc | 8.80 × 10⁶ | 2.76 × 10⁻⁴ | 31.4 |
| | hTβRII-extended hinge-hFc | 1.51 × 10⁷ | 1.39 × 10⁻³ | 92.1 |

FIGURE 4A

|  | TGFβ1 | | |
|---|---|---|---|
| Receptor | $k_a$ (1/Ms) | $k_d$ (1/s) | $K_D$ (pM) |
| hTβRII (G4S)5-hFc | $7.36 \times 10^7$ | $6.48 \times 10^{-4}$ | 8.8 |
| hTβRII (G4S)6-hFc | $1.66 \times 10^8$ | $6.32 \times 10^{-4}$ | 3.8 |

|  | TGFβ3 | | |
|---|---|---|---|
| Receptor | $k_a$ (1/Ms) | $k_d$ (1/s) | $K_D$ (pM) |
| hTβRII (G4S)5-hFc | $1.47 \times 10^8$ | $4.35 \times 10^{-4}$ | 2.96 |
| hTβRII (G4S)6-hFc | $5.99 \times 10^7$ | $2.75 \times 10^{-4}$ | 4.60 |

Figure 4B

| | TGFβ1 | TGFβ3 | Ratio TGFβ1/TGFβ3 |
|---|---|---|---|
| hTβRII-hFc | 7.69 | 0.18 | 42 |
| hTβRII(G4S)2-hFc | 1.12 | 0.13 | 8.61 |
| hTβRII(G4S)3-hFc | 0.22 | 0.17 | 1.29 |
| hTβRII(G4S)4-hFc | 0.07 | 0.03 | 2.3 |
| hTβRII extended hinge-hFc | 5.67 | 0.11 | 52 |

| Construct | TGFβ1—IC50 (nM) | TGFβ3—IC50 (nM) | Ratio TGFβ1/TGFβ3 |
|---|---|---|---|
| hTBRII (G4S)5-hFc | 0.03 | 0.04 | 0.75 |
| hTBRII (G4S)6-hFc | 0.02 | 0.04 | 0.5 |

FIGURE 5F

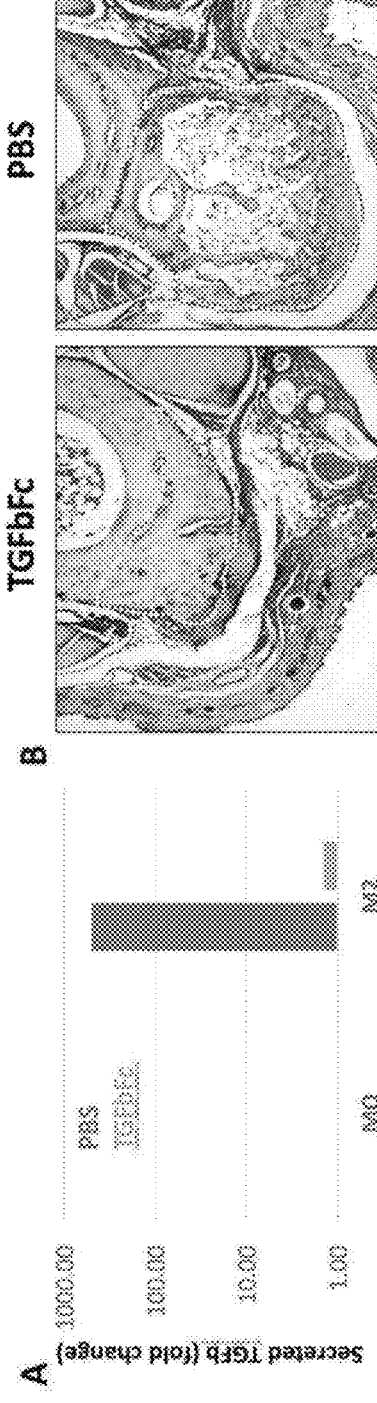
FIGURE 6A
FIGURE 6B
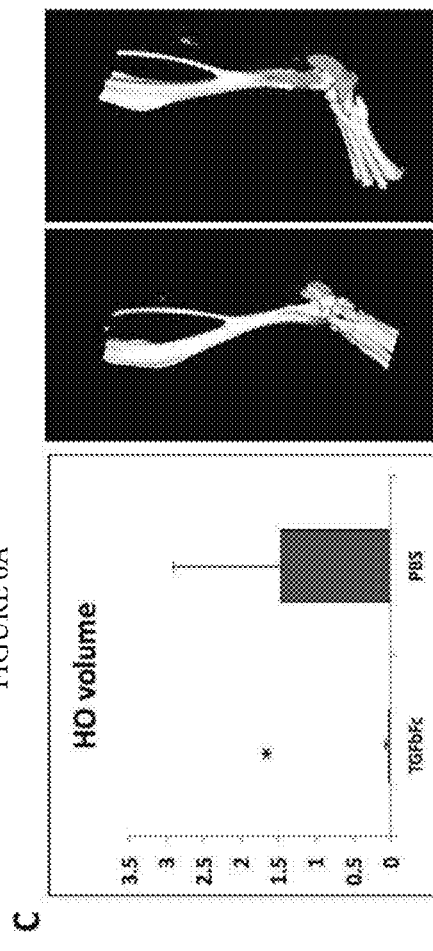
FIGURE 6C

```
IgG1    -------THTCPPCPAPELLGGPSVFLFPPKPKDTLMISRTPEVTCVVVDVSHEDPEVKF  53
IgG4    ----ESKYGPPCPSCPAPEFLGGPSVFLFPPKPKDTLMISRTPEVTCVVVDVSQEDPEVQF  57
IgG2    --------VECPPCPAPPVAG-PSVFLFPPKPKDTLMISRTPEVTCVVVDVSHEDPEVQF  51
IgG3    EPKSCDTPPPCPRCPAPELLGGPSVFLFPPKPKDTLMISRTPEVTCVVVDVSHEDPEVQF  60
                 **  ****  * *******************************:*****:*

IgG1    NWYVDGVEVHNAKTKPREEQYNSTYRVVSVLTVLHQDWLNGKEYKCKVSNKALPAPIEKT  113
IgG4    NWYVDGVEVHNAKTKPREEQFNSTYRVVSVLTVLHQDWLNGKEYKCKVSNKGLPSSIEKT  117
IgG2    NWYVDGVEVHNAKTKPREEQFNSTFRVVSVLTVVHQDWLNGKEYKCKVSNKGLPAPIEKT  111
IgG3    NWYVDGVEVHNAKTKPREEQYNSTFRVVSVLTVLHQDWLNGKEYKCKVSNKALPAPIEKT  120
        ********************:***:*********:*************.:*.:***

IgG1    ISKAKGQPREPQVYTLPPSRDEMTKNQVSLTCLVKGFYPSDIAVEWESNGQPENNYKTTP  173
IgG4    ISKAKGQPREPQVYTLPPSQEEMTKNQVSLTCLVKGFYPSDIAVEWESNGQPENNYKTTP  177
IgG2    ISKTKGQPREPQVYTLPPSREEMTKNQVSLTCLVKGFYPSDIAVEWESNGQPENNYKTTP  171
IgG3    ISKTKGQPREPQVYTLPPSREEMTKNQVSLTCLVKGFYPSDIAVEWESSGQPENNYNTTP  180
        ***.*.**********:::***********************:***

IgG1    PVLDSDGSFFLYSKLTVDKSRWQQGNVFSCSVMHEALHNHYTQKSLSLSPGK  225
IgG4    PVLDSDGSFFLYSRLTVDKSRWQEGNVFSCSVMHEALHNHYTQKSLSLSLGK  229
IgG2    PMLDSDGSFFLYSKLTVDKSRWQQGNVFSCSVMHEALHNHYTQKSLSLSPGK  223
IgG3    PMLDSDGSFFLYSKLTVDKSRWQQGNIFSCSVMHEALHNRFTQKSLSLSPGK  232
        *:***********:*********:**:***********:.:*********  **
```

FIGURE 7

SEQUENCE LISTING

```
<160> NUMBER OF SEQ ID NOS: 87

<210> SEQ ID NO 1
<211> LENGTH: 567
<212> TYPE: PRT
<213> ORGANISM: Homo sapiens

<400> SEQUENCE: 1

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
            20                  25                  30

Asn Asn Asp Met Ile Val Thr Asp Asn Asn Gly Ala Val Lys Phe Pro
        35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80
```

-continued

```
Gln Glu Val Cys Val Ala Val Trp Arg Lys Asn Asp Glu Asn Ile Thr
                85                  90                  95
Leu Glu Thr Val Cys His Asp Pro Lys Leu Pro Tyr His Asp Phe Ile
            100                 105                 110
Leu Glu Asp Ala Ala Ser Pro Lys Cys Ile Met Lys Glu Lys Lys
        115                 120                 125
Pro Gly Glu Thr Phe Phe Met Cys Ser Cys Ser Ser Asp Glu Cys Asn
130                 135                 140
Asp Asn Ile Ile Phe Ser Glu Glu Tyr Asn Thr Ser Asn Pro Asp Leu
145                 150                 155                 160
Leu Leu Val Ile Phe Gln Val Thr Gly Ile Ser Leu Leu Pro Pro Leu
                165                 170                 175
Gly Val Ala Ile Ser Val Ile Ile Phe Tyr Cys Tyr Arg Val Asn
            180                 185                 190
Arg Gln Gln Lys Leu Ser Ser Thr Trp Glu Thr Gly Lys Thr Arg Lys
        195                 200                 205
Leu Met Glu Phe Ser Glu His Cys Ala Ile Ile Leu Glu Asp Asp Arg
210                 215                 220
Ser Asp Ile Ser Ser Thr Cys Ala Asn Asn Ile Asn His Asn Thr Glu
225                 230                 235                 240
Leu Leu Pro Ile Glu Leu Asp Thr Leu Val Gly Lys Gly Arg Phe Ala
                245                 250                 255
Glu Val Tyr Lys Ala Lys Leu Lys Gln Asn Thr Ser Glu Gln Phe Glu
            260                 265                 270
Thr Val Ala Val Lys Ile Phe Pro Tyr Glu Glu Tyr Ala Ser Trp Lys
        275                 280                 285
Thr Glu Lys Asp Ile Phe Ser Asp Ile Asn Leu Lys His Glu Asn Ile
290                 295                 300
Leu Gln Phe Leu Thr Ala Glu Glu Arg Lys Thr Glu Leu Gly Lys Gln
305                 310                 315                 320
Tyr Trp Leu Ile Thr Ala Phe His Ala Lys Gly Asn Leu Gln Glu Tyr
                325                 330                 335
Leu Thr Arg His Val Ile Ser Trp Glu Asp Leu Arg Lys Leu Gly Ser
            340                 345                 350
Ser Leu Ala Arg Gly Ile Ala His Leu His Ser Asp His Thr Pro Cys
        355                 360                 365
Gly Arg Pro Lys Met Pro Ile Val His Arg Asp Leu Lys Ser Ser Asn
370                 375                 380
Ile Leu Val Lys Asn Asp Leu Thr Cys Cys Leu Cys Asp Phe Gly Leu
385                 390                 395                 400
Ser Leu Arg Leu Asp Pro Thr Leu Ser Val Asp Asp Leu Ala Asn Ser
                405                 410                 415
Gly Gln Val Gly Thr Ala Arg Tyr Met Ala Pro Glu Val Leu Glu Ser
            420                 425                 430
Arg Met Asn Leu Glu Asn Val Glu Ser Phe Lys Gln Thr Asp Val Tyr
        435                 440                 445
Ser Met Ala Leu Val Leu Trp Glu Met Thr Ser Arg Cys Asn Ala Val
450                 455                 460
Gly Glu Val Lys Asp Tyr Glu Pro Pro Phe Gly Ser Lys Val Arg Glu
465                 470                 475                 480
His Pro Cys Val Glu Ser Met Lys Asp Asn Val Leu Arg Asp Arg Gly
                485                 490                 495
```

```
Arg Pro Glu Ile Pro Ser Phe Trp Leu Asn His Gln Gly Ile Gln Met
                500                 505                 510

Val Cys Glu Thr Leu Thr Glu Cys Trp Asp His Asp Pro Glu Ala Arg
            515                 520                 525

Leu Thr Ala Gln Cys Val Ala Glu Arg Phe Ser Glu Leu Glu His Leu
        530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565

<210> SEQ ID NO 2
<211> LENGTH: 592
<212> TYPE: PRT
<213> ORGANISM: Homo sapiens

<400> SEQUENCE: 2

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Asp
                20                  25                  30

Val Glu Met Glu Ala Gln Lys Asp Glu Ile Ile Cys Pro Ser Cys Asn
            35                  40                  45

Arg Thr Ala His Pro Leu Arg His Ile Asn Asn Asp Met Ile Val Thr
        50                  55                  60

Asp Asn Asn Gly Ala Val Lys Phe Pro Gln Leu Cys Lys Phe Cys Asp
65                  70                  75                  80

Val Arg Phe Ser Thr Cys Asp Asn Gln Lys Ser Cys Met Ser Asn Cys
                85                  90                  95

Ser Ile Thr Ser Ile Cys Glu Lys Pro Gln Glu Val Cys Val Ala Val
                100                 105                 110

Trp Arg Lys Asn Asp Glu Asn Ile Thr Leu Glu Thr Val Cys His Asp
            115                 120                 125

Pro Lys Leu Pro Tyr His Asp Phe Ile Leu Glu Asp Ala Ala Ser Pro
        130                 135                 140

Lys Cys Ile Met Lys Glu Lys Lys Lys Pro Gly Glu Thr Phe Phe Met
145                 150                 155                 160

Cys Ser Cys Ser Ser Asp Glu Cys Asn Asp Asn Ile Ile Phe Ser Glu
                165                 170                 175

Glu Tyr Asn Thr Ser Asn Pro Asp Leu Leu Leu Val Ile Phe Gln Val
                180                 185                 190

Thr Gly Ile Ser Leu Leu Pro Pro Leu Gly Val Ala Ile Ser Val Ile
            195                 200                 205

Ile Ile Phe Tyr Cys Tyr Arg Val Asn Arg Gln Gln Lys Leu Ser Ser
        210                 215                 220

Thr Trp Glu Thr Gly Lys Thr Arg Lys Leu Met Glu Phe Ser Glu His
225                 230                 235                 240

Cys Ala Ile Ile Leu Glu Asp Asp Arg Ser Asp Ile Ser Ser Thr Cys
                245                 250                 255

Ala Asn Asn Ile Asn His Asn Thr Glu Leu Leu Pro Ile Glu Leu Asp
                260                 265                 270

Thr Leu Val Gly Lys Gly Arg Phe Ala Glu Val Tyr Lys Ala Lys Leu
            275                 280                 285

Lys Gln Asn Thr Ser Glu Gln Phe Glu Thr Val Ala Val Lys Ile Phe
        290                 295                 300
```

Pro Tyr Glu Glu Tyr Ala Ser Trp Lys Thr Glu Lys Asp Ile Phe Ser
305                 310                 315                 320

Asp Ile Asn Leu Lys His Glu Asn Ile Leu Gln Phe Leu Thr Ala Glu
            325                 330                 335

Glu Arg Lys Thr Glu Leu Gly Lys Gln Tyr Trp Leu Ile Thr Ala Phe
        340                 345                 350

His Ala Lys Gly Asn Leu Gln Glu Tyr Leu Thr Arg His Val Ile Ser
    355                 360                 365

Trp Glu Asp Leu Arg Lys Leu Gly Ser Ser Leu Ala Arg Gly Ile Ala
370                 375                 380

His Leu His Ser Asp His Thr Pro Cys Gly Arg Pro Lys Met Pro Ile
385                 390                 395                 400

Val His Arg Asp Leu Lys Ser Ser Asn Ile Leu Val Lys Asn Asp Leu
            405                 410                 415

Thr Cys Cys Leu Cys Asp Phe Gly Leu Ser Leu Arg Leu Asp Pro Thr
        420                 425                 430

Leu Ser Val Asp Asp Leu Ala Asn Ser Gly Gln Val Gly Thr Ala Arg
    435                 440                 445

Tyr Met Ala Pro Glu Val Leu Glu Ser Arg Met Asn Leu Glu Asn Val
450                 455                 460

Glu Ser Phe Lys Gln Thr Asp Val Tyr Ser Met Ala Leu Val Leu Trp
465                 470                 475                 480

Glu Met Thr Ser Arg Cys Asn Ala Val Gly Glu Val Lys Asp Tyr Glu
            485                 490                 495

Pro Pro Phe Gly Ser Lys Val Arg Glu His Pro Cys Val Glu Ser Met
        500                 505                 510

Lys Asp Asn Val Leu Arg Asp Arg Gly Arg Pro Glu Ile Pro Ser Phe
    515                 520                 525

Trp Leu Asn His Gln Gly Ile Gln Met Val Cys Glu Thr Leu Thr Glu
530                 535                 540

Cys Trp Asp His Asp Pro Glu Ala Arg Leu Thr Ala Gln Cys Val Ala
545                 550                 555                 560

Glu Arg Phe Ser Glu Leu Glu His Leu Asp Arg Leu Ser Gly Arg Ser
            565                 570                 575

Cys Ser Glu Glu Lys Ile Pro Glu Asp Gly Ser Leu Asn Thr Thr Lys
        580                 585                 590

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Gly Gly Gly
1

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

```
Thr Gly Gly Gly Gly Ser Gly Gly Gly Gly Ser
1               5                   10
```

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

```
Thr Gly Gly Gly Gly Ser Gly Gly Gly Gly Ser Gly Gly Gly Gly Ser
1               5                   10                  15
```

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Thr Gly Gly Gly Gly Ser Gly Gly Gly Gly Ser Gly Gly Gly Gly Ser
1               5                   10                  15

Gly Gly Gly Gly Ser
            20
```

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Thr Gly Gly Gly Pro Lys Ser Cys Asp Lys
1               5                   10
```

<210> SEQ ID NO 8
<211> LENGTH: 1248
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
atggatgcaa tgaagagagg gctctgctgt gtgctgctgc tgtgtggagc agtcttcgtt      60
tcgcccggcg ccacgatccc accgcacgtt cagaagtcgg atgtggaaat ggaggcccag     120
aaagatgaaa tcatctgccc cagctgtaat aggactgccc atccactgag acatattaat     180
aacgacatga tagtcactga caacaacggt gcagtcaagt tccacaaact gtgtaaattt     240
tgtgatgtga gattttccac ctgtgacaac cagaaatcct gcatgagcaa ctgcagcatc     300
acctccatct gtgagaagcc acaggaagtc tgtgtggctg tatggagaaa gaatgacgag     360
aacataacac tagagacagt tgccatgac ccccaagctcc cctaccatga ctttattctg     420
gaagatgctg cttctccaaa gtgcattatg aaggaaaaaa aaaagcctgg tgagactttc     480
ttcatgtgtt cctgtagctc tgatgagtgc aatgacaaca tcatcttctc agaagaatat     540
aacaccagca atcctgacac cggtggtgga actcacacat gcccaccgtg cccagcacct     600
```

```
gaactcctgg ggggaccgtc agtcttcctc ttccccccaa aacccaagga caccctcatg    660
atctcccgga cccctgaggt cacatgcgtg gtggtggacg tgagccacga agaccctgag    720
gtcaagttca actggtacgt ggacggcgtg gaggtgcata atgccaagac aaagccgcgg    780
gaggagcagt acaacagcac gtaccgtgtg gtcagcgtcc tcaccgtcct gcaccaggac    840
tggctgaatg gcaaggagta caagtgcaag gtctccaaca aagccctccc agcccccatc    900
gagaaaacca tctccaaagc caagggcagc cccgagaac acaggtgta caccctgccc    960 ccatcccggg aggagatgac caagaaccag gtcagcctga cctgcctggt caaaggcttc    1020
tatcccagcg acatcgccgt ggagtgggag agcaatgggc agccggagaa caactacaag    1080
accacgcctc ccgtgctgga ctccgacggc tccttcttcc tctatagcaa gctcaccgtg    1140
gacaagagca ggtggcagca ggggaacgtc ttctcatgct ccgtgatgca tgaggctctg    1200
cacaaccact acacgcagaa gagcctctcc ctgtctccgg gtaaatga    1248
```

<210> SEQ ID NO 9
<211> LENGTH: 415
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Asp Val Glu Met Glu Ala Gln Lys Asp Glu Ile Ile Cys Pro Ser
        35                  40                  45

Cys Asn Arg Thr Ala His Pro Leu Arg His Ile Asn Asn Asp Met Ile
    50                  55                  60

Val Thr Asp Asn Asn Gly Ala Val Lys Phe Pro Gln Leu Cys Lys Phe
65                  70                  75                  80

Cys Asp Val Arg Phe Ser Thr Cys Asp Asn Gln Lys Ser Cys Met Ser
                85                  90                  95

Asn Cys Ser Ile Thr Ser Ile Cys Glu Lys Pro Gln Glu Val Cys Val
            100                 105                 110

Ala Val Trp Arg Lys Asn Asp Glu Asn Ile Thr Leu Glu Thr Val Cys
        115                 120                 125

His Asp Pro Lys Leu Pro Tyr His Asp Phe Ile Leu Glu Asp Ala Ala
    130                 135                 140

Ser Pro Lys Cys Ile Met Lys Glu Lys Lys Lys Pro Gly Glu Thr Phe
145                 150                 155                 160

Phe Met Cys Ser Cys Ser Ser Asp Glu Cys Asn Asp Asn Ile Ile Phe
                165                 170                 175

Ser Glu Glu Tyr Asn Thr Ser Asn Pro Asp Thr Gly Gly Gly Thr His
            180                 185                 190

Thr Cys Pro Pro Cys Pro Ala Pro Glu Leu Leu Gly Gly Pro Ser Val
        195                 200                 205

Phe Leu Phe Pro Pro Lys Pro Lys Asp Thr Leu Met Ile Ser Arg Thr
    210                 215                 220

Pro Glu Val Thr Cys Val Val Val Asp Val Ser His Glu Asp Pro Glu
225                 230                 235                 240
```

```
Val Lys Phe Asn Trp Tyr Val Asp Gly Val Glu His Asn Ala Lys
            245                 250                 255

Thr Lys Pro Arg Glu Glu Gln Tyr Asn Ser Thr Tyr Arg Val Val Ser
        260                 265                 270

Val Leu Thr Val Leu His Gln Asp Trp Leu Asn Gly Lys Glu Tyr Lys
        275                 280                 285

Cys Lys Val Ser Asn Lys Ala Leu Pro Ala Pro Ile Glu Lys Thr Ile
        290                 295                 300

Ser Lys Ala Lys Gly Gln Pro Arg Glu Pro Gln Val Tyr Thr Leu Pro
305                 310                 315                 320

Pro Ser Arg Glu Glu Met Thr Lys Asn Gln Val Ser Leu Thr Cys Leu
                325                 330                 335

Val Lys Gly Phe Tyr Pro Ser Asp Ile Ala Val Glu Trp Glu Ser Asn
            340                 345                 350

Gly Gln Pro Glu Asn Asn Tyr Lys Thr Thr Pro Pro Val Leu Asp Ser
        355                 360                 365

Asp Gly Ser Phe Phe Leu Tyr Ser Lys Leu Thr Val Asp Lys Ser Arg
370                 375                 380

Trp Gln Gln Gly Asn Val Phe Ser Cys Ser Val Met His Glu Ala Leu
385                 390                 395                 400

His Asn His Tyr Thr Gln Lys Ser Leu Ser Leu Ser Pro Gly Lys
                405                 410                 415

<210> SEQ ID NO 10
<211> LENGTH: 1284
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
atggatgcaa tgaagagagg gctctgctgt gtgctgctgc tgtgtggagc agtcttcgtt      60
tcgcccggcg ccacgatccc accgcacgtt cagaagtcgg atgtggaaat ggaggcccag     120
aaagatgaaa tcatctgccc cagctgtaat aggactgccc atccactgag acatattaat     180
aacgacatga tagtcactga caacaacggt gcagtcaagt tccacaact gtgtaaattt     240 tgtgatgtga gattttccac ctgtgacaac cagaaatcct gcatgagcaa ctgcagcatc     300
acctccatct gtgagaagcc acaggaagtc tgtgtggctg tatggagaaa gaatgacgag     360
aacataacac tagagacagt ttgccatgac cccaagctcc cctaccatga ctttattctg     420
gaagatgctg cttctccaaa gtgcattatg aaggaaaaaa aaaagcctgg tgagactttc     480
ttcatgtgtt cctgtagctc tgatgagtgc aatgacaaca tcatcttctc agaagaaatt     540
aacaccagca atcctgacac cggtggtgga ggaagtggtg gaggtggttc tggaggtggt     600
ggaagtactc acacatgccc accgtgccca gcacctgaac tcctgggggg accgtcagtc     660
ttcctcttcc ccccaaaacc caaggacacc ctcatgatct cccggacccc tgaggtcaca     720
tgcgtggtgg tggacgtgag ccacgaagac cctgaggtca agttcaactg gtacgtggac     780
ggcgtggagg tgcataatgc caagacaaag ccgcgggagg agcagtacaa cagcacgtac     840
cgtgtggtca gcgtcctcac cgtcctgcac caggactggc tgaatggcaa ggagtacaag     900
tgcaaggtct ccaacaaagc cctcccagcc ccatcgaga aaaccatctc caaagccaaa     960
gggcagcccc gagaaccaca ggtgtacacc ctgcccccat cccgggagga gatgaccaag    1020
aaccaggtca gcctgacctg cctggtcaaa ggcttctatc ccagcgacat cgccgtggag    1080
```

```
tgggagagca atgggcagcc ggagaacaac tacaagacca cgcctcccgt gctggactcc    1140
gacggctcct tcttcctcta tagcaagctc accgtggaca agagcaggtg gcagcagggg    1200
aacgtcttct catgctccgt gatgcatgag gctctgcaca accactacac gcagaagagc    1260 ctctcccctgt ctccgggtaa atga                                          1284
```

<210> SEQ ID NO 11
<211> LENGTH: 427
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

```
Met Asp Ala Met Lys Arg Gly Leu Cys Cys Val Leu Leu Leu Cys Gly
 1               5                  10                  15

Ala Val Phe Val Ser Pro Gly Ala Thr Ile Pro Pro His Val Gln Lys
            20                  25                  30

Ser Asp Val Glu Met Glu Ala Gln Lys Asp Glu Ile Ile Cys Pro Ser
        35                  40                  45

Cys Asn Arg Thr Ala His Pro Leu Arg His Ile Asn Asn Asp Met Ile
    50                  55                  60

Val Thr Asp Asn Asn Gly Ala Val Lys Phe Pro Gln Leu Cys Lys Phe
65                  70                  75                  80

Cys Asp Val Arg Phe Ser Thr Cys Asp Asn Gln Lys Ser Cys Met Ser
                85                  90                  95

Asn Cys Ser Ile Thr Ser Ile Cys Glu Lys Pro Gln Glu Val Cys Val
           100                 105                 110

Ala Val Trp Arg Lys Asn Asp Glu Asn Ile Thr Leu Glu Thr Val Cys
       115                 120                 125

His Asp Pro Lys Leu Pro Tyr His Asp Phe Ile Leu Glu Asp Ala Ala
   130                 135                 140

Ser Pro Lys Cys Ile Met Lys Glu Lys Lys Pro Gly Glu Thr Phe Phe
145                 150                 155                 160

Phe Met Cys Ser Cys Ser Ser Asp Glu Cys Asn Asp Asn Ile Ile Phe
                165                 170                 175

Ser Glu Glu Tyr Asn Thr Ser Asn Pro Asp Thr Gly Gly Gly Gly Ser
            180                 185                 190

Gly Gly Gly Gly Ser Gly Gly Gly Ser Thr His Thr Cys Pro Pro
        195                 200                 205

Cys Pro Ala Pro Glu Leu Leu Gly Gly Pro Ser Val Phe Leu Phe Pro
    210                 215                 220

Pro Lys Pro Lys Asp Thr Leu Met Ile Ser Arg Thr Pro Glu Val Thr
225                 230                 235                 240

Cys Val Val Val Asp Val Ser His Glu Asp Pro Glu Val Lys Phe Asn
                245                 250                 255

Trp Tyr Val Asp Gly Val Glu Val His Asn Ala Lys Thr Lys Pro Arg
            260                 265                 270

Glu Glu Gln Tyr Asn Ser Thr Tyr Arg Val Val Ser Val Leu Thr Val
        275                 280                 285

Leu His Gln Asp Trp Leu Asn Gly Lys Glu Tyr Lys Cys Lys Val Ser
    290                 295                 300

Asn Lys Ala Leu Pro Ala Pro Ile Glu Lys Thr Ile Ser Lys Ala Lys
305                 310                 315                 320
```

```
Gly Gln Pro Arg Glu Pro Gln Val Tyr Thr Leu Pro Pro Ser Arg Glu
            325                 330                 335

Glu Met Thr Lys Asn Gln Val Ser Leu Thr Cys Leu Val Lys Gly Phe
            340                 345                 350

Tyr Pro Ser Asp Ile Ala Val Glu Trp Glu Ser Asn Gly Gln Pro Glu
            355                 360                 365

Asn Asn Tyr Lys Thr Thr Pro Pro Val Leu Asp Ser Asp Gly Ser Phe
            370                 375                 380

Phe Leu Tyr Ser Lys Leu Thr Val Asp Lys Ser Arg Trp Gln Gln Gly
385                 390                 395                 400

Asn Val Phe Ser Cys Ser Val Met His Glu Ala Leu His Asn His Tyr
                405                 410                 415

Thr Gln Lys Ser Leu Ser Leu Ser Pro Gly Lys
            420                 425

<210> SEQ ID NO 12
<211> LENGTH: 1299
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
atggatgcaa tgaagagagg ctctgctgt gtgctgctgc tgtgtggagc agtcttcgtt    60
tcgcccggcg ccacgatccc accgcacgtt cagaagtcgg atgtggaaat ggaggcccag   120
aaagatgaaa tcatctgccc cagctgtaat aggactgccc atccactgag acatattaat   180
aacgacatga tagtcactga caacaacggt gcagtcaagt ttccacaact gtgtaaattt   240
tgtgatgtga gattttccac ctgtgacaac cagaaatcct gcatgagcaa ctgcagcatc   300
acctccatct gtgagaagcc acaggaagtc tgtgtggctg tatggagaaa gaatgacgag   360
aacataacac tagagacagt ttgccatgac cccaagctcc cctaccatga ctttattctg   420
gaagatgctg cttctccaaa gtgcattatg aaggaaaaaa aaaagcctgg tgagactttc   480
ttcatgtgtt cctgtagctc tgatgagtgc aatgacaaca tcatcttctc agaagaatat   540
aacaccagca atcctgacac cggtggtgga ggttctggag gtggaggaag tggtggaggt   600
ggttctggag gtggtggaag tactcacaca tgcccaccgt gcccagcacc tgaactcctg   660
gggggaccgt cagtcttcct cttccccca aaacccaagg acaccctcat gatctcccgg   720
acccctgagg tcacatgcgt ggtggtggac gtgagccacg aagaccctga ggtcaagttc   780
aactggtacg tggacggcgt ggaggtgcat aatgccaaga caaagccgcg ggaggagcag   840
tacaacagca cgtaccgtgt ggtcagcgtc ctcaccgtcc tgcaccagga ctggctgaat   900
ggcaaggagt acaagtgcaa ggtctccaac aaagccctcc cagcccccat cgagaaaacc   960
atctccaaag ccaagggca gccccgagaa ccacaggtgt acaccctgcc cccatcccgg  1020
gaggagatga ccaagaacca ggtcagcctg acctgcctgg tcaaaggctt ctatcccagc  1080
gacatcgccg tggagtggga gagcaatggg cagccggaga caactacaa gaccacgcct  1140 cccgtgctgg actccgacgg ctccttcttc ctctatagca agctcaccgt ggacaagagc  1200
aggtggcagc aggggaacgt cttctcatgc tccgtgatgc atgaggctct gcacaaccac  1260
tacacgcaga agagcctctc cctgtctccg ggtaaatga                         1299

<210> SEQ ID NO 13
```

<211> LENGTH: 432
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Asp Val Glu Met Glu Ala Gln Lys Asp Glu Ile Ile Cys Pro Ser
        35                  40                  45

Cys Asn Arg Thr Ala His Pro Leu Arg His Ile Asn Asn Asp Met Ile
    50                  55                  60

Val Thr Asp Asn Asn Gly Ala Val Lys Phe Pro Gln Leu Cys Lys Phe
65                  70                  75                  80

Cys Asp Val Arg Phe Ser Thr Cys Asp Asn Gln Lys Ser Cys Met Ser
                85                  90                  95

Asn Cys Ser Ile Thr Ser Ile Cys Glu Lys Pro Gln Glu Val Cys Val
            100                 105                 110

Ala Val Trp Arg Lys Asn Asp Glu Asn Ile Thr Leu Glu Thr Val Cys
        115                 120                 125

His Asp Pro Lys Leu Pro Tyr His Asp Phe Ile Leu Glu Asp Ala Ala
    130                 135                 140

Ser Pro Lys Cys Ile Met Lys Glu Lys Lys Pro Gly Glu Thr Phe
145                 150                 155                 160

Phe Met Cys Ser Cys Ser Ser Asp Glu Cys Asn Asp Asn Ile Ile Phe
                165                 170                 175

Ser Glu Glu Tyr Asn Thr Ser Asn Pro Asp Thr Gly Gly Gly Gly Ser
            180                 185                 190

Gly Gly Gly Gly Ser Gly Gly Gly Ser Gly Gly Gly Gly Ser Thr
        195                 200                 205

His Thr Cys Pro Pro Cys Pro Ala Pro Glu Leu Leu Gly Gly Pro Ser
    210                 215                 220

Val Phe Leu Phe Pro Pro Lys Pro Lys Asp Thr Leu Met Ile Ser Arg
225                 230                 235                 240

Thr Pro Glu Val Thr Cys Val Val Val Asp Val Ser His Glu Asp Pro
                245                 250                 255

Glu Val Lys Phe Asn Trp Tyr Val Asp Gly Val Glu Val His Asn Ala
            260                 265                 270

Lys Thr Lys Pro Arg Glu Glu Gln Tyr Asn Ser Thr Tyr Arg Val Val
        275                 280                 285

Ser Val Leu Thr Val Leu His Gln Asp Trp Leu Asn Gly Lys Glu Tyr
    290                 295                 300

Lys Cys Lys Val Ser Asn Lys Ala Leu Pro Ala Pro Ile Glu Lys Thr
305                 310                 315                 320

Ile Ser Lys Ala Lys Gly Gln Pro Arg Glu Pro Gln Val Tyr Thr Leu
                325                 330                 335

Pro Pro Ser Arg Glu Glu Met Thr Lys Asn Gln Val Ser Leu Thr Cys
            340                 345                 350

Leu Val Lys Gly Phe Tyr Pro Ser Asp Ile Ala Val Glu Trp Glu Ser
        355                 360                 365

Asn Gly Gln Pro Glu Asn Asn Tyr Lys Thr Thr Pro Pro Val Leu Asp
```

Ser Asp Gly Ser Phe Phe Leu Tyr Ser Lys Leu Thr Val Asp Lys Ser
385                 390                 395                 400

Arg Trp Gln Gln Gly Asn Val Phe Ser Cys Ser Val Met His Glu Ala
            405                 410                 415

Leu His Asn His Tyr Thr Gln Lys Ser Leu Ser Leu Ser Pro Gly Lys
        420                 425                 430

<210> SEQ ID NO 14
<211> LENGTH: 1269
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
atggatgcaa tgaagagagg gctctgctgt gtgctgctgc tgtgtggagc agtcttcgtt      60
tcgcccggcg ccacgatccc accgcacgtt cagaagtcgg atgtggaaat ggaggcccag     120
aaagatgaaa tcatctgccc cagctgtaat aggactgccc atccactgag acatattaat     180
aacgacatga tagtcactga caacaacggt gcagtcaagt tccacaact gtgtaaattt      240 tgtgatgtga gattttccac ctgtgacaac cagaaatcct gcatgagcaa ctgcagcatc     300
acctccatct gtgagaagcc acaggaagtc tgtgtggctg tatggagaaa gaatgacgag     360
aacataacac tagagacagt ttgccatgac cccaagctcc cctaccatga ctttattctg     420
gaagatgctg cttctccaaa gtgcattatg aaggaaaaaa aaaagcctgg tgagactttc     480
ttcatgtgtt cctgtagctc tgatgagtgc aatgacaaca tcatcttctc agaagaatat     540
aacaccagca tcctgacac cggtggaggt ggttctggag tggtggaag tactcacaca      600 tgcccaccgt gcccagcacc tgaactcctg ggggaccgt cagtcttcct cttcccccca     660
aaacccaagg acaccctcat gatctcccgg acccctgagg tcacatgcgt ggtggtggac    720
gtgagccacg aagaccctga ggtcaagttc aactggtacg tggacggcgt ggaggtgcat    780
aatgccaaga caaagccgcg ggaggagcag tacaacagca cgtaccgtgt ggtcagcgtc    840
ctcaccgtcc tgcaccagga ctggctgaat ggcaaggagt acaagtgcaa ggtctccaac    900
aaagccctcc cagcccccat cgagaaaacc atctccaaag ccaaagggca gccccgagaa    960
ccacaggtgt acaccctgcc cccatcccgg gaggagatga ccaagaacca ggtcagcctg   1020
acctgcctgg tcaaaggctt ctatcccagc gacatcgccg tggagtggga gagcaatggg   1080
cagccggaga caactacaa gaccacgcct cccgtgctgg actccgacgg ctccttcttc     1140
ctctatagca agctcaccgt ggacaagagc aggtggcagc aggggaacgt cttctcatgc    1200
tccgtgatgc atgaggctct gcacaaccac tacacgcaga gagcctctc cctgtctccg    1260 ggtaaatga                                                             1269

<210> SEQ ID NO 15
<211> LENGTH: 422
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Asp Ala Met Lys Arg Gly Leu Cys Cys Val Leu Leu Leu Cys Gly
1               5                   10                  15

```
Ala Val Phe Val Ser Pro Gly Ala Thr Ile Pro Pro His Val Gln Lys
         20                  25                  30

Ser Asp Val Glu Met Glu Ala Gln Lys Asp Glu Ile Ile Cys Pro Ser
             35                  40                  45

Cys Asn Arg Thr Ala His Pro Leu Arg His Ile Asn Asn Asp Met Ile
 50                  55                  60

Val Thr Asp Asn Asn Gly Ala Val Lys Phe Pro Gln Leu Cys Lys Phe
 65                  70                  75                  80

Cys Asp Val Arg Phe Ser Thr Cys Asp Asn Gln Lys Ser Cys Met Ser
                 85                  90                  95

Asn Cys Ser Ile Thr Ser Ile Cys Glu Lys Pro Gln Glu Val Cys Val
             100                 105                 110

Ala Val Trp Arg Lys Asn Asp Glu Asn Ile Thr Leu Glu Thr Val Cys
             115                 120                 125

His Asp Pro Lys Leu Pro Tyr His Asp Phe Ile Leu Glu Asp Ala Ala
         130                 135                 140

Ser Pro Lys Cys Ile Met Lys Glu Lys Lys Pro Gly Glu Thr Phe
145                 150                 155                 160

Phe Met Cys Ser Cys Ser Ser Asp Glu Cys Asn Asp Asn Ile Ile Phe
                 165                 170                 175

Ser Glu Glu Tyr Asn Thr Ser Asn Pro Asp Thr Gly Gly Gly Ser
             180                 185                 190

Gly Gly Gly Gly Ser Thr His Thr Cys Pro Pro Cys Pro Ala Pro Glu
             195                 200                 205

Leu Leu Gly Gly Pro Ser Val Phe Leu Phe Pro Pro Lys Pro Lys Asp
         210                 215                 220

Thr Leu Met Ile Ser Arg Thr Pro Glu Val Thr Cys Val Val Val Asp
225                 230                 235                 240

Val Ser His Glu Asp Pro Glu Val Lys Phe Asn Trp Tyr Val Asp Gly
             245                 250                 255

Val Glu Val His Asn Ala Lys Thr Lys Pro Arg Glu Glu Gln Tyr Asn
             260                 265                 270

Ser Thr Tyr Arg Val Val Ser Val Leu Thr Val Leu His Gln Asp Trp
         275                 280                 285

Leu Asn Gly Lys Glu Tyr Lys Cys Lys Val Ser Asn Lys Ala Leu Pro
         290                 295                 300

Ala Pro Ile Glu Lys Thr Ile Ser Lys Ala Lys Gly Gln Pro Arg Glu
305                 310                 315                 320

Pro Gln Val Tyr Thr Leu Pro Pro Ser Arg Glu Glu Met Thr Lys Asn
                 325                 330                 335

Gln Val Ser Leu Thr Cys Leu Val Lys Gly Phe Tyr Pro Ser Asp Ile
             340                 345                 350

Ala Val Glu Trp Glu Ser Asn Gly Gln Pro Glu Asn Asn Tyr Lys Thr
             355                 360                 365

Thr Pro Pro Val Leu Asp Ser Asp Gly Ser Phe Phe Leu Tyr Ser Lys
         370                 375                 380

Leu Thr Val Asp Lys Ser Arg Trp Gln Gln Gly Asn Val Phe Ser Cys
385                 390                 395                 400

Ser Val Met His Glu Ala Leu His Asn His Tyr Thr Gln Lys Ser Leu
                 405                 410                 415

Ser Leu Ser Pro Gly Lys
             420
```

<210> SEQ ID NO 16
<211> LENGTH: 1266
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16

| | | | | | |
|---|---|---|---|---|---|
| atggatgcaa | tgaagagagg | ctctgctgt | gtgctgctgc | tgtgtggagc | agtcttcgtt | 60 |
| tcgcccggcg | ccacgatccc | accgcacgtt | cagaagtcgg | atgtggaaat | ggaggcccag | 120 |
| aaagatgaaa | tcatctgccc | cagctgtaat | aggactgccc | atccactgag | acatattaat | 180 |
| aacgacatga | tagtcactga | caacaacggt | gcagtcaagt | tccacaact | gtgtaaattt | 240 |
| tgtgatgtga | gattttccac | ctgtgacaac | cagaaatcct | gcatgagcaa | ctgcagcatc | 300 |
| acctccatct | gtgagaagcc | acaggaagtc | tgtgtggctg | tatggagaaa | gaatgacgag | 360 |
| aacataacac | tagagacagt | ttgccatgac | cccaagctcc | cctaccatga | ctttattctg | 420 |
| gaagatgctg | cttctccaaa | gtgcattatg | aaggaaaaaa | aaaagcctgg | tgagactttc | 480 |
| ttcatgtgtt | cctgtagctc | tgatgagtgc | aatgacaaca | tcatcttctc | agaagaatat | 540 |
| aacaccagca | atcctgacac | cggtggtgga | cccaaatctt | gtgacaaaac | tcacacatgc | 600 |
| ccaccgtgcc | cagcacctga | actcctgggg | ggaccgtcag | tcttcctctt | ccccccaaaa | 660 |
| cccaaggaca | ccctcatgat | ctcccggacc | cctgaggtca | catgcgtggt | ggtggacgtg | 720 |
| agccacgaag | accctgaggt | caagttcaac | tggtacgtgg | acggcgtgga | ggtgcataat | 780 |
| gccaagacaa | agccgcggga | ggagcagtac | aacagcacgt | accgtgtggt | cagcgtcctc | 840 |
| accgtcctgc | accaggactg | gctgaatggc | aaggagtaca | agtgcaaggt | ctccaacaaa | 900 |
| gccctcccag | ccccatcga | gaaaaccatc | tccaaagcca | aagggcagcc | ccgagaacca | 960 |
| caggtgtaca | ccctgccccc | atcccgggag | gagatgacca | agaaccaggt | cagcctgacc | 1020 |
| tgcctggtca | aaggcttcta | tcccagcgac | atcgccgtgg | agtgggagag | caatgggcag | 1080 |
| ccggagaaca | actacaagac | cacgcctccc | gtgctggact | ccgacggctc | cttcttcctc | 1140 |
| tatagcaagc | tcaccgtgga | caagagcagg | tggcagcagg | ggaacgtctt | ctcatgctcc | 1200 |
| gtgatgcatg | aggctctgca | caaccactac | acgcagaaga | gcctctccct | gtccccgggt | 1260 |
| aaatga | | | | | | 1266 |

<210> SEQ ID NO 17
<211> LENGTH: 421
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

Met Asp Ala Met Lys Arg Gly Leu Cys Cys Val Leu Leu Cys Gly
1               5                   10                  15

Ala Val Phe Val Ser Pro Gly Ala Thr Ile Pro Pro His Val Gln Lys
            20                  25                  30

Ser Asp Val Glu Met Glu Ala Gln Lys Asp Glu Ile Ile Cys Pro Ser
        35                  40                  45

Cys Asn Arg Thr Ala His Pro Leu Arg His Ile Asn Asn Asp Met Ile
    50                  55                  60

Val Thr Asp Asn Asn Gly Ala Val Lys Phe Pro Gln Leu Cys Lys Phe

```
            65                  70                  75                  80
Cys Asp Val Arg Phe Ser Thr Cys Asp Asn Gln Lys Ser Cys Met Ser
                85                  90                  95

Asn Cys Ser Ile Thr Ser Ile Cys Glu Lys Pro Gln Glu Val Cys Val
            100                 105                 110

Ala Val Trp Arg Lys Asn Asp Glu Asn Ile Thr Leu Glu Thr Val Cys
            115                 120                 125

His Asp Pro Lys Leu Pro Tyr His Asp Phe Ile Leu Glu Asp Ala Ala
130                 135                 140

Ser Pro Lys Cys Ile Met Lys Glu Lys Lys Pro Gly Glu Thr Phe
145                 150                 155                 160

Phe Met Cys Ser Cys Ser Ser Asp Glu Cys Asn Asp Asn Ile Ile Phe
                165                 170                 175

Ser Glu Glu Tyr Asn Thr Ser Asn Pro Asp Thr Gly Gly Gly Pro Lys
            180                 185                 190

Ser Cys Asp Lys Thr His Thr Cys Pro Pro Cys Pro Ala Pro Glu Leu
            195                 200                 205

Leu Gly Gly Pro Ser Val Phe Leu Phe Pro Pro Lys Pro Lys Asp Thr
210                 215                 220

Leu Met Ile Ser Arg Thr Pro Glu Val Thr Cys Val Val Val Asp Val
225                 230                 235                 240

Ser His Glu Asp Pro Glu Val Lys Phe Asn Trp Tyr Val Asp Gly Val
                245                 250                 255

Glu Val His Asn Ala Lys Thr Lys Pro Arg Glu Glu Gln Tyr Asn Ser
            260                 265                 270

Thr Tyr Arg Val Val Ser Val Leu Thr Val Leu His Gln Asp Trp Leu
            275                 280                 285

Asn Gly Lys Glu Tyr Lys Cys Lys Val Ser Asn Lys Ala Leu Pro Ala
            290                 295                 300

Pro Ile Glu Lys Thr Ile Ser Lys Ala Lys Gly Gln Pro Arg Glu Pro
305                 310                 315                 320

Gln Val Tyr Thr Leu Pro Pro Ser Arg Glu Glu Met Thr Lys Asn Gln
                325                 330                 335

Val Ser Leu Thr Cys Leu Val Lys Gly Phe Tyr Pro Ser Asp Ile Ala
            340                 345                 350

Val Glu Trp Glu Ser Asn Gly Gln Pro Glu Asn Asn Tyr Lys Thr Thr
            355                 360                 365

Pro Pro Val Leu Asp Ser Asp Gly Ser Phe Phe Leu Tyr Ser Lys Leu
            370                 375                 380

Thr Val Asp Lys Ser Arg Trp Gln Gln Gly Asn Val Phe Ser Cys Ser
385                 390                 395                 400

Val Met His Glu Ala Leu His Asn His Tyr Thr Gln Lys Ser Leu Ser
                405                 410                 415

Leu Ser Pro Gly Lys
            420

<210> SEQ ID NO 18
<211> LENGTH: 162
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18
```

```
Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Lys Pro Gly Thr Phe Phe Met Cys Ser Cys Ser Ser Asp
    130                 135                 140

Glu Cys Asn Asp Asn Ile Ile Phe Ser Glu Glu Tyr Asn Thr Ser Asn
145                 150                 155                 160

Pro Asp

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gly Gly Gly Ser
1               5

<210> SEQ ID NO 20
<211> LENGTH: 162
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
```

-continued

```
                115                 120                 125
Lys Lys Lys Pro Gly Glu Thr Phe Phe Met Cys Ser Cys Ser Ser Asp
        130                 135                 140

Glu Cys Asn Asp Asn Ile Ile Phe Ser Glu Glu Tyr Asn Thr Ser Asn
145                 150                 155                 160

Pro Asp

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gly Gly Gly Ser Gly Gly Gly Gly Ser
1               5                   10

<210> SEQ ID NO 22
<211> LENGTH: 22
<212> TYPE: PRT
<213> ORGANISM: Unknown
<220> FEATURE:
<223> OTHER INFORMATION: Description of Unknown:
      native leader sequence

<400> SEQUENCE: 22

Met Gly Arg Gly Leu Leu Arg Gly Leu Trp Pro Leu His Ile Val Leu
1               5                   10                  15

Trp Thr Arg Ile Ala Ser
            20

<210> SEQ ID NO 23
<211> LENGTH: 22
<212> TYPE: PRT
<213> ORGANISM: Unknown
<220> FEATURE:
<223> OTHER INFORMATION: Description of Unknown:
      Tissue plasminogen activator sequence

<400> SEQUENCE: 23

Met Asp Ala Met Lys Arg Gly Leu Cys Cys Val Leu Leu Leu Cys Gly
1               5                   10                  15

Ala Val Phe Val Ser Pro
            20

<210> SEQ ID NO 24
<211> LENGTH: 21
<212> TYPE: PRT
<213> ORGANISM: Apis sp.

<400> SEQUENCE: 24

Met Lys Phe Leu Val Asn Val Ala Leu Val Phe Met Val Val Tyr Ile
1               5                   10                  15

Ser Tyr Ile Tyr Ala
            20

<210> SEQ ID NO 25
<211> LENGTH: 26
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 25

Thr Gly Gly Gly Gly Ser Gly Gly Gly Ser Gly Gly Gly Gly Ser
1               5                   10                  15

Gly Gly Gly Gly Ser Gly Gly Gly Gly Ser
            20                  25

<210> SEQ ID NO 26
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Thr Gly Gly Gly Gly Ser Gly Gly Gly Ser Gly Gly Gly Gly Ser
1               5                   10                  15

Gly Gly Gly Gly Ser Gly Gly Gly Ser Gly Gly Gly Gly Ser
            20                  25                  30

<210> SEQ ID NO 27
<211> LENGTH: 137
<212> TYPE: PRT
<213> ORGANISM: Homo sapiens

<400> SEQUENCE: 27

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser
                85                  90                  95

Pro Lys Cys Ile Met Lys Glu Lys Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr Asn Thr Ser Asn Pro Asp
    130                 135

<210> SEQ ID NO 28
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Lys Ser Val Asn Asn Asp Met Ile Val Thr Asp Asn Asn Gly Ala
1               5                   10                  15

Val Lys Phe Pro Gln Leu Cys Lys Phe Cys Asp Val Arg Phe Ser Thr
            20                  25                  30
```

```
Cys Asp Asn Gln Lys Ser Cys Met Ser Asn Cys Ser Ile Thr Ser Ile
            35                  40                  45

Cys Glu Lys Pro Gln Glu Val Cys Val Ala Val Trp Arg Lys Asn Asp
 50                  55                  60

Glu Asn Ile Thr Leu Glu Thr Val Cys His Asp Pro Lys Leu Pro Tyr
 65                  70                  75                  80

His Asp Phe Ile Leu Glu Asp Ala Ala Ser Pro Lys Cys Ile Met Lys
                 85                  90                  95

Glu Lys Lys Lys Pro Gly Glu Thr Phe Phe Met Cys Ser Cys Ser Ser
            100                 105                 110

Asp Glu Cys Asn Asp Asn Ile Ile Phe Ser Glu Glu Tyr Asn Thr Ser
            115                 120                 125

Asn Pro Asp
        130

<210> SEQ ID NO 29
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Met Ile Val Thr Asp Asn Asn Gly Ala Val Lys Phe Pro Gln Leu
 1               5                  10                  15

Cys Lys Phe Cys Asp Val Arg Phe Ser Thr Cys Asp Asn Gln Lys Ser
             20                  25                  30

Cys Met Ser Asn Cys Ser Ile Thr Ser Ile Cys Glu Lys Pro Gln Glu
         35                  40                  45

Val Cys Val Ala Val Trp Arg Lys Asn Asp Glu Asn Ile Thr Leu Glu
 50                  55                  60

Thr Val Cys His Asp Pro Lys Leu Pro Tyr His Asp Phe Ile Leu Glu
 65                  70                  75                  80

Asp Ala Ala Ser Pro Lys Cys Ile Met Lys Glu Lys Lys Lys Pro Gly
                 85                  90                  95

Glu Thr Phe Phe Met Cys Ser Cys Ser Ser Asp Glu Cys Asn Asp Asn
            100                 105                 110

Ile Ile Phe Ser Glu Glu Tyr Asn Thr Ser Asn Pro Asp
            115                 120                 125

<210> SEQ ID NO 30
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Thr Ile Pro Pro His Val Gln Lys Ser Val Asn Asn Asp Met Ile Val
 1               5                  10                  15

Thr Asp Asn Asn Gly Ala Val Lys Phe Pro Gln Leu Cys Lys Phe Cys
             20                  25                  30

Asp Val Arg Phe Ser Thr Cys Asp Asn Gln Lys Ser Cys Met Ser Asn
         35                  40                  45

Cys Ser Ile Thr Ser Ile Cys Glu Lys Pro Gln Glu Val Cys Val Ala
 50                  55                  60
```

```
Val Trp Arg Lys Asn Asp Glu Asn Ile Thr Leu Glu Thr Val Cys His
 65                  70                  75                  80

Asp Pro Lys Leu Pro Tyr His Asp Phe Ile Leu Glu Asp Ala Ala Ser
                 85                  90                  95

Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
            115                 120                 125

Glu Glu Tyr
    130

<210> SEQ ID NO 31
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Gln Lys Ser Val Asn Asn Asp Met Ile Val Thr Asp Asn Asn Gly Ala
 1               5                  10                  15

Val Lys Phe Pro Gln Leu Cys Lys Phe Cys Asp Val Arg Phe Ser Thr
             20                  25                  30

Cys Asp Asn Gln Lys Ser Cys Met Ser Asn Cys Ser Ile Thr Ser Ile
            35                  40                  45

Cys Glu Lys Pro Gln Glu Val Cys Val Ala Val Trp Arg Lys Asn Asp
         50                  55                  60

Glu Asn Ile Thr Leu Glu Thr Val Cys His Asp Pro Lys Leu Pro Tyr
 65                  70                  75                  80

His Asp Phe Ile Leu Glu Asp Ala Ala Ser Pro Lys Cys Ile Met Lys
                 85                  90                  95

Glu Lys Lys Pro Gly Glu Thr Phe Phe Met Cys Ser Cys Ser Ser
            100                 105                 110

Asp Glu Cys Asn Asp Asn Ile Ile Phe Ser Glu Glu Tyr
            115                 120                 125

<210> SEQ ID NO 32
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Asp Met Ile Val Thr Asp Asn Asn Gly Ala Val Lys Phe Pro Gln Leu
 1               5                  10                  15

Cys Lys Phe Cys Asp Val Arg Phe Ser Thr Cys Asp Asn Gln Lys Ser
             20                  25                  30

Cys Met Ser Asn Cys Ser Ile Thr Ser Ile Cys Glu Lys Pro Gln Glu
            35                  40                  45

Val Cys Val Ala Val Trp Arg Lys Asn Asp Glu Asn Ile Thr Leu Glu
         50                  55                  60

Thr Val Cys His Asp Pro Lys Leu Pro Tyr His Asp Phe Ile Leu Glu
 65                  70                  75                  80

Asp Ala Ala Ser Pro Lys Cys Ile Met Lys Glu Lys Lys Pro Gly
                 85                  90                  95
```

```
Glu Thr Phe Phe Met Cys Ser Cys Ser Ser Asp Glu Cys Asn Asp Asn
            100                 105                 110

Ile Ile Phe Ser Glu Glu Tyr
        115

<210> SEQ ID NO 33
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Lys Ser Asp Val Glu Met Glu Ala Gln Lys Asp Glu Ile Ile Cys
1               5                   10                  15

Pro Ser Cys Asn Arg Thr Ala His Pro Leu Arg His Ile Asn Asn Asp
            20                  25                  30

Met Ile Val Thr Asp Asn Asn Gly Ala Val Lys Phe Pro Gln Leu Cys
        35                  40                  45

Lys Phe Cys Asp Val Arg Phe Ser Thr Cys Asp Asn Gln Lys Ser Cys
    50                  55                  60

Met Ser Asn Cys Ser Ile Thr Ser Ile Cys Glu Lys Pro Gln Glu Val
65                  70                  75                  80

Cys Val Ala Val Trp Arg Lys Asn Asp Glu Asn Ile Thr Leu Glu Thr
                85                  90                  95

Val Cys His Asp Pro Lys Leu Pro Tyr His Asp Phe Ile Leu Glu Asp
            100                 105                 110

Ala Ala Ser Pro Lys Cys Ile Met Lys Glu Lys Lys Pro Gly Glu
        115                 120                 125

Thr Phe Phe Met Cys Ser Cys Ser Asp Glu Cys Asn Asp Asn Ile
    130                 135                 140

Ile Phe Ser Glu Glu Tyr Asn Thr Ser Asn Pro Asp
145                 150                 155

<210> SEQ ID NO 34
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110
```

Asp Phe Ile Leu Glu Asp Ala Ala Ser Pro Lys Cys Ile Met Lys Glu
            115                 120                 125

Lys Lys Lys Pro Gly Glu Thr Phe Phe Met Cys Ser Cys Ser Ser Asp
130                 135                 140

Glu Cys Asn Asp Asn Ile Ile Phe Ser Glu Glu Tyr
145                 150                 155

<210> SEQ ID NO 35
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Lys Ser Asp Val Glu Met Glu Ala Gln Lys Asp Glu Ile Ile Cys
1               5                   10                  15

Pro Ser Cys Asn Arg Thr Ala His Pro Leu Arg His Ile Asn Asn Asp
            20                  25                  30

Met Ile Val Thr Asp Asn Asn Gly Ala Val Lys Phe Pro Gln Leu Cys
        35                  40                  45

Lys Phe Cys Asp Val Arg Phe Ser Thr Cys Asp Asn Gln Lys Ser Cys
50                  55                  60

Met Ser Asn Cys Ser Ile Thr Ser Ile Cys Glu Lys Pro Gln Glu Val
65                  70                  75                  80

Cys Val Ala Val Trp Arg Lys Asn Asp Glu Asn Ile Thr Leu Glu Thr
                85                  90                  95

Val Cys His Asp Pro Lys Leu Pro Tyr His Asp Phe Ile Leu Glu Asp
            100                 105                 110

Ala Ala Ser Pro Lys Cys Ile Met Lys Glu Lys Lys Lys Pro Gly Glu
        115                 120                 125

Thr Phe Phe Met Cys Ser Cys Ser Ser Asp Glu Cys Asn Asp Asn Ile
    130                 135                 140

Ile Phe Ser Glu Glu Tyr
145                 150

<210> SEQ ID NO 36
<211> LENGTH: 137
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asn
        35                  40                  45

Cys Ser Ile Thr Ser Ile Cys Glu Lys Pro Gln Glu Val Cys Val Ala
50                  55                  60

Val Trp Arg Lys Asn Asp Glu Asn Ile Thr Leu Glu Thr Val Cys His
65                  70                  75                  80

Asp Pro Lys Leu Pro Tyr His Lys Phe Ile Leu Glu Asp Ala Ala Ser
                85                  90                  95

Pro Lys Cys Ile Met Lys Glu Lys Lys Pro Gly Glu Thr Phe Phe
        100                 105                 110

Met Cys Ser Cys Ser Ser Asp Glu Cys Asn Asp Asn Ile Ile Phe Ser
            115                 120                 125

Glu Glu Tyr Asn Thr Ser Asn Pro Asp
    130                 135

<210> SEQ ID NO 37
<211> LENGTH: 162
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Lys Phe Ile Leu Glu Asp Ala Ala Ser Pro Lys Cys Ile Met Lys Glu
        115                 120                 125

Lys Lys Lys Pro Gly Glu Thr Phe Phe Met Cys Ser Cys Ser Ser Asp
    130                 135                 140

Glu Cys Asn Asp Asn Ile Ile Phe Ser Glu Glu Tyr Asn Thr Ser Asn
145                 150                 155                 160

Pro Asp

<210> SEQ ID NO 38
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Thr Ile Pro Pro His Val Gln Lys Ser Val Asn Asn Asp Met Ile Val
1               5                   10                  15

Thr Asp Asn Asn Gly Ala Val Lys Phe Pro Gln Leu Cys Lys Phe Cys
            20                  25                  30

Asp Val Arg Phe Ser Thr Cys Asp Asn Gln Lys Ser Cys Met Ser Asp
        35                  40                  45

Cys Ser Ile Thr Ser Ile Cys Glu Lys Pro Gln Glu Val Cys Val Ala
    50                  55                  60

Val Trp Arg Lys Asn Asp Glu Asn Ile Thr Leu Glu Thr Val Cys His
65                  70                  75                  80

Asp Pro Lys Leu Pro Tyr His Asp Phe Ile Leu Glu Asp Ala Ala Ser

```
                85                  90                  95
Pro Lys Cys Ile Met Lys Glu Lys Lys Pro Gly Glu Thr Phe Phe
            100                 105                 110

Met Cys Ser Cys Ser Ser Asp Glu Cys Asn Asp Asn Ile Ile Phe Ser
        115                 120                 125

Glu Glu Tyr
    130

<210> SEQ ID NO 39
<211> LENGTH: 156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asp Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Lys Pro Gly Glu Thr Phe Phe Met Cys Ser Cys Ser Ser Asp
    130                 135                 140

Glu Cys Asn Asp Asn Ile Ile Phe Ser Glu Glu Tyr
145                 150                 155

<210> SEQ ID NO 40
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Thr Gly Gly Gly Gly Ser Gly Gly Gly Gly Ser Gly Gly Gly Gly Ser
1               5                   10                  15

Gly Gly Gly Gly Ser Gly Gly Gly Ser Gly Gly Gly Gly Ser Gly
            20                  25                  30

Gly Gly Gly Ser
        35

<210> SEQ ID NO 41
<211> LENGTH: 36
<212> TYPE: PRT
<213> ORGANISM: Homo sapiens

<400> SEQUENCE: 41
```

```
Gly Arg Cys Lys Ile Arg His Ile Gly Ser Asn Asn Arg Leu Gln Arg
1               5                   10                  15

Ser Thr Cys Gln Asn Thr Gly Trp Glu Ser Ala His Val Met Lys Thr
            20                  25                  30

Pro Gly Phe Arg
        35
```

<210> SEQ ID NO 42
<211> LENGTH: 223
<212> TYPE: PRT
<213> ORGANISM: Homo sapiens

<400> SEQUENCE: 42

```
Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Asp Val Ser His Glu Asp Pro Glu
        35                  40                  45

Val Gln Phe Asn Trp Tyr Val Asp Gly Val Glu Val His Asn Ala Lys
50                  55                  60

Thr Lys Pro Arg Glu Glu Gln Phe Asn Ser Thr Phe Arg Val Val Ser
65              70                  75                  80

Val Leu Thr Val Val His Gln Asp Trp Leu Asn Gly Lys Glu Tyr Lys
                85                  90                  95

Cys Lys Val Ser Asn Lys Gly Leu Pro Ala Pro Ile Glu Lys Thr Ile
                100                 105                 110

Ser Lys Thr Lys Gly Gln Pro Arg Glu Pro Gln Val Tyr Thr Leu Pro
            115                 120                 125

Pro Ser Arg Glu Glu Met Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220
```

<210> SEQ ID NO 43
<211> LENGTH: 233
<212> TYPE: PRT
<213> ORGANISM: Homo sapiens

<400> SEQUENCE: 43

```
Gly Gly Pro Lys Ser Cys Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
        35                  40                  45

Val Val Asp Val Ser His Glu Asp Pro Glu Val Lys Phe Asn Trp Tyr
    50                  55                  60
```

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
        115                 120                 125

Pro Arg Glu Pro Gln Val Tyr Thr Leu Pro Pro Ser Arg Glu Glu Met
130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Ala Leu His Asn His Tyr Thr Gln
    210                 215                 220

Lys Ser Leu Ser Leu Ser Pro Gly Lys
225                 230

<210> SEQ ID NO 44
<211> LENGTH: 437
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Asp Val Glu Met Glu Ala Gln Lys Asp Glu Ile Ile Cys Pro Ser
        35                  40                  45

Cys Asn Arg Thr Ala His Pro Leu Arg His Ile Asn Asn Asp Met Ile
    50                  55                  60

Val Thr Asp Asn Asn Gly Ala Val Lys Phe Pro Gln Leu Cys Lys Phe
65                  70                  75                  80

Cys Asp Val Arg Phe Ser Thr Cys Asp Asn Gln Lys Ser Cys Met Ser
                85                  90                  95

Asn Cys Ser Ile Thr Ser Ile Cys Glu Lys Pro Gln Glu Val Cys Val
            100                 105                 110

Ala Val Trp Arg Lys Asn Asp Glu Asn Ile Thr Leu Glu Thr Val Cys
        115                 120                 125

His Asp Pro Lys Leu Pro Tyr His Asp Phe Ile Leu Glu Asp Ala Ala
130                 135                 140

Ser Pro Lys Cys Ile Met Lys Glu Lys Lys Pro Gly Glu Thr Phe
145                 150                 155                 160

Phe Met Cys Ser Cys Ser Ser Asp Glu Cys Asn Asp Asn Ile Ile Phe
                165                 170                 175

Ser Glu Glu Tyr Asn Thr Ser Asn Pro Asp Thr Gly Gly Gly Gly Ser

```
                180                 185                 190
Gly Gly Gly Gly Ser Gly Gly Gly Ser Gly Gly Gly Ser Gly
            195                 200                 205

Gly Gly Gly Ser Thr His Thr Cys Pro Pro Cys Pro Ala Pro Glu Leu
            210                 215                 220

Leu Gly Gly Pro Ser Val Phe Leu Phe Pro Pro Lys Pro Lys Asp Thr
225                 230                 235                 240

Leu Met Ile Ser Arg Thr Pro Glu Val Thr Cys Val Val Val Asp Val
                245                 250                 255

Ser His Glu Asp Pro Glu Val Lys Phe Asn Trp Tyr Val Asp Gly Val
            260                 265                 270

Glu Val His Asn Ala Lys Thr Lys Pro Arg Glu Glu Gln Tyr Asn Ser
        275                 280                 285

Thr Tyr Arg Val Val Ser Val Leu Thr Val Leu His Gln Asp Trp Leu
    290                 295                 300

Asn Gly Lys Glu Tyr Lys Cys Lys Val Ser Asn Lys Ala Leu Pro Ala
305                 310                 315                 320

Pro Ile Glu Lys Thr Ile Ser Lys Ala Lys Gly Gln Pro Arg Glu Pro
                325                 330                 335

Gln Val Tyr Thr Leu Pro Pro Ser Arg Glu Glu Met Thr Lys Asn Gln
            340                 345                 350

Val Ser Leu Thr Cys Leu Val Lys Gly Phe Tyr Pro Ser Asp Ile Ala
        355                 360                 365

Val Glu Trp Glu Ser Asn Gly Gln Pro Glu Asn Asn Tyr Lys Thr Thr
    370                 375                 380

Pro Pro Val Leu Asp Ser Asp Gly Ser Phe Phe Leu Tyr Ser Lys Leu
385                 390                 395                 400

Thr Val Asp Lys Ser Arg Trp Gln Gln Gly Asn Val Phe Ser Cys Ser
                405                 410                 415

Val Met His Glu Ala Leu His Asn His Tyr Thr Gln Lys Ser Leu Ser
            420                 425                 430

Leu Ser Pro Gly Lys
        435

<210> SEQ ID NO 45
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Met Asp Ala Met Lys Arg Gly Leu Cys Cys Val Leu Leu Leu Cys Gly
1               5                   10                  15

Ala Val Phe Val Ser Pro Gly Ala Thr Ile Pro Pro His Val Gln Lys
            20                  25                  30

Ser Asp Val Glu Met Glu Ala Gln Lys Asp Glu Ile Ile Cys Pro Ser
        35                  40                  45

Cys Asn Arg Thr Ala His Pro Leu Arg His Ile Asn Asn Asp Met Ile
    50                  55                  60

Val Thr Asp Asn Asn Gly Ala Val Lys Phe Pro Gln Leu Cys Lys Phe
65                  70                  75                  80

Cys Asp Val Arg Phe Ser Thr Cys Asp Asn Gln Lys Ser Cys Met Ser
                85                  90                  95
```

```
Asn Cys Ser Ile Thr Ser Ile Cys Glu Lys Pro Gln Glu Val Cys Val
            100                 105                 110

Ala Val Trp Arg Lys Asn Asp Glu Asn Ile Thr Leu Glu Thr Val Cys
        115                 120                 125

His Asp Pro Lys Leu Pro Tyr His Asp Phe Ile Leu Glu Asp Ala Ala
        130                 135                 140

Ser Pro Lys Cys Ile Met Lys Glu Lys Lys Pro Gly Glu Thr Phe
145                 150                 155                 160

Phe Met Cys Ser Cys Ser Ser Asp Glu Cys Asn Asp Asn Ile Ile Phe
                165                 170                 175

Ser Glu Glu Tyr Asn Thr Ser Asn Pro Asp Thr Gly Gly Gly Ser
            180                 185                 190

Gly Gly Gly Gly Ser Gly Gly Gly Ser Gly Gly Gly Ser Gly
            195                 200                 205

Gly Gly Ser Gly Gly Gly Ser Thr His Thr Cys Pro Pro Cys
        210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
            260                 265                 270

Tyr Val Asp Gly Val Glu Val His Asn Ala Lys Thr Lys Pro Arg Glu
        275                 280                 285

Glu Gln Tyr Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 46
<211> LENGTH: 1314
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
atggatgcaa tgaagagagg gctctgctgt gtgctgctgc tgtgtggagc agtcttcgtt      60
```

```
tcgcccggcg ccacgatccc accgcacgtt cagaagtcgg atgtggaaat ggaggcccag      120
aaagatgaaa tcatctgccc cagctgtaat aggactgccc atccactgag acatattaat      180
aacgacatga tagtcactga caacaacggt gcagtcaagt ttccacaact gtgtaaattt      240
tgtgatgtga gattttccac ctgtgacaac cagaaatcct gcatgagcaa ctgcagcatc      300
acctccatct gtgagaagcc acaggaagtc tgtgtggctg tatggagaaa gaatgacgag      360
aacataacac tagagacagt ttgccatgac cccaagctcc cctaccatga ctttattctg      420
gaagatgctg cttctccaaa gtgcattatg aaggaaaaaa aaaagcctgg tgagactttc      480
ttcatgtgtt cctgtagctc tgatgagtgc aatgacaaca tcatcttctc agaagaatat      540
aacaccagca atcctgacac cggtggagga ggttctggtg gtggaggttc tggaggtgga      600
ggaagtggtg gaggtggttc tggaggtggt ggaagtactc acacatgccc accgtgccca      660
gcacctgaac tcctgggggg accgtcagtc ttcctcttcc ccccaaaacc caaggacacc      720
ctcatgatct cccggacccc tgaggtcaca tgcgtggtgg tggacgtgag ccacgaagac      780
cctgaggtca agttcaactg gtacgtggac ggcgtggagg tgcataatgc caagacaaag      840
ccgcgggagg agcagtacaa cagcacgtac cgtgtggtca gcgtcctcac cgtcctgcac      900
caggactggc tgaatggcaa ggagtacaag tgcaaggtct ccaacaaagc cctcccagcc      960
cccatcgaga aaaccatctc caaagccaaa gggcagcccc gagaaccaca ggtgtacacc     1020
ctgcccccat cccgggagga tgaccaagaa ccaggtca gcctgacctg cctggtcaaa     1080
ggcttctatc ccagcgacat cgccgtggag tgggagagca atgggcagcc ggagaacaac     1140
tacaagacca cgcctcccgt gctggactcc gacggctcct tcttcctcta tagcaagctc     1200
accgtggaca agagcaggtg gcagcagggg aacgtcttct catgctccgt gatgcatgag     1260
gctctgcaca accactacac gcagaagagc ctctccctgt ctccgggtaa atga           1314

<210> SEQ ID NO 47
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47
atggatgcaa tgaagagagg gctctgctgt gtgctgctgc tgtgtggagc agtcttcgtt       60
tcgcccggcg ccacgatccc accgcacgtt cagaagtcgg atgtggaaat ggaggcccag      120
aaagatgaaa tcatctgccc cagctgtaat aggactgccc atccactgag acatattaat      180
aacgacatga tagtcactga caacaacggt gcagtcaagt ttccacaact gtgtaaattt      240
tgtgatgtga gattttccac ctgtgacaac cagaaatcct gcatgagcaa ctgcagcatc      300
acctccatct gtgagaagcc acaggaagtc tgtgtggctg tatggagaaa gaatgacgag      360
aacataacac tagagacagt ttgccatgac cccaagctcc cctaccatga ctttattctg      420
gaagatgctg cttctccaaa gtgcattatg aaggaaaaaa aaaagcctgg tgagactttc      480
ttcatgtgtt cctgtagctc tgatgagtgc aatgacaaca tcatcttctc agaagaatat      540
aacaccagca atcctgacac cggtggaggt ggaagtggtg gaggaggttc tggtggtgga      600
ggttctggag gtggaggaag tggtggaggt ggttctggag gtggtggaag tactcacaca      660
tgcccaccgt gcccagcacc tgaactcctg ggggaccgt cagtcttcct cttcccccca      720
aaacccaagg acaccctcat gatctcccgg acccctgagg tcacatgcgt ggtggtggac      780
```

-continued

```
gtgagccacg aagaccctga ggtcaagttc aactggtacg tggacggcgt ggaggtgcat    840
aatgccaaga caaagccgcg ggaggagcag tacaacagca cgtaccgtgt ggtcagcgtc    900
ctcaccgtcc tgcaccagga ctggctgaat ggcaaggagt acaagtgcaa ggtctccaac    960
aaagccctcc cagcccccat cgagaaaacc atctccaaag ccaagggca gccccgagaa     1020 ccacaggtgt acaccctgcc cccatcccgg gaggagatga ccaagaacca ggtcagcctg    1080
acctgcctgg tcaaaggctt ctatcccagc gacatcgccg tggagtggga gagcaatggg    1140
cagccggaga acaactacaa gaccacgcct cccgtgctgg actccgacgg ctccttcttc    1200
ctctatagca agctcaccgt ggacaagagc aggtggcagc aggggaacgt cttctcatgc    1260
tccgtgatgc atgaggctct gcacaaccac tacacgcaga agagcctctc cctgtctccg    1320
ggtaaatga                                                             1329
```

<210> SEQ ID NO 48
<211> LENGTH: 408
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

```
Thr Ile Pro Pro His Val Gln Lys Ser Asp Val Glu Met Glu Ala Gln
1               5                   10                  15

Lys Asp Glu Ile Ile Cys Pro Ser Cys Asn Arg Thr Ala His Pro Leu
            20                  25                  30

Arg His Ile Asn Asn Asp Met Ile Val Thr Asp Asn Asn Gly Ala Val
        35                  40                  45

Lys Phe Pro Gln Leu Cys Lys Phe Cys Asp Val Arg Phe Ser Thr Cys
    50                  55                  60

Asp Asn Gln Lys Ser Cys Met Ser Asn Cys Ser Ile Thr Ser Ile Cys
65                  70                  75                  80

Glu Lys Pro Gln Glu Val Cys Val Ala Val Trp Arg Lys Asn Asp Glu
                85                  90                  95

Asn Ile Thr Leu Glu Thr Val Cys His Asp Pro Lys Leu Pro Tyr His
            100                 105                 110

Asp Phe Ile Leu Glu Asp Ala Ala Ser Pro Lys Cys Ile Met Lys Glu
        115                 120                 125

Lys Lys Lys Pro Gly Glu Thr Phe Phe Met Cys Ser Cys Ser Ser Asp
    130                 135                 140

Glu Cys Asn Asp Asn Ile Ile Phe Ser Glu Glu Tyr Asn Thr Ser Asn
145                 150                 155                 160

Pro Asp Thr Gly Gly Gly Gly Ser Gly Gly Gly Ser Gly Gly Gly
                165                 170                 175

Gly Ser Gly Gly Gly Gly Ser Thr His Thr Cys Pro Pro Cys Pro Ala
            180                 185                 190

Pro Glu Leu Leu Gly Gly Pro Ser Val Phe Leu Phe Pro Pro Lys Pro
        195                 200                 205

Lys Asp Thr Leu Met Ile Ser Arg Thr Pro Glu Val Thr Cys Val Val
    210                 215                 220

Val Asp Val Ser His Glu Asp Pro Glu Val Lys Phe Asn Trp Tyr Val
225                 230                 235                 240

Asp Gly Val Glu Val His Asn Ala Lys Thr Lys Pro Arg Glu Glu Gln
                245                 250                 255
```

-continued

Tyr Asn Ser Thr Tyr Arg Val Val Ser Val Leu Thr Val Leu His Gln
                260                 265                 270

Asp Trp Leu Asn Gly Lys Glu Tyr Lys Cys Lys Val Ser Asn Lys Ala
            275                 280                 285

Leu Pro Ala Pro Ile Glu Lys Thr Ile Ser Lys Ala Lys Gly Gln Pro
        290                 295                 300

Arg Glu Pro Gln Val Tyr Thr Leu Pro Pro Ser Arg Glu Glu Met Thr
305                 310                 315                 320

Lys Asn Gln Val Ser Leu Thr Cys Leu Val Lys Gly Phe Tyr Pro Ser
                325                 330                 335

Asp Ile Ala Val Glu Trp Glu Ser Asn Gly Gln Pro Glu Asn Asn Tyr
            340                 345                 350

Lys Thr Thr Pro Pro Val Leu Asp Ser Asp Gly Ser Phe Phe Leu Tyr
        355                 360                 365

Ser Lys Leu Thr Val Asp Lys Ser Arg Trp Gln Gln Gly Asn Val Phe
370                 375                 380

Ser Cys Ser Val Met His Glu Ala Leu His Asn His Tyr Thr Gln Lys
385                 390                 395                 400

Ser Leu Ser Leu Ser Pro Gly Lys
                405

<210> SEQ ID NO 49
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Lys Val Ser Asn Lys Ala Leu Pro Ala Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220
Lys
225

<210> SEQ ID NO 50
<211> LENGTH: 851
<212> TYPE: PRT
<213> ORGANISM: Homo sapiens

<400> SEQUENCE: 50

Met Thr Ser His Tyr Val Ile Ala Ile Phe Ala Leu Met Ser Ser Cys
1               5                   10                  15

Leu Ala Thr Ala Gly Pro Glu Pro Gly Ala Leu Cys Glu Leu Ser Pro
                20                  25                  30

Val Ser Ala Ser His Pro Val Gln Ala Leu Met Glu Ser Phe Thr Val
            35                  40                  45

Leu Ser Gly Cys Ala Ser Arg Gly Thr Thr Gly Leu Pro Gln Glu Val
    50                  55                  60

His Val Leu Asn Leu Arg Thr Ala Gly Gln Gly Pro Gly Gln Leu Gln
65                  70                  75                  80

Arg Glu Val Thr Leu His Leu Asn Pro Ile Ser Ser Val His Ile His
                85                  90                  95

His Lys Ser Val Val Phe Leu Leu Asn Ser Pro His Pro Leu Val Trp
                100                 105                 110

His Leu Lys Thr Glu Arg Leu Ala Thr Gly Val Ser Arg Leu Phe Leu
            115                 120                 125

Val Ser Glu Gly Ser Val Val Gln Phe Ser Ser Ala Asn Phe Ser Leu
    130                 135                 140

Thr Ala Glu Thr Glu Glu Arg Asn Phe Pro His Gly Asn Glu His Leu
145                 150                 155                 160

Leu Asn Trp Ala Arg Lys Glu Tyr Gly Ala Val Thr Ser Phe Thr Glu
                165                 170                 175

Leu Lys Ile Ala Arg Asn Ile Tyr Ile Lys Val Gly Glu Asp Gln Val
            180                 185                 190

Phe Pro Pro Lys Cys Asn Ile Gly Lys Asn Phe Leu Ser Leu Asn Tyr
    195                 200                 205

Leu Ala Glu Tyr Leu Gln Pro Lys Ala Ala Glu Gly Cys Val Met Ser
    210                 215                 220

Ser Gln Pro Gln Asn Glu Glu Val His Ile Ile Glu Leu Ile Thr Pro
225                 230                 235                 240

Asn Ser Asn Pro Tyr Ser Ala Phe Gln Val Asp Ile Thr Ile Asp Ile
                245                 250                 255

Arg Pro Ser Gln Glu Asp Leu Glu Val Val Lys Asn Leu Ile Leu Ile
            260                 265                 270

Leu Lys Cys Lys Lys Ser Val Asn Trp Val Ile Lys Ser Phe Asp Val
    275                 280                 285

Lys Gly Ser Leu Lys Ile Ile Ala Pro Asn Ser Ile Gly Phe Gly Lys
    290                 295                 300

Glu Ser Glu Arg Ser Met Thr Met Thr Lys Ser Ile Arg Asp Asp Ile
305                 310                 315                 320

Pro Ser Thr Gln Gly Asn Leu Val Lys Trp Ala Leu Asp Asn Gly Tyr
                325                 330                 335

Ser Pro Ile Thr Ser Tyr Thr Met Ala Pro Val Ala Asn Arg Phe His

-continued

```
               340                 345                 350
Leu Arg Leu Glu Asn Asn Ala Glu Glu Met Gly Asp Glu Glu Val His
            355                 360                 365
Thr Ile Pro Pro Glu Leu Arg Ile Leu Leu Asp Pro Gly Ala Leu Pro
            370                 375                 380
Ala Leu Gln Asn Pro Pro Ile Arg Gly Gly Glu Gly Gln Asn Gly Gly
385                 390                 395                 400
Leu Pro Phe Pro Phe Pro Asp Ile Ser Arg Arg Val Trp Asn Glu Glu
                405                 410                 415
Gly Glu Asp Gly Leu Pro Arg Pro Lys Asp Pro Val Ile Pro Ser Ile
            420                 425                 430
Gln Leu Phe Pro Gly Leu Arg Glu Pro Glu Glu Val Gln Gly Ser Val
            435                 440                 445
Asp Ile Ala Leu Ser Val Lys Cys Asp Asn Glu Lys Met Ile Val Ala
            450                 455                 460
Val Glu Lys Asp Ser Phe Gln Ala Ser Gly Tyr Ser Gly Met Asp Val
465                 470                 475                 480
Thr Leu Leu Asp Pro Thr Cys Lys Ala Lys Met Asn Gly Thr His Phe
                485                 490                 495
Val Leu Glu Ser Pro Leu Asn Gly Cys Gly Thr Arg Pro Arg Trp Ser
                500                 505                 510
Ala Leu Asp Gly Val Val Tyr Tyr Asn Ser Ile Val Ile Gln Val Pro
            515                 520                 525
Ala Leu Gly Asp Ser Ser Gly Trp Pro Asp Gly Tyr Glu Asp Leu Glu
            530                 535                 540
Ser Gly Asp Asn Gly Phe Pro Gly Asp Met Asp Glu Gly Asp Ala Ser
545                 550                 555                 560
Leu Phe Thr Arg Pro Glu Ile Val Val Phe Asn Cys Ser Leu Gln Gln
                565                 570                 575
Val Arg Asn Pro Ser Ser Phe Gln Glu Gln Pro His Gly Asn Ile Thr
                580                 585                 590
Phe Asn Met Glu Leu Tyr Asn Thr Asp Leu Phe Leu Val Pro Ser Gln
            595                 600                 605
Gly Val Phe Ser Val Pro Glu Asn Gly His Val Tyr Val Glu Val Ser
            610                 615                 620
Val Thr Lys Ala Glu Gln Glu Leu Gly Phe Ala Ile Gln Thr Cys Phe
625                 630                 635                 640
Ile Ser Pro Tyr Ser Asn Pro Asp Arg Met Ser His Tyr Thr Ile Ile
                645                 650                 655
Glu Asn Ile Cys Pro Lys Asp Glu Ser Val Lys Phe Tyr Ser Pro Lys
            660                 665                 670
Arg Val His Phe Pro Ile Pro Gln Ala Asp Met Asp Lys Lys Arg Phe
            675                 680                 685
Ser Phe Val Phe Lys Pro Val Phe Asn Thr Ser Leu Leu Phe Leu Gln
            690                 695                 700
Cys Glu Leu Thr Leu Cys Thr Lys Met Glu Lys His Pro Gln Lys Leu
705                 710                 715                 720
Pro Lys Cys Val Pro Pro Asp Glu Ala Cys Thr Ser Leu Asp Ala Ser
                725                 730                 735
Ile Ile Trp Ala Met Met Gln Asn Lys Lys Thr Phe Thr Lys Pro Leu
                740                 745                 750
Ala Val Ile His His Glu Ala Glu Ser Lys Glu Lys Gly Pro Ser Met
            755                 760                 765
```

```
Lys Glu Pro Asn Pro Ile Ser Pro Pro Ile Phe His Gly Leu Asp Thr
            770                 775                 780

Leu Thr Val Met Gly Ile Ala Phe Ala Ala Phe Val Ile Gly Ala Leu
785                 790                 795                 800

Leu Thr Gly Ala Leu Trp Tyr Ile Tyr Ser His Thr Gly Glu Thr Ala
                805                 810                 815

Gly Arg Gln Gln Val Pro Thr Ser Pro Pro Ala Ser Glu Asn Ser Ser
                820                 825                 830

Ala Ala His Ser Ile Gly Ser Thr Gln Ser Thr Pro Cys Ser Ser Ser
                835                 840                 845

Ser Thr Ala
    850

<210> SEQ ID NO 51
<211> LENGTH: 767
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gly Pro Glu Pro Gly Ala Leu Cys Glu Leu Ser Pro Val Ser Ala Ser
1               5                   10                  15

His Pro Val Gln Ala Leu Met Glu Ser Phe Thr Val Leu Ser Gly Cys
                20                  25                  30

Ala Ser Arg Gly Thr Thr Gly Leu Pro Gln Glu Val His Val Leu Asn
            35                  40                  45

Leu Arg Thr Ala Gly Gln Gly Pro Gly Gln Leu Gln Arg Glu Val Thr
50                  55                  60

Leu His Leu Asn Pro Ile Ser Ser Val His Ile His His Lys Ser Val
65                  70                  75                  80

Val Phe Leu Leu Asn Ser Pro His Pro Leu Val Trp His Leu Lys Thr
                85                  90                  95

Glu Arg Leu Ala Thr Gly Val Ser Arg Leu Phe Leu Val Ser Glu Gly
            100                 105                 110

Ser Val Val Gln Phe Ser Ser Ala Asn Phe Ser Leu Thr Ala Glu Thr
        115                 120                 125

Glu Glu Arg Asn Phe Pro His Gly Asn Glu His Leu Leu Asn Trp Ala
    130                 135                 140

Arg Lys Glu Tyr Gly Ala Val Thr Ser Phe Thr Glu Leu Lys Ile Ala
145                 150                 155                 160

Arg Asn Ile Tyr Ile Lys Val Gly Glu Asp Gln Val Phe Pro Pro Lys
                165                 170                 175

Cys Asn Ile Gly Lys Asn Phe Leu Ser Leu Asn Tyr Leu Ala Glu Tyr
            180                 185                 190

Leu Gln Pro Lys Ala Ala Glu Gly Cys Val Met Ser Ser Gln Pro Gln
        195                 200                 205

Asn Glu Glu Val His Ile Ile Glu Leu Ile Thr Pro Asn Ser Asn Pro
    210                 215                 220

Tyr Ser Ala Phe Gln Val Asp Ile Thr Ile Asp Ile Arg Pro Ser Gln
225                 230                 235                 240

Glu Asp Leu Glu Val Val Lys Asn Leu Ile Leu Ile Leu Lys Cys Lys
                245                 250                 255

Lys Ser Val Asn Trp Val Ile Lys Ser Phe Asp Val Lys Gly Ser Leu
```

```
                260                 265                 270
Lys Ile Ile Ala Pro Asn Ser Ile Gly Phe Gly Lys Glu Ser Glu Arg
        275                 280                 285

Ser Met Thr Met Thr Lys Ser Ile Arg Asp Asp Ile Pro Ser Thr Gln
        290                 295                 300

Gly Asn Leu Val Lys Trp Ala Leu Asp Asn Gly Tyr Ser Pro Ile Thr
305                 310                 315                 320

Ser Tyr Thr Met Ala Pro Val Ala Asn Arg Phe His Leu Arg Leu Glu
                325                 330                 335

Asn Asn Ala Glu Glu Met Gly Asp Glu Glu Val His Thr Ile Pro Pro
            340                 345                 350

Glu Leu Arg Ile Leu Leu Asp Pro Gly Ala Leu Pro Ala Leu Gln Asn
        355                 360                 365

Pro Pro Ile Arg Gly Gly Glu Gly Gln Asn Gly Gly Leu Pro Phe Pro
    370                 375                 380

Phe Pro Asp Ile Ser Arg Arg Val Trp Asn Glu Glu Gly Glu Asp Gly
385                 390                 395                 400

Leu Pro Arg Pro Lys Asp Pro Val Ile Pro Ser Ile Gln Leu Phe Pro
                405                 410                 415

Gly Leu Arg Glu Pro Glu Val Gln Gly Ser Val Asp Ile Ala Leu
            420                 425                 430

Ser Val Lys Cys Asp Asn Glu Lys Met Ile Val Ala Val Glu Lys Asp
        435                 440                 445

Ser Phe Gln Ala Ser Gly Tyr Ser Gly Met Asp Val Thr Leu Leu Asp
    450                 455                 460

Pro Thr Cys Lys Ala Lys Met Asn Gly Thr His Phe Val Leu Glu Ser
465                 470                 475                 480

Pro Leu Asn Gly Cys Gly Thr Arg Pro Arg Trp Ser Ala Leu Asp Gly
                485                 490                 495

Val Val Tyr Tyr Asn Ser Ile Val Ile Gln Val Pro Ala Leu Gly Asp
            500                 505                 510

Ser Ser Gly Trp Pro Asp Gly Tyr Glu Asp Leu Glu Ser Gly Asp Asn
        515                 520                 525

Gly Phe Pro Gly Asp Met Asp Glu Gly Asp Ala Ser Leu Phe Thr Arg
    530                 535                 540

Pro Glu Ile Val Val Phe Asn Cys Ser Leu Gln Gln Val Arg Asn Pro
545                 550                 555                 560

Ser Ser Phe Gln Glu Gln Pro His Gly Asn Ile Thr Phe Asn Met Glu
                565                 570                 575

Leu Tyr Asn Thr Asp Leu Phe Leu Val Pro Ser Gln Gly Val Phe Ser
            580                 585                 590

Val Pro Glu Asn Gly His Val Tyr Val Glu Val Ser Val Thr Lys Ala
        595                 600                 605

Glu Gln Glu Leu Gly Phe Ala Ile Gln Thr Cys Phe Ile Ser Pro Tyr
    610                 615                 620

Ser Asn Pro Asp Arg Met Ser His Tyr Thr Ile Ile Glu Asn Ile Cys
625                 630                 635                 640

Pro Lys Asp Glu Ser Val Lys Phe Tyr Ser Pro Lys Arg Val His Phe
                645                 650                 655

Pro Ile Pro Gln Ala Asp Met Asp Lys Lys Arg Phe Ser Phe Val Phe
            660                 665                 670

Lys Pro Val Phe Asn Thr Ser Leu Leu Phe Leu Gln Cys Glu Leu Thr
        675                 680                 685
```

```
Leu Cys Thr Lys Met Glu Lys His Pro Gln Lys Leu Pro Lys Cys Val
            690                 695                 700

Pro Pro Asp Glu Ala Cys Thr Ser Leu Asp Ala Ser Ile Ile Trp Ala
705                 710                 715                 720

Met Met Gln Asn Lys Lys Thr Phe Thr Lys Pro Leu Ala Val Ile His
                725                 730                 735

His Glu Ala Glu Ser Lys Glu Lys Gly Pro Ser Met Lys Glu Pro Asn
            740                 745                 750

Pro Ile Ser Pro Pro Ile Phe His Gly Leu Asp Thr Leu Thr Val
            755                 760                 765

<210> SEQ ID NO 52
<211> LENGTH: 2553
<212> TYPE: DNA
<213> ORGANISM: Homo sapiens

<400> SEQUENCE: 52
atgacttccc attatgtgat tgccatcttt gccctgatga gctcctgttt agccactgca     60
ggtccagagc ctggtgcact gtgtgaactg tcacctgtca gtgcctccca tcctgtccag    120
gccttgatgg agagcttcac tgttttgtca ggctgtgcca gcagaggcac aactgggctg    180
ccacaggagg tgcatgtcct gaatctccgc actgcaggcc aggggcctgg ccagctacag    240
agagaggtca cacttcacct gaatcccatc tcctcagtcc acatccacca agtctgtt     300 gtgttcctgc tcaactcccc acaccccctg gtgtggcatc tgaagacaga gagacttgcc    360
actggggtct ccagactgtt tttggtgtct gagggttctg tggtccagtt ttcatcagca    420
aacttctcct tgacagcaga aacagaagaa aggaacttcc ccatggaaa tgaacatctg    480 ttaaattggg cccgaaaaga gtatggagca gttacttcat tcaccgaact caagatagca    540
agaaacattt atattaaagt gggggaagat caagtgttcc ctccaaagtg caacataggg    600
aagaattttc tctcactcaa ttaccttgct gagtaccttc aacccaaagc agcagaaggg    660
tgtgtgatgt ccagccagcc ccagaatgag gaagtacaca tcatcgagct aatcaccccc    720
aactctaacc cctacagtgc tttccaggtg gatataacaa ttgatataag accttctcaa    780
gaggatcttg aagtggtcaa aaatctcatc ctgatcttga agtgcaaaaa gtctgtcaac    840
tgggtgatca atctttttga tgttaaggga agcctgaaaa ttattgctcc taacagtatt    900
ggctttggaa aagagagtga agatctatg acaatgacca atcaataag agatgacatt    960 ccttcaaccc aagggaatct ggtgaagtgg gcttttggaca atggctatag tccaataact   1020
tcatacacaa tggctcctgt ggctaataga tttcatcttc ggcttgaaaa taatgcagag   1080
gagatgggag atgaggaagt ccacactatt cctcctgagc tacggatcct gctggaccct   1140
ggtgccctgc ctgccctgca gaacccgccc atccggggag gggaaggcca aaatggaggc   1200
cttccgtttc ctttcccaga tatttccagg agagtctgga atgaagaggg agaagatggg   1260
ctccctcggc caaaggaccc tgtcattccc agcatacaac tgtttcctgg tctcagagag   1320
ccagaagagg tgcaagggag cgtggatatt gccctgtctg tcaaatgtga caatgagaag   1380
atgatcgtgg ctgtagaaaa agattctttt caggccagtg gctactcggg gatgacgtc   1440 accctgttgg atcctacctg caaggccaag atgaatggca cacactttgt tttggagtct   1500
cctctgaatg gctgcggtac tcggccccgg tggtcagccc ttgatggtgt ggtctactat   1560
aactccattg tgatacaggt tccagccctt ggggacagta gtggttggcc agatggttat   1620
gaagatctgg agtcaggtga taatggattt ccgggagata tggatgaagg agatgcttcc   1680
```

```
ctgttcaccc gacctgaaat cgtggtgttt aattgcagcc ttcagcaggt gaggaacccc    1740
agcagcttcc aggaacagcc ccacggaaac atcaccttca acatggagct atacaacact    1800
gacctctttt tggtgccctc ccagggcgtc ttctctgtgc cagagaatgg acacgtttat    1860
gttgaggtat ctgttactaa ggctgaacaa gaactgggat tgccatcca acgtgcttt     1920 atctctccat attcgaaccc tgataggatg tctcattaca ccattattga gaatatttgt    1980
cctaaagatg aatctgtgaa attctacagt cccaagagag tgcactttcc tatcccgcaa    2040
gctgacatgg ataagaagcg attcagcttt gtcttcaagc ctgtcttcaa cacctcactg    2100 ctcttctac agtgtgagct gacgctgtgt acgaagatgg agaagcaccc ccagaagttg      2160
cctaagtgtg tgcctcctga cgaagcctgc acctcgctgg acgcctcgat aatctgggcc    2220
atgatgcaga ataagaagac gttcactaag ccccttgctg tgatccacca tgaagcagaa    2280
tctaaagaaa aaggtccaag catgaaggaa ccaaatccaa tttctccacc aattttccat    2340
ggtctggaca ccctaaccgt gatgggcatt gcgtttgcag cctttgtgat cggagcactc    2400
ctgacggggg ccttgtggta catctattct cacacagggg agacagcagg aaggcagcaa    2460
gtccccacct ccccgccagc ctcggaaaac agcagtgctg cccacagcat cggcagcacg    2520
cagagcacgc cttgctccag cagcagcacg gcc                                 2553

<210> SEQ ID NO 53
<211> LENGTH: 2301
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
ggtccagagc ctggtgcact gtgtgaactg tcacctgtca gtgcctccca tcctgtccag      60
gccttgatgg agagcttcac tgtttttgtca ggctgtgcca gcagaggcac aactgggctg    120
ccacaggagg tgcatgtcct gaatctccgc actgcaggcc agggggcctgg ccagctacag    180 agagaggtca cacttcacct gaatcccatc tcctcagtcc acatccacca caagtctgtt    240
gtgttcctgc tcaactcccc acaccccctg gtgtggcatc tgaagacaga gagacttgcc    300 actgggtct ccagactgtt tttggtgtct gagggttctg tggtccagtt ttcatcagca     360
aacttctcct tgacagcaga aacagaagaa aggaacttcc cccatggaaa tgaacatctg    420
ttaaattggg cccgaaaaga gtatggagca gttacttcat tcaccgaact caagatagca    480
agaaacattt atattaaagt gggggaagat caagtgttcc ctccaaagtg caacataggg    540
aagaattttc tctcactcaa ttaccttgct gagtaccttc aacccaaagc agcagaaggg    600
tgtgtgatgt ccagccagcc ccagaatgag gaagtacaca tcatcgagct aatcaccccc    660
aactctaacc cctacagtgc tttccaggtg gatataacaa ttgatataag accttctcaa    720
gaggatcttg aagtggtcaa aaatctcatc ctgatcttga agtgcaaaaa gtctgtcaac    780
tgggtgatca atctttttga tgttaaggga agcctgaaaa ttattgctcc taacagtatt    840
ggctttggaa aagagagtga agatctctatg acaatgacca atcaataag agatgacatt    900 ccttcaaccc aagggaatct ggtgaagtgg ctttggaca atggctatag tccaataact    960
tcatacacaa tggctcctgt ggctaataga tttcatcttc ggcttgaaaa taatgcagag    1020
gagatgggga tgaggaagt ccacactatt cctcctgagc tacggatcct gctggaccct    1080
ggtgccctgc ctgccctgca gaacccgccc atccggggag gggaaggcca aatggaggc    1140
```

-continued

```
cttccgtttc ctttcccaga tatttccagg agagtctgga atgaagaggg agaagatggg    1200
ctccctcggc caaaggaccc tgtcattccc agcatacaac tgtttcctgg tctcagagag    1260
ccagaagagg tgcaagggag cgtggatatt gccctgtctg tcaaatgtga caatgagaag    1320
atgatcgtgg ctgtagaaaa agattctttt caggccagtg gctactcggg gatggacgtc    1380
accctgttgg atcctacctg caaggccaag atgaatggca cacactttgt tttggagtct    1440
cctctgaatg gctgcggtac tcggccccgg tggtcagccc ttgatggtgt ggtctactat    1500
aactccattg tgatacaggt tccagccctt ggggacagta gtggttggcc agatggttat    1560
gaagatctgg agtcaggtga taatggattt ccgggagata tggatgaagg agatgcttcc    1620
ctgttcaccc gacctgaaat cgtggtgttt aattgcagcc ttcagcaggt gaggaacccc    1680
agcagcttcc aggaacagcc ccacggaaac atcaccttca acatggagct atacaacact    1740
gacctctttt tggtgccctc ccagggcgtc ttctctgtgc cagagaatgg acacgtttat    1800
gttgaggtat ctgttactaa ggctgaacaa gaactgggat ttgccatcca aacgtgcttt    1860
atctctccat attcgaaccc tgataggatg tctcattaca ccattattga gaatatttgt    1920
cctaaagatg aatctgtgaa attctacagt cccaagagag tgcactttcc tatcccgcaa    1980
gctgacatgg ataagaagcg attcagcttt gtcttcaagc ctgtcttcaa cacctcactg    2040
ctctttctac agtgtgagct gacgctgtgt acgaagatgg agaagcaccc ccagaagttg    2100
cctaagtgtg tgcctcctga cgaagcctgc acctcgctgg acgcctcgat aatctgggcc    2160
atgatgcaga ataagaagac gttcactaag ccccttgctg tgatccacca tgaagcagaa    2220
tctaaagaaa aaggtccaag catgaaggaa ccaaatccaa tttctccacc aattttccat    2280
ggtctggaca ccctaaccgt g                                              2301
```

<210> SEQ ID NO 54
<211> LENGTH: 850
<212> TYPE: PRT
<213> ORGANISM: Homo sapiens

<400> SEQUENCE: 54

```
Met Thr Ser His Tyr Val Ile Ala Ile Phe Ala Leu Met Ser Ser Cys
1               5                   10                  15

Leu Ala Thr Ala Gly Pro Glu Pro Gly Ala Leu Cys Glu Leu Ser Pro
            20                  25                  30

Val Ser Ala Ser His Pro Val Gln Ala Leu Met Glu Ser Phe Thr Val
        35                  40                  45

Leu Ser Gly Cys Ala Ser Arg Gly Thr Thr Gly Leu Pro Gln Glu Val
    50                  55                  60

His Val Leu Asn Leu Arg Thr Ala Gly Gln Gly Pro Gly Gln Leu Gln
65                  70                  75                  80

Arg Glu Val Thr Leu His Leu Asn Pro Ile Ser Ser Val His Ile His
                85                  90                  95

His Lys Ser Val Val Phe Leu Leu Asn Ser Pro His Pro Leu Val Trp
            100                 105                 110

His Leu Lys Thr Glu Arg Leu Ala Thr Gly Val Ser Arg Leu Phe Leu
        115                 120                 125

Val Ser Glu Gly Ser Val Val Gln Phe Ser Ser Ala Asn Phe Ser Leu
    130                 135                 140

Thr Ala Glu Thr Glu Glu Arg Asn Phe Pro His Gly Asn Glu His Leu
145                 150                 155                 160
```

```
Leu Asn Trp Ala Arg Lys Glu Tyr Gly Ala Val Thr Ser Phe Thr Glu
                165                 170                 175

Leu Lys Ile Ala Arg Asn Ile Tyr Ile Lys Val Gly Glu Asp Gln Val
            180                 185                 190

Phe Pro Pro Lys Cys Asn Ile Gly Lys Asn Phe Leu Ser Leu Asn Tyr
        195                 200                 205

Leu Ala Glu Tyr Leu Gln Pro Lys Ala Ala Glu Gly Cys Val Met Ser
    210                 215                 220

Ser Gln Pro Gln Asn Glu Val His Ile Ile Glu Leu Ile Thr Pro
225                 230                 235                 240

Asn Ser Asn Pro Tyr Ser Ala Phe Gln Val Asp Ile Thr Ile Asp Ile
                245                 250                 255

Arg Pro Ser Gln Glu Asp Leu Glu Val Val Lys Asn Leu Ile Leu Ile
            260                 265                 270

Leu Lys Cys Lys Lys Ser Val Asn Trp Val Ile Lys Ser Phe Asp Val
        275                 280                 285

Lys Gly Ser Leu Lys Ile Ile Ala Pro Asn Ser Ile Gly Phe Gly Lys
    290                 295                 300

Glu Ser Glu Arg Ser Met Thr Met Thr Lys Ser Ile Arg Asp Asp Ile
305                 310                 315                 320

Pro Ser Thr Gln Gly Asn Leu Val Lys Trp Ala Leu Asp Asn Gly Tyr
                325                 330                 335

Ser Pro Ile Thr Ser Tyr Thr Met Ala Pro Val Ala Asn Arg Phe His
            340                 345                 350

Leu Arg Leu Glu Asn Asn Glu Glu Met Gly Asp Glu Glu Val His Thr
        355                 360                 365

Ile Pro Pro Glu Leu Arg Ile Leu Leu Asp Pro Gly Ala Leu Pro Ala
    370                 375                 380

Leu Gln Asn Pro Pro Ile Arg Gly Gly Glu Gly Gln Asn Gly Gly Leu
385                 390                 395                 400

Pro Phe Pro Phe Pro Asp Ile Ser Arg Arg Val Trp Asn Glu Glu Gly
                405                 410                 415

Glu Asp Gly Leu Pro Arg Pro Lys Asp Pro Val Ile Pro Ser Ile Gln
            420                 425                 430

Leu Phe Pro Gly Leu Arg Glu Pro Glu Val Gln Gly Ser Val Asp
        435                 440                 445

Ile Ala Leu Ser Val Lys Cys Asp Asn Glu Lys Met Ile Val Ala Val
    450                 455                 460

Glu Lys Asp Ser Phe Gln Ala Ser Gly Tyr Ser Gly Met Asp Val Thr
465                 470                 475                 480

Leu Leu Asp Pro Thr Cys Lys Ala Lys Met Asn Gly Thr His Phe Val
                485                 490                 495

Leu Glu Ser Pro Leu Asn Gly Cys Gly Thr Arg Pro Arg Trp Ser Ala
            500                 505                 510

Leu Asp Gly Val Val Tyr Tyr Asn Ser Ile Val Ile Gln Val Pro Ala
        515                 520                 525

Leu Gly Asp Ser Ser Gly Trp Pro Asp Gly Tyr Glu Asp Leu Glu Ser
    530                 535                 540

Gly Asp Asn Gly Phe Pro Gly Asp Met Asp Glu Gly Asp Ala Ser Leu
545                 550                 555                 560

Phe Thr Arg Pro Glu Ile Val Val Phe Asn Cys Ser Leu Gln Gln Val
                565                 570                 575

Arg Asn Pro Ser Ser Phe Gln Glu Gln Pro His Gly Asn Ile Thr Phe
```

```
                580             585             590
Asn Met Glu Leu Tyr Asn Thr Asp Leu Phe Leu Val Pro Ser Gln Gly
            595             600             605

Val Phe Ser Val Pro Glu Asn Gly His Val Tyr Val Glu Val Ser Val
610             615             620

Thr Lys Ala Glu Gln Glu Leu Gly Phe Ala Ile Gln Thr Cys Phe Ile
625             630             635             640

Ser Pro Tyr Ser Asn Pro Asp Arg Met Ser His Tyr Thr Ile Ile Glu
            645             650             655

Asn Ile Cys Pro Lys Asp Glu Ser Val Lys Phe Tyr Ser Pro Lys Arg
            660             665             670

Val His Phe Pro Ile Pro Gln Ala Asp Met Asp Lys Arg Phe Ser
            675             680             685

Phe Val Phe Lys Pro Val Phe Asn Thr Ser Leu Leu Phe Leu Gln Cys
            690             695             700

Glu Leu Thr Leu Cys Thr Lys Met Glu Lys His Pro Gln Lys Leu Pro
705             710             715             720

Lys Cys Val Pro Pro Asp Glu Ala Cys Thr Ser Leu Asp Ala Ser Ile
            725             730             735

Ile Trp Ala Met Met Gln Asn Lys Lys Thr Phe Thr Lys Pro Leu Ala
            740             745             750

Val Ile His His Glu Ala Glu Ser Lys Glu Lys Gly Pro Ser Met Lys
            755             760             765

Glu Pro Asn Pro Ile Ser Pro Pro Ile Phe His Gly Leu Asp Thr Leu
770             775             780

Thr Val Met Gly Ile Ala Phe Ala Ala Phe Val Ile Gly Ala Leu Leu
785             790             795             800

Thr Gly Ala Leu Trp Tyr Ile Tyr Ser His Thr Gly Glu Thr Ala Gly
            805             810             815

Arg Gln Gln Val Pro Thr Ser Pro Pro Ala Ser Glu Asn Ser Ser Ala
            820             825             830

Ala His Ser Ile Gly Ser Thr Gln Ser Thr Pro Cys Ser Ser Ser Ser
            835             840             845

Thr Ala
    850

<210> SEQ ID NO 55
<211> LENGTH: 766
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gly Pro Glu Pro Gly Ala Leu Cys Glu Leu Ser Pro Val Ser Ala Ser
1               5                   10                  15

His Pro Val Gln Ala Leu Met Glu Ser Phe Thr Val Leu Ser Gly Cys
            20                  25                  30

Ala Ser Arg Gly Thr Thr Gly Leu Pro Gln Glu Val His Val Leu Asn
        35                  40                  45

Leu Arg Thr Ala Gly Gln Gly Pro Gly Gln Leu Gln Arg Glu Val Thr
    50                  55                  60

Leu His Leu Asn Pro Ile Ser Ser Val His Ile His His Lys Ser Val
65                  70                  75                  80
```

-continued

Val Phe Leu Leu Asn Ser Pro His Pro Leu Trp His Leu Lys Thr
                85                  90                  95

Glu Arg Leu Ala Thr Gly Val Ser Arg Leu Phe Leu Val Ser Glu Gly
            100                 105                 110

Ser Val Val Gln Phe Ser Ser Ala Asn Phe Ser Leu Thr Ala Glu Thr
            115                 120                 125

Glu Glu Arg Asn Phe Pro His Gly Asn Glu His Leu Leu Asn Trp Ala
        130                 135                 140

Arg Lys Glu Tyr Gly Ala Val Thr Ser Phe Thr Glu Leu Lys Ile Ala
145                 150                 155                 160

Arg Asn Ile Tyr Ile Lys Val Gly Glu Asp Gln Val Phe Pro Pro Lys
                165                 170                 175

Cys Asn Ile Gly Lys Asn Phe Leu Ser Leu Asn Tyr Leu Ala Glu Tyr
            180                 185                 190

Leu Gln Pro Lys Ala Ala Glu Gly Cys Val Met Ser Ser Gln Pro Gln
        195                 200                 205

Asn Glu Glu Val His Ile Ile Glu Leu Ile Thr Pro Asn Ser Asn Pro
    210                 215                 220

Tyr Ser Ala Phe Gln Val Asp Ile Thr Ile Asp Ile Arg Pro Ser Gln
225                 230                 235                 240

Glu Asp Leu Glu Val Val Lys Asn Leu Ile Leu Ile Leu Lys Cys Lys
                245                 250                 255

Lys Ser Val Asn Trp Val Ile Lys Ser Phe Asp Val Lys Gly Ser Leu
            260                 265                 270

Lys Ile Ile Ala Pro Asn Ser Ile Gly Phe Gly Lys Glu Ser Glu Arg
        275                 280                 285

Ser Met Thr Met Thr Lys Ser Ile Arg Asp Asp Ile Pro Ser Thr Gln
    290                 295                 300

Gly Asn Leu Val Lys Trp Ala Leu Asp Asn Gly Tyr Ser Pro Ile Thr
305                 310                 315                 320

Ser Tyr Thr Met Ala Pro Val Ala Asn Arg Phe His Leu Arg Leu Glu
                325                 330                 335

Asn Asn Glu Glu Met Gly Asp Glu Glu Val His Thr Ile Pro Pro Glu
            340                 345                 350

Leu Arg Ile Leu Leu Asp Pro Gly Ala Leu Pro Ala Leu Gln Asn Pro
        355                 360                 365

Pro Ile Arg Gly Gly Glu Gly Gln Asn Gly Gly Leu Pro Phe Pro Phe
    370                 375                 380

Pro Asp Ile Ser Arg Arg Val Trp Asn Glu Glu Gly Glu Asp Gly Leu
385                 390                 395                 400

Pro Arg Pro Lys Asp Pro Val Ile Pro Ser Ile Gln Leu Phe Pro Gly
                405                 410                 415

Leu Arg Glu Pro Glu Glu Val Gln Gly Ser Val Asp Ile Ala Leu Ser
            420                 425                 430

Val Lys Cys Asp Asn Glu Lys Met Ile Val Ala Val Glu Lys Asp Ser
        435                 440                 445

Phe Gln Ala Ser Gly Tyr Ser Gly Met Asp Val Thr Leu Leu Asp Pro
    450                 455                 460

Thr Cys Lys Ala Lys Met Asn Gly Thr His Phe Val Leu Glu Ser Pro
465                 470                 475                 480

Leu Asn Gly Cys Gly Thr Arg Pro Arg Trp Ser Ala Leu Asp Gly Val
                485                 490                 495

Val Tyr Tyr Asn Ser Ile Val Ile Gln Val Pro Ala Leu Gly Asp Ser

```
            500                 505                 510
Ser Gly Trp Pro Asp Gly Tyr Glu Asp Leu Glu Ser Gly Asp Asn Gly
            515                 520                 525

Phe Pro Gly Asp Met Asp Glu Gly Asp Ala Ser Leu Phe Thr Arg Pro
            530                 535                 540

Glu Ile Val Val Phe Asn Cys Ser Leu Gln Gln Val Arg Asn Pro Ser
545                 550                 555                 560

Ser Phe Gln Glu Gln Pro His Gly Asn Ile Thr Phe Asn Met Glu Leu
                565                 570                 575

Tyr Asn Thr Asp Leu Phe Leu Val Pro Ser Gln Gly Val Phe Ser Val
            580                 585                 590

Pro Glu Asn Gly His Val Tyr Val Glu Val Ser Val Thr Lys Ala Glu
            595                 600                 605

Gln Glu Leu Gly Phe Ala Ile Gln Thr Cys Phe Ile Ser Pro Tyr Ser
            610                 615                 620

Asn Pro Asp Arg Met Ser His Tyr Thr Ile Ile Glu Asn Ile Cys Pro
625                 630                 635                 640

Lys Asp Glu Ser Val Lys Phe Tyr Ser Pro Lys Arg Val His Phe Pro
                645                 650                 655

Ile Pro Gln Ala Asp Met Asp Lys Lys Arg Phe Ser Phe Val Phe Lys
                660                 665                 670

Pro Val Phe Asn Thr Ser Leu Leu Phe Leu Gln Cys Glu Leu Thr Leu
            675                 680                 685

Cys Thr Lys Met Glu Lys His Pro Gln Lys Leu Pro Lys Cys Val Pro
            690                 695                 700

Pro Asp Glu Ala Cys Thr Ser Leu Asp Ala Ser Ile Ile Trp Ala Met
705                 710                 715                 720

Met Gln Asn Lys Lys Thr Phe Thr Lys Pro Leu Ala Val Ile His His
                725                 730                 735

Glu Ala Glu Ser Lys Glu Lys Gly Pro Ser Met Lys Glu Pro Asn Pro
            740                 745                 750

Ile Ser Pro Pro Ile Phe His Gly Leu Asp Thr Leu Thr Val
            755                 760                 765

<210> SEQ ID NO 56
<211> LENGTH: 2550
<212> TYPE: DNA
<213> ORGANISM: Homo sapiens

<400> SEQUENCE: 56
atgacttccc attatgtgat tgccatcttt gccctgatga gctcctgttt agccactgca    60
ggtccagagc ctggtgcact gtgtgaactg tcacctgtca gtgcctccca tcctgtccag   120
gccttgatgg agagcttcac tgttttgtca ggctgtgcca gcagaggcac aactgggctg   180
ccacaggagg tgcatgtcct gaatctccgc actgcaggcc aggggcctgg ccagctacag   240
agagaggtca cacttcacct gaatcccatc tcctcagtcc acatccacca caagtctgtt   300
gtgttcctgc tcaactcccc acacccctg gtgtggcatc tgaagacaga gagacttgcc   360 actgggtct ccagactgtt tttggtgtct gagggttctg tggtccagtt ttcatcagca   420
aacttctcct tgacagcaga aacagaagaa aggaacttcc cccatggaaa tgaacatctg   480
ttaaattggg cccgaaaaga gtatggagca gttacttcat tcaccgaact caagatagca   540
agaaacattt atattaaagt gggggaagat caagtgttcc ctccaaagtg caacataggg   600
aagaattttc tctcactcaa ttaccttgct gagtaccttc aacccaaagc agcagaaggg   660
```

```
tgtgtgatgt ccagccagcc ccagaatgag gaagtacaca tcatcgagct aatcaccccc    720
aactctaacc cctacagtgc tttccaggtg gatataacaa ttgatataag accttctcaa    780
gaggatcttg aagtggtcaa aaatctcatc ctgatcttga agtgcaaaaa gtctgtcaac    840
tgggtgatca aatcttttga tgttaaggga agcctgaaaa ttattgctcc taacagtatt    900
ggctttggaa aagagagtga aagatctatg acaatgacca aatcaataag agatgacatt    960
ccttcaaccc aagggaatct ggtgaagtgg gctttggaca atggctatag tccaataact   1020
tcatacacaa tggctcctgt ggctaataga tttcatcttc ggcttgaaaa taatgaggag   1080
atgggagatg aggaagtcca cactattcct cctgagctac ggatcctgct ggaccctggt   1140
gccctgcctg ccctgcagaa cccgcccatc cggggagggg aaggccaaaa tggaggcctt   1200
ccgtttcctt tcccagatat ttccaggaga gtctggaatg aagagggaga gatgggctc    1260 cctcggccaa aggaccctgt cattcccagc atacaactgt ttcctggtct cagagagcca   1320
gaagaggtgc aagggagcgt ggatattgcc ctgtctgtca aatgtgacaa tgagaagatg   1380
atcgtggctg tagaaaaaga ttcttttcag gccagtggct actcggggat ggacgtcacc   1440
ctgttggatc ctacctgcaa ggccaagatg aatggcacac actttgtttt ggagtctcct   1500
ctgaatggct gcggtactcg gccccggtgg tcagcccttg atggtgtggt ctactataac   1560
tccattgtga tacaggttcc agcccttggg gacagtagtg gttggccaga tggttatgaa   1620
gatctggagt caggtgataa tggatttccg ggagatatgg atgaaggaga tgcttccctg   1680
ttcacccgac ctgaaatcgt ggtgtttaat tgcagccttc agcaggtgag gaaccccagc   1740
agcttccagg aacagcccca cggaaacatc accttcaaca tggagctata caacactgac   1800 ctcttttttgg tgccctccca gggcgtcttc tctgtgccag agaatggaca cgtttatgtt   1860
gaggtatctg ttactaaggc tgaacaagaa ctgggatttg ccatccaaac gtgctttatc   1920
tctccatatt cgaaccctga taggatgtct cattacacca ttattgagaa tatttgtcct   1980
aaagatgaat ctgtgaaatt ctacagtccc aagagagtgc actttcctat cccgcaagct   2040
gacatggata agaagcgatt cagctttgtc ttcaagcctg tcttcaacac ctcactgctc   2100
tttctacagt gtgagctgac gctgtgtacg aagatggaga agcaccccca gaagttgcct   2160
aagtgtgtgc ctcctgacga agcctgcacc tcgctggacg cctcgataat ctgggccatg   2220
atgcagaata agaagacgtt cactaagccc cttgctgtga tccaccatga agcagaatct   2280
aaagaaaaag gtccaagcat gaaggaacca aatccaattt ctccaccaat tttccatggt   2340
ctggacaccc taaccgtgat gggcattgcg tttgcagcct ttgtgatcgg agcactcctg   2400 acggggggcct tgtggtacat ctattctcac acaggggaga cagcaggaag gcagcaagtc   2460
cccacctccc cgccagcctc ggaaaacagc agtgctgccc acagcatcgg cagcacgcag   2520
agcacgcctt gctccagcag cagcacggcc                                   2550
```

<210> SEQ ID NO 57
<211> LENGTH: 2298
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
ggtccagagc ctggtgcact gtgtgaactg tcacctgtca gtgcctccca tcctgtccag     60
gccttgatgg agagcttcac tgttttgtca ggctgtgcca gcagaggcac aactgggctg    120
```

```
ccacaggagg tgcatgtcct gaatctccgc actgcaggcc aggggcctgg ccagctacag      180
agagaggtca cacttcacct gaatcccatc tcctcagtcc acatccacca caagtctgtt      240
gtgttcctgc tcaactcccc acacccctg tgtggcatc tgaagacaga gagacttgcc        300
actgggtct ccagactgtt tttggtgtct gagggttctg tggtccagtt ttcatcagca        360
aacttctcct tgacagcaga aacagaagaa aggaacttcc cccatggaaa tgaacatctg      420
ttaaattggg cccgaaaaga gtatggagca gttacttcat tcaccgaact caagatagca      480
agaaacattt atattaaagt gggggaagat caagtgttcc ctccaaagtg caacataggg      540
aagaattttc tctcactcaa ttaccttgct gagtaccttc aacccaaagc agcagaaggg      600
tgtgtgatgt ccagccagcc ccagaatgag gaagtacaca tcatcgagct aatcaccccc      660
aactctaacc cctacagtgc tttccaggtg gatataacaa ttgatataag accttctcaa      720
gaggatcttg aagtggtcaa aaatctcatc ctgatcttga agtgcaaaaa gtctgtcaac      780
tgggtgatca aatcttttga tgttaaggga agcctgaaaa ttattgctcc taacagtatt      840
ggctttggaa aagagagtga aagatctatg acaatgacca aatcaataag agatgacatt      900
ccttcaaccc aagggaatct ggtgaagtgg gctttggaca atggctatag tccaataact      960
tcatacacaa tggctcctgt ggctaataga tttcatcttc ggcttgaaaa taatgaggag      1020
atgggagatg aggaagtcca cactattcct cctgagctac ggatcctgct ggaccctggt      1080
gccctgcctg ccctgcagaa cccgcccatc cggggagggg aaggccaaaa tggaggcctt      1140
ccgtttcctt tcccagatat ttccaggaga gtctggaatg aagagggaga agatgggctc      1200
cctcggccaa aggaccctgt cattcccagc atacaactgt ttcctggtct cagagagcca      1260
gaagaggtgc aagggagcgt ggatattgcc ctgtctgtca aatgtgacaa tgagaagatg      1320
atcgtggctg tagaaaaaga ttcttttcag gccagtggct actcggggat ggacgtcacc      1380
ctgttggatc ctacctgcaa ggccaagatg aatggcacac actttgtttt ggagtctcct      1440
ctgaatggct gcggtactcg gccccggtgg tcagcccttg atggtgtggt ctactataac      1500
tccattgtga tacaggttcc agcccttggg gacagtagtg gttggccaga tggttatgaa      1560
gatctggagt caggtgataa tggatttccg ggagatatgg atgaaggaga tgcttccctg      1620
ttcacccgac ctgaaatcgt ggtgtttaat tgcagccttc agcaggtgag gaaccccagc      1680
agcttccagg aacagcccca cggaaacatc accttcaaca tggagctata caacactgac      1740
ctcttttttgg tgccctccca gggcgtcttc tctgtgccag agaatggaca cgtttatgtt      1800
gaggtatctg ttactaaggc tgaacaagaa ctgggatttg ccatccaaac gtgctttatc      1860
tctccatatt cgaaccctga taggatgtct cattacacca ttattgagaa tatttgtcct      1920
aaagatgaat ctgtgaaatt ctacagtccc aagagagtgc actttcctat cccgcaagct      1980
gacatggata agaagcgatt cagctttgtc ttcaagcctg tcttcaacac ctcactgctc      2040
tttctacagt gtgagctgac gctgtgtacg aagatggaga agcaccccca gaagttgcct      2100
aagtgtgtgc ctcctgacga agcctgcacc tcgctggacg cctcgataat ctgggccatg      2160
atgcagaata gaagacgtt cactaagccc cttgctgtga tccaccatga agcagaatct      2220
aaagaaaaag gtccaagcat gaaggaacca atccaatttt ctccaccaat tttccatggt      2280
ctggacaccc taaccgtg                                                    2298

<210> SEQ ID NO 58
<211> LENGTH: 225
<212> TYPE: PRT
```

<213> ORGANISM: Homo sapiens

<400> SEQUENCE: 58

```
Thr His Thr Cys Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
                35                  40                  45

Pro Glu Val Lys Phe Asn Trp Tyr Val Asp Gly Val Glu Val His Asn
        50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
            85                  90                  95

Tyr Lys Cys Lys Val Ser Asn Lys Ala Leu Pro Ala Pro Ile Glu Lys
        100                 105                 110

Thr Ile Ser Lys Ala Lys Gly Gln Pro Arg Glu Pro Gln Val Tyr Thr
            115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
            165                 170                 175

Asp Ser Asp Gly Ser Phe Phe Leu Tyr Ser Lys Leu Thr Val Asp Lys
        180                 185                 190

Ser Arg Trp Gln Gln Gly Asn Val Phe Ser Cys Ser Val Met His Glu
    195                 200                 205

Ala Leu His Asn His Tyr Thr Gln Lys Ser Leu Ser Leu Ser Pro Gly
    210                 215                 220

Lys
225
```

<210> SEQ ID NO 59
<211> LENGTH: 223
<212> TYPE: PRT
<213> ORGANISM: Homo sapiens

<400> SEQUENCE: 59

```
Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Gln Phe Asn Trp Tyr Val Asp Gly Val Glu Val His Asn Ala Lys
    50                  55                  60

Thr Lys Pro Arg Glu Glu Gln Phe Asn Ser Thr Phe Arg Val Val Ser
65                  70                  75                  80

Val Leu Thr Val Val His Gln Asp Trp Leu Asn Gly Lys Glu Tyr Lys
            85                  90                  95

Cys Lys Val Ser Asn Lys Gly Leu Pro Ala Pro Ile Glu Lys Thr Ile
        100                 105                 110

Ser Lys Thr Lys Gly Gln Pro Arg Glu Pro Gln Val Tyr Thr Leu Pro
```

```
            115                 120                 125
Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Met Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220
```

<210> SEQ ID NO 60
<211> LENGTH: 232
<212> TYPE: PRT
<213> ORGANISM: Homo sapiens

<400> SEQUENCE: 60

```
Glu Pro Lys Ser Cys Asp Thr Pro Pro Cys Pro Arg Cys Pro Ala
1               5                   10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Gln Phe Lys Trp Tyr Val
50                  55                  60

Asp Gly Val Glu Val His Asn Ala Lys Thr Lys Pro Arg Glu Glu Gln
65                  70                  75                  80

Tyr Asn Ser Thr Phe Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Thr Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Ser Gly Gln Pro Glu Asn Asn Tyr
                165                 170                 175

Asn Thr Thr Pro Pro Met Leu Asp Ser Asp Gly Ser Phe Phe Leu Tyr
            180                 185                 190

Ser Lys Leu Thr Val Asp Lys Ser Arg Trp Gln Gln Gly Asn Ile Phe
        195                 200                 205

Ser Cys Ser Val Met His Glu Ala Leu His Asn Arg Phe Thr Gln Lys
    210                 215                 220

Ser Leu Ser Leu Ser Pro Gly Lys
225                 230
```

<210> SEQ ID NO 61
<211> LENGTH: 279
<212> TYPE: PRT
<213> ORGANISM: Homo sapiens

<400> SEQUENCE: 61

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro Ala Pro
    50                  55                  60

Glu Leu Leu Gly Gly Pro Ser Val Phe Leu Phe Pro Pro Lys Pro Lys
65                  70                  75                  80

Asp Thr Leu Met Ile Ser Arg Thr Pro Glu Val Thr Cys Val Val Val
                85                  90                  95

Asp Val Ser His Glu Asp Pro Glu Val Gln Phe Lys Trp Tyr Val Asp
                100                 105                 110

Gly Val Glu Val His Asn Ala Lys Thr Lys Pro Arg Glu Glu Gln Tyr
            115                 120                 125

Asn Ser Thr Phe Arg Val Val Ser Val Leu Thr Val Leu His Gln Asp
    130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
        195                 200                 205

Ile Ala Val Glu Trp Glu Ser Ser Gly Gln Pro Glu Asn Asn Tyr Asn
    210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270

Leu Ser Leu Ser Pro Gly Lys
        275

<210> SEQ ID NO 62
<211> LENGTH: 229
<212> TYPE: PRT
<213> ORGANISM: Homo sapiens

<400> SEQUENCE: 62

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys
225

<210> SEQ ID NO 63
<211> LENGTH: 410
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gly Ala Thr Ile Pro Pro His Val Gln Lys Ser Asp Val Glu Met Glu
1               5                   10                  15

Ala Gln Lys Asp Glu Ile Ile Cys Pro Ser Cys Asn Arg Thr Ala His
            20                  25                  30

Pro Leu Arg His Ile Asn Asn Asp Met Ile Val Thr Asp Asn Asn Gly
        35                  40                  45

Ala Val Lys Phe Pro Gln Leu Cys Lys Phe Cys Asp Val Arg Phe Ser
    50                  55                  60

Thr Cys Asp Asn Gln Lys Ser Cys Met Ser Asn Cys Ser Ile Thr Ser
65                  70                  75                  80

Ile Cys Glu Lys Pro Gln Glu Val Cys Val Ala Val Trp Arg Lys Asn
                85                  90                  95

Asp Glu Asn Ile Thr Leu Glu Thr Val Cys His Asp Pro Lys Leu Pro
            100                 105                 110

Tyr His Asp Phe Ile Leu Glu Asp Ala Ala Ser Pro Lys Cys Ile Met
        115                 120                 125

Lys Glu Lys Lys Lys Pro Gly Glu Thr Phe Phe Met Cys Ser Cys Ser
    130                 135                 140

Ser Asp Glu Cys Asn Asp Asn Ile Ile Phe Ser Glu Glu Tyr Asn Thr
145                 150                 155                 160

Ser Asn Pro Asp Thr Gly Gly Gly Gly Ser Gly Gly Gly Gly Ser Gly
                165                 170                 175

Gly Gly Gly Ser Gly Gly Gly Gly Ser Thr His Thr Cys Pro Pro Cys
            180                 185                 190

Pro Ala Pro Glu Leu Leu Gly Gly Pro Ser Val Phe Leu Phe Pro Pro
        195                 200                 205

```
Lys Pro Lys Asp Thr Leu Met Ile Ser Arg Thr Pro Glu Val Thr Cys
            210                 215                 220

Val Val Val Asp Val Ser His Glu Asp Pro Glu Val Lys Phe Asn Trp
225                 230                 235                 240

Tyr Val Asp Gly Val Glu Val His Asn Ala Lys Thr Lys Pro Arg Glu
                245                 250                 255

Glu Gln Tyr Asn Ser Thr Tyr Arg Val Val Ser Val Leu Thr Val Leu
            260                 265                 270

His Gln Asp Trp Leu Asn Gly Lys Glu Tyr Lys Cys Lys Val Ser Asn
        275                 280                 285

Lys Ala Leu Pro Ala Pro Ile Glu Lys Thr Ile Ser Lys Ala Lys Gly
290                 295                 300

Gln Pro Arg Glu Pro Gln Val Tyr Thr Leu Pro Pro Ser Arg Glu Glu
305                 310                 315                 320

Met Thr Lys Asn Gln Val Ser Leu Thr Cys Leu Val Lys Gly Phe Tyr
                325                 330                 335

Pro Ser Asp Ile Ala Val Glu Trp Glu Ser Asn Gly Gln Pro Glu Asn
            340                 345                 350

Asn Tyr Lys Thr Thr Pro Pro Val Leu Asp Ser Asp Gly Ser Phe Phe
        355                 360                 365

Leu Tyr Ser Lys Leu Thr Val Asp Lys Ser Arg Trp Gln Gln Gly Asn
370                 375                 380

Val Phe Ser Cys Ser Val Met His Glu Ala Leu His Asn His Tyr Thr
385                 390                 395                 400

Gln Lys Ser Leu Ser Leu Ser Pro Gly Lys
                405                 410

<210> SEQ ID NO 64
<211> LENGTH: 409
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Ala Thr Ile Pro Pro His Val Gln Lys Ser Asp Val Glu Met Glu Ala
1               5                   10                  15

Gln Lys Asp Glu Ile Ile Cys Pro Ser Cys Asn Arg Thr Ala His Pro
            20                  25                  30

Leu Arg His Ile Asn Asn Asp Met Ile Val Thr Asp Asn Asn Gly Ala
        35                  40                  45

Val Lys Phe Pro Gln Leu Cys Lys Phe Cys Asp Val Arg Phe Ser Thr
50                  55                  60

Cys Asp Asn Gln Lys Ser Cys Met Ser Asn Cys Ser Ile Thr Ser Ile
65                  70                  75                  80

Cys Glu Lys Pro Gln Glu Val Cys Val Ala Val Trp Arg Lys Asn Asp
                85                  90                  95

Glu Asn Ile Thr Leu Glu Thr Val Cys His Asp Pro Lys Leu Pro Tyr
            100                 105                 110

His Asp Phe Ile Leu Glu Asp Ala Ala Ser Pro Lys Cys Ile Met Lys
        115                 120                 125

Glu Lys Lys Lys Pro Gly Glu Thr Phe Phe Met Cys Ser Cys Ser Ser
130                 135                 140

Asp Glu Cys Asn Asp Asn Ile Ile Phe Ser Glu Glu Tyr Asn Thr Ser
```

```
                    145                 150                 155                 160
Asn Pro Asp Thr Gly Gly Gly Ser Gly Gly Gly Ser Gly Gly
                165                 170                 175

Gly Gly Ser Gly Gly Gly Ser Thr His Thr Cys Pro Cys Pro
            180                 185                 190

Ala Pro Glu Leu Leu Gly Gly Pro Ser Val Phe Leu Phe Pro Pro Lys
            195                 200                 205

Pro Lys Asp Thr Leu Met Ile Ser Arg Thr Pro Glu Val Thr Cys Val
210                 215                 220

Val Val Asp Val Ser His Glu Asp Pro Glu Val Lys Phe Asn Trp Tyr
225                 230                 235                 240

Val Asp Gly Val Glu Val His Asn Ala Lys Thr Lys Pro Arg Glu Glu
                245                 250                 255

Gln Tyr Asn Ser Thr Tyr Arg Val Val Ser Val Leu Thr Val Leu His
            260                 265                 270

Gln Asp Trp Leu Asn Gly Lys Glu Tyr Lys Cys Lys Val Ser Asn Lys
            275                 280                 285

Ala Leu Pro Ala Pro Ile Glu Lys Thr Ile Ser Lys Ala Lys Gly Gln
290                 295                 300

Pro Arg Glu Pro Gln Val Tyr Thr Leu Pro Pro Ser Arg Glu Glu Met
305                 310                 315                 320

Thr Lys Asn Gln Val Ser Leu Thr Cys Leu Val Lys Gly Phe Tyr Pro
                325                 330                 335

Ser Asp Ile Ala Val Glu Trp Glu Ser Asn Gly Gln Pro Glu Asn Asn
            340                 345                 350

Tyr Lys Thr Thr Pro Pro Val Leu Asp Ser Asp Gly Ser Phe Phe Leu
            355                 360                 365

Tyr Ser Lys Leu Thr Val Asp Lys Ser Arg Trp Gln Gln Gly Asn Val
370                 375                 380

Phe Ser Cys Ser Val Met His Glu Ala Leu His Asn His Tyr Thr Gln
385                 390                 395                 400

Lys Ser Leu Ser Leu Ser Pro Gly Lys
                405

<210> SEQ ID NO 65
<211> LENGTH: 407
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Ile Pro Pro His Val Gln Lys Ser Asp Val Glu Met Glu Ala Gln Lys
1               5                   10                  15

Asp Glu Ile Ile Cys Pro Ser Cys Asn Arg Thr Ala His Pro Leu Arg
            20                  25                  30

His Ile Asn Asn Asp Met Ile Val Thr Asp Asn Gly Ala Val Lys
        35                  40                  45

Phe Pro Gln Leu Cys Lys Phe Cys Asp Val Arg Phe Ser Thr Cys Asp
    50                  55                  60

Asn Gln Lys Ser Cys Met Ser Asn Cys Ser Ile Thr Ser Ile Cys Glu
65                  70                  75                  80

Lys Pro Gln Glu Val Cys Val Ala Val Trp Arg Lys Asn Asp Glu Asn
                85                  90                  95
```

Ile Thr Leu Glu Thr Val Cys His Asp Pro Lys Leu Pro Tyr His Asp
            100                 105                 110

Phe Ile Leu Glu Asp Ala Ala Ser Pro Lys Cys Ile Met Lys Glu Lys
            115                 120                 125

Lys Lys Pro Gly Glu Thr Phe Phe Met Cys Ser Cys Ser Ser Asp Glu
130                 135                 140

Cys Asn Asp Asn Ile Ile Phe Ser Glu Glu Tyr Asn Thr Ser Asn Pro
145                 150                 155                 160

Asp Thr Gly Gly Gly Ser Gly Gly Gly Ser Gly Gly Gly Gly Gly Gly
                165                 170                 175

Ser Gly Gly Gly Ser Thr His Thr Cys Pro Pro Cys Pro Ala Pro
            180                 185                 190

Glu Leu Leu Gly Gly Pro Ser Val Phe Leu Phe Pro Pro Lys Pro Lys
            195                 200                 205

Asp Thr Leu Met Ile Ser Arg Thr Pro Glu Val Thr Cys Val Val Val
            210                 215                 220

Asp Val Ser His Glu Asp Pro Glu Val Lys Phe Asn Trp Tyr Val Asp
225                 230                 235                 240

Gly Val Glu Val His Asn Ala Lys Thr Lys Pro Arg Glu Glu Gln Tyr
                245                 250                 255

Asn Ser Thr Tyr Arg Val Val Ser Val Leu Thr Val Leu His Gln Asp
            260                 265                 270

Trp Leu Asn Gly Lys Glu Tyr Lys Cys Lys Val Ser Asn Lys Ala Leu
            275                 280                 285

Pro Ala Pro Ile Glu Lys Thr Ile Ser Lys Ala Lys Gly Gln Pro Arg
290                 295                 300

Glu Pro Gln Val Tyr Thr Leu Pro Pro Ser Arg Glu Glu Met Thr Lys
305                 310                 315                 320

Asn Gln Val Ser Leu Thr Cys Leu Val Lys Gly Phe Tyr Pro Ser Asp
                325                 330                 335

Ile Ala Val Glu Trp Glu Ser Asn Gly Gln Pro Glu Asn Asn Tyr Lys
            340                 345                 350

Thr Thr Pro Pro Val Leu Asp Ser Asp Gly Ser Phe Phe Leu Tyr Ser
            355                 360                 365

Lys Leu Thr Val Asp Lys Ser Arg Trp Gln Gln Gly Asn Val Phe Ser
            370                 375                 380

Cys Ser Val Met His Glu Ala Leu His Asn His Tyr Thr Gln Lys Ser
385                 390                 395                 400

Leu Ser Leu Ser Pro Gly Lys
                405

<210> SEQ ID NO 66
<211> LENGTH: 406
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Pro Pro His Val Gln Lys Ser Asp Val Glu Met Glu Ala Gln Lys Asp
1               5                   10                  15

Glu Ile Ile Cys Pro Ser Cys Asn Arg Thr Ala His Pro Leu Arg His
            20                  25                  30

Ile Asn Asn Asp Met Ile Val Thr Asp Asn Asn Gly Ala Val Lys Phe
        35                  40                  45

```
Pro Gln Leu Cys Lys Phe Cys Asp Val Arg Phe Ser Thr Cys Asp Asn
 50                  55                  60

Gln Lys Ser Cys Met Ser Asn Cys Ser Ile Thr Ser Ile Cys Glu Lys
 65                  70                  75                  80

Pro Gln Glu Val Cys Val Ala Val Trp Arg Lys Asn Asp Glu Asn Ile
                 85                  90                  95

Thr Leu Glu Thr Val Cys His Asp Pro Lys Leu Pro Tyr His Asp Phe
                100                 105                 110

Ile Leu Glu Asp Ala Ala Ser Pro Lys Cys Ile Met Lys Glu Lys Lys
                115                 120                 125

Lys Pro Gly Glu Thr Phe Phe Met Cys Ser Cys Ser Ser Asp Glu Cys
130                 135                 140

Asn Asp Asn Ile Ile Phe Ser Glu Glu Tyr Asn Thr Ser Asn Pro Asp
145                 150                 155                 160

Thr Gly Gly Gly Gly Ser Gly Gly Gly Ser Gly Gly Gly Gly Ser
                165                 170                 175

Gly Gly Gly Gly Ser Thr His Thr Cys Pro Pro Cys Pro Ala Pro Glu
                180                 185                 190

Leu Leu Gly Gly Pro Ser Val Phe Leu Phe Pro Pro Lys Pro Lys Asp
                195                 200                 205

Thr Leu Met Ile Ser Arg Thr Pro Glu Val Thr Cys Val Val Val Asp
210                 215                 220

Val Ser His Glu Asp Pro Glu Val Lys Phe Asn Trp Tyr Val Asp Gly
225                 230                 235                 240

Val Glu Val His Asn Ala Lys Thr Lys Pro Arg Glu Glu Gln Tyr Asn
                245                 250                 255

Ser Thr Tyr Arg Val Val Ser Val Leu Thr Val Leu His Gln Asp Trp
                260                 265                 270

Leu Asn Gly Lys Glu Tyr Lys Cys Lys Val Ser Asn Lys Ala Leu Pro
                275                 280                 285

Ala Pro Ile Glu Lys Thr Ile Ser Lys Ala Lys Gly Gln Pro Arg Glu
                290                 295                 300

Pro Gln Val Tyr Thr Leu Pro Pro Ser Arg Glu Glu Met Thr Lys Asn
305                 310                 315                 320

Gln Val Ser Leu Thr Cys Leu Val Lys Gly Phe Tyr Pro Ser Asp Ile
                325                 330                 335

Ala Val Glu Trp Glu Ser Asn Gly Gln Pro Glu Asn Asn Tyr Lys Thr
                340                 345                 350

Thr Pro Pro Val Leu Asp Ser Asp Gly Ser Phe Phe Leu Tyr Ser Lys
                355                 360                 365

Leu Thr Val Asp Lys Ser Arg Trp Gln Gln Gly Asn Val Phe Ser Cys
                370                 375                 380

Ser Val Met His Glu Ala Leu His Asn His Tyr Thr Gln Lys Ser Leu
385                 390                 395                 400

Ser Leu Ser Pro Gly Lys
                405

<210> SEQ ID NO 67
<211> LENGTH: 405
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 67

```
Pro His Val Gln Lys Ser Asp Val Glu Met Glu Ala Gln Lys Asp Glu
1               5                   10                  15

Ile Ile Cys Pro Ser Cys Asn Arg Thr Ala His Pro Leu Arg His Ile
            20                  25                  30

Asn Asn Asp Met Ile Val Thr Asp Asn Asn Gly Ala Val Lys Phe Pro
            35                  40                  45

Gln Leu Cys Lys Phe Cys Asp Val Arg Phe Ser Thr Cys Asp Asn Gln
    50                  55                  60

Lys Ser Cys Met Ser Asn Cys Ser Ile Thr Ser Ile Cys Glu Lys Pro
65                  70                  75                  80

Gln Glu Val Cys Val Ala Val Trp Arg Lys Asn Asp Glu Asn Ile Thr
                85                  90                  95

Leu Glu Thr Val Cys His Asp Pro Lys Leu Pro Tyr His Asp Phe Ile
            100                 105                 110

Leu Glu Asp Ala Ala Ser Pro Lys Cys Ile Met Lys Glu Lys Lys Lys
        115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Thr
145                 150                 155                 160

Gly Gly Gly Gly Ser Gly Gly Gly Ser Gly Gly Gly Gly Ser Gly
                165                 170                 175

Gly Gly Gly Ser Thr His Thr Cys Pro Pro Cys Pro Ala Pro Glu Leu
            180                 185                 190

Leu Gly Gly Pro Ser Val Phe Leu Phe Pro Pro Lys Pro Lys Asp Thr
        195                 200                 205

Leu Met Ile Ser Arg Thr Pro Glu Val Thr Cys Val Val Val Asp Val
    210                 215                 220

Ser His Glu Asp Pro Glu Val Lys Phe Asn Trp Tyr Val Asp Gly Val
225                 230                 235                 240

Glu Val His Asn Ala Lys Thr Lys Pro Arg Glu Glu Gln Tyr Asn Ser
                245                 250                 255

Thr Tyr Arg Val Val Ser Val Leu Thr Val Leu His Gln Asp Trp Leu
            260                 265                 270

Asn Gly Lys Glu Tyr Lys Cys Lys Val Ser Asn Lys Ala Leu Pro Ala
        275                 280                 285

Pro Ile Glu Lys Thr Ile Ser Lys Ala Lys Gly Gln Pro Arg Glu Pro
    290                 295                 300

Gln Val Tyr Thr Leu Pro Pro Ser Arg Glu Glu Met Thr Lys Asn Gln
305                 310                 315                 320

Val Ser Leu Thr Cys Leu Val Lys Gly Phe Tyr Pro Ser Asp Ile Ala
                325                 330                 335

Val Glu Trp Glu Ser Asn Gly Gln Pro Glu Asn Asn Tyr Lys Thr Thr
            340                 345                 350

Pro Pro Val Leu Asp Ser Asp Gly Ser Phe Phe Leu Tyr Ser Lys Leu
        355                 360                 365

Thr Val Asp Lys Ser Arg Trp Gln Gln Gly Asn Val Phe Ser Cys Ser
    370                 375                 380

Val Met His Glu Ala Leu His Asn His Tyr Thr Gln Lys Ser Leu Ser
385                 390                 395                 400

Leu Ser Pro Gly Lys
                405
```

<210> SEQ ID NO 68
<211> LENGTH: 404
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

```
His Val Gln Lys Ser Asp Val Glu Met Glu Ala Gln Lys Asp Glu Ile
1               5                   10                  15

Ile Cys Pro Ser Cys Asn Arg Thr Ala His Pro Leu Arg His Ile Asn
            20                  25                  30

Asn Asp Met Ile Val Thr Asp Asn Asn Gly Ala Val Lys Phe Pro Gln
        35                  40                  45

Leu Cys Lys Phe Cys Asp Val Arg Phe Ser Thr Cys Asp Asn Gln Lys
    50                  55                  60

Ser Cys Met Ser Asn Cys Ser Ile Thr Ser Ile Cys Glu Lys Pro Gln
65                  70                  75                  80

Glu Val Cys Val Ala Val Trp Arg Lys Asn Asp Glu Asn Ile Thr Leu
                85                  90                  95

Glu Thr Val Cys His Asp Pro Lys Leu Pro Tyr His Asp Phe Ile Leu
            100                 105                 110

Glu Asp Ala Ala Ser Pro Lys Cys Ile Met Lys Glu Lys Lys Lys Pro
        115                 120                 125

Gly Glu Thr Phe Phe Met Cys Ser Cys Ser Ser Asp Glu Cys Asn Asp
130                 135                 140

Asn Ile Ile Phe Ser Glu Glu Tyr Asn Thr Ser Asn Pro Asp Thr Gly
145                 150                 155                 160

Gly Gly Gly Ser Gly Gly Gly Ser Gly Gly Gly Ser Gly Gly
                165                 170                 175

Gly Gly Ser Thr His Thr Cys Pro Pro Cys Pro Ala Pro Glu Leu Leu
            180                 185                 190

Gly Gly Pro Ser Val Phe Leu Phe Pro Pro Lys Pro Lys Asp Thr Leu
        195                 200                 205

Met Ile Ser Arg Thr Pro Glu Val Thr Cys Val Val Val Asp Val Ser
    210                 215                 220

His Glu Asp Pro Glu Val Lys Phe Asn Trp Tyr Val Asp Gly Val Glu
225                 230                 235                 240

Val His Asn Ala Lys Thr Lys Pro Arg Glu Glu Gln Tyr Asn Ser Thr
                245                 250                 255

Tyr Arg Val Val Ser Val Leu Thr Val Leu His Gln Asp Trp Leu Asn
            260                 265                 270

Gly Lys Glu Tyr Lys Cys Lys Val Ser Asn Lys Ala Leu Pro Ala Pro
        275                 280                 285

Ile Glu Lys Thr Ile Ser Lys Ala Lys Gly Gln Pro Arg Glu Pro Gln
    290                 295                 300

Val Tyr Thr Leu Pro Pro Ser Arg Glu Glu Met Thr Lys Asn Gln Val
305                 310                 315                 320

Ser Leu Thr Cys Leu Val Lys Gly Phe Tyr Pro Ser Asp Ile Ala Val
                325                 330                 335

Glu Trp Glu Ser Asn Gly Gln Pro Glu Asn Asn Tyr Lys Thr Thr Pro
            340                 345                 350

Pro Val Leu Asp Ser Asp Gly Ser Phe Phe Leu Tyr Ser Lys Leu Thr
```

```
            355                 360                 365
Val Asp Lys Ser Arg Trp Gln Gln Gly Asn Val Phe Ser Cys Ser Val
370                 375                 380

Met His Glu Ala Leu His Asn His Tyr Thr Gln Lys Ser Leu Ser Leu
385                 390                 395                 400

Ser Pro Gly Lys

<210> SEQ ID NO 69
<211> LENGTH: 503
<212> TYPE: PRT
<213> ORGANISM: Homo sapiens

<400> SEQUENCE: 69

Met Glu Ala Ala Val Ala Ala Pro Arg Pro Arg Leu Leu Leu Leu Val
1               5                   10                  15

Leu Ala Ala Ala Ala Ala Ala Ala Leu Leu Pro Gly Ala Thr
                20                  25                  30

Ala Leu Gln Cys Phe Cys His Leu Cys Thr Lys Asp Asn Phe Thr Cys
            35                  40                  45

Val Thr Asp Gly Leu Cys Phe Val Ser Val Thr Glu Thr Thr Asp Lys
        50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu Ala Ala
        115                 120                 125

Val Ile Ala Gly Pro Val Cys Phe Val Cys Ile Ser Leu Met Leu Met
130                 135                 140

Val Tyr Ile Cys His Asn Arg Thr Val Ile His His Arg Val Pro Asn
145                 150                 155                 160

Glu Glu Asp Pro Ser Leu Asp Arg Pro Phe Ile Ser Glu Gly Thr Thr
                165                 170                 175

Leu Lys Asp Leu Ile Tyr Asp Met Thr Thr Ser Gly Ser Gly Ser Gly
            180                 185                 190

Leu Pro Leu Leu Val Gln Arg Thr Ile Ala Arg Thr Ile Val Leu Gln
        195                 200                 205

Glu Ser Ile Gly Lys Gly Arg Phe Gly Glu Val Trp Arg Gly Lys Trp
210                 215                 220

Arg Gly Glu Glu Val Ala Val Lys Ile Phe Ser Ser Arg Glu Glu Arg
225                 230                 235                 240

Ser Trp Phe Arg Glu Ala Glu Ile Tyr Gln Thr Val Met Leu Arg His
                245                 250                 255

Glu Asn Ile Leu Gly Phe Ile Ala Ala Asp Asn Lys Asp Asn Gly Thr
            260                 265                 270

Trp Thr Gln Leu Trp Leu Val Ser Asp Tyr His Glu His Gly Ser Leu
        275                 280                 285

Phe Asp Tyr Leu Asn Arg Tyr Thr Val Thr Val Glu Gly Met Ile Lys
            290                 295                 300

Leu Ala Leu Ser Thr Ala Ser Gly Leu Ala His Leu His Met Glu Ile
305                 310                 315                 320

Val Gly Thr Gln Gly Lys Pro Ala Ile Ala His Arg Asp Leu Lys Ser
```

325                 330                 335
Lys Asn Ile Leu Val Lys Lys Asn Gly Thr Cys Cys Ile Ala Asp Leu
            340                 345                 350
Gly Leu Ala Val Arg His Asp Ser Ala Thr Asp Thr Ile Asp Ile Ala
        355                 360                 365
Pro Asn His Arg Val Gly Thr Lys Arg Tyr Met Ala Pro Glu Val Leu
370                 375                 380
Asp Asp Ser Ile Asn Met Lys His Phe Glu Ser Phe Lys Arg Ala Asp
385                 390                 395                 400
Ile Tyr Ala Met Gly Leu Val Phe Trp Glu Ile Ala Arg Arg Cys Ser
            405                 410                 415
Ile Gly Gly Ile His Glu Asp Tyr Gln Leu Pro Tyr Tyr Asp Leu Val
            420                 425                 430
Pro Ser Asp Pro Ser Val Glu Glu Met Arg Lys Val Val Cys Glu Gln
        435                 440                 445
Lys Leu Arg Pro Asn Ile Pro Asn Arg Trp Gln Ser Cys Glu Ala Leu
    450                 455                 460
Arg Val Met Ala Lys Ile Met Arg Glu Cys Trp Tyr Ala Asn Gly Ala
465                 470                 475                 480
Ala Arg Leu Thr Ala Leu Arg Ile Lys Lys Thr Leu Ser Gln Leu Ser
            485                 490                 495
Gln Gln Glu Gly Ile Lys Met
            500

<210> SEQ ID NO 70
<211> LENGTH: 102
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Ala Ala Leu Leu Pro Gly Ala Thr Ala Leu Gln Cys Phe Cys His Leu
1               5                   10                  15
Cys Thr Lys Asp Asn Phe Thr Cys Val Thr Asp Gly Leu Cys Phe Val
            20                  25                  30
Ser Val Thr Glu Thr Thr Asp Lys Val Ile His Asn Ser Met Cys Ile
        35                  40                  45
Ala Glu Ile Asp Leu Ile Pro Arg Asp Arg Pro Phe Val Cys Ala Pro
    50                  55                  60
Ser Ser Lys Thr Gly Ser Val Thr Thr Thr Tyr Cys Cys Asn Gln Asp
65                  70                  75                  80
His Cys Asn Lys Ile Glu Leu Pro Thr Thr Val Lys Ser Ser Pro Gly
            85                  90                  95
Leu Gly Pro Val Glu Leu
            100

<210> SEQ ID NO 71
<211> LENGTH: 1509
<212> TYPE: DNA
<213> ORGANISM: Homo sapiens

<400> SEQUENCE: 71
atggaggcgg cggtcgctgc tccgcgtccc cggctgctcc tcctcgtgct ggcggcggcg      60
gcggcggcgg cggcggcgct gctcccgggg gcgacggcgt tacagtgttt ctgccacctc     120

```
tgtacaaaag acaattttac ttgtgtgaca gatgggctct gctttgtctc tgtcacagag      180
accacagaca aagttataca caacagcatg tgtatagctg aaattgactt aattcctcga      240
gataggccgt tgtatgtgc accctcttca aaaactgggt ctgtgactac aacatattgc      300
tgcaatcagg accattgcaa taaaatagaa cttccaacta ctgtaaagtc atcacctggc      360
cttggtcctg tggaactggc agctgtcatt gctggaccag tgtgcttcgt ctgcatctca      420
ctcatgttga tggtctatat ctgccacaac cgcactgtca ttcaccatcg agtgccaaat      480
gaagaggacc cttcattaga tcgcccttt atttcagagg gtactacgtt gaaagactta      540
atttatgata tgcaacgtc aggttctggc tcaggtttac cattgcttgt tcagagaaca      600
attgcgagaa ctattgtgtt acaagaaagc attggcaaag gtcgatttgg agaagtttgg      660
agaggaaagt ggcggggaga agaagttgct gttaagatat tctcctctag agaagaacgt      720
tcgtggttcc gtgaggcaga gatttatcaa actgtaatgt tacgtcatga aacatcctg      780 ggatttatag cagcagacaa taagacaat ggtacttgga ctcagctctg gttggtgtca      840
gattatcatg agcatggatc cctttttgat tacttaaaca gatacacagt tactgtggaa      900
ggaatgataa aacttgctct gtccacggcg agcggtcttg cccatcttca catggagatt      960
gttggtaccc aaggaaagcc agccattgct catagagatt tgaaatcaaa gaatatcttg     1020
gtaaagaaga atggaacttg ctgtattgca gacttaggac tggcagtaag acatgattca     1080
gccacagata ccattgatat tgctccaaac cacagagtgg gaacaaaaag gtacatggcc     1140
cctgaagttc tcgatgattc cataaatatg aaacattttg aatccttcaa acgtgctgac     1200
atctatgcaa tgggcttagt attctgggaa attgctcgac gatgttccat ggtggaattt     1260
catgaagatt accaactgcc ttattatgat cttgtacctt ctgacccatc agttgaagaa     1320
atgagaaaag ttgtttgtga acagaagtta aggccaaata tcccaaacag atggcagagc     1380
tgtgaagcct tgagagtaat ggctaaaatt atgagagaat gttggtatgc caatggagca     1440
gctaggctta cagcattgcg gattaagaaa acattatcgc aactcagtca acaggaaggc     1500
atcaaaatg                                                             1509
```

<210> SEQ ID NO 72
<211> LENGTH: 306
<212> TYPE: DNA
<213> ORGANISM: Homo sapiens

<400> SEQUENCE: 72

```
gcggcgctgc tcccgggggc gacggcgtta cagtgtttct gccacctctg tacaaaagac       60
aattttactt gtgtgacaga tgggctctgc tttgtctctg tcacagagac cacagacaaa      120
gttatacaca acagcatgtg tatagctgaa attgacttaa ttcctcgaga taggccgttt      180
gtatgtgcac cctcttcaaa aactgggtct gtgactacaa catattgctg caatcaggac      240
cattgcaata aaatagaact tccaactact gtaaagtcat cacctggcct tggtcctgtg      300
gaactg                                                                 306
```

<210> SEQ ID NO 73
<211> LENGTH: 507
<212> TYPE: PRT
<213> ORGANISM: Homo sapiens

<400> SEQUENCE: 73

Met Glu Ala Ala Val Ala Ala Pro Arg Pro Arg Leu Leu Leu Leu Val
1               5                   10                  15

```
Leu Ala Ala Ala Ala Ala Ala Ala Leu Leu Pro Gly Ala Thr
         20                  25              30

Ala Leu Gln Cys Phe Cys His Leu Cys Thr Lys Asp Asn Phe Thr Cys
         35              40                  45

Val Thr Asp Gly Leu Cys Phe Val Ser Val Thr Glu Thr Thr Asp Lys
 50                      55                  60

Val Ile His Asn Ser Met Cys Ile Ala Glu Ile Asp Leu Ile Pro Arg
 65              70                  75                      80

Asp Arg Pro Phe Val Cys Ala Pro Ser Ser Lys Thr Gly Ser Val Thr
                 85                  90                  95

Thr Thr Tyr Cys Cys Asn Gln Asp His Cys Asn Lys Ile Glu Leu Pro
             100                 105             110

Thr Thr Gly Pro Phe Ser Val Lys Ser Ser Pro Gly Leu Gly Pro Val
         115                 120                 125

Glu Leu Ala Ala Val Ile Ala Gly Pro Val Cys Phe Val Cys Ile Ser
     130                 135                 140

Leu Met Leu Met Val Tyr Ile Cys His Asn Arg Thr Val Ile His His
145                 150                 155                 160

Arg Val Pro Asn Glu Glu Asp Pro Ser Leu Asp Arg Pro Phe Ile Ser
                 165                 170                 175

Glu Gly Thr Thr Leu Lys Asp Leu Ile Tyr Asp Met Thr Thr Ser Gly
             180                 185                 190

Ser Gly Ser Gly Leu Pro Leu Leu Val Gln Arg Thr Ile Ala Arg Thr
         195                 200                 205

Ile Val Leu Gln Glu Ser Ile Gly Lys Gly Arg Phe Gly Glu Val Trp
210                 215                 220

Arg Gly Lys Trp Arg Gly Glu Glu Val Ala Val Lys Ile Phe Ser Ser
225                 230                 235                 240

Arg Glu Glu Arg Ser Trp Phe Arg Glu Ala Glu Ile Tyr Gln Thr Val
                 245                 250                 255

Met Leu Arg His Glu Asn Ile Leu Gly Phe Ile Ala Ala Asp Asn Lys
             260                 265                 270

Asp Asn Gly Thr Trp Thr Gln Leu Trp Leu Val Ser Asp Tyr His Glu
         275                 280                 285

His Gly Ser Leu Phe Asp Tyr Leu Asn Arg Tyr Thr Val Thr Val Glu
     290                 295                 300

Gly Met Ile Lys Leu Ala Leu Ser Thr Ala Ser Gly Leu Ala His Leu
305                 310                 315                 320

His Met Glu Ile Val Gly Thr Gln Gly Lys Pro Ala Ile Ala His Arg
                 325                 330                 335

Asp Leu Lys Ser Lys Asn Ile Leu Val Lys Lys Asn Gly Thr Cys Cys
             340                 345                 350

Ile Ala Asp Leu Gly Leu Ala Val Arg His Asp Ser Ala Thr Asp Thr
     355                 360                 365

Ile Asp Ile Ala Pro Asn His Arg Val Gly Thr Lys Arg Tyr Met Ala
370                 375                 380

Pro Glu Val Leu Asp Asp Ser Ile Asn Met Lys His Phe Glu Ser Phe
385                 390                 395                 400

Lys Arg Ala Asp Ile Tyr Ala Met Gly Leu Val Phe Trp Glu Ile Ala
                 405                 410                 415

Arg Arg Cys Ser Ile Gly Gly Ile His Glu Asp Tyr Gln Leu Pro Tyr
             420                 425                 430

Tyr Asp Leu Val Pro Ser Asp Pro Ser Val Glu Glu Met Arg Lys Val
```

```
              435                 440                 445
Val Cys Glu Gln Lys Leu Arg Pro Asn Ile Pro Asn Arg Trp Gln Ser
        450                 455                 460

Cys Glu Ala Leu Arg Val Met Ala Lys Ile Met Arg Glu Cys Trp Tyr
465                 470                 475                 480

Ala Asn Gly Ala Ala Arg Leu Thr Ala Leu Arg Ile Lys Lys Thr Leu
                485                 490                 495

Ser Gln Leu Ser Gln Gln Glu Gly Ile Lys Met
        500                 505
```

<210> SEQ ID NO 74
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

```
Ala Ala Leu Leu Pro Gly Ala Thr Ala Leu Gln Cys Phe Cys His Leu
1               5                   10                  15

Cys Thr Lys Asp Asn Phe Thr Cys Val Thr Asp Gly Leu Cys Phe Val
            20                  25                  30

Ser Val Thr Glu Thr Thr Asp Lys Val Ile His Asn Ser Met Cys Ile
        35                  40                  45

Ala Glu Ile Asp Leu Ile Pro Arg Asp Arg Pro Phe Val Cys Ala Pro
50                  55                  60

Ser Ser Lys Thr Gly Ser Val Thr Thr Thr Tyr Cys Cys Asn Gln Asp
65                  70                  75                  80

His Cys Asn Lys Ile Glu Leu Pro Thr Thr Gly Pro Phe Ser Val Lys
                85                  90                  95

Ser Ser Pro Gly Leu Gly Pro Val Glu Leu
            100                 105
```

<210> SEQ ID NO 75
<211> LENGTH: 1521
<212> TYPE: DNA
<213> ORGANISM: Homo sapiens

<400> SEQUENCE: 75

```
atggaggcgg cggtcgctgc tccgcgtccc cggctgctcc tcctcgtgct ggcggcggcg      60
gcggcggcgg cggcggcgct gctcccgggg gcgacggcgt acagtgtttt ctgccacctc     120
tgtacaaaag acaattttac ttgtgtgaca gatgggctct gctttgtctc tgtcacagag     180
accacagaca agttatacaa caacagcatg tgtatagctg aaattgactt aattcctcga     240
gataggccgt ttgtatgtgc accctcttca aaaactgggt ctgtgactac aacatattgc     300
tgcaatcagg accattgcaa taaaatagaa cttccaacta ctggcccttt ttcagtaaag     360
tcatcacctg gccttggtcc tgtggaactg cagctgtca ttgctggacc agtgtgcttc      420
gtctgcatct cactcatgtt gatggtctat atctgccaca accgcactgt cattcaccat     480
cgagtgccaa atgaagagga cccttcatta gatcgccctt ttatttcaga gggtactacg     540
ttgaaagact aatttatga tatgcaacg tcaggttctg gctcaggttt accattgctt       600
gttcagagaa caattgcgag aactattgtg ttacaagaaa gcattggcaa aggtcgattt     660
ggagaagttt ggagaggaaa gtggcgggga aagaagttg ctgttaagat attctctct       720 agagaagaac gttcgtggtt ccgtgaggca gagatttatc aaactgtaat gttacgtcat     780
```

```
gaaaacatcc tgggatttat agcagcagac aataaagaca atggtacttg gactcagctc      840
tggttggtgt cagattatca tgagcatgga tcccttttg attacttaaa cagatacaca      900
gttactgtgg aaggaatgat aaaacttgct ctgtccacgg cgagcggtct tgcccatctt      960
cacatggaga ttgttggtac caaggaaag ccagccattg ctcatagaga tttgaaatca     1020
aagaatatct tggtaaagaa gaatggaact tgctgtattg cagacttagg actggcagta    1080
agacatgatt cagccacaga taccattgat attgctccaa accacagagt gggaacaaaa    1140
aggtacatgg cccctgaagt tctcgatgat tccataaata tgaaacattt tgaatccttc    1200
aaacgtgctg acatctatgc aatgggctta gtattctggg aaattgctcg acgatgttcc    1260
attggtggaa ttcatgaaga ttaccaactg ccttattatg atcttgtacc ttctgaccca    1320
tcagttgaag aaatgagaaa agttgtttgt gaacagaagt taaggccaaa tatcccaaac    1380
agatggcaga gctgtgaagc cttgagagta atggctaaaa ttatgagaga atgttggtat    1440
gccaatggag cagctaggct tacagcattg cggattaaga aaacattatc gcaactcagt    1500
caacaggaag gcatcaaaat g                                             1521
```

<210> SEQ ID NO 76
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76

```
gcggcgctgc tcccggggc gacggcgtta cagtgtttct gccacctctg tacaaaagac       60
aattttactt gtgtgacaga tgggctctgc tttgtctctg tcacagagac cacagacaaa     120
gttatacaca acagcatgtg tatagctgaa attgacttaa ttcctcgaga taggccgttt     180
gtatgtgcac cctcttcaaa aactgggtct gtgactacaa catattgctg caatcaggac     240
cattgcaata aaatagaact tccaactact ggccctttt cagtaaagtc atcacctggc      300
cttggtcctg tggaactg                                                  318
```

<210> SEQ ID NO 77
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 77

Gly Gly Gly Gly Ser Gly Gly Gly Gly Ser
1               5                   10

<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments -continued

```
<400> SEQUENCE: 78

Gly Gly Gly Gly Ser Gly Gly Gly Ser Gly Gly Gly Gly Ser
1               5                   10                  15

<210> SEQ ID NO 79
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 79

Gly Gly Gly Gly Ser Gly Gly Gly Gly Ser Gly Gly Gly Gly Ser Gly
1               5                   10                  15

Gly Gly Gly Ser
            20

<210> SEQ ID NO 80
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: See specification as filed for detailed
      description of substitutions and preferred embodiments

<400> SEQUENCE: 80

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 81
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Gly Gly Gly Ser Gly Gly Gly Gly Ser Gly Gly Gly Gly Ser Gly
1               5                   10                  15

Gly Gly Gly Ser
            20

<210> SEQ ID NO 82
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Asn Thr Ser Asn Pro Asp Thr Gly Gly Gly Thr His Thr Cys Pro Pro
1               5                   10                  15

Cys
```

```
<210> SEQ ID NO 83
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Asn Thr Ser Asn Pro Asp Thr Gly Gly Gly Gly Ser Gly Gly Gly Gly
1               5                   10                  15

Ser Thr His Thr Cys Pro Pro Cys
            20

<210> SEQ ID NO 84
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Asn Thr Ser Asn Pro Asp Thr Gly Gly Gly Gly Ser Gly Gly Gly Gly
1               5                   10                  15

Ser Gly Gly Gly Gly Ser Thr His Thr Cys Pro Pro Cys
            20                  25

<210> SEQ ID NO 85
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Asn Thr Ser Asn Pro Asp Thr Gly Gly Gly Gly Ser Gly Gly Gly Gly
1               5                   10                  15

Ser Gly Gly Gly Gly Ser Gly Gly Gly Gly Ser Thr His Thr Cys Pro
            20                  25                  30

Pro Cys

<210> SEQ ID NO 86
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Asn Thr Ser Asn Pro Asp Thr Gly Gly Gly Pro Lys Ser Cys Asp Lys
1               5                   10                  15

Thr His Thr Cys Pro Pro Cys
            20

<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag
```

```
<400> SEQUENCE: 87

His His His His His His
1               5
```

METHODS FOR TREATING HETEROTOPIC OSSIFICATION

CROSS-REFERENCE TO RELATED APPLICATIONS

This application is a national stage filing under 35 U.S.C. § 371 of International Application No. PCT/US2019/017297, filed on Feb. 8, 2019, which claims the benefit of and priority to U.S. Provisional Application No. 62/628,649, filed on Feb. 9, 2018 and U.S. Provisional Application No. 62/666,235, filed on May 3, 2018. The specifications of each of the foregoing applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Aug. 3, 2020, is named 1848179-125-301_Seq.txt and is 177,924 bytes in size.

BACKGROUND OF THE INVENTION

Heterotopic ossification (HO) is the pathologic formation of extra-skeletal bone in soft tissues. Vanden Bossche and Vanderstraeten, J Rehabil Med 27, 129 (2005). In general, this process occurs in patient populations with severe trauma including large-surface area burns, musculoskeletal injury, orthopedic operations, and spinal cord injury, and in patient populations with a genetic disease known as fibrodysplasia ossificans progressiva (FOP). FOP is caused by a hyperactivating mutation in the type I bone morphogenetic protein (BMP) receptor ACVR1, and patients with FOP develop ectopic bone lesions in the absence of any substantial trauma. The clinical sequela of these pathologic ectopic bone formations, whether in the setting of trauma or genetic mutations, include non-healing wounds, chronic pain, and joint immobility. In the case of FOP, progressive ossification may lead to death due to loss of thoracic cage compliance.

Treatment options for HO are limited as bone often recurs following surgical resection, and some patients may have non-resectable HO due to its sensitive location. The risk of an operation may outweigh the benefits of excision, especially in the face of recurrence. Thus, there is a high unmet need for effective therapies for treating HO.

SUMMARY OF THE INVENTION

In part, the present disclosure relates to the discovery that a TGFβ antagonist (inhibitor) can be used to treat heterotopic ossification (HO). In particular, the data presented herein shows that a soluble TβRII polypeptide, which binds to TGFβ1 and TGFβ3, is effective at attenuating development of HO anlagen with decreased osseous deposition and marrow space formation in a mouse model of HO. Furthermore, treatment with the TβRII polypeptide significantly reduced the volume of mature HO in this animal model. While not wishing to be bound to any particular mechanism, it is expected that the effects of TβRII polypeptides are caused primarily by TGFβ signaling antagonist effect, particularly of TGFβ1 and/or TGFβ3. Therefore, it is expected that other TGFβ antagonists [e.g., antagonists of the TβRII receptor, antagonists of one or more TβRII-binding ligand (e.g., TGFβ1, TGFβ2, and TGFβ3), antagonists of one or more TβRII-associated type I receptor (e.g., ALK5), antagonists of one or more TβRII-associated co-receptor (betaglycan), antagonists of one or more TβRII downstream signaling components (e.g., Smads), or combination of such antagonists] will useful in the treatment of HO. Such agents are collectively referred to herein as "TGFβ antagonists" or "TGFβ inhibitors".

In certain aspects, the disclosure relates to methods for treating HO comprising administering to a patient in need thereof an effective amount of a Transforming Growth Factor-β (TGFβ) antagonist. In some embodiments, the methods prevent or reduce the severity and/or duration of one or more complications of HO. For example, treatment with a TGFβ antagonist may prevent or reduce the severity and/or duration of one or more complications of HO selected from the group consisting of: joint contracture, ankylosis, pain, spasticity, swelling fever, neurovascular compression, and pressure ulcers. In some embodiments, the methods relate to treating HO that is associated with one or more disorders or conditions selected from the group consisting of: spinal cord injury, trauma, brain injuries, burns, fractures, muscle contusion, joint arthroplasty/replacement, hip surgery/replacement, acetabular surgery/replacement, elbow fracture, fracture of the long bones of the lower leg, combat-related trauma, amputation, neuromuscular blockade used to manage adult respiratory distress syndrome, nontraumatic myelopathies. In some embodiments, the disclosure relates to methods of treating fibrodysplasia ossificans progressiva (FOP) comprising administering to a patient in need thereof an effective amount of a TGFβ antagonist. For example, the methods prevent or reduce the severity and/or duration of one or more complications of FOP (e.g., heterotopic ossification). In some embodiments, the disclosure relates to methods of treating fibrodysplasia ossificans progressiva (FOP) comprising administering to a patient in need thereof an effective amount of a TGFβ antagonist. For example, the methods prevent or reduce the severity and/or duration of one or more complications of FOP (e.g., heterotopic ossification). In some embodiments, the disclosure relates to methods of treating fibrous dysplasia comprising administering to a patient in need thereof an effective amount of a TGFβ antagonist. For example, the methods prevent or reduce the severity and/or duration of one or more complications of fibrous dysplasia (e.g., heterotopic ossification). In some embodiments, heterotopic ossification occurs in one or more tissues selected from the group consisting of: bone, skin, subcutaneous tissue, skeletal muscle, fibrosis tissue adjacent to joints, walls of blood vessels, and ligaments. Optionally, such methods described herein further comprise administering to the patient an effective amount of one or more additional active agents or supportive therapies for treating HO. For example, such additional active agents or supportive therapies include isotretinoin, etidronate with oral corticosteroids, perhexiline maleate, ALK2 small-molecule inhibitors, palovarotene, retinoic acid receptor gamma agonists, retinoic acid receptor alpha agonists, activin antibodies (e.g., activin A antibodies such as REGN 2477), allele-specific RNA interference of ALK2, bisphosphonates, radiation therapy anti-inflammatory agents (e.g., indomethacin, ibuprofen and aspirin), and conservative treatments such as passive range of motion exercises or other mobilization techniques. In some embodiments, the additional active agent or supportive therapy is treatment with an activin antagonist. In some embodiments, the activin antagonist is an activin antibody. In some embodiments, the activin antibody is an activin A antibody. In some embodiments, TGFβ antagonist is a multi-specific antibody that binds to and inhibits signaling mediated by one or more of TGFβ1, TGFβ2, and TGFβ3 and further binds to and inhibits activin (e.g., activin A).

In certain aspects, a TGFβ antagonist, or combination of antagonists, to be used in accordance with methods and uses described herein is an agent that inhibits at least TGFβ1 (e.g., a TGFβ1 antagonist). Effects on TGFβ1 inhibition may be determined, for example, using a cell-based assay including those described herein (e.g., Smad signaling assay). Therefore, in some embodiments, a TGFβ antagonist, or combination of antagonists, of the disclosure may bind to at least TGFβ1. Ligand binding activity may be determined, for example, using a binding affinity assay including those described herein. In some embodiments, a TGFβ antagonist, or combination of antagonists, of the disclosure binds to at least TGFβ1 with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M). As described herein, various TGFβ antagonists that inhibit TGFβ1 can be used in accordance with the methods and uses described herein including, for example, ligand traps (e.g., TβRII polypeptides and variants thereof), antibodies, small molecules, nucleotide sequences, and combinations thereof. In certain embodiments, a TGFβ antagonist, or combination of antagonists, that inhibits TGFβ1 may further inhibit one or more of: TGFβ2, TGFβ3, TβRII, ALK5, and betaglycan. In some embodiments, a TGFβ antagonist, or combination of antagonists, that inhibits TGFβ1 further inhibits TGFβ3. In some embodiments, a TGFβ antagonist, or combination of antagonists, that inhibits TGFβ1 does not inhibit or does not substantially inhibit TGFβ2. In some embodiments, a TGFβ antagonist, or combination of antagonists, that inhibits TGFβ1 further inhibits TGFβ3 but does not inhibit or does not substantially inhibit TGFβ2.

In certain aspects, a TGFβ antagonist, or combination of antagonists, to be used in accordance with methods and uses described herein is an agent that inhibits at least TGFβ2 (e.g., a TGFβ2 antagonist). Effects on TGFβ2 inhibition may be determined, for example, using a cell-based assay including those described herein (e.g., Smad signaling assay). Therefore, in some embodiments, a TGFβ antagonist, or combination of antagonists, of the disclosure may bind to at least TGFβ2. Ligand binding activity may be determined, for example, using a binding affinity assay including those described herein. In some embodiments, a TGFβ antagonist, or combination of antagonists, of the disclosure binds to at least TGFβ2 with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M). As described herein, various TGFβ antagonists that inhibit TGFβ2 can be used in accordance with the methods and uses described herein including, for example, ligand traps (e.g., TβRII polypeptides and variants thereof), antibodies, small molecules, nucleotide sequences, and combinations thereof. In certain embodiments, a TGFβ antagonist, or combination of antagonists, that inhibits TGFβ2 may further inhibit one or more of: TGFβ1, TGFβ3, TβRII, ALK5, and betaglycan.

In certain aspects, a TGFβ antagonist, or combination of antagonists, to be used in accordance with methods and uses described herein is an agent that inhibits at least TGFβ3 (e.g., a TGFβ3 antagonist). Effects on TGFβ3 inhibition may be determined, for example, using a cell-based assay including those described herein (e.g., Smad signaling assay). Therefore, in some embodiments, a TGFβ antagonist, or combination of antagonists, of the disclosure may bind to at least TGFβ3. Ligand binding activity may be determined, for example, using a binding affinity assay including those described herein. In some embodiments, a TGFβ antagonist, or combination of antagonists, of the disclosure binds to at least TGFβ3 with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-12}$ M). As described herein, various TGFβ antagonists that inhibit TGFβ3 can be used in accordance with the methods and uses described herein including, for example, ligand traps (e.g., TβRII polypeptides and variants thereof), antibodies, small molecules, nucleotide sequences, and combinations thereof. In certain embodiments, a TGFβ antagonist, or combination of antagonists, that inhibits TGFβ3 may further inhibit one or more of: TGFβ1, TGFβ2, TβRII, ALK5, and betaglycan. In some embodiments, a TGFβ antagonist, or combination of antagonists, that inhibits TGFβ3 further inhibits TGFβ1. In some embodiments, a TGFβ antagonist, or combination of antagonists, that inhibits TGFβ3 does not inhibit or does not substantially inhibit TGFβ2. In some embodiments, a TGFβ antagonist, or combination of antagonists, that inhibits TGFβ3 further inhibits TGFβ1 but does not inhibit or does not substantially inhibit TGFβ2.

In certain aspects, a TGFβ antagonist, or combination of antagonists, to be used in accordance with methods and uses described herein is an agent that inhibits at least TβRII (e.g., a TβRII receptor antagonist). Effects on TβRII inhibition may be determined, for example, using a cell-based assay including those described herein (e.g., Smad signaling assay). Therefore, in some embodiments, a TGFβ antagonist, or combination of antagonists, of the disclosure may bind to at least TβRII. Ligand binding activity may be determined, for example, using a binding affinity assay including those described herein. In some embodiments, a TGFβ antagonist, or combination of antagonists, of the disclosure binds to at least TβRII with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-1}$ M). As described herein, various TGFβ antagonists that inhibit TβRII can be used in accordance with the methods and uses described herein including, for example, ligand traps (e.g., TβRII polypeptides and variants thereof), antibodies, small molecules, nucleotide sequences, and combinations thereof. In certain embodiments, a TGFβ antagonist, or combination of antagonists, that inhibits TβRII may further inhibit one or more of: TGFβ1, TGFβ2, TGFβ3, ALK5, and betaglycan. In some embodiments, a TGFβ antagonist, or combination of antagonists, that inhibits TβRII does not inhibit or does not substantially inhibit TGFβ2.

In certain aspects, a TGFβ antagonist, or combination of antagonists, to be used in accordance with methods and uses described herein is an agent that inhibits at least ALK5 (e.g., na ALK5 antagonist). Effects on ALK5 inhibition may be determined, for example, using a cell-based assay including those described herein (e.g., Smad signaling assay). Therefore, in some embodiments, a TGFβ antagonist, or combination of antagonists, of the disclosure may bind to at least ALK5. Ligand binding activity may be determined, for example, using a binding affinity assay including those described herein. In some embodiments, an ALK5 antagonist, or combination of antagonists, of the disclosure binds to at least ALK5 with a $K_D$ of at least $1\times10^{-7}$ M (e.g., at least $1\times10^{-8}$ M, at least $1\times10^{-9}$ M, at least $1\times10^{-10}$ M, at least $1\times10^{-11}$ M, or at least $1\times10^{-1}$ M). As described herein, various TGFβ antagonists that inhibit ALK5 can be used in accordance with the methods and uses described herein including, for example, ligand traps (e.g., TβRII polypeptides and variants thereof), antibodies, small molecules, nucleotide sequences, and combinations thereof. In certain embodiments, a TGFβ antagonist, or combination of antagonists, that inhibits ALK5 may further inhibit one or more of: TGFβ1, TGFβ2, TGFβ3, TβRII, and betaglycan. In some embodiments, a TGFβ antagonist, or combination of antagonists, that inhibits ALK5 does not inhibit or does not substantially inhibit TGFβ2.

In certain aspects, a TGFβ antagonist, or combination of antagonists, to be used in accordance with methods and uses described herein is an agent that inhibits at least betaglycan (e.g., a betaglycan antagonist). Effects on betaglycan inhibition may be determined, for example, using a cell-based assay including those described herein (e.g., Smad signaling assay). Therefore, in some embodiments, a TGFβ antagonist, or combination of antagonists, of the disclosure may bind to at least betaglycan. Ligand binding activity may be determined, for example, using a binding affinity assay including those described herein. In some embodiments, a betaglycan antagonist, or combination of antagonists, of the disclosure binds to at least betaglycan with a $K_D$ of at least $1\times10^{-7}$ M (e.g., at least $1\times10^{-1}$ M, at least $1\times10^{-9}$ M, at least $1\times10^{-10}$ M, at least $1\times10^{-11}$ M, or at least $1\times10^{-12}$ M). As described herein, various TGFβ antagonists that inhibit betaglycan can be used in accordance with the methods and uses described herein including, for example, ligand traps (e.g., TβRII polypeptides and variants thereof), antibodies, small molecules, nucleotide sequences, and combinations thereof. In certain embodiments, a TGFβ antagonist, or combination of antagonists, that inhibits betaglycan may further inhibit one or more of TGFβ1, TGFβ2, TGFβ3, TβRII, and ALK5. In some embodiments, a TGFβ antagonist, or combination of antagonists, that inhibits betaglycan does not inhibit or does not substantially inhibit TGFβ2.

In certain aspects, the disclosure provides TβRII polypeptides and the use of such TβRII polypeptides as selective antagonists for TGFβ1 and/or TGFβ3. As described herein, polypeptides comprising part or all of the TβRII extracellular domain (ECD), with or without additional mutations, bind to and/or inhibit TGFβ1 and/or TGFβ3 with varying affinities. Thus, in certain aspects, the disclosure provides TβRII polypeptides for use in selectively inhibiting TGFβ superfamily associated disorders.

In part, the disclosure provides TβRII polypeptide fusion proteins and the use of such fusion proteins as selective antagonists for TGFβ1 or TGFβ3. As described herein, polypeptides comprising part or all of the TβRII extracellular domain (ECD), with or without additional mutations, bind to and/or inhibit TGFβ1 or TGFβ3 with varying affinities. In particular, TβRII polypeptides comprising a heterologous portion (e.g., an Fc immunoglobulin domain) and a linker of at least 10 amino acids in length (e.g., a linker having the amino acid sequence of SEQ ID NO: 6) are associated with surprisingly superior TGFβ1 and TGFβ3 binding properties as compared to TβRII polypeptides having a shorter linker. Thus, in certain aspects, the disclosure provides TβRII polypeptides for use in selectively inhibiting TGFβ superfamily associated disorders.

In some embodiments, the disclosure provides for a Transforming Growth Factor-β Receptor II (TβRII) fusion polypeptide comprising: a) an extracellular domain of a TβRII portion; b) a heterologous portion, and c) a linker portion; wherein the linker is at least 10 amino acids in length; and wherein the TβRII extracellular domain portion comprises an amino acid sequence at least 80% identical to: i) a sequence beginning at any of positions 23 to 35 of SEQ ID NO: 1 and ending at any of positions 153 to 159 of SEQ ID NO: 1 or ii) a sequence beginning at any of positions 23 to 60 of SEQ ID NO: 2 and ending at any of positions 178 to 184 of SEQ ID NO: 2. In some embodiments, the TβRII extracellular domain portion comprises an amino acid sequence at least 80% identical to a sequence beginning at any of positions 23 to 35 of SEQ ID NO: 1 and ending at any of positions 153 to 159 of SEQ ID NO: 1. In some embodiments, the TβRII extracellular domain portion comprises an amino acid sequence at least 90% identical to a sequence beginning at any of positions 23 to 35 of SEQ ID NO: 1 and ending at any of positions 153 to 159 of SEQ ID NO: 1. In some embodiments, the TβRII extracellular domain portion comprises an amino acid sequence at least 95% identical to a sequence beginning at any of positions 23 to 35 of SEQ ID NO: 1 and ending at any of positions 153 to 159 of SEQ ID NO: 1. In some embodiments, the TβRII extracellular domain portion comprises an amino acid sequence at least 97% identical to a sequence beginning at any of positions 23 to 35 of SEQ ID NO: 1 and ending at any of positions 153 to 159 of SEQ ID NO: 1. In some embodiments, the TβRII extracellular domain portion comprises an amino acid sequence beginning at any of positions 23 to 35 of SEQ ID NO: 1 and ending at any of positions 153 to 159 of SEQ ID NO: 1. In some embodiments, the TβRII extracellular domain portion comprises an amino acid sequence at least 80% identical to a sequence beginning at any of positions 23 to 60 of SEQ ID NO: 2 and ending at any of positions 178 to 184 of SEQ ID NO: 2. In some embodiments, the TβRII extracellular domain portion comprises an amino acid sequence at least 90% identical to a sequence beginning at any of positions 23 to 60 of SEQ ID NO: 2 and ending at any of positions 178 to 184 of SEQ ID NO: 2. In some embodiments, the TβRII extracellular domain portion comprises an amino acid sequence at least 95% identical to a sequence beginning at any of positions 23 to 60 of SEQ ID NO: 2 and ending at any of positions 178 to 184 of SEQ ID NO: 2. In some embodiments, the TβRII extracellular domain portion comprises an amino acid sequence at least 97% identical to a sequence beginning at any of positions 23 to 60 of SEQ ID NO: 2 and ending at any of positions 178 to 184 of SEQ ID NO: 2. In some embodiments, the TβRII extracellular domain portion comprises an amino acid sequence beginning at any of positions 23 to 60 of SEQ ID NO: 2 and ending at any of positions 178 to 184 of SEQ ID NO: 2. In some embodiments, the TβRII extracellular domain portion comprises an amino acid sequence at least 80% identical to SEQ ID NO: 18. In some embodiments, the TβRII extracellular domain portion comprises an amino acid sequence at least 90% identical to SEQ ID NO: 18. In some embodiments, the TβRII extracellular domain portion comprises an amino acid sequence at least 95% identical to SEQ ID NO: 18. In some embodiments, the TβRII extracellular domain portion comprises an amino acid sequence at least 97% identical to SEQ ID NO: 18. In some embodiments, the TβRII extracellular domain portion comprises the amino acid sequence of SEQ ID NO: 18. In some embodiments, the TβRII extracellular domain portion consists of an amino acid sequence at least 80% identical to a sequence beginning at any of positions 23 to 35 of SEQ ID NO: 1 and ending at any of positions 153 to 159 of SEQ ID NO: 1. In some embodiments, the TβRII extracellular domain portion consists of an amino acid sequence at least 90% identical to a sequence beginning at any of positions 23 to 35 of SEQ ID NO: 1 and ending at any of positions 153 to 159 of SEQ ID NO: 1. In some embodiments, the TβRII extracellular domain portion consists of an amino acid sequence at least 95% identical to a sequence beginning at any of positions 23 to 35 of SEQ ID NO: 1 and ending at any of positions 153 to 159 of SEQ ID NO: 1. In some embodiments, the TβRII extracellular domain portion consists of an amino acid sequence at least 97% identical to a sequence beginning at any of positions 23 to 35 of SEQ ID NO: 1 and ending at any of positions 153 to 159 of SEQ ID NO: 1. In some embodiments, the TβRII extracellular domain portion consists of an amino acid sequence beginning at any of positions 23 to 35 of SEQ ID NO: 1 and ending at any of positions 153 to 159 of SEQ ID NO: 1. In some embodiments, the TβRII extracellular domain portion consists of an amino acid sequence at least 80% identical to a sequence beginning at any of positions 23 to 60 of SEQ ID NO: 2 and ending at any of positions 178 to 184 of SEQ ID NO: 2. In some embodiments, the TβRII extracellular domain portion consists of an amino acid sequence at least 90% identical to a sequence beginning at any of positions 23 to 60 of SEQ ID NO: 2 and ending at any of positions 178 to 184 of SEQ ID NO: 2. In some embodiments, the TβRII extracellular domain portion consists of an amino acid sequence at least 95% identical to a sequence beginning at any of positions 23 to 60 of SEQ ID NO: 2 and ending at any of positions 178 to 184 of SEQ ID NO: 2. In some embodiments, the TβRII extracellular domain portion consists of an amino acid sequence at least 97% identical to a sequence beginning at any of positions 23 to 60 of SEQ ID NO: 2 and ending at any of positions 178 to 184 of SEQ ID NO: 2. In some embodiments, the TβRII extracellular domain portion consists of an amino acid sequence beginning at any of positions 23 to 60 of SEQ ID NO: 2 and ending at any of positions 178 to 184 of SEQ ID NO: 2. In some embodiments, the TβRII extracellular domain portion consists of an amino acid sequence at least 80% identical to SEQ ID NO: 18. In some embodiments, the TβRII extracellular domain portion consists of an amino acid sequence at least 90% identical to SEQ ID NO: 18. In some embodiments, the TβRII extracellular domain portion consists of an amino acid sequence at least 95% identical to SEQ ID NO: 18. In some embodiments, the TβRII extracellular domain portion consists of an amino acid sequence at least 97% identical to SEQ ID NO: 18. In some embodiments, the TβRII extracellular domain portion consists of the amino acid sequence of SEQ ID NO: 18. In some embodiments, the polypeptide comprises an N-terminal leader sequence. In some embodiments, the N-terminal leader sequence comprises the amino acid sequence of any one of SEQ ID NOs: 22-24. In some embodiments, the N-terminal leader sequence comprises the amino acid sequence of SEQ ID NO: 23. In some embodiments, the heterologous portion is an immunoglobulin Fc domain. In some embodiments, the immunoglobulin Fc domain is a human immunoglobulin Fc domain. In some embodiments, the heterologous portion comprises an amino acid sequence that is at least 80% identical to SEQ ID NO: 49. In some embodiments, the heterologous portion comprises an amino acid sequence that is at least 90% identical to SEQ ID NO: 49. In some embodiments, the heterologous portion comprises an amino acid sequence that is at least 95% identical to SEQ ID NO: 49. In some embodiments, the heterologous portion comprises an amino acid sequence that is at least 97% identical to SEQ ID NO: 49. In some embodiments, the heterologous portion comprises the amino acid sequence of SEQ ID NO: 49. In some embodiments, the linker is less than 25 amino acids in length. In some embodiments, the linker is between 10 and 25 amino acids in length. In some embodiments, the linker is between 15 and 25 amino acids in length. In some embodiments, the linker is between 17 and 22 amino acids in length. In some embodiments, the linker is 21 amino acids in length. In some embodiments, the linker comprises (GGGGS)n, wherein n=≥2. In some embodiments, the linker comprises (GGGGS)n, wherein n=≥3. In some embodiments, the linker comprises (GGGGS)n, wherein n=≥4. In some embodiments, the linker comprises (GGGGS)$_n$, wherein n≠≥5. In some embodiments, the linker comprises the amino acid sequence of SEQ ID NO: 21. In some embodiments, the linker comprises the amino acid sequence of any one of SEQ ID NOs: 4-7. In some embodiments, the linker comprises the amino acid sequence of SEQ ID NO: 6. In some embodiments, the polypeptide comprises an amino acid sequence that is at least 80% identical to the amino acid sequence of SEQ ID NO: 11. In some embodiments, the polypeptide comprises an amino acid sequence that is at least 90% identical to the amino acid sequence of SEQ ID NO: 11. In some embodiments, the polypeptide comprises an amino acid sequence that is at least 95% identical to the amino acid sequence of SEQ ID NO: 11. In some embodiments, the polypeptide comprises the amino acid sequence of SEQ ID NO: 11. In some embodiments, the polypeptide comprises an amino acid sequence that is at least 80% identical to the amino acid sequence of SEQ ID NO: 13. In some embodiments, the polypeptide comprises an amino acid sequence that is at least 90% identical to the amino acid sequence of SEQ ID NO: 13. In some embodiments, the polypeptide comprises an amino acid sequence that is at least 95% identical to the amino acid sequence of SEQ ID NO: 13. In some embodiments, the polypeptide comprises the amino acid sequence of SEQ ID NO: 13. In some embodiments, the polypeptide comprises an amino acid sequence that is at least 80% identical to the amino acid sequence of SEQ ID NO: 63. In some embodiments, the polypeptide comprises an amino acid sequence that is at least 90% identical to the amino acid sequence of SEQ ID NO: 63. In some embodiments, the polypeptide comprises an amino acid sequence that is at least 95% identical to the amino acid sequence of SEQ ID NO: 63. In some embodiments, the polypeptide comprises the amino acid sequence of SEQ ID NO: 63. In some embodiments, the polypeptide comprises an amino acid sequence that is at least 80% identical to the amino acid sequence of SEQ ID NO: 48. In some embodiments, the polypeptide comprises an amino acid sequence that is at least 90% identical to the amino acid sequence of SEQ ID NO: 48. In some embodiments, the polypeptide comprises an amino acid sequence that is at least 95% identical to the amino acid sequence of SEQ ID NO: 48. In some embodiments, the polypeptide comprises the amino acid sequence of SEQ ID NO: 48. In some embodiments, the polypeptide comprises an amino acid sequence that is at least 80% identical to the amino acid sequence of SEQ ID NO: 65. In some embodiments, the polypeptide comprises an amino acid sequence that is at least 90% identical to the amino acid sequence of SEQ ID NO: 65. In some embodiments, the polypeptide comprises an amino acid sequence that is at least 95% identical to the amino acid sequence of SEQ ID NO: 65. In some embodiments, the polypeptide comprises the amino acid sequence of SEQ ID NO: 65. In some embodiments, the polypeptide comprises an amino acid sequence that is at least 80% identical to the amino acid sequence of SEQ ID NO: 68. In some embodiments, the polypeptide comprises an amino acid sequence that is at least 90% identical to the amino acid sequence of SEQ ID NO: 68. In some embodiments, the polypeptide comprises an amino acid sequence that is at least 95% identical to the amino acid sequence of SEQ ID NO: 68. In some embodiments, the polypeptide comprises the amino acid sequence of SEQ ID NO: 68. In some embodiments, the polypeptide comprises an amino acid sequence that is at least 80% identical to the amino acid sequence of SEQ ID NO: 15. In some embodiments, the polypeptide comprises an amino acid sequence that is at least 90% identical to the amino acid sequence of SEQ ID NO: 15. In some embodiments, the polypeptide comprises an amino acid sequence that is at least 95% identical to the amino acid sequence of SEQ ID NO: 15. In some embodiments, the polypeptide comprises the amino acid sequence of SEQ ID NO: 15. In some embodiments, the TβRII polypeptide does not include amino acids 185-592 of SEQ ID NO: 2. In some embodiments, the TβRII polypeptide does not include amino acids 1-22 of SEQ ID NO: 2. In some embodiments, the polypeptide consists of or consists essentially of: a) a TβRII polypeptide portion comprising an amino acid sequence that is at least 85%, 90%, 95%, 97%, or 99% identical to the amino acid sequence of SEQ ID NO: 18 and no more than 10, 9, 8, 7, 6, 5, 4, 3, 2 or 1 additional amino acids; b) a linker portion comprising an amino acid sequence that is at least 85%, 90%, 95%, 97%, or 99% identical to the amino acid sequence of SEQ ID NO: 6 and no more than 5, 4, 3, 2 or 1 additional amino acids; c) a heterologous portion comprising an amino acid sequence that is at least 85%, 90%, 95%, 97%, or 99% identical to the amino acid sequence of SEQ ID NO: 49 and no more than 25, 20, 15, 10, 5, 4, 3, 2, or 1 additional amino acids; and d) optionally a leader sequence (e.g., SEQ ID NO: 23). In some embodiments, the polypeptide consists of or consists essentially of: a) a TβRII polypeptide portion comprising the amino acid sequence of SEQ ID NO: 18 and no more than 10, 9, 8, 7, 6, 5, 4, 3, 2 or 1 additional amino acids; b) a linker portion comprising the amino acid sequence of SEQ ID NO: 6 and no more than 5, 4, 3, 2 or 1 additional amino acids; c) a heterologous portion comprising the amino acid sequence of SEQ ID NO: 49 and no more than 25, 20, 15, 10, 5, 4, 3, 2, or 1 additional amino acids; and d) optionally a leader sequence (e.g., SEQ ID NO: 23). In some embodiments, the polypeptide comprises: a) an extracellular domain of a TβRII portion; wherein the extracellular domain comprises an amino acid sequence that is at least 85%, 90%, 95%, 97%, or 99% identical to the sequence of SEQ ID NO: 18; b) a heterologous portion, wherein the heterologous portion comprises an amino acid sequence that is at least 85%, 90%, 95%, 97%, or 99% identical to the sequence of SEQ ID NO: 49; and c) a linker portion connecting the extracellular domain and the heterologous portion; wherein the linker comprises an amino acid sequence that is at least 85%, 90%, 95%, 97%, or 99% identical to the amino acid sequence of SEQ ID NO: 6. In some embodiments, the polypeptide comprises: a) an extracellular domain of a TβRII portion; wherein the extracellular domain comprises the amino acid sequence of SEQ ID NO: 18; b) a heterologous portion, wherein the heterologous portion comprises the amino acid sequence of SEQ ID NO: 49; and c) a linker portion connecting the extracellular domain and the heterologous portion; wherein the linker comprises the amino acid sequence of SEQ ID NO: 6. In some embodiments, the polypeptide comprises an amino acid sequence that is at least 85%, 90%, 95%, 97%, or 99% identical to the amino acid sequence of SEQ ID NO: 48. In some embodiments, the polypeptide comprises the amino acid sequence of SEQ ID NO: 48. In some embodiments, the polypeptide does not include a leader sequence, or wherein the leader sequence has been removed. In some embodiments, the polypeptide includes one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent. In some embodiments, the polypeptide is glycosylated. In some embodiments, the polypeptide has a glycosylation pattern characteristic of expression of the polypeptide in CHO cells. In some embodiments, the polypeptide binds human TGFβ1 with an equilibrium dissociation constant ($K_D$) less than 100 pM. In some embodiments, the polypeptide binds human TGFβ1 with an equilibrium dissociation constant ($K_D$) less than 75 pM. In some embodiments, the polypeptide binds human TGFβ3 with an equilibrium dissociation constant ($K_D$) less than 60 pM. In some embodiments, the polypeptide binds human TGFβ3 with an equilibrium dissociation constant ($K_D$) less than 50 pM. In some embodiments, the polypeptide inhibits TGFβ1 with an IC50 of less than 1.0 nM, as determined using a reporter gene assay. In some embodiments, the polypeptide inhibits TGFβ1 with an IC50 of less than 0.25 nM, as determined using a reporter gene assay. In some embodiments, the polypeptide inhibits TGFβ1 with an IC50 of less than 0.1 nM, as determined using a reporter gene assay. In some embodiments, the polypeptide inhibits TGFβ1 with an IC50 of less than 0.05 nM, as determined using a reporter gene assay. In some embodiments, the polypeptide inhibits TGFβ3 with an IC50 of less than 0.3 nM, as determined using a reporter gene assay. In some embodiments, the polypeptide inhibits TGFβ3 with an IC50 of less than 0.1 nM, as determined using a reporter gene assay. In some embodiments, the polypeptide inhibits TGFβ3 with an IC50 of less than 0.05 nM, as determined using a reporter gene assay. In some embodiments, the polypeptide inhibits TGFβ3 with an IC50 of less than 0.04 nM, as determined using a reporter gene assay. In some embodiments, the reporter gene assay is a CAGA reporter assay.

In some embodiments, the disclosure provides for a homodimer comprising any two of the polypeptides disclosed herein.

In some embodiments, the disclosure provides for an isolated polynucleotide comprising a coding sequence for any of the polypeptides disclosed herein. In some embodiments, the disclosure provides for a recombinant polynucleotide comprising a promoter sequence operably linked to any of the polynucleotides disclosed herein. In some embodiments, the polynucleotide comprises a nucleotide sequence that is at least 80%, 85%, 90%, 95%, 97% or 100% identical to any one of SEQ ID NOs: 10, 12, 14, 46 or 47.

In some embodiments, the disclosure provides for a cell transformed with any of the polynucleotides disclosed herein. In some embodiments, cell is a mammalian cell. In some embodiments, the cell is a CHO cell or a human cell.

In some embodiments, the disclosure provides for a pharmaceutical preparation comprising pharmaceutically acceptable excipient and any of the polypeptides disclosed herein or any of the homodimers disclosed herein.

In certain aspects, a TGFβ antagonist is an antibody, or combination of antibodies. In certain aspects, the antibody binds to at least TβRII. In some embodiments a TGFβ antagonist antibody that binds to TβRII inhibits TβRII signaling, optionally as measured in a cell-based assay such as those described herein. In some embodiments, a TGFβ antagonist antibody that binds to TβRII inhibits one or more TGF-beta superfamily ligands, TGFβ superfamily type I receptors, or TGFβ superfamily co-receptors from binding to TβRII. In some embodiments, a TGFβ antagonist antibody that binds to TβRII inhibits one or more TGF-beta superfamily ligands from binding to TβRII selected from the group consisting of: TGFβ1, TGFβ2, and TGFβ3. In certain aspects, the antibody binds to at least ALK5. In some embodiments a TGFβ antagonist antibody that binds to ALK5 inhibits ALK5 signaling, optionally as measured in a cell-based assay such as those described herein. In some embodiments, a TGFβ antagonist antibody that binds to ALK5 inhibits one or more TGF-beta superfamily ligands, TGFβ superfamily type II receptors, or TGFβ superfamily co-receptors from binding to ALK5. In some embodiments a TGFβ antagonist antibody that binds to ALK5 inhibits one or more TGF-beta superfamily ligands from binding to ALK5 selected from the group consisting of: TGFβ1, TGFβ2, and TGFβ3. In certain aspects, the antibody binds to at least betaglycan. In some embodiments a TGFβ antagonist antibody that binds to betaglycan inhibits betaglycan signaling, optionally as measured in a cell-based assay such as those described herein. In some embodiments, a TGFβ antagonist antibody that binds to betaglycan inhibits one or more TGF-beta superfamily ligands, TGFβ superfamily type I receptors, or TGFβ superfamily type II receptors from binding to betaglycan. In some embodiments a TGFβ antagonist antibody that binds to betaglycan inhibits one or more TGF-beta superfamily ligands from binding to betaglycan selected from the group consisting of: TGFβ1, TGFβ2, and TGFβ3. In certain aspects, a TGFβ antagonist antibody binds to at least TGFβ1. In some embodiments, a TGFβ antagonist antibody that binds to TGFβ1 inhibits TβRII signaling, optionally as measured in a cell-based assay such as those described herein. In some embodiments, a TGFβ antagonist antibody that binds to TGFβ1 inhibits TGFβ1-TβRII, TGFβ1-ALK5, and/or TGFβ1-betaglycan binding. In certain aspects, a TGFβ antagonist antibody binds to at least TGFβ2. In some embodiments, a TGFβ antagonist antibody that binds to TGFβ2 inhibits TβRII signaling, optionally as measured in a cell-based assay such as those described herein. In some embodiments, a TGFβ antagonist antibody that binds to TGFβ2 inhibits TGFβ2-TβRII, TGFβ1-ALK5, and/or TGFβ1-betaglycan binding. In certain embodiments, a TGFβ antagonist antibody binds to at least TGFβ3. In some embodiments, a TGFβ antagonist antibody that binds to TGFβ3 inhibits TβRII signaling, optionally as measured in a cell-based assay such as those described herein. In some embodiments, a TGFβ antagonist antibody that binds to TGFβ3 inhibits TGFβ3-TβRII, TGFβ1-ALK5, and/or TGFβ1-betaglycan binding. In some embodiments, a TGFβ antagonist antibody is a multispecific antibody, or a combination of multispecific antibodies, inhibits signaling in a cell-based assay of one or more of: TGFβ1, TGFβ2, TGFβ3, TβRII, ALK5, and betaglycan. In some embodiments, antibody is a chimeric antibody, a humanized antibody, or a human antibody. In some embodiments, the antibody is a single-chain antibody, an F(ab')2 fragment, a single-chain diabody, a tandem single-chain Fv fragment, a tandem single-chain diabody, or a fusion protein comprising a single-chain diabody and at least a portion of an immunoglobulin heavy-chain constant region.

In certain aspects, a TGFβ antagonist is a small molecule inhibitor or combination of small molecule inhibitors. In some embodiments, a TGFβ antagonist small molecule inhibitor is an inhibitor of at least TβRII. In some embodiments, a TGFβ antagonist small molecule inhibitor is an inhibitor of at least ALK5. In some embodiments, a TGFβ antagonist small molecule inhibitor is an inhibitor of at least betaglycan. In some embodiments, a TGFβ antagonist small molecule inhibitor is an inhibitor of at least TGFβ1. In some embodiments, a TGFβ antagonist small molecule inhibitor is an inhibitor of at least TGFβ2. In some embodiments, a TGFβ antagonist small molecule inhibitor is an inhibitor of at least TGFβ3.

In certain aspects, a TGFβ antagonist is a nucleic acid inhibitor or combination of nucleic acid inhibitors. In some embodiments, a TGFβ antagonist nucleic acid inhibitor is an inhibitor of at least TβRII. In some embodiments, a TGFβ antagonist nucleic acid inhibitor is an inhibitor of at least ALK5. In some embodiments, a TGFβ antagonist nucleic acid inhibitor is an inhibitor of at least betaglycan. In some embodiments, a TGFβ antagonist nucleic acid inhibitor is an inhibitor of at least TGFβ1. In some embodiments, a TGFβ antagonist nucleic acid inhibitor is an inhibitor of at least TGFβ2. In some embodiments, a TGFβ antagonist nucleic acid inhibitor is an inhibitor of at least TGFβ3.

BRIEF DESCRIPTION OF THE DRAWINGS

FIG. 1 shows the amino acid sequence of native precursor for the B (short) isoform of human TGFβ receptor type II (hTβRII) (NP_003233.4). Solid underline indicates the mature extracellular domain (ECD) (residues 23-159), and double underline indicates valine that is replaced in the A (long) isoform. Dotted underline denotes leader (residues 1-22).

FIG. 2 shows the amino acid sequence of native precursor for the A (long) isoform of human TβRII (NP_001020018.1). Solid underline indicates the mature ECD (residues 23-184), and double underline indicates the splice-generated isoleucine substitution. Dotted underline denotes leader (residues 1-22).

FIGS. 4A and 4B show in tabular form the binding affinity between TGFβ1 and TGFβ3 and one of several different TβRII-Fc fusion protein constructs.

FIGS. 5E and 5F provide $IC_{50}$ data from these same experiments in tabular form.

FIGS. 6A, 6B, and 6C show the effects of mTβRII-mFc in an in vitro inflammation model as well as an animal model of heterotopic ossification. FIG. 6A shows that mTβRII-mFc can abrogate TGFβ1 secretion by regenerative M2 macrophages in an inflammatory environment in vitro. FIG. 6B shows that treatment with mTβRII-mFc decreases osseous deposition and marrow space formation in an animal model of traumatic heterotopic ossification. FIG. 6C shows that treatment with mTβRII-mFc significantly decreases the volume of mature HO in an animal model of traumatic heterotopic ossification.

FIG. 7 shows multiple sequence alignment of Fc domains from human IgG isotypes using Clustal 2.1. Hinge regions are indicated by dotted underline. Double underline indicates examples of positions engineered in IgG1 Fc to promote asymmetric chain pairing and the corresponding positions with respect to other isotypes IgG2, IgG3 and IgG4.

DETAILED DESCRIPTION OF THE INVENTION

1. Overview

Figure 3:
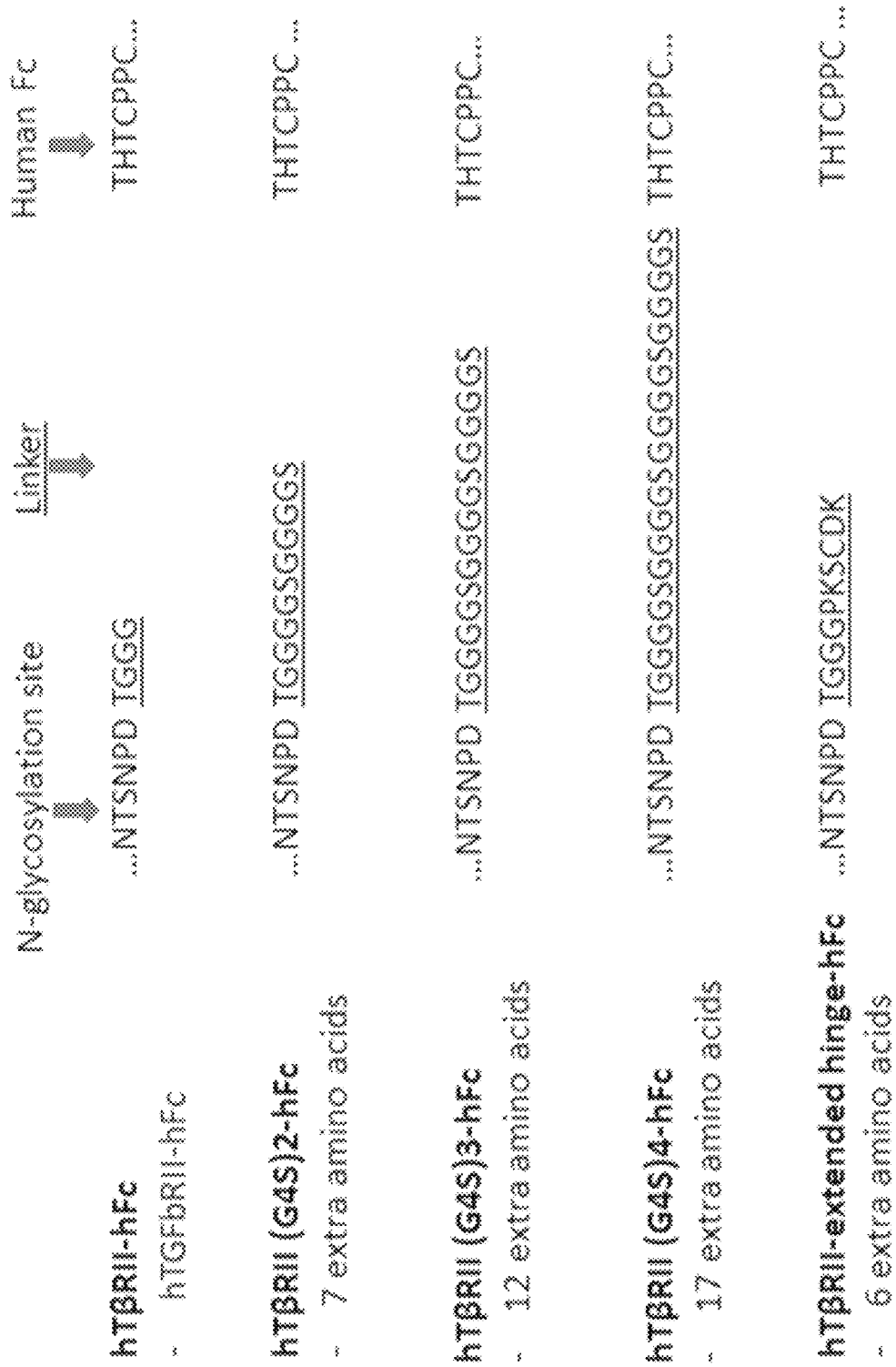
FIG. 3 shows a comparison of the linker sequences of five different TβRII constructs.

Proteins described herein are the human forms, unless otherwise specified. NCBI references for the proteins are as follows: human TβRII isoform A (hTβRI$_{long}$), NP_001020018.1 and human TβRII isoform B (hTβRII$_{short}$), (NP_003233.4). Sequences of native TβRII proteins from human are set forth in FIGS. 1 and 2. In some embodiments, the TβRII proteins are from non-human animals, such as a mouse, rat, cow or monkey.

The TGFβ superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. By manipulating the activity of a member of the TGFβ family, it is often possible to cause significant physiological changes in an organism. For example, the Piedmontese and Belgian Blue cattle breeds carry a loss-of-function mutation in the GDF8 (also called myostatin) gene that causes a marked increase in muscle mass. Grobet et al., Nat Genet. 1997, 17(1):71-4. Similarly, in humans, inactive alleles of GDF8 are associated with increased muscle mass and, reportedly, exceptional strength. Schuelke et al., N Engl J Med 2004, 350: 2682-8.

TGFβ signals are mediated by heteromeric complexes of type I (e.g. TβRI) and type II (e.g. TβRII) serine/threonine kinase receptors, which phosphorylate and activate downstream SMAD proteins upon ligand stimulation (Massague, 2000, Nat. Rev. Mol. Cell Biol. 1:169-178). These type I and type II receptors are transmembrane proteins, composed of a ligand-binding extracellular domain with cysteine-rich region, a transmembrane domain, and a cytoplasmic domain with predicted serine/threonine specificity. Type I receptors are essential for signaling; and type II receptors are required for binding ligands and for expression of type I receptors. Type I and II receptors form a stable complex after ligand binding, resulting in phosphorylation of type I receptors by type II receptors. TGFβ has three mammalian isoforms, TGFβ1, TGFβ2 and TGFβ3, each with distinct functions in vivo. The binding of TGFβs to TβRII is a crucial step in initiating activation of the TGFβ signaling pathway, leading to phosphorylation of SMAD2, and translocation of the activated SMAD2/SMAD4 complex to the nucleus to modulate gene expression.

Thus, in certain aspects, the disclosure provides TβRII polypeptides as antagonists of TGFβ1 or TGFβ3 for use in treating various TGFβ1- or TGFβ3-associated disorders. While not wishing to be bound to any particular mechanism of action, it is expected that such polypeptides act by binding to TGFβ1 or TGFβ3 and inhibiting the ability of these ligands to form ternary signaling complexes.

The disclosure provides for fusion proteins comprising TβRII polypeptides and a heterologous portion (e.g., an Fc portion). In particular embodiments, the TβRII portion and the heterologous portion are fused by means of a linker. As described in greater detail below, the disclosure demonstrates that TβRII-Fc fusion proteins comprising linkers of certain lengths (e.g., a linker having 21 amino acids) were surprisingly able to bind TGFβ-1 and TGFβ-3 with stronger affinity than TβRII-Fc fusion proteins having a linker of only four amino acids.

As demonstrated herein, a soluble TβRII polypeptide, which binds to TGFβ1 and TGFβ3, is effective at substantially attenuating development of heterotopic ossification (HO) anlagen with decreased osseous deposition and marrow space formation in a mouse model of HO. Furthermore, treatment with the TβRII polypeptide significantly reduced the volume of mature HO in this animal model. While not wishing to be bound to any particular mechanism, it is expected that the effects of TβRII polypeptides are caused primarily by TGFβ signaling antagonist effect, particularly of TGFβ1 and/or TGFβ3. Regardless of the mechanism, it is apparent from the data presented herein the TGFβ signaling antagonists do reduce the severity of osseous deposition in HO. It should be noted that heterotopic ossification is dynamic, which changes depending on a balance of factors that increase HO and factors that decrease HO. HO can be decreased by increasing factors that reduce HO; decreasing factors that increase HO; or both. Therefore, the term decreasing (reducing) HO refers to the observable physical changes in osseous deposition and are intended to be neutral as to the mechanisms by which the changes occur.

The animal model for HO that was used in the studies descried herein are considered to be predicative of efficacy in humans, and therefore, this disclosure provides methods for using TGFβ signaling antagonist to treat HO particularly preventing or reducing the severity or duration of one or more complications of HO, in humans. As disclosed herein, the term TGFβ antagonist refers a variety of agents that may be used to antagonize TGFβ signaling including, for example, antagonists that inhibit one or more TGFβ ligands [e.g., TGFβ1, TGFβ2, and/or TGFβ3]; antagonists that inhibit one or more TGFβ-interacting type I-, type II-, or co-receptor (e.g., TβRII, ALK5 and betaglycan); and antagonists that inhibit one or more downstream signaling components (e.g., Smad proteins such as Smads 2 and 3). TGFβ antagonists to be used in accordance with the methods and uses of the disclosure include a variety of forms, for example, ligand traps (e.g., soluble TβRII polypeptides and betaglycan polypeptides), antibody antagonists (e.g., antibodies that inhibit one or more of TGFβ1, TGFβ2, TGFβ3, TβRII, and betaglycan), small molecule antagonists [e.g., small molecules that inhibit one or more of TGFβ1, TGFβ2, TGFβ3, TβRII, betaglycan, and one or more Smad proteins (e.g., Smads 2 and 3)], and nucleotide antagonists [e.g., nucleotide sequences that inhibit one or more of TGFβ1, TGFβ2, TGFβ3, TβRII, betaglycan, and one or more Smad proteins (e.g., Smads 2 and 3)].

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions. The term "sequence similarity," in all its grammatical forms, refers to the degree of identity or correspondence between nucleic acid or amino acid sequences that may or may not share a common evolutionary origin. However, in common usage and in the instant application, the term "homologous," when modified with an adverb such as "highly," may refer to sequence similarity and may or may not relate to a common evolutionary origin.

"Percent (%) sequence identity" or "percent (%) identical" with respect to a reference polypeptide (or nucleotide) sequence is defined as the percentage of amino acid residues (or nucleic acids) in a candidate sequence that are identical to the amino acid residues (or nucleic acids) in the reference polypeptide (nucleotide) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid (nucleic acid) sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

"Agonize", in all its grammatical forms, refers to the process of activating a protein and/or gene (e.g., by activating or amplifying that protein's gene expression or by inducing an inactive protein to enter an active state) or increasing a protein's and/or gene's activity.

"Antagonize", in all its grammatical forms, refers to the process of inhibiting a protein and/or gene (e.g., by inhibiting or decreasing that protein's gene expression or by inducing an active protein to enter an inactive state) or decreasing a protein's and/or gene's activity.

The terms "about" and "approximately" as used in connection with a numerical value throughout the specification and the claims denotes an interval of accuracy, familiar and acceptable to a person skilled in the art.

Numeric ranges disclosed herein are inclusive of the numbers defining the ranges.

The terms "a" and "an" include plural referents unless the context in which the term is used clearly dictates otherwise. The terms "a" (or "an"), as well as the terms "one or more," and "at least one" can be used interchangeably herein. Furthermore, "and/or" where used herein is to be taken as specific disclosure of each of the two or more specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Throughout this specification, the word "comprise" or variations such as "comprises" or "comprising" will be understood to imply the inclusion of a stated integer or groups of integers but not the exclusion of any other integer or group of integers. As used herein, the term "comprises" also encompasses the use of the narrower terms "consisting" and "consisting essentially of."

The term "consisting essentially of" is limited to the specified materials or steps and those that do not materially affect the basic and novel characteristics of the invention(s) disclosed herein.

The term "appreciable affinity" as used herein means binding with a dissociation constant ($K_D$) of less than 50 nM.

The terms "polypeptide", "oligopeptide", "peptide" and "protein" are used interchangeably herein to refer to chains of amino acids of any length. The chain may be linear or branched, it may comprise modified amino acids, and/or may be interrupted by non-amino acids. The terms also encompass an amino acid chain that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that the polypeptides can occur as single chains or associated chains.

2. TGFβ Antagonists

As disclosed herein, the term TGFβ antagonist refers a variety of agents that may be used to antagonize TGFβ-mediated signaling including, for example, antagonists that inhibit one or more TGFβ ligands [e.g., TGFβ1, TGFβ2, and/or TGFβ3]; antagonists that inhibit one or more TGFβ-interacting type I-, type II-, or co-receptor (e.g., TβRII, ALK5 and betaglycan); and antagonists that inhibit one or more downstream signaling components (e.g., Smad proteins such as Smads 2 and 3). TGFβ antagonists to be used in accordance with the methods and uses of the disclosure include a variety of forms, for example, ligand traps (e.g., soluble TβRII polypeptides and betaglycan polypeptides), antibody antagonists (e.g., antibodies that inhibit one or more of TGFβ1, TGFβ2, TGFβ3, TβRII, and betaglycan), small molecule antagonists [e.g., small molecules that inhibit one or more of TGFβ1, TGFβ2, TGFβ3, TβRII, betaglycan, and one or more Smad proteins (e.g., Smads 2 and 3)], and nucleotide antagonists [e.g., nucleotide sequences that inhibit one or more of TGFβ1, TGFβ2, TGFβ3, TβRII, betaglycan, and one or more Smad proteins (e.g., Smads 2 and 3)].

A. TβRII and Betaglycan Polypeptides

Naturally occurring TβRII proteins are transmembrane proteins, with a portion of the protein positioned outside the cell (the extracellular portion) and a portion of the protein positioned inside the cell (the intracellular portion). Aspects of the present disclosure encompass variant TβRII polypeptides comprising mutations within the extracellular domain and/or truncated portions of the extracellular domain of TβRII. As described above, human TβRII occurs naturally in at least two isoforms—A (long) and B (short)—generated by alternative splicing in the extracellular domain (ECD) (FIGS. 1 and 2 and SEQ ID NOS: 1 and 2). SEQ ID NO: 27, which corresponds to residues 23-159 of SEQ ID NO: 1, depicts the native full-length extracellular domain of the short isoform of TβRII. SEQ ID NO: 18, which corresponds to residues 23-184 of SEQ ID NO: 2, depicts the native full-length extracellular domain of the long isoform of TβRII. Unless noted otherwise, amino acid position numbering with regard to variants based on the TβRII short and long isoforms refers to the corresponding position in the native precursors, SEQ ID NO: 1 and SEQ ID NO: 2, respectively.

In certain embodiments, the disclosure provides variant TβRII polypeptides. A TβRII polypeptide of the disclosure may bind to and inhibit the function of a TGFβ superfamily member, such as but not limited to, TGFβ1 or TGFβ3. TβRII polypeptides may include a polypeptide consisting of, or comprising, an amino acid sequence at least 70% identical, and optionally at least 70%, 75%, 80%, 85%, 90%, 91%, 92%, 93%, 94%, 95%, 96%, 97%, 98%, 99%, or 100% identical to a truncated ECD domain of a naturally occurring TβRII polypeptide, whose C-terminus occurs at any of amino acids 153-159 of SEQ ID NO: 1. TβRII polypeptides may include a polypeptide consisting of, or comprising, an amino acid sequence at least 70% identical, and optionally at least 70%, 75%, 80%, 85%, 90%, 91%, 92%, 93%, 94%, 95%, 96%, 97%, 98%, 99%, or 100% identical to a truncated ECD domain of a naturally occurring TβRII polypeptide, whose C-terminus occurs at any of amino acids 178-184 of SEQ ID NO: 2. In particular embodiments, the TβRII polypeptides comprise an amino acid sequence at least 70% identical, and optionally at least 70%, 75%, 80%, 85%, 90%, 91%, 92%, 93%, 94%, 95%, 96%, 97%, 98%, 99%, or 100% identical to the amino acid sequence of SEQ ID NO: 18. Optionally, a TβRII polypeptide does not include more than 5 consecutive amino acids, or more than 10, 20, 30, 40, 50, 52, 60, 70, 80, 90, 100, 150 or 200 or more consecutive amino acids from a sequence consisting of amino acids 160-567 of SEQ ID NO: 1 or from a sequence consisting of amino acids 185-592 of SEQ ID NO: 2. In some embodiments, the TβRII polypeptide does not include amino acids 160-567 of SEQ ID NO: 1. In some embodiments, the TβRII polypeptide does not include amino acids 1-22 of SEQ ID NO: 1. In some embodiments, the TβRII polypeptide does not include amino acids 1-22 and 160-567 of SEQ ID NO: 1. In some embodiments, the TβRII polypeptide does not include amino acids 185-592 of SEQ ID NO: 2. In some embodiments, the TβRII polypeptide does not include amino acids 1-22 of SEQ ID NO: 2. In some embodiments, the TβRII polypeptide does not include amino acids 1-22 and 185-592 of SEQ ID NO: 2. The unprocessed TβRII polypeptide may either include or exclude any signal sequence, as well as any sequence N-terminal to the signal sequence. As elaborated herein, the N-terminus of the mature (processed) TβRII polypeptide may occur at any of amino acids 23-35 of SEQ ID NO: 1 or 23-60 of SEQ ID NO: 2. Examples of mature TβRII polypeptides include, but are not limited to, amino acids 23-159 of SEQ ID NO: 1 (set forth in SEQ ID NO: 27), amino acids 29-159 of SEQ ID NO: 1 (set forth in SEQ ID NO: 28), amino acids 35-159 of SEQ ID NO: 1 (set forth in SEQ ID NO: 29), amino acids 23-153 of SEQ ID NO: 1 (set forth in SEQ ID NO: 30), amino acids 29-153 of SEQ ID NO: 1 (set forth in SEQ ID NO: 31), amino acids 35-153 of SEQ ID NO: 1 (set forth in SEQ ID NO: 32), amino acids 23-184 of SEQ ID NO: 2 (set forth in SEQ ID NO: 18), amino acids 29-184 of SEQ ID NO: 2 (set forth in SEQ ID NO: 33), amino acids 60-184 of SEQ ID NO: 2 (set forth in SEQ ID NO: 29), amino acids 23-178 of SEQ ID NO: 2 (set forth in SEQ ID NO: 34), amino acids 29-178 of SEQ ID NO: 2 (set forth in SEQ ID NO: 35), and amino acids 60-178 of SEQ ID NO: 2 (set forth in SEQ ID NO: 32). It will be understood by one of skill in the art that corresponding variants based on the long isoform of TβRII will include nucleotide sequences encoding the 25-amino acid insertion along with a conservative Val-Ile substitution at the flanking position C-terminal to the insertion. The TβRII polypeptides accordingly may include isolated extracellular portions of TβRII polypeptides, including both the short and the long isoforms, variants thereof (including variants that comprise, for example, no more than 2, 3, 4, 5, 10, 15, 20, 25, 30, or 35 amino acid substitutions in the sequence corresponding to amino acids 23-159 of SEQ ID NO: 1 or amino acids 23-184 of SEQ ID NO: 2), fragments thereof, and fusion proteins comprising any of the foregoing, but in each case preferably any of the foregoing TβRII polypeptides will retain substantial affinity for at least one of, or both of, TGFβ1 or TGFβ3. Generally, a TβRII polypeptide will be designed to be soluble in aqueous solutions at biologically relevant temperatures, pH levels, and osmolarity.

In some embodiments, the variant TβRII polypeptides of the disclosure comprise one or more mutations in the extracellular domain that confer an altered ligand binding profile. A TβRII polypeptide may include one, two, five or more alterations in the amino acid sequence relative to the corresponding portion of a naturally occurring TβRII polypeptide. In some embodiments, the mutation results in a substitution, insertion, or deletion at the position corresponding to position 70 of SEQ ID NO: 1. In some embodiments, the mutation results in a substitution, insertion, or deletion at the position corresponding to position 110 of SEQ ID NO: 1. Examples include, but are not limited to, an N to D substitution or a D to K substitution in the positions corresponding to positions 70 and 110, respectively, of SEQ ID NO: 1. Examples of such variant TβRII polypeptides include, but are not limited to, the sequences set forth in SEQ ID NOs: 36-39. A TβRII polypeptide may comprise a polypeptide or portion thereof that is encoded by any one of SEQ ID NOs: 8, 10, 12, 14, 16, 46 or 47, or silent variants thereof or nucleic acids that hybridize to the complement thereof under stringent hybridization conditions. In particular embodiments, a TβRII polypeptide may comprise a polypeptide or portion thereof that is encoded by any one of SEQ ID NO: 12, or silent variants thereof or nucleic acids that hybridize to the complement thereof under stringent hybridization conditions.

In some embodiments, the variant TβRII polypeptides of the disclosure further comprise an insertion of 36 amino acids (SEQ ID NO: 41) between the pair of glutamate residues (positions 151 and 152 of SEQ ID NO: 1, or positions 176 and 177 of SEQ ID NO: 2) located near the C-terminus of the human TβRII ECD, as occurs naturally in the human TβRII isoform C (Konrad et al., BMC Genomics 8:318, 2007).

It has been demonstrated that TβRII polypeptides can be modified to selectively antagonize TβRII ligands. The N70 residue represents a potential glycosylation site. In some embodiments, the TβRII polypeptides are aglycosylated. In some embodiments, the TβRII polypeptides are aglycosylated or have reduced glycosylation at position Asn157. In some embodiments, the TβRII polypeptides are aglycosylated or have reduced glycosylation at position Asn73.

In certain embodiments, a TβRII polypeptide binds to TGFβ1, and the TβRII polypeptide does not show substantial binding to TGFβ3. In certain embodiments, a TβRII polypeptide binds to TGFβ3, and the TβRII polypeptide does not show substantial binding to TGFβ1. Binding may be assessed using purified proteins in solution or in a surface plasmon resonance system, such as a Biacore™ system.

In certain embodiments, a TβRII polypeptide inhibits TGFβ1 cellular signaling, and the TβRII polypeptide has an intermediate or limited inhibitory effect on TGFβ3 signaling. In certain embodiments, a TβRII polypeptide inhibits TGFβ3 cellular signaling, and the TβRII polypeptide has an intermediate or limited inhibitory effect on TGFβ1 signaling. Inhibitory effect on cell signaling can be assayed by methods known in the art.

Taken together, an active portion of a TβRII polypeptide may comprise amino acid sequences 23-153, 23-154, 23-155, 23-156, 23-157, or 23-158 of SEQ ID NO: 1, as well as variants of these sequences starting at any of amino acids 24-35 of SEQ ID NO: 1. Similarly, an active portion of a TβRII polypeptide may comprise amino acid sequences 23-178, 23-179, 23-180, 23-181, 23-182, or 23-183 of SEQ ID NO: 2, as well as variants of these sequences starting at any of amino acids 24-60 of SEQ ID NO: 2. Exemplary TβRII polypeptides comprise amino acid sequences 29-159, 35-159, 23-153, 29-153 and 35-153 of SEQ ID NO: 1 or amino acid sequences 29-184, 60-184, 23-178, 29-178 and 60-178 of SEQ ID NO: 2. Variants within these ranges are also contemplated, particularly those having at least 70%, 75%, 80%, 85%, 90%, 91%, 92%, 93%, 94%, 95%, 96%, 97%, 98%, or 99% identity to the corresponding portion of SEQ ID NO: 1 or SEQ ID NO: 2. A TβRII polypeptide may be selected that does not include the sequence consisting of amino acids 160-567 of SEQ ID NO: 1 or amino acids 185-592 of SEQ ID NO: 2. In particular embodiments, the TβRII polypeptides comprise an amino acid sequence at least 70% identical, and optionally at least 70%, 75%, 80%, 85%, 90%, 91%, 92%, 93%, 94%, 95%, 96%, 97%, 98%, 99%, or 100% identical to the amino acid sequence of SEQ ID NO: 18.

The term "betaglycan polypeptide" includes polypeptides comprising any naturally occurring betaglycan protein (encoded by TGFBR3 or one of its nonhuman orthologs) as well as any variants thereof (including mutants, fragments, fusions, and peptidomimetic forms) that retain a useful activity.

The human betaglycan isoform A precursor protein sequence (NCBI Ref Seq NP_003234.2) is as follows:

transmembrane domain is indicated by dotted underline. This isoform differs from betaglycan isoform B by insertion of a single alanine indicated above by double underline.

A processed betaglycan isoform A polypeptide sequence is as follows:

```
                                               (SEQ ID NO: 51)
GPEPGALCELSPVSASHPVQALMESFTVLSGCASRGTTGLPQEVHVLNLR

TAGQGPGQLQREVTLHLNPISSVHIHHKSVVFLLNSPHPLVWHLKTERLA

TGVSRLFLVSEGSVVQFSSANFSLTAETEERNFPHGNEHLLNWARKEYGA

VISFTELKIARNIYIKVGEDQVFPPKCNIGKNELSLNYLAEYLQPKAAEG

CVMSSQPQNEEVHIIELITPNSNPYSAFQVDITIDIRPSQEDLEVVKNLI

LILKCKKSVNWVIKSFDVKGSLKIIAPNSIGEGKESERSMTMTKSIRDDI

PSTQGNLVKWALDNGYSPITSYTMAPVANRFHLRLENNAEEMGDEEVHTI

PPELRILLDPGALPALQNPPIRGGEGQNGGLPFPFPDISRRVWNEEGEDG

LPRPKDPVIPSIQLFPGLREPEEVQGSVDIALSVKCDNEKMIVAVEKDSF

QASGYSGMDVILLDPICKAKMNGTHFVLESPLNGCGTRPRWSALDGVVYY

NSIVIQVPALGDSSGWPDGYEDLESGDNGFPGDMDEGDASLFTRPEIVVE

NCSLQQVRNPSSFQEQPHGNITFNMELYNTDLFLVPSQGVESVPENGHVY

VEVSVIKAEQELGFAIQTCFISPYSNPDRMSHYTIIENICPKDESVKFYS

PKRVHFPIPQADMDKKRFSFVFKPVFNISLLFLQCELTLCIKMEKHPQKL

PKCVPPDEACTSLDASIIWAMMQNKKTFTKPLAVIHHEAESKEKGPSMKE

PNPISPPIFHGLDILTV
```

A nucleic acid sequence encoding the unprocessed precursor protein of human betaglycan isoform A is shown below (SEQ ID NO: 52), corresponding to nucleotides 516-3068 of NCBI Reference Sequence NM_003243.4. The

```
                                               (SEQ ID NO: 50)
  1 MTSHYVIAIF ALMSSCLATA GPEPGALCEL SPVSASHPVQ ALMESFTVLS GCASRGTTGL

61 PQEVHVLNLR TAGQGPGQLQ REVTLHLNPI SSVHIHHKSV VFLLNSPHPL VWHLKTERLA

121 TGVSRLFLVS EGSVVQFSSA NFSLTAETEE RNFPHGNEHL LNWARKEYGA VTSFTELKIA

181 RNIYIKVGED QVFPPKCNIG KNFLSLNYLA EYLQPKAAEG CVMSSQPQNE EVHIIELITP

241 NSNPYSAFQV DITIDIRPSQ EDLEVVKNLI LILKCKKSVN WVIKSFDVKG SLKIIAPNSI

301 GFGKESERSM TMTKSIRDDI PSTQGNLVKW ALDNGYSPIT SYTMAPVANR FHLRLENNAE

361 EMGDEEVHTI PPELRILLDP GALPALQNPP IRGGEGQNGG LPFPFPDISR RVWNEEGEDG

421 LPRPKDPVIP SIQLFPGLRE PEEVQGSVDI ALSVKCDNEK MIVAVEKDSF QASGYSGMDV

481 TLLDPTCKAK MNGTHFVLES PLNGCGTRPR WSALDGVVYY NSIVIQVPAL GDSSGWPDGY

541 EDLESGDNGF PGDMDEGDAS LFTRPEIVVF NCSLQQVRNP SSFQEQPHGN ITFNMELYNT

601 DLFLVPSQGV FSVPENGHVY VEVSVTKAEQ ELGFAIQTCF ISPYSNPDRM SHYTIIENIC

661 PKDESVEFYS PKRVHFPIPQ ADMDKERFSF VFKPVFNTSL LFLQCELTLC TKMEKHPQKL

721 PKCVPPDEAC TSLDASIIWA MMQNKKTFTK PLAVIHHEAE SKEKGPSMEE PNPISPPIFH

781 GLDTLIVMGI AFAAFVIGAL LTGALWYIYS HTGETAGRQQ VPTSPPASEN SSAAHSIGST

841 QSTPCSSSST A
```

The signal peptide is indicated by single underline, the extracellular domain is indicated in bold font, and the signal sequence is indicated by solid underline and the transmembrane region by dotted underline.

(SEQ ID NO: 52)
ATGACTTCCCATTATGTGATTGCCATCTTTGCCCTGATGAGCTCCTGTTTAGCCACTGCAGGTCCAGAGCCTGGT

GCACTGTGTGAACTGTCACCTGTCAGTGCCTCCCATCCTGTCCAGGCCTTGATGGAGAGCTTCACTGTTTTGTCA

GGCTGTGCCAGCAGAGGCACAACTGGGCTGCCACAGGAGGTGCATGTCCTGAATCTCCGCACTGCAGGCCAGGGG

CCTGGCCAGCTACAGAGAGAGGTCACACTTCACCTGAATCCCATCTCCTCAGTCCACATCCACCACAAGTCTGTT

GTGTTCCTGCTCAACTCCCCACACCCCCTGGTGTGGCATCTGAAGACAGAGAGACTTGCCACTGGGGTCTCCAGA

CTGTTTTTGGTGTCTGAGGGTTCTGTGGTCCAGTTTTCATCAGCAAACTTCTCCTTGACAGCAGAAACAGAAGAA

AGGAACTTCCCCCATGGAAATGAACATCTGTTAAATTGGGCCCGAAAAGAGTATGGAGCAGTTACTTCATTCACC

GAACTCAAGATAGCAAGAAACATTTATATTAAAGTGGGGAAGATCAAGTGTTCCCTCCAAAGTGCAACATAGGG

AAGAATTTTCTCTCACTCAATTACCTTGCTGAGTACCTTCAACCCAAAGCAGCAGAAGGGTGTGTGATGTCCAGC

CAGCCCCAGAATGAGGAAGTACACATCATCGAGCTAATCACCCCCAACTCTAACCCCTACAGTGCTTTCCAGGTG

GATATAACAATTGATATAAGACCTTCTCAAGAGGATCTTGAAGTGGTCAAAAATCTCATCCTGATCTTGAAGTGC

AAAAAGTCTGTCAACTGGGTGATCAAATCTTTTGATGTTAAGGGAAGCCTGAAAATTATTGCTCCTAACAGTATT

GGCTTTGGAAAAGAGAGTGAAAGATCTATGACAATGACCAAATCAATAAGAGATGACATTCCTTCAACCCAAGGG

AATCTGGTGAAGTGGGCTTTGGACAATGGCTATAGTCCAATAACTTCATACACAATGGCTCCTGTGGCTAATAGA

TTTCATCTTCGGCTTGAAAATAATGCAGAGGAGATGGGAGATGAGGAAGTCCACACTATTCCTCCTGAGCTACGG

ATCCTGCTGGACCCTGGTGCCCTGCCTGCCCTGCAGAACCCGCCCATCCGGGGAGGGGAAGGCCAAAATGGAGGC

CTTCCGTTTCCTTTCCCAGATATTTCCAGGAGAGTCTGGAATGAAGAGGGAGAAGATGGGCTCCCTCGGCCAAAG

GACCCTGTCATTCCCAGCATACAACTGTTTCCTGGTCTCAGAGAGCCAGAAGAGGTGCAAGGGAGCGTGGATATT

GCCCTGTCTGTCAAATGTGACAATGAGAAGATGATCGTGGCTGTAGAAAAGATTCTTTTCAGGCCAGTGGCTAC

TCGGGGATGGACGTCACCCTGTTGGATCCTACCTGCAAGGCCAAGATGAATGGCACACACTTTGTTTTGGAGTCT

CCTCTGAATGGCTGCGGTACTCGGCCCCGGTGGTCAGCCCTTGATGGTGTGGTCTACTATAACTCCATTGTGATA

CAGGTTCCAGCCCTTGGGGACAGTAGTGGTTGGCCAGATGGTTATGAAGATCTGGAGTCAGGTGATAATGGATTT

CCGGGAGATATGGATGAAGGAGATGCTTCCCTGTTCACCCGACCTGAAATCGTGGTGTTTAATTGCAGCCTTCAG

CAGGTGAGGAACCCCAGCAGCTTCCAGGAACAGCCCCACGGAAACATCACCTTCAACATGGAGCTATACAACACT

GACCTCTTTTTGGTGCCCTCCCAGGGCGTCTTCTCTGTGCCAGAGAATGGACACGTTTATGTTGAGGTATCTGTT

ACTAAGGCTGAACAAGAACTGGGATTTGCCATCCAAACGTGCTTTATCTCTCCATATTCGAACCCTGATAGGATG

TCTCATTACACCATTATTGAGAATATTTGTCCTAAAGATGAATCTGTGAAATTCTACAGTCCCAAGAGAGTGCAC

TTTCCTATCCCGCAAGCTGACATGGATAAGAAGCGATTCAGCTTTGTCTTCAAGCCTGTCTTCAACACCTCACTG

CTCTTTCTACAGTGTGAGCTGACGCTGTGTACGAAGATGGAGAAGCACCCCCAGAAGTTGCCTAAGTGTGTGCCT

CCTGACGAAGCCTGCACCTCGCTGGACGCCTCGATAATCTGGGCCATGATGCAGAATAAGAAGACGTTCACTAAG

CCCCTTGCTGTGATCCACCATGAAGCAGAATCTAAAGAAAAAGGTCCAAGCATGAAGGAACCAAATCCAATTTCT

CCACCAATTTTCCATGGTCTGGACACCCTAACCGT<u>GATGGGCATTGCGTTTGCAGCCTTTGTGATCGGAGCACTC</u>

<u>CTGACGGGGCCTTGTGGTACATCTATT</u>CTCACACAGGGGAGACAGCAGGAAGGCAGCAAGTCCCCACCTCCCCG

CCAGCCTCGGAAAACAGCAGTGCTGCCCACAGCATCGGCAGCACGCAGAGCACGCCTTGCTCCAGCAGCAGCACG

GCC

A nucleic acid sequence encoding a processed extracellular domain of betaglycan isoform A is shown below (SEQ ID NO: 53):

(SEQ ID NO: 53)
GGTCCAGAGCCTGGTGCACTGTGTGAACTGTCACCTGTCAGTGCCTCCA
TCCTGTCCAGGCCTTGATGGAGAGCTTCACTGTTTTGTCAGGCTGTGCCA
GCAGAGGCACAACTGGGCTGCCACAGGAGGTGCATGTCCTGAATCTCCGC
ACTGCAGGCCAGGGGCCTGGCCAGCTACAGAGAGAGGTCACACTTCACCT
GAATCCCATCTCCTCAGTCCACATCCACCACAAGTCTGTTGTGTTCCTGC
TCAACTCCCCACACCCCCTGGTGTGGCATCTGAAGACAGAGAGACTTGCC
ACTGGGGTCTCCAGACTGTTTTGGTGTCTGAGGGTTCTGTGGTCCAGTT
TTCATCAGCAAACTTCTCCTTGACAGCAGAAACAGAAGAAAGGAACTTCC
CCCATGGAAATGAACATCTGTTAAATTGGGCCCGAAAAGAGTATGGAGCA
GTTACTTCATTCACCGAACTCAAGATAGCAAGAAACATTTATATTAAAGT
GGGGGAAGATCAAGTGTTCCCTCCAAAGTGCAACATAGGGAAGAATTTTC
TCTCACTCAATTACCTTGCTGAGTACCTTCAACCCAAAGCAGCAGAAGGG
TGTGTGATGTCCAGCCAGCCCCAGAATGAGGAAGTACACATCATCGAGCT
AATCACCCCCAACTCTAACCCCTACAGTGCTTTCCAGGTGGATATAACAA
TTGATATAAGACCTTCTCAAGAGGATCTTGAAGTGGTCAAAAATCTCATC
CTGATCTTGAAGTGCAAAAAGTCTGTCAACTGGGTGATCAAATCTTTTGA
TGTTAAGGGAAGCCTGAAAATTATTGCTCCTAACAGTATTGGCTTTGGAA
AAGAGAGTGAAAGATCTATGACAATGACCAAATCAATAAGAGATGACATT
CCTTCAACCCAAGGGAATCTGGTGAAGTGGGCTTTGGACAATGGCTATAG
TCCAATAACTTCATACACAATGGCTCCTGTGGCTAATAGATTTCATCTTC
GGCTTGAAAATAATGCAGAGGAGATGGGAGATGAGGAAGTCCACACTATT
CCTCCTGAGCTACGGATCCTGCTGGACCCTGGTGCCCTGCCTGCCCTGCA
GAACCCGCCCATCCGGGGAGGGGAAGGCCAAAATGGAGGCCTTCCGTTTC
CTTTCCCAGATATTTCCAGGAGAGTCTGGAATGAAGAGGGAGAAGATGGG
CTCCCTCGGCCAAAGGACCCTGTCATTCCCAGCATACAACTGTTTCCTGG
TCTCAGAGAGCCAGAAGAGGTGCAAGGGAGCGTGGATATTGCCCTGTCTG
TCAAATGTGACAATGAGAAGATGATCGTGGCTGTAGAAAAAGATTCTTTT
CAGGCCAGTGGCTACTCGGGGATGGACGTCACCCTGTTGGATCCTACCTG
CAAGGCCAAGATGAATGGCACACACTTTGTTTTGGAGTCTCCTCTGAATG
GCTGCGGTACTCGGCCCCGGTGGTCAGCCCTTGATGGTGTGGTCTACTAT
AACTCCATTGTGATACAGGTTCCAGCCCTTGGGGACAGTAGTGGTTGGCC
AGATGGTTATGAAGATCTGGAGTCAGGTGATAATGGATTTCCGGGAGATA
TGGATGAAGGAGATGCTTCCCTGTTCACCCGACCTGAAATCGTGGTGTTT
AATTGCAGCCTTCAGCAGGTGAGGAACCCCAGCAGCTTCCAGGAACAGCC
CCACGGAAACATCACCTTCAACATGGAGCTATACAACACTGACCTCTTTT
TGGTGCCCTCCCAGGGCGTCTTCTCTGTGCCAGAGAATGGACACGTTTAT
GTTGAGGTATCTGTTACTAAGGCTGAACAAGAACTGGGATTTGCCATCCA
AACGTGCTTTATCTCTCCATATTCGAACCCTGATAGGATGTCTCATTACA
CCATTATTGAGAATATTTGTCCTAAAGATGAATCTGTGAAATTCTACAGT
CCCAAGAGAGTGCACTTTCCTATCCCGCAAGCTGACATGGATAAGAAGCG
ATTCAGCTTTGTCTTCAAGCCTGTCTTCAACACCTCACTGCTCTTTCTAC
AGTGTGAGCTGACGCTGTGTACGAAGATGGAGAAGCACCCCCAGAAGTTG
CCTAAGTGTGTGCCTCCTGACGAAGCCTGCACCTCGCTGGACGCCTCGAT
AATCTGGGCCATGATGCAGAATAAGAAGACGTTCACTAAGCCCCTTGCTG
TGATCCACCATGAAGCAGAATCTAAAGAAAAAGGTCCAAGCATGAAGGAA
CCAAATCCAATTTCTCCACCAATTTTCCATGGTCTGGACACCCTAACCGT
G

A human betaglycan isoform B precursor protein sequence (NCBI Ref Seq NP_001182612.1) is as follows:

(SEQ ID NO: 54)
```
  1 MTSHYVIAIF ALMSSCLATA GPEPGALCEL SPVSASHPVQ ALMESFTVLS GCASRGTTGL

61 PQEVHVLNLR TAGQGPGQLQ REVTLHLNPI SSVHIHHKSV VFLLNSPHPL VWHLKTERLA

121 TGVSRLFLVS EGSVVQFSSA NFSLTAETEE RNFPHGNEHL LNWARKEYGA VTSFTELKIA

181 RNIYIKVGED QVFPPKCNIG KNFLSLNYLA EYLQPKAAEG CVMSSQPQNE EVHIIELITP

241 NSNPYSAFQV DITIDIRPSQ EDLEVVKNLI LILKCKKSVN WVIKSFDVKG SLKIIAPNSI

301 GFGKESERSM TMTKSIRDDI PSTQGNLVKW ALDNGYSPIT SYTMAPVANR FHLRLENNEE

361 MGDEEVHTIP PELRILLDPG ALPALQNPPI RGGEGQNGGL PFPFPDISRR VWNEEGEDGL

421 PRPKDPVIPS IQLFPGLREP EEVQGSVDIA LSVKCDNEKM IVAVEKDSFQ ASGYSGMDVT

481 LLDPTCKAKM NGTHFVLESP LNGCGTRPRW SALDGVVYYN SIVIQVPALG DSSGWPDGYE

541 DLESGDNGFP GDMDEGDASL FTRPEIVVFN CSLQQVRNPS SFQEQPHGNI TFNMELYNTD

601 LFLVPSQGVF SVPENGHVYV EVSVTKAEQE LGFAIQTCFI SPYSNPDRMS HYTIIENICP

661 KDESVKFYSP KRVHFPIPQA DMDKERFSFV FKPVFNTSLL FLQCELTLCT KMEKHPQKLP
```

```
721 KCVPPDEACT SLDASIIWAM MQNKKTFTKP LAVIHHEAES KEKGPSMKEP NPISPPIFHG

781 LDTLTVMGIA FAAFVIGALL TGALWYIYSH TGETAGRQQV PTSPPASENS SAAHSIGSTQ

841 STPCSSSSTA
```

The signal peptide is indicated by single underline, the extracellular domain is indicated in bold font, and the transmembrane domain is indicated by dotted underline.

A processed betaglycan isoform B polypeptide sequence is as follows:

```
                                            (SEQ ID NO: 55)
GPEPGALCELSPVSASHPVQALMESFTVLSGCASRGTTGLPQEVHVLNLR

TAGQGPGQLQREVTLHLNPISSVHIHHKSVVFLLNSPHPLVWHLKTERLA

TGVSRLFLVSEGSVVQFSSANFSLTAETEERNFPHGNEHLLNWARKEYGA

VTSFTELKIARNIYIKVGEDQVFPPKCNIGKNFLSLNYLAEYLQPKAAEG

CVMSSQPQNEEVHIIELITPNSNPYSAFQVDITIDIRPSQEDLEVVKNLI

LILKCKKSVNWVIKSFDVKGSLKIIAPNSIGFGKESERSMTMTKSIRDDI

PSTQGNLVKWALDNGYSPITSYTMAPVANRFHLRLENNEEMGDEEVHTIP

PELRILLDPGALPALQNPPIRGGEGQNGGLPFPFPDISRRVWNEEGEDGL
```

```
                                            -continued
PRPKDPVIPSIQLFPGLREPEEVQGSVDIALSVKCDNEKMIVAVEKDSFQ

ASGYSGMDVTLLDPTCKAKMNGTHFVLESPLNGCGTRPRWSALDGVVYYN

SIVIQVPALGDSSGWPDGYEDLESGDNGFPGDMDEGDASLFTRPEIVVFN

CSLQQVRNPSSFQEQPHGNITFNMELYNTDLFLVPSQGVFSVPENGHVYV

EVSVTKAEQELGFAIQTCFISPYSNPDRMSHYTIIENICPKDESVKFYSP

KRVHFPIPQADMDKKRFSFVFKPVFNTSLLFLQCELTLCTKMEKHPQKLP

KCVPPDEACTSLDASIIWAMMQNKKTFTKPLAVIHHEAESKEKGPSMKEP

NPISPPIFHGLDTLTV
```

A nucleic acid sequence encoding the unprocessed precursor protein of human betaglycan isoform B is shown below (SEQ ID NO: 56), corresponding to nucleotides 516-3065 of NCBI Reference Sequence NM_001195683.1. The signal sequence is indicated by solid underline and the transmembrane region by dotted underline.

```
                                            (SEQ ID NO: 56)
ATGACTTCCCATTATGTGATTGCCATCTTTGCCCTGATGAGCTCCTGTTTAGCCACTGCAGGTCCAGAGCCTGGT

GCACTGTGTGAACTGTCACCTGTCAGTGCCTCCCATCCTGTCCAGGCCTTGATGGAGAGCTTCACTGTTTTGTCA

GGCTGTGCCAGCAGAGGCACAACTGGGCTGCCACAGGAGGTGCATGTCCTGAATCTCCGCACTGCAGGCCAGGGG

CCTGGCCAGCTACAGAGAGAGGTCACACTTCACCTGAATCCCATCTCCTCAGTCCACATCCACCACAAGTCTGTT

GTGTTCCTGCTCAACTCCCCACACCCCCTGGTGTGGCATCTGAAGACAGAGAGACTTGCCACTGGGGTCTCCAGA

CTGTTTTTGGTGTCTGAGGGTTCTGTGGTCCAGTTTTCATCAGCAAACTTCTCCTTGACAGCAGAAACAGAAGAA

AGGAACTTCCCCCATGGAAATGAACATCGTTAAATTGGGCCCGAAAAGAGTATGGAGCAGTTACTTCATTCACC

GAACTCAAGATAGCAAGAAACATTTATATTAAAGTGGGGGAAGATCAAGTGTTCCCTCCAAAGTGCAACATAGGG

AAGAATTTTCTCTCACTCAATTACCTTGCTGAGTACCTTCAACCCAAAGCAGCAGAAGGGTGTGTGATGTCCAGC

CAGCCCCAGAATGAGGAAGTACACATCATCGAGCTAATCACCCCCAACTCTAACCCCTACAGTGCTTTCCAGGTG

GATATAACAATTGATATAAGACCTTCTCAAGAGGATCTTGAAGTGGTCAAAAATCTCATCCTGATCTTGAAGTGC

AAAAAGTCTGTCAACTGGGTGATCAAATCTTTTGATGTTAAGGGAAGCCTGAAAATTATTGCTCCTAACAGTATT

GGCTTTGGAAAAGAGAGTGAAAGATCTATGACAATGACCAAATCAATAAGAGATGACATTCCTTCAACCCAAGGG

AATCTGGTGAAGTGGGCTTTGGACAATGGCTATAGTCCAATAACTTCATACACAATGGCTCCTGTGGCTAATAGA

TTTCATCTTCGGCTTGAAAATAATGAGGAGATGGGAGATGAGGAAGTCCACACTATTCCTCCTGAGCTACGGATC

CTGCTGGACCCTGGTGCCCTGCCTGCCCTGCAGAACCCGCCCATCCGGGGAGGGGAAGGCCAAAATGGAGGCCTT

CCGTTTCCTTTCCCAGATATTTCCAGGAGAGTCTGGAATGAAGAGGGAGAAGATGGGCTCCCTCGGCCAAAGGAC

CCTGTCATTCCCAGCATACAACTGTTTCCTGGTCTCAGAGAGCCAGAAGAGGTGCAAGGGAGCGTGGATATTGCC

CTGTCTGTCAAATGTGACAATGAGAAGATGATCGTGGCTGTAGAAAAAGATTCTTTTCAGGCCAGTGGCTACTCG

GGGATGGACGTCACCCTGTTGGATCCTACCTGCAAGGCCAAGATGAATGGCACACACTTTGTTTTGGAGTCTCCT

CTGAATGGCTGCGGTACTCGGCCCCGGTGGTCAGCCCTTGATGGTGTGGTCTACTATAACTCCATTGTGATACAG

GTTCCAGCCCTTGGGGACAGTAGTGGTTGGCCAGATGGTTATGAAGATCTGGAGTCAGGTGATAATGGATTTCCG
```

```
GGAGATATGGATGAAGGAGATGCTTCCCTGTTCACCCGACCTGAAATCGTGGTGTTTAATTGCAGCCTTCAGCAG

GTGAGGAACCCCAGCAGCTTCCAGGAACAGCCCCACGGAAACATCACCTTCAACATGGAGCTATACAACACTGAC

CTCTTTTTGGTGCCCTCCCAGGGCGTCTTCTCTGTGCCAGAGAATGGACACGTTTATGTTGAGGTATCTGTTACT

AAGGCTGAACAAGAACTGGGATTTGCCATCCAAACGTGCTTTATCTCTCCATATTCGAACCCTGATAGGATGTCT

CATTACACCATTATTGAGAATATTTGTCCTAAAGATGAATCTGTGAAATTCTACAGTCCCAAGAGAGTGCACTTT

CCTATCCCGCAAGCTGACATGGATAAGAAGCGATTCAGCTTTGTCTTCAAGCCTGTCTTCAACACCTCACTGCTC

TTTCTACAGTGTGAGCTGACGCTGTGTACGAAGATGGAGAAGCACCCCCAGAAGTTGCCTAAGTGTGTGCCTCCT

GACGAAGCCTGCACCTCGCTGGACGCCTCGATAATCTGGGCCATGATGCAGAATAAGAAGACGTTCACTAAGCCC

CTTGCTGTGATCCACCATGAAGCAGAATCTAAAGAAAAAGGTCCAAGCATGAAGGAACCAAATCCAATTTCTCCA

CCAATTTTCCATGGTCTGGACACCCTAACCGTGATGGGCATTGCGTTTGCAGCCTTTGTGATCGGAGCACTCCTG

ACGGGGCCTTGTGGTACATCTATTCTCACACAGGGGAGACAGCAGGAAGGCAGCAAGTCCCCACCTCCCCGCCA

GCCTCGGAAAACAGCAGTGCTGCCCACAGCATCGGCAGCACGCAGAGCACGCCTTGCTCCAGCAGCAGCACGGCC
```

A nucleic acid sequence encoding a processed extracellular domain of betaglycan isoform B is shown below (SEQ ID NO: 57):

```
                                              (SEQ ID NO: 57)
GGTCCAGAGCCTGGTGCACTGTGTGAACTGTCACCTGTCAGTGCCTCCCA

TCCTGTCCAGGCCTTGATGGAGAGCTTCACTGTTTTGTCAGGCTGTGCCA

GCAGAGGCACAACTGGGCTGCCACAGGAGGTGCATGTCCTGAATCTCCGC

ACTGCAGGCCAGGGGCCTGGCCAGCTACAGAGAGAGGTCACACTTCACCT

GAATCCCATCTCCTCAGTCCACATCCACCACAAGTCTGTTGTGTTCCTGC

TCAACTCCCCACACCCCCTGGTGTGGCATCTGAAGACAGAGACTTGCC

ACTGGGGTCTCCAGACTGTTTTGGTGTCTGAGGGTTCTGTGGTCCAGTT

TTCATCAGCAAACTTCTCCTTGACAGCAGAAACAGAAGAAAGGAACTTCC

CCCATGGAAATGAACATCTGTTAAATTGGGCCCGAAAAGAGTATGGAGCA

GTTACTTCATTCACCGAACTCAAGATAGCAAGAAACATTTATATTAAAGT

GGGGGAAGATCAAGTGTTCCCTCCAAAGTGCAACATAGGGAAGAATTTTC

TCTCACTCAATTACCTTGCTGAGTACCTTCAACCCAAAGCAGCAGAAGGG

TGTGTGATGTCCAGCCAGCCCCAGAATGAGGAAGTACACATCATCGAGCT

AATCACCCCCAACTCTAACCCCTACAGTGCTTTCCAGGTGGATATAACAA

TTGATATAAGACCTTCTCAAGAGGATCTTGAAGTGGTCAAAAATCTCATC

CTGATCTTGAAGTGCAAAAAGTCTGTCAACTGGGTGATCAAATCTTTTGA

TGTTAAGGGAAGCCTGAAAATTATTGCTCCTAACAGTATTGGCTTTGGAA

AAGAGAGTGAAAGATCTATGACAATGACCAAATCAATAAGAGATGACATT

CCTTCAACCCAAGGGAATCTGGTGAAGTGGGCTTTGGACAATGGCTATAG

TCCAATAACTTCATACACAATGGCTCCTGTGGCTAATAGATTTCATCTTC

GGCTTGAAAATAATGAGGAGATGGGAGATGAGGAAGTCCACACTATTCCT

CCTGAGCTACGGATCCTGCTGGACCCTGGTGCCCTGCCTGCCCTGCAGAA

CCCGCCCATCCGGGGAGGGGAAGGCCAAAATGGAGGCCTTCCGTTTCCTT

TCCCAGATATTTCCAGGAGAGTCTGGAATGAAGAGGGAGAAGATGGGCTC

CCTCGGCCAAAGGACCCTGTCATTCCCAGCATACAACTGTTTCCTGGTCT

CAGAGAGCCAGAAGAGGTGCAAGGGAGCGTGGATATTGCCCTGTCTGTCA

AATGTGACAATGAGAAGATGATCGTGGCTGTAGAAAAAGATTCTTTTCAG

GCCAGTGGCTACTCGGGGATGGACGTCACCCTGTTGGATCCTACCTGCAA

GGCCAAGATGAATGGCACACACTTTGTTTTGGAGTCTCCTCTGAATGGCT

GCGGTACTCGGCCCCGGTGGTCAGCCCTTGATGGTGTGGTCTACTATAAC

TCCATTGTGATACAGGTTCCAGCCCTTGGGGACAGTAGTGGTTGGCCAGA

TGGTTATGAAGATCTGGAGTCAGGTGATAATGGATTTCCGGGAGATATGG

ATGAAGGAGATGCTTCCCTGTTCACCCGACCTGAAATCGTGGTGTTTAAT

TGCAGCCTTCAGCAGGTGAGGAACCCCAGCAGCTTCCAGGAACAGCCCCA

CGGAAACATCACCTTCAACATGGAGCTATACAACACTGACCTCTTTTTGG

TGCCCTCCCAGGGCGTCTTCTCTGTGCCAGAGAATGGACACGTTTATGTT

GAGGTATCTGTTACTAAGGCTGAACAAGAACTGGGATTTGCCATCCAAAC

GTGCTTTATCTCTCCATATTCGAACCCTGATAGGATGTCTCATTACACCA

TTATTGAGAATATTTGTCCTAAAGATGAATCTGTGAAATTCTACAGTCCC

AAGAGAGTGCACTTTCCTATCCCGCAAGCTGACATGGATAAGAAGCGATT

CAGCTTTGTCTTCAAGCCTGTCTTCAACACCTCACTGCTCTTTCTACAGT

GTGAGCTGACGCTGTGTACGAAGATGGAGAAGCACCCCCAGAAGTTGCCT

AAGTGTGTGCCTCCTGACGAAGCCTGCACCTCGCTGGACGCCTCGATAAT

CTGGGCCATGATGCAGAATAAGAAGACGTTCACTAAGCCCCTTGCTGTGA

TCCACCATGAAGCAGAATCTAAAGAAAAAGGTCCAAGCATGAAGGAACCA

AATCCAATTTCTCCACCAATTTTCCATGGTCTGGACACCCTAACCGTG
```

In certain embodiments, the disclosure relates to betaglycan polypeptide, which includes fragments, functional variants, and modified forms thereof. Preferably, betaglycan polypeptides for use in accordance with inventions of the disclosure are soluble (e.g., comprise an extracellular domain of betaglycan). In other preferred embodiments, betaglycan polypeptides for use in accordance with the inventions of the disclosure bind to and/or inhibit (antagonize) activity (e.g., Smad signaling) of one or more TGF-beta superfamily ligands. In some embodiments, betaglycan polypeptide comprise an amino acid sequence that is at least 70%, 75%, 80%, 85%, 90%, 91%, 92%, 93%, 94%, 95%, 96%, 97%, 98%, 99%, or 100% identical to the amino acid sequence of SEQ ID NOs: 50, 51, 54, or 55. In some embodiments, betaglycan polypeptides comprise an amino acid sequence that is at least 70%, 75%, 80%, 85%, 90%, 91%, 92%, 93%, 94%, 95%, 96%, 97%, 98%, 99%, or 100% identical to a polypeptide that begins at any one of amino acids of 21-28 of SEQ ID NO: 50, and ends at any one of amino acids 381-787 of SEQ ID NO: 50. In some embodiments, polypeptides of the disclosure comprise at least one betaglycan polypeptide that is at least 70%, 75%, 80%, 85%, 90%, 91%, 92%, 93%, 94%, 95%, 96%, 97%, 98%, 99%, or 100% identical to amino acids of 21-381 of SEQ ID NO: 50. In some embodiments, polypeptides of the disclosure comprise at least one betaglycan polypeptide that is at least 70%, 75%, 80%, 85%, 90%, 91%, 92%, 93%, 94%, 95%, 96%, 97%, 98%, 99%, or 100% identical to amino acids of 21-787 of SEQ ID NO: 50. In some embodiments, polypeptides of the disclosure comprise at least one betaglycan polypeptide that is at least 70%, 75%, 80%, 85%, 90%, 91%, 92%, 93%, 94%, 95%, 96%, 97%, 98%, 99%, or 100% identical to amino acids of 28-381 of SEQ ID NO: 50. In some embodiments, polypeptides of the disclosure comprise at least one betaglycan polypeptide that is at least 70%, 75%, 80%, 85%, 90%, 91%, 92%, 93%, 94%, 95%, 96%, 97%, 98%, 99%, or 100% identical to amino acids of 28-787 of SEQ ID NO: 50. In some embodiments, polypeptides of the disclosure comprise of at least one betaglycan polypeptide that is at least 70%, 75%, 80%, 85%, 90%, 91%, 92%, 93%, 94%, 95%, 96%, 97%, 98%, 99%, or 100% identical to amino acids of 21-781 of SEQ ID NO: 50. In some embodiments, polypeptides of the disclosure comprise at least one betaglycan polypeptide that is at least 70%, 75%, 80%, 85%, 90%, 91%, 92%, 93%, 94%, 95%, 96%, 97%, 98%, 99%, or 100% identical to amino acids of 28-781 of SEQ ID NO: 50. In some embodiments, polypeptides of the disclosure comprise at least one betaglycan polypeptide that is at least 70%, 75%, 80%, 85%, 90%, 91%, 92%, 93%, 94%, 95%, 96%, 97%, 98%, 99%, or 100% identical to a polypeptide that begins at any one of amino acids of 21-28 of SEQ ID NO: 54, and ends at any one of amino acids 380-786 of SEQ ID NO: 54. In some embodiments, polypeptides of the disclosure comprise at least one betaglycan polypeptide that is at least 70%, 75%, 80%, 85%, 90%, 91%, 92%, 93%, 94%, 95%, 96%, 97%, 98%, 99%, or 100% identical to amino acids of 21-380 of SEQ ID NO: 54. In some embodiments, polypeptides of the disclosure comprise at least one betaglycan polypeptide that is at least 70%, 75%, 80%, 85%, 90%, 91%, 92%, 93%, 94%, 95%, 96%, 97%, 98%, 99%, or 100% identical to amino acids of 21-786 of SEQ ID NO: 54. In some embodiments, polypeptides of the disclosure comprise at least one betaglycan polypeptide that is at least 70%, 75%, 80%, 85%, 90%, 91%, 92%, 93%, 94%, 95%, 96%, 97%, 98%, 99%, or 100% identical to amino acids of 28-380 of SEQ ID NO: 54. In some embodiments, polypeptides of the disclosure comprise at least one betaglycan polypeptide that is at least 70%, 75%, 80%, 85%, 90%, 91%, 92%, 93%, 94%, 95%, 96%, 97%, 98%, 99%, or 100% identical to amino acids of 28-786 of SEQ ID NO: 54. In some embodiments, polypeptides of the disclosure comprise at least one betaglycan polypeptide that is at least 70%, 75%, 80%, 85%, 90%, 91%, 92%, 93%, 94%, 95%, 96%, 97%, 98%, 99%, or 100% identical to amino acids of 21-780 of SEQ ID NO: 54. In some embodiments, polypeptides of the disclosure comprise at least one betaglycan polypeptide that is at least 70%, 75%, 80%, 85%, 90%, 91%, 92%, 93%, 94%, 95%, 96%, 97%, 98%, 99%, or 100% identical to amino acids of 28-780 of SEQ ID NO: 54. In some embodiments, polypeptides of the disclosure comprise at least one betaglycan polypeptide that is at least 70%, 75%, 80%, 85%, 90%, 91%, 92%, 93%, 94%, 95%, 96%, 97%, 98%, 99%, or 100% identical to a polypeptide that begins at any one of amino acids of 21-28 of SEQ ID NO: 50, and ends at any one of amino acids 730-787 of SEQ ID NO: 50. In some embodiments, polypeptides of the disclosure comprise at least one betaglycan polypeptide that is at least 70%, 75%, 80%, 85%, 90%, 91%, 92%, 93%, 94%, 95%, 96%, 97%, 98%, 99%, or 100% identical to amino acids of 21-787 of SEQ ID NO: 50. In some embodiments, polypeptides of the disclosure comprise at least one betaglycan polypeptide that is at least 70%, 75%, 80%, 85%, 90%, 91%, 92%, 93%, 94%, 95%, 96%, 97%, 98%, 99%, or 100% identical to amino acids of 28-730 of SEQ ID NO: 50. In some embodiments, polypeptides of the disclosure comprise at least one betaglycan polypeptide that is at least 70%, 75%, 80%, 85%, 90%, 91%, 92%, 93%, 94%, 95%, 96%, 97%, 98%, 99%, or 100% identical to a polypeptide that begins at any one of amino acids of 21-28 of SEQ ID NO: 50, and ends at any one of amino acids 730-787 of SEQ ID NO: 50. In some embodiments, polypeptides of the disclosure comprise at least one betaglycan polypeptide that is at least 70%, 75%, 80%, 85%, 90%, 91%, 92%, 93%, 94%, 95%, 96%, 97%, 98%, 99%, or 100% identical to amino acids of 21-787 of SEQ ID NO: 50. In some embodiments, polypeptides of the disclosure comprise at least one betaglycan polypeptide that is at least 70%, 75%, 80%, 85%, 90%, 91%, 92%, 93%, 94%, 95%, 96%, 97%, 98%, 99%, or 100% identical to amino acids of 28-730 of SEQ ID NO: 50. In some embodiments, polypeptides of the disclosure comprise at least one betaglycan polypeptide that is at least 70%, 75%, 80%, 85%, 90%, 91%, 92%, 93%, 94%, 95%, 96%, 97%, 98%, 99%, or 100% identical to a polypeptide that begins at any one of amino acids of 21-28 (e.g., amino acid residues of SEQ ID NO: 54, and ends at any one of amino acids 730-787 of SEQ ID NO: 54. In some embodiments, polypeptides of the disclosure comprise at least one betaglycan polypeptide that is at least 70%, 75%, 80%, 85%, 90%, 91%, 92%, 93%, 94%, 95%, 96%, 97%, 98%, 99%, or 100% identical to amino acids of 21-786 of SEQ ID NO: 54. In some embodiments, polypeptides of the disclosure comprise at least one betaglycan polypeptide that is at least 70%, 75%, 80%, 85%, 90%, 91%, 92%, 93%, 94%, 95%, 96%, 97%, 98%, 99%, or 100% identical to amino acids of 28-729 of SEQ ID NO: 54.

In certain aspects, the present disclosure relates to heteromultimers that comprise an ALK5 polypeptide. As used herein, the term "ALK5" refers to a family of activin receptor-like kinase-5 proteins from any species and variants derived from such ALK4 proteins by mutagenesis or other modification. Reference to ALK5 herein is understood to be a reference to any one of the currently identified forms. Members of the ALK5 family are generally transmembrane proteins, composed of a ligand-binding extracellular domain with a cysteine-rich region, a transmembrane domain, and a cytoplasmic domain with predicted serine/threonine kinase activity.

The term "ALK5 polypeptide" includes polypeptides comprising any naturally occurring polypeptide of an ALK5 family member as well as any variants thereof (including mutants, fragments, fusions, and peptidomimetic forms) that retain a useful activity.

The human ALK5 precursor protein, isoform 1 sequence (NCBI Ref Seq NP_004603.1) is as follows:

```
                                      (SEQ ID NO: 69)
  1 MEAAVAAPRP RLLLLVLAAA AAAAAALLPG ATALQCFCHL

CTKDNFTCVT DGLCFVSVTE

61 TTDKVIHNSM CIAEIDLIPR DRPFVCAPSS KTGSVTTTYC

CNQDHCNKIE LPTTVKSSPG

121 LGPVELAAVI AGPVCFVCIS LMLMVYICHN RTVIHHRVPN

EEDPSLDRPF ISEGTTLKDL

181 IYDMTTSGSG SGLPLLVQRT IARTIVLQES IGKGRFGEVW

RGKWRGEEVA VKIFSSREER

241 SWFREAEIYQ TVMLRHENIL GFIAADNKDN GTWTQLWLVS

DYHEHGSLFD YLNRYTVTVE

301 GMIKLALSTA SGLAHLHMEI VGTQGKPAIA HRDLKSKNIL

VKKNGTCCIA DLGLAVRHDS

361 ATDTIDIAPN HRVGTKRYMA PEVLDDSINM KHFESFKRAD

IYAMGLVFWE IARRCSIGGI

421 HEDYQLPYYD LVPSDPSVEE MRKVVCEQKL RPNIPNRWQS

CEALRVMAKI MRECWYANGA

481 ARLTALRIKK TLSQLSQQEG IKM
```

The signal peptide is indicated by a single underline and the extracellular domain is indicated in bold font.

A processed extracellular ALK5 polypeptide sequence is as follows:

```
                                      (SEQ ID NO: 70)
AALLPGATALQCFCHLCTKDNFTCVTDGLCFVSVTETTDKVIHNSMCIAE

IDLIPRDRPFVCAPSSKTGSVTTTYCCNQDHCNKIELPTTVKSSPGLGPV

EL
```

A nucleic acid sequence encoding the ALK5 precursor protein is shown below (SEQ ID NO: 32), corresponding to nucleotides 77-1585 of Genbank Reference Sequence NM_004612.2. The signal sequence is underlined and the extracellular domain is indicated in bold font.

```
                                      (SEQ ID NO: 71)
ATGGAGGCGGCGGTCGCTGCTCCGCGTCCCCGGCTGCTCCTCCTCGTGCT

GGCGGCGGCGGCGGCGGCGGCGGCGGCGCTGCTCCCGGGGGCGACGGCGT

TACAGTGTTTCTGCCACCTCTGTACAAAAGACAATTTTACTTGTGTGACA

GATGGGCTCTGCTTTGTCTCTGTCACAGAGACCACAGACAAAGTTATACA

CAACAGCATGTGTATAGCTGAAATTGACTTAATTCCTCGAGATAGGCCGT

TTGTATGTGCACCCTCTTCAAAAACTGGGTCTGTGACTACAACATATTGC

TGCAATCAGGACCATTGCAATAAAATAGAACTTCCAACTACTGTAAAGTC

ATCACCTGGCCTTGGTCCTGTGGAACTGGCAGCTGTCATTGCTGGACCAG

TGTGCTTCGTCTGCATCTCACTCATGTTGATGGTCTATATCTGCCACAAC

CGCACTGTCATTCACCATCGAGTGCCAAATGAAGAGGACCCTTCATTAGA

TCGCCCTTTTATTTCAGAGGGTACTACGTTGAAAGACTTAATTTATGATA

TGACAACGTCAGGTTCTGGCTCAGGTTTACCATTGCTTGTTCAGAGAACA

ATTGCGAGAACTATTGTGTTACAAGAAAGCATTGGCAAAGGTCGATTTGG

AGAAGTTTGGAGAGGAAAGTGGCGGGGAGAAGAAGTTGCTGTTAAGATAT

TCTCCTCTAGAGAAGAACGTTCGTGGTTCCGTGAGGCAGAGATTTATCAA

ACTGTAATGTTACGTCATGAAAACATCCTGGGATTTATAGCAGCAGACAA

TAAAGACAATGGTACTTGGACTCAGCTCTGGTTGGTGTCAGATTATCATG

AGCATGGATCCCTTTTTGATTACTTAAACAGATACACAGTTACTGTGGAA

GGAATGATAAAACTTGCTCTGTCCACGGCGAGCGGTCTTGCCCATCTTCA

CATGGAGATTGTTGGTACCCAAGGAAAGCCAGCCATTGCTCATAGAGATT

TGAAATCAAAGAATATCTTGGTAAAGAAGAATGGAACTTGCTGTATTGCA

GACTTAGGACTGGCAGTAAGACATGATTCAGCCACAGATACCATTGATAT

TGCTCCAAACCACAGAGTGGGAACAAAAAGGTACATGGCCCCTGAAGTTC

TCGATGATTCCATAAATATGAAACATTTTGAATCCTTCAAACGTGCTGAC

ATCTATGCAATGGGCTTAGTATTCTGGGAAATTGCTCGACGATGTTCCAT

TGGTGGAATTCATGAAGATTACCAACTGCCTTATTATGATCTTGTACCTT

CTGACCCATCAGTTGAAGAAATGAGAAAAGTTGTTTGTGAACAGAAGTTA

AGGCCAAATATCCCAAACAGATGGCAGAGCTGTGAAGCCTTGAGAGTAAT

GGCTAAAATTATGAGAGAATGTTGGTATGCCAATGGAGCAGCTAGGCTTA

CAGCATTGCGGATTAAGAAAACATTATCGCAACTCAGTCAACAGGAAGGC

ATCAAAATG
```

A nucleic acid sequence encoding an extracellular human ALK5 polypeptide is as follows:

```
                                      (SEQ ID NO: 72)
GCGGCGCTGCTCCCGGGGGCGACGGCGTTACAGTGT

TTCTGCCACCTCTGTACAAAAGACAATTTTACTTG

TGTGACAGATGGGCTCTGCTTTGTCTCTGTCACAG

AGACCACAGACAAAGTTATACACAACAGCATGTGT

ATAGCTGAAATTGACTTAATTCCTCGAGATAGGCC

GTTTGTATGTGCACCCTCTTCAAAAACTGGGTCTG

TGACTACAACATATTGCTGCAATCAGGACCATTGC

AATAAAATAGAACTTCCAACTACTGTAAAGTCATC

ACCTGGCCTTGGTCCTGTGGAACTG
```

An alternative isoform of the human ALK5 precursor protein sequence, isoform 2 (NCBI Ref Seq XP_005252207.1), is as follows:

```
                                      (SEQ ID NO: 73)
  1 MEAAVAAPRP RLLLLVLAAA AAAAALLPG

ATALQCFCHL CTKDNFTCVT DGLCFVSVTE
```

```
 61 TTDKVIHNSM CIAEIDLIPR DRPFVCAPSS
    KTGSVTTTYC CNQDHCNKIE LPTTGPFSVK
121 SSPGLGPVEL AAVIAGPVCF VCISLMLMVY
    ICHNRTVIHH RVPNEEDPSL DRPFISEGTT
181 LKDLIYDMTT SGSGSGLPLL VQRTIARTIV
    LQESIGKGRF GEVWRGKWRG EEVAVKIFSS
241 REERSWFREA EIYQTVMLRH ENILGFIAAD
    NKDNGTWTQL WLVSDYHEHG SLFDYLNRYT
301 VTVEGMIKLA LSTASGLAHL HMEIVGTQGK
    PAIAHRDLKS KNILVKKNGT CCIADLGLAV
361 RHDSATDTID IAPNHRVGTK RYMAPEVLDD
    SINMKHFESF KRADIYAMGL VFWEIARRCS
421 IGGIHEDYQL PYYDLVPSDP SVEEMRKWC
    EQKLRPNIPN RWQSCEALRV MAKIMRECWY
481 ANGAARLTAL RIKKTLSQLS QQEGIKM
```

The signal peptide is indicated by a single underline and the extracellular domain is indicated in bold font.

A processed extracellular ALK5 polypeptide sequence (isoform 2) is as follows:

```
                                       (SEQ ID NO: 74)
AALLPGATALQCFCHLCTKDNFTCVTDGLCFVSVTE

TTDKVIHNSMCIAEIDLIPRDRPFVCAPSSKTGSVT

TTYCCNQDHCNKIELPTTGPFSVKSSPGLGPVEL
```

A nucleic acid sequence encoding human ALK5 precursor protein (isoform 2) is shown below (SEQ ID NO: 75), corresponding to nucleotides 77-1597 of Genbank Reference Sequence XM_005252150.1. The signal sequence is underlined and the extracellular domain is indicated in bold font.

```
(SEQ ID NO: 75)
ATGGAGGCGGCGGTCGCTGCTCCGCGTCCCCGGCT

GCTCCTCCTCGTGCTGGCGGCGGCGGCGGCGGCGG

CGGCGGCGCTGCTCCCGGGGGCGACGGCGTTACAG

TGTTTCTGCCACCTCTGTACAAAAGACAATTTTAC

TTGTGTGACAGATGGGCTCTGCTTTGTCTCTGTCA

CAGAGACCACAGACAAAGTTATACACAACAGCATG

TGTATAGCTGAAATTGACTTAATTCCTCGAGATAG

GCCGTTTGTATGTGCACCCTCTTCAAAAACTGGGT

CTGTGACTACAACATATTGCTGCAATCAGGACCAT

TGCAATAAAATAGAACTTCCAACTACTGGCCCTTT

TTCAGTAAAGTCATCACCTGGCCTTGGTCCTGTGG

AACTGGCAGCTGTCATTGCTGGACCAGTGTGCTTC

GTCTGCATCTCACTCATGTTGATGGTCTATATCTG

CCACAACCGCACTGTCATTCACCATCGAGTGCCAA

ATGAAGAGGACCCTTCATTAGATCGCCCTTTTATT

TCAGAGGGTACTACGTTGAAAGACTTAATTTATGA

TATGACAACGTCAGGTTCTGGCTCAGGTTTACCAT

TGCTTGTTCAGAGAACAATTGCGAGAACTATTGTG

TTACAAGAAAGCATTGGCAAAGGTCGATTTGGAGA

AGTTTGGAGAGGAAAGTGGCGGGGAGAAGAAGTTG

CTGTTAAGATATTCTCCTCTAGAGAAGAACGTTCG

TGGTTCCGTGAGGCAGAGATTTATCAAACTGTAAT

GTTACGTCATGAAAACATCCTGGGATTTATAGCAG

CAGACAATAAAGACAATGGTACTTGGACTCAGCTC

TGGTTGGTGTCAGATTATCATGAGCATGGATCCCT

TTTTGATTACTTAAACAGATACACAGTTACTGTGG

AAGGAATGATAAAACTTGCTCTGTCCACGGCGAGC

GGTCTTGCCCATCTTCACATGGAGATTGTTGGTAC

CCAAGGAAAGCCAGCCATTGCTCATAGAGATTTGA

AATCAAAGAATATCTTGGTAAAGAAGAATGGAACT

TGCTGTATTGCAGACTTAGGACTGGCAGTAAGACA

TGATTCAGCCACAGATACCATTGATATTGCTCCAA

ACCACAGAGTGGGAACAAAAAGGTACATGGCCCCT

GAAGTTCTCGATGATTCCATAAATATGAAACATTT

TGAATCCTTCAAACGTGCTGACATCTATGCAATGG

GCTTAGTATTCTGGGAAATTGCTCGACGATGTTCC

ATTGGTGGAATTCATGAAGATTACCAACTGCCTTA

TTATGATCTTGTACCTTCTGACCCATCAGTTGAAG

AAATGAGAAAAGTTGTTTGTGAACAGAAGTTAAGG

CCAAATATCCCAAACAGATGGCAGAGCTGTGAAGC

CTTGAGAGTAATGGCTAAAATTATGAGAGAATGTT

GGTATGCCAATGGAGCAGCTAGGCTTACAGCATTG

CGGATTAAGAAAACATTATCGCAACTCAGTCAACA

GGAAGGCATCAAAATG
```

A nucleic acid sequence encoding an processed extracellular ALK5 polypeptide is as follows:

```
                                       (SEQ ID NO: 76)
GCGGCGCTGCTCCCGGGGGCGACGGCGTTACAGTG

TTTCTGCCACCTCTGTACAAAAGACAATTTTACTT

GTGTGACAGATGGGCTCTGCTTTGTCTCTGTCACA

GAGACCACAGACAAAGTTATACACAACAGCATGTG

TATAGCTGAAATTGACTTAATTCCTCGAGATAGGC

CGTTTGTATGTGCACCCTCTTCAAAAACTGGGTCT
```

-continued

```
GTGACTACAACATATTGCTGCAATCAGGACCATTG

CAATAAAATAGAACTTCCAACTACTGGCCCTTTTT

CAGTAAAGTCATCACCTGGCCTTGGTCCTGTGGAA

CTG
```

In certain embodiments, the disclosure relates to heteromultimers that comprise at least one ALK5 polypeptide, which includes fragments, functional variants, and modified forms thereof. Preferably, ALK5 polypeptides for use in accordance with the disclosure (e.g., heteromultimers comprising an ALK5 polypeptide and uses thereof) are soluble (e.g., an extracellular domain of ALK5). In other preferred embodiments, ALK5 polypeptides for use in accordance with the disclosure bind to and/or inhibit (antagonize) activity (e.g., Smad signaling) of one or more TGF-beta superfamily ligands. In some embodiments, heteromultimers of the disclosure comprise at least one ALK5 polypeptide that is at least 70%, 75%, 80%, 85%, 90%, 91%, 92%, 93%, 94%, 95%, 96%, 97%, 98%, 99%, or 100% identical to the amino acid sequence of SEQ ID NOs: 69, 70, 73, or 74. In some embodiments, heteromultimers of the disclosure comprise at least one ALK5 polypeptide that is at least 70%, 75%, 80%, 85%, 90%, 91%, 92%, 93%, 94%, 95%, 96%, 97%, 98%, 99%, or 100% identical to a polypeptide that begins at any one of amino acids of 25-36 (e.g., amino acid residues 25, 26, 27, 28, 29, 30, 31, 32, 33, 34, 35, or 36) of SEQ ID NO: 69, and ends at any one of amino acids 101-126 (e.g., amino acid residues 101, 102, 103, 104, 105, 106, 107, 108, 109, 110, 111, 112,113, 114, 115, 116, 117, 118, 119, 120, 121, 122, 123, 124, 125, or 126) of SEQ ID NO: 69. In some embodiments, heteromultimers of the disclosure comprise at least one ALK5 polypeptide that is at least 70%, 75%, 80%, 85%, 90%, 91%, 92%, 93%, 94%, 95%, 96%, 97%, 98%, 99%, or 100% identical to amino acids of 25-101 of SEQ ID NO: 69. In some embodiments, heteromultimers of the disclosure comprise at least one ALK5 polypeptide that is at least 70%, 75%, 80%, 85%, 90%, 91%, 92%, 93%, 94%, 95%, 96%, 97%, 98%, 99%, or 100% identical to amino acids of 25-126 of SEQ ID NO: 69. In some embodiments, heteromultimers of the disclosure comprise at least one ALK5 polypeptide that is at least 70%, 75%, 80%, 85%, 90%, 91%, 92%, 93%, 94%, 95%, 96%, 97%, 98%, 99%, or 100% identical to amino acids of 36-101 of SEQ ID NO: 69. In some embodiments, heteromultimers of the disclosure comprise at least one ALK5 polypeptide that is at least 70%, 75%, 80%, 85%, 90%, 91%, 92%, 93%, 94%, 95%, 96%, 97%, 98%, 99%, or 100% identical to amino acids of 36-126 of SEQ ID NO: 69. In some embodiments, heteromultimers of the disclosure comprise at least one ALK5 polypeptide that is at least 70%, 75%, 80%, 85%, 90%, 91%, 92%, 93%, 94%, 95%, 96%, 97%, 98%, 99%, or 100% identical to a polypeptide that begins at any one of amino acids of 25-36 (e.g., amino acid residues 25, 26, 27, 28, 29, 30, 31, 32, 33, 34, 35, or 36) of SEQ ID NO: 73, and ends at any one of amino acids 101-130 (e.g., amino acid residues 101, 102, 103, 104, 105, 106, 107, 108, 109, 110, 111, 112,113, 114, 115, 116, 117, 118, 119, 120, 121, 122, 123, 124, 125, 126, 127, 128, 129 or 130) of SEQ ID NO: 73. In some embodiments, heteromultimers of the disclosure comprise at least one ALK5 polypeptide that is at least 70%, 75%, 80%, 85%, 90%, 91%, 92%, 93%, 94%, 95%, 96%, 97%, 98%, 99%, or 100% identical to amino acids of 25-101 of SEQ ID NO: 73. In some embodiments, heteromultimers of the disclosure comprise at least one ALK5 polypeptide that is at least 70%, 75%, 80%, 85%, 90%, 91%, 92%, 93%, 94%, 95%, 96%, 97%, 98%, 99%, or 100% identical to amino acids of 25-130 of SEQ ID NO: 73. In some embodiments, heteromultimers of the disclosure comprise at least one ALK5 polypeptide that is at least 70%, 75%, 80%, 85%, 90%, 91%, 92%, 93%, 94%, 95%, 96%, 97%, 98%, 99%, or 100% identical to amino acids of 36-101 of SEQ ID NO: 73. In some embodiments, heteromultimers of the disclosure comprise at least one ALK5 polypeptide that is at least 70%, 75%, 80%, 85%, 90%, 91%, 92%, 93%, 94%, 95%, 96%, 97%, 98%, 99%, or 100% identical to amino acids of 36-130 of SEQ ID NO: 73.

As described above, the disclosure provides TβRII or betaglycan polypeptides sharing a specified degree of sequence identity or similarity to a naturally occurring TβRII or betaglycan polypeptide. To determine the percent identity of two amino acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The amino acid residues at corresponding amino acid positions are then compared. When a position in the first sequence is occupied by the same amino acid residue as the corresponding position in the second sequence, then the molecules are identical at that position (as used herein amino acid "identity" is equivalent to amino acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

In one embodiment, the percent identity between two amino acid sequences is determined using the Needleman and Wunsch (J Mol. Biol. (48):444-453 (1970)) algorithm which has been incorporated into the GAP program in the GCG software package (available at http://www.gcg.com). In a specific embodiment, the following parameters are used in the GAP program: either a Blosum 62 matrix or a PAM250 matrix, and a gap weight of 16, 14, 12, 10, 8, 6, or 4 and a length weight of 1, 2, 3, 4, 5, or 6. In yet another embodiment, the percent identity between two nucleotide sequences is determined using the GAP program in the GCG software package (Devereux, J., et al., Nucleic Acids Res. 12(1):387 (1984)) (available at http://www.gcg.com). Exemplary parameters include using a NWSgapdna.CMP matrix and a gap weight of 40, 50, 60, 70, or 80 and a length weight of 1, 2, 3, 4, 5, or 6. Unless otherwise specified, percent identity between two amino acid sequences is to be determined using the GAP program using a Blosum 62 matrix, a GAP weight of 10 and a length weight of 3, and if such algorithm cannot compute the desired percent identity, a suitable alternative disclosed herein should be selected.

In another embodiment, the percent identity between two amino acid sequences is determined using the algorithm of E. Myers and W. Miller (CABIOS, 4:11-17 (1989)) which has been incorporated into the ALIGN program (version 2.0), using a PAM120 weight residue table, a gap length penalty of 12 and a gap penalty of 4.

Another embodiment for determining the best overall alignment between two amino acid sequences can be determined using the FASTDB computer program based on the algorithm of Brutlag et al. (*Comp. App. Biosci.,* 6:237-245 (1990)). In a sequence alignment the query and subject sequences are both amino acid sequences. The result of said global sequence alignment is presented in terms of percent identity. In one embodiment, amino acid sequence identity is performed using the FASTDB computer program based on the algorithm of Brutlag et al. (*Comp. App. Biosci.,* 6:237-245 (1990)). In a specific embodiment, parameters employed to calculate percent identity and similarity of an amino acid alignment comprise: Matrix=PAM 150, k-tuple=2, Mismatch Penalty=1, Joining Penalty=20, Randomization Group Length=0, Cutoff Score=1, Gap Penalty=5 and Gap Size Penalty=0.05.

Polypeptides of the disclosure (e.g., TβRII or betaglycan polypeptides) may additionally include any of various leader sequences at the N-terminus. Such a sequence would allow the peptides to be expressed and targeted to the secretion pathway in a eukaryotic system. See, e.g., Ernst et al., U.S. Pat. No. 5,082,783 (1992). Alternatively, a native signal sequence (e.g., native TβRII or betaglycan signal sequence) may be used to effect extrusion from the cell. Possible leader sequences include native leaders, tissue plasminogen activator (TPA) and honeybee mellitin (SEQ ID NOs. 22-24, respectively). Examples of TβRII-Fc fusion proteins incorporating a TPA leader sequence include SEQ ID NOs: 11, 13, 15 and 17. Processing of signal peptides may vary depending on the leader sequence chosen, the cell type used and culture conditions, among other variables, and therefore actual N-terminal start sites for mature polypeptides may shift by 1, 2, 3, 4 or 5 amino acids in either the N-terminal or C-terminal direction. Examples of TβRII-Fc fusion proteins include SEQ ID NOs: 11, 13, 15 and 17. It will be understood by one of skill in the art that corresponding variants based on the long isoform of TβRII will include the 25-amino acid insertion along with a conservative Val-Ile substitution at the flanking position C-terminal to the insertion.

In some embodiments, any of the TβRII polypeptides disclosed herein are at least 80%, 85%, 90%, 92%, 94%, 95%, 97%, 99% or 100% identical to the amino acid sequence of any one of SEQ ID NOs: 18, 20, 27, 30, 34, 36, 37, 38, 39, or 48, but lack one or more N-terminal amino acids as compared to the amino acid sequences of SEQ ID NO: 18, 20, 27, 30, 34, 36, 37, 38, 39, or 48. In some embodiments, the TβRII polypeptide lacks the amino acid corresponding to the first amino acid (threonine) of any one of SEQ ID NOs: 18, 20, 27, 30, 34, 36, 37, 38, 39, or 48. In some embodiments, the TβRII polypeptide lacks the amino acids corresponding to the first and second amino acids (threonine and isoleucine, respectively) of any one of SEQ ID NOs: 18, 20, 27, 30, 34, 36, 37, 38, 39, or 48. In some embodiments, the TβRII polypeptide lacks the amino acids corresponding to the first, second and third amino acids (threonine, isoleucine, and proline, respectively) of any one of SEQ ID NOs: 18, 20, 27, 30, 34, 36, 37, 38, 39, or 48. In some embodiments, the TβRII polypeptide lacks the amino acids corresponding to the first, second, third and fourth amino acids (threonine, isoleucine, proline, proline, respectively) of any one of SEQ ID NOs: 18, 20, 27, 30, 34, 36, 37, 38, 39, or 48.

In some embodiments, any of the TβRII polypeptides disclosed herein are at least 80%, 85%, 90%, 92%, 94%, 95%, 97%, 99% or 100% identical to the amino acid sequence of any one of SEQ ID NOs: 18 or 48, but lack the amino acid corresponding to the first amino acid (threonine) of SEQ ID NO: 18 or 48. In some embodiments, the TβRII polypeptide lacks the amino acids corresponding to the first and second amino acids (threonine and isoleucine, respectively) of SEQ ID NO: 18 or 48. In some embodiments, the TβRII polypeptide lacks the amino acids corresponding to the first, second and third amino acids (threonine, isoleucine, and proline, respectively) of SEQ ID NO: 18 or 48. In some embodiments, the TβRII polypeptide lacks the amino acids corresponding to the first, second, third and fourth amino acids (threonine, isoleucine, proline, proline, respectively) of SEQ ID NO: 18 or 48.

In some embodiments, the disclosure provides for a composition comprising a mixture of TβRII polypeptides, wherein the TβRII polypeptides in the composition each comprise an amino acid sequence that is at least 80%, 85%, 90%, 92%, 94%, 95%, 97%, 99% or 100% identical to the amino acid sequence of any one of SEQ ID NOs: 18, 20, 27, 30, 34, 36, 37, 38, 39, or 48; but wherein at least a portion of the TβRII polypeptides (e.g., at least 1%, 3%, 4%, 5%0, 1, 15%, 20%, 25%, 30%, 40%, 50%, 60%, 70%, 80%, 90%, 95%) in the composition include the amino acids corresponding to the first, second, third and fourth amino acids (threonine, isoleucine, proline and proline, respectively) of any one of SEQ ID NOs: 18, 20, 27, 30, 34, 36, 37, 38, 39, or 48; and wherein at least a portion of the TβRII polypeptides (e.g., at least 1%, 3%, 4%, 5%, 10%, 15%, 20%, 25%, 30%, 40%, 50%, 60%, 70%, 80%, 90%, 95%) in the composition lack one or more of the amino acids corresponding to the first, second, third and fourth amino acids (threonine, isoleucine, proline and proline, respectively) of any one of SEQ ID NOs: 18, 20, 27, 30, 34, 36, 37, 38, 39, or 48. In some embodiments, the disclosure provides for a composition comprising a mixture of TβRII polypeptides, wherein the TβRII polypeptides are at least 80%, 85%, 90%, 92%, 94%, 95%, 97%, 99% or 100% identical to the amino acid sequence of any one of SEQ ID NOs: 18 or 48, but wherein at least 30% to 80% of the TβRII polypeptides in the composition lack the amino acid corresponding to the first amino acid (threonine) of SEQ ID NO: 18 or 48. In some embodiments, the TβRII polypeptides are at least 80%, 85%, 90%, 92%, 94%, 95%, 97%, 99% or 100% identical to the amino acid sequence of any one of SEQ ID NOs: 63-68. In some embodiments, the TβRII polypeptides are at least 80%, 85%, 90%, 92%, 94%, 95%, 97%, 99% or 100% identical to the amino acid sequence of SEQ ID NO: 68.

In certain embodiments, the present disclosure contemplates specific mutations of the polypeptides (e.g., TβRII or betaglycan polypeptides) so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine (or asparagine-X-serine) (where "X" is any amino acid) which is specifically recognized by appropriate cellular glycosylation enzymes. The alteration may also be made by the addition of, or substitution by, one or more serine or threonine residues to the sequence of the wild-type polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a polypeptide is by chemical or enzymatic coupling of glycosides to the polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 published Sep. 11, 1987, and in Aplin and Wriston (1981) CRC Crit. Rev. Biochem., pp. 259-306, incorporated by reference herein. Removal of one or more carbohydrate moieties present on a polypeptide may be accomplished chemically and/or enzymatically. Chemical deglycosylation may involve, for example, exposure of the polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on polypeptides can be achieved by the use of a variety of endo- and exo-glycosidases as described by Thotakura et al. (1987) Meth. Enzymol. 138:350. The sequence of a polypeptide may be adjusted, as appropriate, depending on the type of expression system used, as mammalian, yeast, insect and plant cells may all introduce differing glycosylation patterns that can be affected by the amino acid sequence of the peptide. In general, polypeptides (e.g., TβRII or betaglycan polypeptides) for use in humans will be expressed in a mammalian cell line that provides proper glycosylation, such as HEK293 or CHO cell lines, although other mammalian expression cell lines, yeast cell lines with engineered glycosylation enzymes, and insect cells are expected to be useful as well.

This disclosure further contemplates a method of generating mutants, particularly sets of combinatorial mutants of a polypeptide (e.g., TβRII or betaglycan polypeptides), as well as truncation mutants; pools of combinatorial mutants are especially useful for identifying functional variant sequences. The purpose of screening such combinatorial libraries may be to generate, for example, polypeptide variants which can act as either agonists or antagonist, or alternatively, which possess novel activities all together. A variety of screening assays are provided below, and such assays may be used to evaluate variants. For example, a TβRII polypeptide variant may be screened for ability to bind to a TβRII ligand, to prevent binding of a TβRII ligand to a TβRII polypeptide or to interfere with signaling caused by a TβRII ligand. The activity of a TβRII polypeptide or its variants may also be tested in a cell-based or in vivo assay, particularly any of the assays disclosed in the Examples.

Combinatorially-derived variants can be generated which have a selective or generally increased potency relative to a polypeptide (e.g., TβRII or betaglycan polypeptides) comprising an extracellular domain of a naturally occurring polypeptide. Likewise, mutagenesis can give rise to variants which have serum half-lives dramatically different than the corresponding wild-type polypeptide. For example, the altered protein can be rendered either more stable or less stable to proteolytic degradation or other processes which result in destruction of, or otherwise elimination or inactivation of, a native TβRII polypeptide. Such variants, and the genes which encode them, can be utilized to alter TβRII polypeptide levels by modulating the half-life of the TβRII polypeptides. For instance, a short half-life can give rise to more transient biological effects and can allow tighter control of recombinant polypeptide levels within the patient. In an Fc fusion protein, mutations may be made in the linker (if any) and/or the Fc portion to alter the half-life of the protein.

A combinatorial library may be produced by way of a degenerate library of genes encoding a library of polypeptides which each include at least a portion of potential polypeptide (e.g., TβRII or betaglycan polypeptides) sequences. For instance, a mixture of synthetic oligonucleotides can be enzymatically ligated into gene sequences such that the degenerate set of potential polypeptide nucleotide sequences are expressible as individual polypeptides, or alternatively, as a set of larger fusion proteins (e.g., for phage display).

There are many ways by which the library of potential polypeptide (e.g., TβRII or betaglycan polypeptide) variants can be generated from a degenerate oligonucleotide sequence. Chemical synthesis of a degenerate gene sequence can be carried out in an automatic DNA synthesizer, and the synthetic genes then be ligated into an appropriate vector for expression. The synthesis of degenerate oligonucleotides is well known in the art (see for example, Narang, SA (1983) Tetrahedron 39:3; Itakura et al., (1981) Recombinant DNA, Proc. 3rd Cleveland Sympos. Macromolecules, ed. AG Walton, Amsterdam: Elsevier pp 273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, polypeptide (e.g., TβRII or betaglycan polypeptide) variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268: 2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of polypeptides (e.g., TβRII or betaglycan polypeptides). The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include ligand binding assays and ligand-mediated cell signaling assays.

In certain embodiments, the polypeptides (e.g., TβRII or betaglycan polypeptides) of the disclosure may further comprise post-translational modifications in addition to any that are naturally present in the native polypeptides. Such modifications include, but are not limited to, acetylation, carboxylation, glycosylation, phosphorylation, lipidation, pegylation (polyethylene glycol) and acylation. As a result, the modified polypeptides may contain non-amino acid elements, such as polyethylene glycols, lipids, mono- or poly-saccharides, and phosphates. Effects of such non-amino acid elements on the functionality of a polypeptide may be tested as described herein for other polypeptide variants. When a polypeptide is produced in cells by cleaving a nascent form of the polypeptide, post-translational processing may also be important for correct folding and/or function of the protein. Different cells (such as CHO, HeLa, MDCK, 293, WI38, NIH-3T3 or HEK-293) have specific cellular machinery and characteristic mechanisms for such post-translational activities and may be chosen to ensure the correct modification and processing of the polypeptides.

In certain aspects, the disclosure provides for fusion proteins (e.g., TβRII or betaglycan fusion proteins), and in some embodiments, a first portion (e.g., a TβRII or betaglycan polypeptide portion) is connected to a heterologous portion (e.g., Fc portion) by means of a linker. In some embodiments, the linkers are glycine and serine rich linkers. Other near neutral amino acids, such as, but not limited to, Thr, Asn, Pro and Ala, may also be used in the linker sequence. In some embodiments, the linker comprises various permutations of amino acid sequences containing Gly and Ser. In some embodiments, the linker is greater than 10 amino acids in length. In further embodiments, the linkers have a length of at least 12, 15, 20, 21, 25, 30, 35, 40, 45 or 50 amino acids. In some embodiments, the linker is less than 40, 35, 30, 25, 22 or 20 amino acids. In some embodiments, the linker is 10-50, 10-40, 10-30, 10-25, 10-21, 10-15, 10, 15-25, 17-22, 20, or 21 amino acids in length. In some preferred embodiments, the linker comprises the amino acid sequence GlyGlyGlyGlySer (GGGGS) (SEQ ID NO: 19), or repetitions thereof (GGGGS)n, where n≥2. In particular embodiments n≥3, or n=3-10. The application teaches the surprising finding that proteins comprising a TβRII portion and a heterologous portion fused together by means of a (GGGGS)$_4$ linker were associated with a stronger affinity for TGFβ1 and TGFβ3 as compared to a TβRII fusion protein where n<4. As such, in preferred embodiments, n≥4, or n=4-10. The application also teaches that proteins comprising (GGGGS)n linkers in which n>4 had similar inhibitory properties as proteins having the (GGGGS)$_4$ linker. As such, in some embodiments, n is not greater than 4 in a (GGGGS)n linker. In some embodiments, n=4-10, 4-9, 4-8, 4-7, 4-6, 4-5, 5-8, 5-7, or 5-6. In some embodiments, n=3, 4, 5, 6, or 7. In particular embodiments, n=4. In some embodiments, a linker comprising a (GGGGS)$_n$ sequence also comprises an N-terminal threonine. In some embodiments, the linker is any one of the following:

```
GGGGSGGGGS                                    (SEQ ID NO: 21)

TGGGGSGGGGS                                   (SEQ ID NO: 4)

TGGGGSGGGGSGGGGS                              (SEQ ID NO: 5)

TGGGGSGGGGSGGGGSGGGGS                         (SEQ ID NO: 6)

TGGGGSGGGGSGGGGSGGGGSGGGGS                    (SEQ ID NO: 25)

TGGGGSGGGGSGGGGSGGGGSGGGGSGGGGS               (SEQ ID NO: 26)
or
TGGGGSGGGGSGGGGSGGGGSGGGGSGGGGSGGGGS.         (SEQ ID NO: 40)
```

In some embodiments, the linker comprises the amino acid sequence of TGGGPKSCDK (SEQ ID NO: 7). In some embodiments, the linker is any one of SEQ ID NOs: 21, 4-7, 25-26 or 40 lacking the N-terminal threonine. In some embodiments, the linker does not comprise the amino acid sequence of SEQ ID NO: 26 or 40.

In certain aspects, functional variants or modified forms of the TβRII (or betaglycan) polypeptides include fusion proteins having at least a portion of the TβRII (or betaglycan) polypeptides and one or more heterologous portions. Well-known examples of such heterologous portions include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A heterologous portion may be selected so as to confer a desired property. For example, some heterologous portions are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS6) fusion partners. As another example, a heterologous portion may be selected so as to facilitate detection of the TβRII (or betaglycan) polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the heterologous portions have a protease cleavage site, such as for Factor Xa or Thrombin, which allows the relevant protease to partially digest the fusion proteins and thereby liberate the recombinant proteins therefrom. The liberated proteins can then be isolated from the heterologous portion by subsequent chromatographic separation. In certain preferred embodiments, a TβRII (or betaglycan) polypeptide is fused with a domain that stabilizes the TβRII polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Likewise, fusions to human serum albumin can confer desirable properties. Other types of heterologous portions that may be selected include multimerizing (e.g., dimerizing, tetramerizing) domains and functional domains.

As specific examples, the present disclosure provides fusion proteins comprising variants of TβRII polypeptides fused to an Fc domain sequence of SEQ ID NO: 49. Optionally, the Fc domain has one or more mutations at residues such as Asp-265, Lys-322, and Asn-434 (numbered in accordance with the corresponding full-length IgG). In certain cases, the mutant Fc domain having one or more of these mutations (e.g., Asp-265 mutation) has reduced ability of binding to the Fcγ receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wildtype Fc domain.

In one embodiment, the class of immunoglobulin from which the heavy chain constant region is derived is IgG (Igγ) (γ subclasses 1, 2, 3, or 4).

An example of a native amino acid sequence that may be used for the Fc portion of human IgG1 (G1Fc) is shown below (SEQ ID NO: 58). Dotted underline indicates the hinge region, and solid underline indicates positions with naturally occurring variants. In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NO: 58. Naturally occurring variants in G1Fc would include E134D and M136L according to the numbering system used in SEQ ID NO: 58 (see Uniprot P01857).

```
                                                              (SEQ ID NO: 58)
  1 THTCPPCPAP ELLGGPSVFL FPPKPKDTLM ISRTPEVTCV VVDVSHEDPE

51 VKFNWYVDGV EVHNAKTKPR EEQYNSTYRV VSVLTVLHQD WLNGKEYKCK

101 VSNKALPAPI EKTISKAKGQ PREPQVYTLP PSREEMTKNQ VSLTCLVKGF

151 YPSDIAVEWE SNGQPENNYK TTPPVLDSDG SFFLYSKLTV DKSRWQQGNV

201 FSCSVMHEAL HNHYTQKSLS LSPGK
```

It is understood that different elements of the fusion proteins may be arranged in any manner that is consistent with the desired functionality. For example, a TβRII (or betaglycan) polypeptide may be placed C-terminal to a heterologous domain, or, alternatively, a heterologous domain may be placed C-terminal to a TβRII (or betaglycan) polypeptide. The TβRII (or betaglycan) polypeptide domain and the heterologous domain need not be adjacent in a fusion protein, and additional domains or amino acid sequences may be included C- or N-terminal to either domain or between the domains.

As used herein, the term "immunoglobulin Fc domain" or simply "Fc" is understood to mean the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region. In a preferred embodiment the immunoglobulin Fc region comprises at least an immunoglobulin hinge region a CH2 domain and a CH3 domain, and preferably lacks the CH1 domain. In some embodiments, the immunoglobulin Fc region is a human immunoglobulin Fc region.

Optionally, the IgG1 Fc domain has one or more mutations at residues such as Asp-265, lysine 322, and Asn-434. In certain cases, the mutant IgG1 Fc domain having one or more of these mutations (e.g., Asp-265 mutation) has reduced ability of binding to the Fcγ receptor relative to a wild-type Fc domain. In other cases, the mutant Fc domain having one or more of these mutations (e.g., Asn-434 mutation) has increased ability of binding to the MHC class I-related Fc-receptor (FcRN) relative to a wild-type IgG1 Fc domain.

An example of a native amino acid sequence that may be used for the Fc portion of human IgG2 (G2Fc) is shown below (SEQ ID NO: 59). Dotted underline indicates the hinge region and double underline indicates positions where there are data base conflicts in the sequence (according to UniProt P01859). In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NO: 59.

```
                                                              (SEQ ID NO: 59)
  1 VECPPCPAPP VAGPSVFLFP PKPKDTLMIS RTPEVTCVVV DVSHEDPEVQ

51 FNWYVDGVEV HNAKTKPREE QFNSTFRVVS VLTVVHQDWL NGKEYKCKVS

101 NKGLPAPIEK TISKTKGQPR EPQVYTLPPS REEMTKNQVS LTCLVKGFYP

151 SDIAVEWESN GQPENNYKTT PPMLDSDGSF FLYSKLTVDK SRWQQGNVFS

201 CSVMHEALHN HYTQKSLSLS PGK
```

Two examples of amino acid sequences that may be used for the Fc portion of human IgG3 (G3Fc) are shown below. The hinge region in G3Fc can be up to four times as long as in other Fc chains and contains three identical 15-residue segments preceded by a similar 17-residue segment. The first G3Fc sequence shown below (SEQ ID NO: 60) contains a short hinge region consisting of a single 15-residue segment, whereas the second G3Fc sequence (SEQ ID NO: 61)

contains a full-length hinge region. In each case, dotted underline indicates the hinge region, and solid underline indicates positions with naturally occurring variants according to UniProt P01859. In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NOs: 60 or 61.

```
                                                         (SEQ ID NO: 60)
  1 EPKSCDTPPP CPRCPAPELL GGPSVFLFPP KPKDTLMISR TPEVTCVVVD

51 VSHEDPEVQF KWYVDGVEVH NAKTKPREEQ YNSTFRVVSV LTVLHQDWLN

101 GKEYKCKVSN KALPAPIEKT ISKTKGQPRE PQVYTLPPSR EEMTKNQVSL

151 TCLVKGFYPS DIAVEWESSG QPENNYNTTP PMLDSDGSFF LYSKLTVDKS

201 RWQQGNIFSC SVMHEALHNR FTQKSLSLSP GK
```

```
                                                         (SEQ ID NO: 61)
  1 ELKTPLGDTT HTCPRCPEPK SCDTPPPCPR CPEPKSCDTP PPCPRCPEPK

51 SCDTPPPCPR CPAPELLGGP SVFLFPPKPK DTLMISRTPE VTCVVVDVSH

101 EDPEVQFKWY VDGVEVHNAK TKPREEQYNS TFRVVSVLTV LHQDWLNGKE

151 YKCKVSNKAL PAPIEKTISK TKGQPREPQV YTLPPSREEM TKNQVSLTCL

201 VKGFYPSDIA VEWESSGQPE NNYNTTPPML DSDGSFFLYS KLTVDKSRWQ

251 QGNIFSCSVM HEALHNRFTQ KSLSLSPGK
```

Naturally occurring variants in G3Fc (for example, see Uniprot P01860) include E68Q, P76L, E79Q, Y81F, D97N, N100D, T124A, S169N, S169del, F221Y when converted to the numbering system used in SEQ ID NO: 60, and the present disclosure provides fusion proteins comprising G3Fc domains containing one or more of these variations. In addition, the human immunoglobulin IgG3 gene (IGHG3) shows a structural polymorphism characterized by different hinge lengths [see Uniprot P01859]. Specifically, variant WIS is lacking most of the V region and all of the CH1 region. It has an extra interchain disulfide bond at position 7 in addition to the 11 normally present in the hinge region. Variant ZUC lacks most of the V region, all of the CH1 region, and part of the hinge. Variant OMM may represent an allelic form or another gamma chain subclass. The present disclosure provides additional fusion proteins comprising G3Fc domains containing one or more of these variants.

An example of a native amino acid sequence that may be used for the Fc portion of human IgG4 (G4Fc) is shown below (SEQ ID NO: 62). Dotted underline indicates the hinge region. In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NO: 62.

```
                                                         (SEQ ID NO: 62)
  1 ESKYGPPCPS CPAPEFLGGP SVFLFPPKPK DTLMISRTPE VTCVVVDVSQ

51 EDPEVQFNWY VDGVEVHNAK TKPREEQFNS TYRVVSVLTV LHQDWLNGKE

101 YKCKVSNKGL PSSIEKTISK AKGQPREPQV YTLPPSQEEM TKNQVSLTCL

151 VKGFYPSDIA VEWESNGQPE NNYKTTPPVL DSDGSFFLYS RLTVDKSRWQ

201 EGNVFSCSVM HEALHNHYTQ KSLSLSLGK
```

A variety of engineered mutations in the Fc domain are presented herein with respect to the G1Fc sequence (SEQ ID NO: 58), and analogous mutations in G2Fc, G3Fc, and G4Fc can be derived from their alignment with G1Fc in FIG. 7 Due to unequal hinge lengths, analogous Fc positions based on isotype alignment (FIG. 7) possess different amino acid numbers in SEQ ID NOs: 58, 59, 60, 61, and 62. It can also be appreciated that a given amino acid position in an immunoglobulin sequence consisting of hinge, $C_H2$, and $C_H3$ regions (e.g., SEQ ID NOs: 58, 59, 60, 61, and 62) will be identified by a different number than the same position when numbering encompasses the entire IgG1 heavy-chain constant domain (consisting of the $C_H1$, hinge, $C_H2$, and $C_H3$ regions) as in the Uniprot database.

Other classes of immunoglobulin, IgA (Igα), IgD (Igδ), IgE (Igε) and IgM (Igμ), may be used. The choice of appropriate immunoglobulin heavy chain constant region is discussed in detail in U.S. Pat. Nos. 5,541,087 and 5,726,044. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region preferably comprises at least a portion of a hinge domain, and preferably at least a portion of a CH3 domain of Fc gamma or the homologous domains in any of IgA, IgD, IgE, or IgM.

Furthermore, it is contemplated that substitution or deletion of amino acids within the immunoglobulin heavy chain constant regions may be useful in the practice of the methods and compositions disclosed herein. One example would be to introduce amino acid substitutions in the upper CH2 region to create an Fc variant with reduced affinity for Fc receptors (Cole et al. (1997) J. Immunol. 159:3613).

In some embodiments, the disclosure provides for TβRII polypeptides fusion proteins comprising an amino acid sequence that is at least 70%, 75%, 80%, 85%, 90%, 91%, 92%, 93%, 94%, 95%, 96%, 97%, 98%, or 99% identical to the amino acid sequence of any one of SEQ ID NOs: 11, 13, 15 and 17, or biologically active fragments thereof. In some embodiments, the TβRII polypeptides fusion proteins comprise an amino acid sequence that is at least 70%, 75%, 80%, 85%, 90%, 91%, 92%, 93%, 94%, 95%, 96%, 97%, 98%, or 99% identical to the amino acid sequence of any one of SEQ ID NOs: 11, 13, and 15, or biologically active fragments thereof. In some embodiments, the TβRII polypeptides fusion proteins comprise an amino acid sequence that is at least 70%, 75%, 80%, 85%, 90%, 91%, 92%, 93%, 94%, 95%, 96%, 97%, 98%, or 99% identical to the amino acid sequence of any one of SEQ ID NO: 13, or a biologically active fragment thereof. In some embodiments, the TβRII polypeptides fusion proteins comprise an amino acid sequence that is at least 80%, 85%, 90%, 95%, 96%, 97%, 98%, or 99% identical to the amino acid sequence of any one of SEQ ID NO: 63, or a biologically active fragment thereof. In some embodiments, the TβRII polypeptides fusion proteins comprise an amino acid sequence that is at least 80%, 85%, 90%, 95%, 96%, 97%, 98%, or 99% identical to the amino acid sequence of any one of SEQ ID NO: 48, or a biologically active fragment thereof. In some embodiments, the TβRII polypeptides fusion proteins comprise an amino acid sequence that is at least 80%, 85%, 90%, 95%, 96%, 97%, 98%, or 99% identical to the amino acid sequence of any one of SEQ ID NO: 64, or a biologically active fragment thereof. In some embodiments, the TβRII polypeptides fusion proteins comprise an amino acid sequence that is at least 80%, 85%, 90%, 95%, 96%, 97%, 98%, or 99% identical to the amino acid sequence of any one of SEQ ID NO: 65, or a biologically active fragment thereof. In some embodiments, the TβRII polypeptides fusion proteins comprise an amino acid sequence that is at least 80%, 85%, 90%, 95%, 96%, 97%, 98%, or 99% identical to the amino acid sequence of any one of SEQ ID NO: 66, or a biologically active fragment thereof. In some embodiments, the TβRII polypeptides fusion proteins comprise an amino acid sequence that is at least 80%, 85%, 90%, 95%, 96%, 97%, 98%, or 99% identical to the amino acid sequence of any one of SEQ ID NO: 67, or a biologically active fragment thereof. In some embodiments, the TβRII polypeptides fusion proteins comprise an amino acid sequence that is at least 80%, 85%, 90%, 95%, 96%, 97%, 98%, or 99% identical to the amino acid sequence of any one of SEQ ID NO: 68, or a biologically active fragment thereof. In some embodiments, the TβRII polypeptides fusion protein comprises an amino acid sequence that is at least 70%, 75%, 80%, 85%, 90%, 91%, 92%, 93%, 94%, 95%, 96%, 97%, 98%, or 99% identical to the amino acid sequence of SEQ ID NO: 49, or a biologically active fragment thereof.

In some embodiments, the fusion proteins described herein have improved binding affinity for TGFβ1 and TGFβ3. In some embodiments, a fusion protein comprising a linker at least 10 amino acids in length (e.g., a fusion protein having the amino acid sequence of any one of SEQ ID NOs: 11, 13, 15, 48, and 63-68) has improved binding affinity for TGFβ1 and TGFβ3 as compared to a reference fusion protein (e.g., a fusion protein having the amino acid sequence of SEQ ID NO: 9). In some embodiments, the fusion protein binds to TGFβ1 with a $K_D$ of less than 200 pM, less than 150 pM, less than 100 pM, less than 75 pM, less than 50 pM or less than 25 pM. In some embodiments, the fusion protein binds to TGFβ3 with a $K_D$ of less than 75 pM, less than 70 pM, less than 60 pM, less than 50 pM, less than 40 pM, less than 35 pM, less than 25 pM, less than 15, less than 10, or less than 5 pM.

In some embodiments any of the polypeptides disclosed herein inhibits TGFβ1 and/or TGFβ3 in a measurable assay. In some embodiments, the polypeptide inhibits TGFβ1 with an $IC_{50}$ of less than 1.0, 0.9, 0.8, 0.7, 0.6, 0.5, 0.4, 0.3, 0.2, 0.1, 0.08, 0.09, 0.07, 0.06, 0.05, 0.04, 0.03, or 0.02 nM, as determined using a reporter gene assay. In some embodiments, the polypeptide inhibits TGFβ3 with an $IC_{50}$ of less than 1.0, 0.9, 0.8, 0.7, 0.6, 0.5, 0.4, 0.3, 0.2, 0.1, 0.09, 0.08, 0.07, 0.06, 0.05, 0.04, 0.03, or 0.02 nM, as determined using a reporter gene assay. In some embodiments, the reporter gene assay is a CAGA reporter assay. In some embodiments, the CAGA assay is based on a human lung carcinoma cell line transfected with a pGL3(CAGA)12 reporter plasmid (Dennler et al, 1998, EMBO 17: 3091-3100) as well as a Renilla reporter plasmid (pRLCMV) to control for transfection efficiency. The CAGA motif is present in the promoters of TGFβ-responsive genes (for example, PAI-1), so this vector is of general use for factors signaling through SMAD2 and SMAD3. See, e.g., Example 2.

In some embodiments, the disclosure provides for TβRII (or betaglycan) containing fusion polypeptides. The fusion polypeptides may be prepared according to any of the methods disclosed herein or that are known in the art.

In some embodiments, any of the fusion polypeptides disclosed herein comprises the following components: a) any of the TβRII (or betaglycan) polypeptides disclosed herein ("A"), b) any of the linkers disclosed herein ("B"), c) any of the heterologous portions disclosed herein ("C"), and optionally a linker ("X"). In such embodiments, the fusion polypeptide may be arranged in a manner as follows (N-terminus to C-terminus): A-B-C or C-B-A. In such embodiments, the fusion polypeptide may be arranged in a manner as follows (N-terminus to C-terminus): X-A-B-C or X-C-B-A. In some embodiments, the fusion polypeptide comprises each of A, B and C (and optionally a leader sequence such as the amino acid sequence of SEQ ID NO: 23), and comprises no more than 100, 90, 80, 70, 60, 50, 40, 30, 20, 10, 5, 4, 3, 2 or 1 additional amino acids (but which may include further post-translational modifications, such as PEGylation).

In some embodiments, the fusion polypeptide comprises a leader sequence (e.g., SEQ ID NO: 23) positioned in a manner as follows (N-terminus to C-terminus): X-A-B-C, and the fusion polypeptide comprises 1, 2, 3, 4, or 5 amino acids between X and A. In some embodiments, the fusion polypeptide comprises a leader sequence (e.g., SEQ ID NO: 23) positioned in a manner as follows (N-terminus to C-terminus): X-C-B-A, and the fusion polypeptide comprises 1, 2, 3, 4, or 5 amino acids between X and C. In some embodiments, the fusion polypeptide comprises a leader sequence (e.g., SEQ ID NO: 23) positioned in a manner as follows (N-terminus to C-terminus): X-A-B-C, and the fusion polypeptide comprises an alanine between X and A. In some embodiments, the fusion polypeptide comprises a leader sequence (e.g., SEQ ID NO: 23) positioned in a manner as follows (N-terminus to C-terminus): X-C-B-A, and the fusion polypeptide comprises an alanine between X and C. In some embodiments, the fusion polypeptide comprises a leader sequence (e.g., SEQ ID NO: 23) positioned in a manner as follows (N-terminus to C-terminus): X-A-B-C, and the fusion polypeptide comprises a glycine and an alanine between X and A. In some embodiments, the fusion polypeptide comprises a leader sequence (e.g., SEQ ID NO: 23) positioned in a manner as follows (N-terminus to C-terminus): X-C-B-A, and the fusion polypeptide comprises a glycine and an alanine between X and C. In some embodiments, the fusion polypeptide comprises a leader sequence (e.g., SEQ ID NO: 23) positioned in a manner as follows (N-terminus to C-terminus): X-A-B-C, and the fusion polypeptide comprises a threonine between X and A. In some embodiments, the fusion polypeptide comprises a leader sequence (e.g., SEQ ID NO: 23) positioned in a manner as follows (N-terminus to C-terminus): X-C-B-A, and the fusion polypeptide comprises a threonine between X and C.

In some embodiments, the fusion polypeptide comprises an amino acid sequence that is at least 70%, 75%, 80%, 85%, 90%, 91%, 92%, 93%, 94%, 95%, 96%, 97%, 98%, or 99% identical to any of the TβRII polypeptide amino acid sequences disclosed herein (e.g., SEQ ID NO: 18), wherein the TβRII polypeptide portion of the fusion polypeptide comprises no more than 10, 9, 8, 7, 6, 5, 4, 3, 2 or 1 additional amino acids (but which may include further post-translational modifications, such as PEGylation). In some embodiments, the fusion polypeptide comprises an amino acid sequence that is at least 70%, 75%, 80%, 85%, 90%, 91%, 92%, 93%, 94%, 95%, 96%, 97%, 98%, or 99% identical to any of the linker sequences disclosed herein (e.g., SEQ ID NO: 6), wherein the linker portion of the fusion polypeptide comprises no more than 5, 4, 3, 2 or 1 additional amino acids (but which may include further post-translational modifications, such as PEGylation). In some embodiments, the fusion polypeptide comprises an amino acid sequence that is at least 70%, 75%, 80%, 85%, 90%, 91%, 92%, 93%, 94%, 95%, 96%, 97%, 98%, or 99% identical to any of the heterologous portion sequences disclosed herein (e.g., SEQ ID NO: 49), wherein the heterologous portion of the fusion polypeptide comprises no more than 25, 20, 15, 10, 5, 4, 3, 2, or 1 additional amino acids (but which may include further post-translational modifications, such as PEGylation). In some embodiments, the fusion polypeptide comprises any of the TβRII polypeptide amino acid sequences disclosed herein (e.g., SEQ ID NO: 18), wherein the TβRII polypeptide portion of the fusion polypeptide comprises no more than 10, 9, 8, 7, 6, 5, 4, 3, 2 or 1 additional amino acids (but which may include further post-translational modifications, such as PEGylation). In some embodiments, the fusion polypeptide comprises any of the linker sequences disclosed herein (e.g., SEQ ID NO: 6), wherein the linker portion of the fusion polypeptide comprises no more than 5, 4, 3, 2 or 1 additional amino acids (but which may include further post-translational modifications, such as PEGylation). In some embodiments, the fusion polypeptide comprises any of the heterologous portion sequences disclosed herein (e.g., SEQ ID NO: 49), wherein the heterologous portion of the fusion polypeptide comprises no more than 25, 20, 15, 10, 5, 4, 3, 2, or 1 additional amino acids (but which may include further post-translational modifications, such as PEGylation).

In some embodiments, the disclosure provides for a fusion polypeptide, wherein the fusion polypeptide consists or consists essentially of (and not necessarily in the following order): a) an amino acid sequence that is at least 70%, 75%, 80%, 85%, 90%, 91%, 92%, 93%, 94%, 95%, 96%, 97%, 98%, or 99% identical to any of the TβRII polypeptide amino acid sequences disclosed herein (e.g., SEQ ID NO: 18), wherein the TβRII polypeptide portion of the fusion polypeptide comprises no more than 10, 9, 8, 7, 6, 5, 4, 3, 2 or 1 additional amino acids (but which may include further post-translational modifications, such as PEGylation); b) an amino acid sequence that is at least 70%, 75%, 80%, 85%, 90%, 91%, 92%, 93%, 94%, 95%, 96%, 97%, 98%, or 99% identical to any of the linker sequences disclosed herein (e.g., SEQ ID NO: 6), wherein the linker portion of the fusion polypeptide comprises no more than 5, 4, 3, 2 or 1 additional amino acids (but which may include further post-translational modifications, such as PEGylation); and c) an amino acid sequence that is at least 70%, 75%, 80%, 85%, 90%, 91%, 92%, 93%, 94%, 95%, 96%, 97%, 98%, or 99% identical to any of the heterologous portion sequences disclosed herein (e.g., SEQ ID NO: 49), wherein the heterologous portion of the fusion polypeptide comprises no more than 25, 20, 15, 10, 5, 4, 3, 2, or 1 additional amino acids (but which may include further post-translational modifications, such as PEGylation); and d) optionally a leader sequence (e.g., SEQ ID NO: 23). In some embodiments, the disclosure provides for a fusion polypeptide, wherein the fusion polypeptide consists or consists essentially of (and not necessarily in the following order): a) any of the TβRII polypeptide amino acid sequences disclosed herein (e.g., SEQ ID NO: 18), wherein the TβRII polypeptide portion of the fusion polypeptide comprises no more than 10, 9, 8, 7, 6, 5, 4, 3, 2 or 1 additional amino acids (but which may include further post-translational modifications, such as PEGylation); b) any of the linker sequences disclosed herein (e.g., SEQ ID NO: 6), wherein the linker portion of the fusion polypeptide comprises no more than 5, 4, 3, 2 or 1 additional amino acids (but which may include further post-translational modifications, such as PEGylation); and c) any of the heterologous portion sequences disclosed herein (e.g., SEQ ID NO: 49), wherein the heterologous portion of the fusion polypeptide comprises no more than 25, 20, 15, 10, 5, 4, 3, 2, or 1 additional amino acids (but which may include further post-translational modifications, such as PEGylation); and d) optionally a leader sequence (e.g., SEQ ID NO: 23).

In some embodiments, the disclosure provides for a fusion polypeptide consisting of or consisting essentially of (and not necessarily in the following order): a) a TβRII polypeptide portion consisting of an amino acid sequence that is at least 70%, 75%, 80%, 85%, 90%, 91%, 92%, 93%, 94%, 95%, 96%, 97%, 98%, or 99% identical to the amino acid sequence of SEQ ID NO: 18 and no more than 10, 9, 8, 7, 6, 5, 4, 3, 2 or 1 additional amino acids (but which may include further post-translational modifications, such as PEGylation); b) a linker portion consisting of an amino acid sequence that is at least 70%, 75%, 80%, 85%, 90%, 91%, 92%, 93%, 94%, 95%, 96%, 97%, 98%, or 99% identical to the amino acid sequence of SEQ ID NO: 6 and no more than 5, 4, 3, 2 or 1 additional amino acids (but which may include further post-translational modifications, such as PEGylation); and c) a heterologous portion consisting of an amino acid sequence that is at least 70%, 75%, 80%, 85%, 90%, 91%, 92%, 93%, 94%, 95%, 96%, 97%, 98%, or 99% identical to the amino acid sequence of SEQ ID NO: 49 and no more than 25, 20, 15, 10, 5, 4, 3, 2, or 1 additional amino acids (but which may include further post-translational modifications, such as PEGylation); and d) optionally a leader sequence (e.g., SEQ ID NO: 23). In some embodiments, the disclosure provides for a fusion polypeptide consisting or consisting essentially of (and not necessarily in the following order): a) a TβRII polypeptide portion consisting of the amino acid sequence of SEQ ID NO: 18 and no more than 10, 9, 8, 7, 6, 5, 4, 3, 2 or 1 additional amino acids (but which may include further post-translational modifications, such as PEGylation); b) a linker portion consisting of the amino acid sequence of SEQ ID NO: 6 and no more than 5, 4, 3, 2 or 1 additional amino acids (but which may include further post-translational modifications, such as PEGylation); and c) a heterologous portion consisting of the amino acid sequence of SEQ ID NO: 49 and no more than 25, 20, 15, 10, 5, 4, 3, 2, or 1 additional amino acids (but which may include further post-translational modifications, such as PEGylation); and d) optionally a leader sequence (e.g., SEQ ID NO: 23).

In some embodiments, the fusion protein does not comprise a leader sequence. In some embodiments, the fusion protein comprises an amino acid sequence that is at least 70%, 75%, 80%, 85%, 90%, 91%, 92%, 93%, 94%, 95%, 96%, 97%, 98%, or 99% identical to the amino acid sequence of SEQ ID NO: 48.

```
                                  (SEQ ID NO: 48)
TIPPHVQKSDVEMEAQKDEIICPSCNRTAHPLRH

INNDMIVTDNNGAVKFPQLCKFCDVRFSTCDNQK

SCMSNCSITSICEKPQEVCVAVWRKNDENITLET

VCHDPKLPYHDFILEDAASPKCIMKEKKKPGETF

FMCSCSSDECNDNIIFSEEYNTSNPDTGGGGSGG

GGSGGGGSGGGGSTHTCPPCPAPELLGGPSVFLF

PPKPKDTLMISRTPEVTCVVVDVSHEDPEVKFNW

YVDGVEVHNAKTKPREEQYNSTYRVVSVLTVLHQ

DWLNGKEYKCKVSNKALPAPIEKTISKAKGQPRE

PQVYTLPPSREEMTKNQVSLTCLVKGFYPSDIAV

EWESNGQPENNYKTTPPVLDSDGSFFLYSKLTVD

KSRWQQGNVFSCSVMHEALHNHYTQKSLSLSPGK
```

In some embodiments, the disclosure provides for a TβRII fusion polypeptide wherein the polypeptide does not comprise an antibody or antigen-binding portion thereof. In some embodiments, the polypeptide does not bind with appreciable affinity to a cytokine other than a transforming growth factor beta superfamily ligand (e.g., TGFβ1, TGFβ2 and/or TGFβ3). In some embodiments, the polypeptide does not bind with appreciable affinity to a cytokine other than TGFβ1, TGFβ2 and/or TGFβ3. In some embodiments, the polypeptide does not bind with appreciable affinity to a cytokine other than TGFβ1 and/or TGFβ3. In some embodiments, the polypeptide does not bind with appreciable affinity to CD4, CD8, CD25, CTLA-4, IL-10, TGFβ Receptor, PD-1, PD-L1, PD-L2, RANK, RANKL, HER2/neu, EGFR1, CD20, VEGF, TNF-α, TNFR2, FoxP3, CD80, CD86, IFN-α, IFN-β, IFN-γ, GITR, 4-1BB, OX-40, TLR1-10, ErbB-1, HER1, ErbB-3/HER3, ErbB-4/HER4, IGFR, IGFBP, IGF-1R, PDGFR, FGFR, VEGFR, HGFR, TRK receptor, ephrin receptors, AXL receptors, LTK receptors, TIE receptors, angiopoietin1, 2, ROR receptor, DDR receptor, RET receptor, KLG receptor, RYK receptor, MuSK receptor, ILβR, IlαR, TNTRSF, TRAIL receptor, ARTC1, alpha-actinin-4, Bcr-abl, B-RAF, caspases, beta-catenin, fibronectin, GPNMB, GDP-L, LDLR, HLA-A2, MLA-A11, HSP70, KIAA205, MART2, MUM-1, 2, 3, PAP, neo-PAP, NFYC, OGT, OS-9, pml-RARalpha fusion protein, PRDX5, PTPRK, KRAS2, NRAS, HRAS, RBAF600, SIRT2. SNRPDI, SYT-SSX1 or -SSX2 fusion protein, Triosephosphate Isomerase, BAGE, BAGE-1. BAGE-2, 3, 4, 5, GAGE-1, 2, 3, 4, 5, 6, 7, 8, GnT-V, HERV-K MEL, KK-LC, KM-HIN-1, LAGE, LAGE-1, CAMEL, MAGE-1, MAGE-A2, MAGE-A3, MAGE-A4, MAGE-AS, MAGE-A6, MAGE-A8, MAGE-A9, MAGE-A10. MAGE-A11, MAGE-A12, MAGE-3, MAGE-B1, MAGE-B2, MAGE-B5. MAGE-B6, MAGE-C1, MAGE-C2, mucin 1 (MUC1), MART-1/Melan-A (MLANA), gp100, gp100/Pme117 (SILV), tyrosinase (TYR), TRP-1, HAGE, NA-88, NY-ESO-1, NY-ESO-1/LAGE-2, SAGE, Sp17. SSX-1, 2, 3, 4, TRP2-1NT2, carcino-embryonic antigen (CEA), Kallikfein 4, mammaglobm-A, OA1, prostate specific antigen (PSA), prostate specific membrane antigen, TRP-1/, 75. TRP-2, AIM-2. BING-4, CPSF, cyclin D1, Ep-CAM, EpbA3, FGF-5, gp250, iCE), AFP, M-CSF, mdm-2, MUC1, p53 (TP53), PBF, FRAME, PSMA, RAGE-1. RNF43, RU2AS, SOX10, STEAP1, survivin (BIRCS), hTERT, telomerase, WTi, SYCP1, BRDT, SPANX, XAGE, ADAM2, PAGE-5, LIP1, CTAGE-1, CSAGE, MMA1, CAGE, BORIS, HOM-TES-85, AF15qI4, HCA66I, LDHC, MORC, SGY-1, SPO11, TPX1, NY-SAR-35, FTHLI7, NXF2 TDRD1, TEX 15, FATE, TPTE, estrogen receptors (ER), androgen receptors (AR), CD40, CD30, CD20, CD19, CD33, CD4, CD25, CD3, CA 72-4, CA 15-3, CA 27-29, CA 125, CA 19-9, beta-human chorionic gonadotropin, 1-2 microglobulin, squamous cell carcinoma antigen, neuron-specific enoJase, heat shock protein gp96, GM2, sargramostim, CTLA-4, 707-AP, ART-4, CAP-1, CLCA2, Cyp-B, HST-2, HPV proteins, EBV proteins, Hepatitis B or C virus proteins, and/or HIV proteins.

In some embodiments, the disclosure provides for a TβRII fusion polypeptide wherein the polypeptide does not comprise an additional ligand binding domain in addition to the TβRII domain. In some embodiments, the polypeptide comprises a linear amino acid sequence comprising a TβRII domain and a heterologous portion (e.g., an Fc portion), but the linear amino acid sequence does not comprise any additional ligand binding domains. In some embodiments, the polypeptide comprises a linear amino acid sequence comprising a TβRII domain and an Fc portion, but the linear amino acid sequence does not comprise any additional ligand binding domains. In some embodiments, the disclosure provides for a TβRII fusion polypeptide wherein the polypeptide does not comprise multiple ligand binding domains in a single linear amino acid sequence. In some embodiments, the disclosure provides for a TβRII fusion polypeptide wherein the polypeptide does not comprise more than one continuous linker sequence in a single linear amino acid sequence. In some embodiments, the polypeptide does not comprise multiple continuous glycine and/or serine linkers (e.g., a linker comprising (GGGGS)n, wherein n=>4) in a single linear amino acid sequence. In some embodiments, the disclosure provides for a TβRII fusion polypeptide wherein the heterologous portion is an Fc domain, and wherein only one continuous linker is covalently bound to the Fc domain. In some embodiments, the only one continuous linker comprises or consists of a (GGGGS)n linker, wherein n=>4.

The application further provides Fc fusion proteins with engineered or variant Fc regions. Such antibodies and Fc fusion proteins may be useful, for example, in modulating effector functions, such as, antigen-dependent cytotoxicity (ADCC) and complement-dependent cytotoxicity (CDC). Additionally, the modifications may improve the stability of the antibodies and Fc fusion proteins. Amino acid sequence variants of the antibodies and Fc fusion proteins are prepared by introducing appropriate nucleotide changes into the DNA, or by peptide synthesis. Such variants include, for example, deletions from, and/or insertions into and/or substitutions of, residues within the amino acid sequences of the antibodies and Fc fusion proteins disclosed herein. Any combination of deletion, insertion, and substitution is made to arrive at the final construct, provided that the final construct possesses the desired characteristics. The amino acid changes also may alter post-translational processes of the antibodies and Fc fusion proteins, such as changing the number or position of glycosylation sites.

Antibodies and Fc fusion proteins with reduced effector function may be produced by introducing changes in the amino acid sequence, including, but are not limited to, the Ala-Ala mutation described by Bluestone et al. (see WO 94/28027 and WO 98/47531; also see Xu et al. 2000 Cell Immunol 200; 16-26). Thus, in certain embodiments, Fc fusion proteins of the disclosure with mutations within the constant region including the Ala-Ala mutation may be used to reduce or abolish effector function. According to these embodiments, antibodies and Fc fusion proteins may comprise a mutation to an alanine at position 234 or a mutation to an alanine at position 235, or a combination thereof. In one embodiment, the antibody or Fc fusion protein comprises an IgG4 framework, wherein the Ala-Ala mutation would describe a mutation(s) from phenylalanine to alanine at position 234 and/or a mutation from leucine to alanine at position 235. In another embodiment, the antibody or Fc fusion protein comprises an IgG1 framework, wherein the Ala-Ala mutation would describe a mutation(s) from leucine to alanine at position 234 and/or a mutation from leucine to alanine at position 235. The antibody or Fc fusion protein may alternatively or additionally carry other mutations, including the point mutation K322A in the CH2 domain (Hezareh et al. 2001 J Virol. 75: 12161-8).

In particular embodiments, the antibody or Fc fusion protein may be modified to either enhance or inhibit complement dependent cytotoxicity (CDC). Modulated CDC activity may be achieved by introducing one or more amino acid substitutions, insertions, or deletions in an Fc region (see, e.g., U.S. Pat. No. 6,194,551). Alternatively or additionally, cysteine residue(s) may be introduced in the Fc region, thereby allowing interchain disulfide bond formation in this region. The homodimeric antibody thus generated may have improved or reduced internalization capability and/or increased or decreased complement-mediated cell killing. See Caron et al., J. Exp Med. 176:1191-1195 (1992) and Shopes, B. J. Immunol. 148:2918-2922 (1992), WO99/51642, Duncan & Winter Nature 322: 738-40 (1988); U.S. Pat. Nos. 5,648,260; 5,624,821; and WO94/29351.

B. Nucleic Acids and Methods of Manufacture

In certain embodiments, the present disclosure makes available isolated and/or purified forms of polypeptides (e.g., TβRII or betaglycan polypeptides), which are isolated from, or otherwise substantially free of (e.g., at least 80%, 90%, 95%, 96%, 97%, 98%, or 99% free of), other proteins and/or other polypeptide species. Polypeptides will generally be produced by expression from recombinant nucleic acids.

In certain embodiments, the disclosure includes nucleic acids encoding soluble polypeptides (e.g., TβRII or betaglycan polypeptides) comprising the coding sequence for an extracellular portion of a protein (e.g., a TβRII or betaglycan protein). In further embodiments, this disclosure also pertains to a host cell comprising such nucleic acids. The host cell may be any prokaryotic or eukaryotic cell. For example, a polypeptide of the present disclosure may be expressed in bacterial cells such as E. coli, insect cells (e.g., using a baculovirus expression system), yeast, or mammalian cells. Other suitable host cells are known to those skilled in the art. Accordingly, some embodiments of the present disclosure further pertain to methods of producing the polypeptides.

In certain aspects, the disclosure provides isolated and/or recombinant nucleic acids encoding any of the polypeptides (e.g., TβRII or betaglycan polypeptides), including fragments, functional variants and fusion proteins disclosed herein. SEQ ID NOs: 8, 10, 12, 14, 16, 46 or 47 encode variants of TβRII extracellular domain fused to an IgG Fc domain. The subject nucleic acids may be single-stranded or double stranded. Such nucleic acids may be DNA or RNA molecules. These nucleic acids may be used, for example, in methods for making polypeptides or as direct therapeutic agents (e.g., in an antisense, RNAi or gene therapy approach).

In certain aspects, the subject nucleic acids encoding polypeptides are further understood to include nucleic acids that are variants of SEQ ID NOs: 8, 10, 12, 14, 16, 46 or 47. Variant nucleotide sequences include sequences that differ by one or more nucleotide substitutions, additions or deletions, such as allelic variants.

In certain embodiments, the disclosure provides isolated or recombinant nucleic acid sequences that are at least 70%, 75%, 80%, 85%, 90%, 91%, 92%, 93%, 94%, 95%, 96%, 97%, 98%, 99% or 100% identical to SEQ ID NOs: 8, 10, 12, 14, 16, 46 or 47. In particular embodiments, the disclosure provides isolated or recombinant nucleic acid sequences that are at least 70%, 75%, 80%, 85%, 90%, 91%, 92%, 93%, 94%, 95%, 96%, 97%, 98%, 99% or 100% identical to SEQ ID NO: 12, or fragments thereof. One of ordinary skill in the art will appreciate that nucleic acid sequences complementary to SEQ ID NOs: 8, 10, 12, 14, 16, 46 or 47, and variants of SEQ ID NOs: 8, 10, 12, 14, 16, 46 or 47 are also within the scope of this disclosure. In further embodiments, the nucleic acid sequences of the disclosure can be isolated, recombinant, and/or fused with a heterologous nucleotide sequence, or in a DNA library.

In other embodiments, nucleic acids of the disclosure also include nucleotide sequences that hybridize under highly stringent conditions to the nucleotide sequences designated in SEQ ID NOs: 8, 10, 12, 14, 16, 46 or 47 complement sequences of SEQ ID NOs: 8, 10, 12, 14, 16, 46 or 47, or fragments thereof. As discussed above, one of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In some embodiments, the disclosure provides nucleic acids which hybridize under low stringency conditions of 6×SSC at room temperature followed by a wash at 2×SSC at room temperature.

Isolated nucleic acids which differ from the nucleic acids as set forth in SEQ ID NOs: 8, 10, 12, 14, 16, 46 or 47 due to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

It will be appreciated by one of skill in the art that corresponding variants based on the long isoform of TβRII will include nucleotide sequences encoding the 25-amino acid insertion along with a conservative Val-Ile substitution at the flanking position C-terminal to the insertion. It will also be appreciated that corresponding variants based on either the long (A) or short (B) isoforms of TβRII will include variant nucleotide sequences comprising an insertion of 108 nucleotides, encoding a 36-amino-acid insertion (SEQ ID NO: 41), at the same location described for naturally occurring TβRII isoform C.

In certain embodiments, the recombinant nucleic acids of the disclosure may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects disclosed herein, the subject nucleic acid is provided in an expression vector comprising a nucleotide sequence encoding a polypeptide (e.g., TβRII or betaglycan polypeptide) and operably linked to at least one regulatory sequence. Regulatory sequences are art-recognized and are selected to direct expression of the T polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, CA (1990). For instance, any of a wide variety of expression control sequences that control the expression of a DNA sequence when operatively linked to it may be used in these vectors to express DNA sequences encoding a polypeptide (e.g., TβRII or betaglycan polypeptide). Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid included in the disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant polypeptide (e.g., TβRII or betaglycan polypeptide) include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see Molecular Cloning A Laboratory Manual, 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUWI), and pBlueBac-derived vectors (such as the β-gal containing pBlueBac III).

In certain embodiments, a vector will be designed for production of the subject polypeptides (e.g., TβRII or betaglycan polypeptidea) in CHO cells, such as a Pcmv-Script vector (Stratagene, La Jolla, Calif), pcDN4 vectors (Invitrogen, Carlsbad, Calif.) and pCI-neo vectors (Promega, Madison, Wisc.). In a preferred embodiment, a vector will be designed for production of the subject polypeptides in HEK-293 cells. As will be apparent, the subject gene constructs can be used to cause expression of the subject polypeptides in cells propagated in culture, e.g., to produce proteins, including fusion proteins or variant proteins, for purification.

This disclosure also pertains to a host cell transfected with a recombinant gene including a coding sequence (e.g., SEQ ID NOs: 8, 10, 12, 14, 16, 46 or 47) for one or more of the subject polypeptides (e.g., TβRII or betaglycan polypeptides). The host cell may be any prokaryotic or eukaryotic cell. For example, a TβRII polypeptide disclosed herein may be expressed in bacterial cells such as E. coli, insect cells (e.g., using a baculovirus expression system), yeast, or mammalian cells. Other suitable host cells are known to those skilled in the art.

Accordingly, the present disclosure further pertains to methods of producing the subject polypeptides (e.g., TβRII or betaglycan polypeptides). For example, a host cell transfected with an expression vector encoding a polypeptide can be cultured under appropriate conditions to allow expression of the polypeptide to occur. The polypeptide may be secreted and isolated from a mixture of cells and medium containing the polypeptide. Alternatively, the polypeptide may be retained cytoplasmically or in a membrane fraction and the cells harvested, lysed and the protein isolated. A cell culture includes host cells, and media. Suitable media for cell culture are well known in the art. The subject polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the polypeptides and affinity purification with an agent that binds to a domain fused to the polypeptide (e.g., a protein A column may be used to purify an Fc fusion). In a preferred embodiment, the polypeptide is a fusion protein containing a domain which facilitates its purification. As an example, purification may be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange.

In another embodiment, a fusion gene coding for a purification leader sequence, such as a poly-(His)/enterokinase cleavage site sequence at the N-terminus of the desired portion of the recombinant polypeptide (e.g., TβRII or betaglycan polypeptide), can allow purification of the expressed fusion protein by affinity chromatography using a $Ni^{2+}$ metal resin. The purification leader sequence can then be subsequently removed by treatment with enterokinase to provide the purified polypeptide (e.g., see Hochuli et al., (1987) J. Chromatography 411:177; and Janknecht et al., PNAS USA 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al., John Wiley & Sons: 1992).

C. Antibodies

In certain aspects, a TGFβ antagonist to be used in accordance with the methods and uses disclosed herein is an antibody (TGFβ antagonist antibody) or combination of antibodies. A TGFβ antagonist antibody, or combination of antibodies, may inhibit and/or bind to, for example, one or more ligands (e.g., TGFβ1, TGFβ2, and TGFβ3), TβRII receptor, TβRII-associated type I receptor (e.g., ALK5), and/or TβRII co-receptor (e.g., betaglycan). In some embodiments, the ability for a TGFβ antagonist antibody, or combination of antibody, to inhibit signaling (e.g., Smad signaling) and/or bind to a target is determined in an in vitro or cell-based assay including, for example, those described herein. As described herein, a TGFβ antagonist antibody, or combination of antagonist antibodies, may be used alone or in combination with one or more additional supportive therapies or active agents to treat heterotopic ossification, preferably preventing or reducing the severity or duration of one or more complications of heterotopic ossification In certain embodiments, a TGFβ antagonist antibody, or combination of antibodies, is an antibody that inhibits at least TGFβ1. Therefore, in some embodiments, a TGFβ antagonist antibody, or combination of antibodies, binds to at least TGFβ1. As used herein, a TGFβ1 antibody (anti-TGFβ1 antibody) generally refers to an antibody that is capable of binding to TGFβ1 with sufficient affinity such that the antibody is useful as a diagnostic and/or therapeutic agent in targeting TGFβ1. In certain embodiments, the extent of binding of an anti-TGFβ1 antibody to an unrelated, non-TGFβ1 protein is less than about 10%, 9%, 8%, 7%, 6%, 5%, 4%, 3%, 2%, or less than 1% of the binding of the antibody to TGFβ1 as measured, for example, by a radioimmunoassay (RIA). In certain embodiments, an anti-TGFβ1 antibody binds to an epitope of TGFβ1 that is conserved among TGFβ1 from different species. In certain preferred embodiments, an anti-TGFβ1 antibody binds to human TGFβ1. In some embodiments, a TGFβ1 antibody may inhibit TGFβ1 from binding to a type I, type II, and/or co-receptor (e.g., TβRII, ALK5, and/or betaglycan) and thus inhibit TGFβ1 signaling (e.g., Smad signaling). It should be noted that TGFβ1 shares some sequence homology to TGFβ2 and TGFβ3. Therefore antibodies that bind TGFβ1, in some embodiments, may also bind to TGFβ2 and/or TGFβ3. In some embodiments, the disclosure relates to a multispecific antibody (e.g., bi-specific antibody), and uses thereof, that binds to TGFβ1 and further binds to, for example, one or more additional ligands (e.g., TGFβ2, TGFβ3, or TGFβ2 and TGFβ3), one or more type I and/or type II receptors (e.g., TβRII and ALK5), and/or one or more co-receptors (e.g., betaglycan). In some embodiments, a multispecific antibody that binds to TGFβ1 further binds to TGFβ3 but does not bind or does not substantially bind to TGFβ2 (e.g., binds to TGFβ2 with a $K_D$ of greater than $1\times10^{-7}$ M or has relatively modest binding, e.g., about $1\times10^{-8}$ M or about $1\times10^{-9}$ M). In some embodiments, the disclosure relates to combinations of antibodies, and uses thereof, wherein the combination of antibodies comprises a TGFβ1 antibody and one or more additional antibodies that bind to, for example, one or more additional ligands (e.g., TGFβ2, TGFβ3, or TGFβ2 and TGFβ3), one or more type I and/or type II receptors (e.g., TβRII and ALK5), and/or one or more co-receptors (e.g., betaglycan). In some embodiments, a combination of antibodies that comprises a TGFβ1 antibody further comprises a TGFβ3 antibody but does not comprise a TGFβ2 antibody.

In certain embodiments, a TGFβ antagonist antibody, or combination of antibodies, is an antibody that inhibits at least TGFβ2. Therefore, in some embodiments, a Tβ TGFβ RII antagonist antibody, or combination of antibodies, binds to at least TGFβ2. As used herein, a TGFβ2 antibody (anti-TGFβ2 antibody) generally refers to an antibody that is capable of binding to TGFβ2 with sufficient affinity such that the antibody is useful as a diagnostic and/or therapeutic agent in targeting TGFβ2. In certain embodiments, the extent of binding of an anti-TGFβ2 antibody to an unrelated, non-TGFβ2 protein is less than about 10%, 9%, 8%, 7%, 6%, 5%, 4%, 3%, 2%, or less than 1% of the binding of the antibody to TGFβ2 as measured, for example, by a radioimmunoassay (RIA). In certain embodiments, an anti-TGFβ2 antibody binds to an epitope of TGFβ2 that is conserved among TGFβ2 from different species. In certain preferred embodiments, an anti-TGFβ2 antibody binds to human TGFβ2. In some embodiments, a TGFβ2 antibody may inhibit TGFβ2 from binding to a type I, type II, and/or co-receptor (e.g., TβRII, ALK5, and/or betaglycan) and thus inhibit TGFβ2 signaling (e.g., Smad signaling). It should be noted that TGFβ2 shares some sequence homology to TGFβ1 and TGFβ3. Therefore antibodies that bind TGFβ2, in some embodiments, may also bind to TGFβ1 and/or TGFβ3. In some embodiments, the disclosure relates to a multispecific antibody (e.g., bi-specific antibody), and uses thereof, that binds to TGFβ2 and further binds to, for example, one or more additional ligands (e.g., TGFβ1, TGFβ3, or TGFβ1 and TGFβ3), one or more type I and/or type II receptors (e.g., TβRII and ALK5), and/or one or more co-receptors (e.g., betaglycan) In some embodiments, the disclosure relates to combinations of antibodies, and uses thereof, wherein the combination of antibodies comprises a TGFβ2 antibody and one or more additional antibodies that bind to, for example, one or more additional ligands (e.g., TGFβ1, TGFβ3, or TGFβ1 and TGFβ3), one or more type I and/or type II receptors (e.g., TβRII and ALK5), and/or one or more co-receptors (e.g., betaglycan).

In certain embodiments, a TGFβ antagonist antibody, or combination of antibodies, is an antibody that inhibits at least TGFβ3. Therefore, in some embodiments, a TGFβ antagonist antibody, or combination of antibodies, binds to at least TGFβ3. As used herein, a TGFβ3 antibody (anti-TGFβ3 antibody) generally refers to an antibody that is capable of binding to TGFβ3 with sufficient affinity such that the antibody is useful as a diagnostic and/or therapeutic agent in targeting TGFβ3. In certain embodiments, the extent of binding of an anti-TGFβ3 antibody to an unrelated, non-TGFβ3 protein is less than about 10%, 9%, 8%, 7%, 6%, 5%, 4%, 3%, 2%, or less than 1% of the binding of the antibody to TGFβ3 as measured, for example, by a radioimmunoassay (RIA). In certain embodiments, an anti-TGFβ3 antibody binds to an epitope of TGFβ3 that is conserved among TGFβ3 from different species. In certain preferred embodiments, an anti-TGFβ3 antibody binds to human TGFβ3. In some embodiments, a TGFβ3 antibody may inhibit TGFβ3 from binding to a type I, type II, and/or co-receptor (e.g., TβRII, ALK5, and/or betaglycan) and thus inhibit TGFβ3 signaling (e.g., Smad signaling). It should be noted that TGFβ3 shares some sequence homology to TGFβ2 and TGFβ1. Therefore antibodies that bind TGFβ3, in some embodiments, may also bind to TGFβ2 and/or TGFβ1. In some embodiments, the disclosure relates to a multispecific antibody (e.g., bi-specific antibody), and uses thereof, that binds to TGFβ3 and further binds to, for example, one or more additional TβRII ligands (e.g., TGFβ2, TGFβ1, or TGFβ2 and TGFβ1), one or more type I and/or type II receptors (e.g., TβRII and ALK5), and/or one or more co-receptors (e.g., betaglycan). In some embodiments, a multispecific antibody that binds to TGFβ3 does not bind or does not substantially bind to TGFβ2 (e.g., binds to TGFβ2 with a $K_D$ of greater than $1\times10^{-7}$ M or has relatively modest binding, e.g., about $1\times10^{-8}$ M or about $1\times10^{-9}$ M). In some embodiments, a multispecific antibody that binds to TGFβ3 further binds to TGFβ1 but does not bind or does not substantially bind to TGFβ2 (e.g., binds to TGFβ2 with a $K_D$ of greater than $1\times10^{-7}$ M or has relatively modest binding, e.g., about $1\times10^{-8}$ M or about $1\times10^{-9}$ M). In some embodiments, the disclosure relates to combinations of antibodies, and uses thereof, wherein the combination of antibodies comprises a TGFβ3 antibody and one or more additional antibodies that bind to, for example, one or more additional ligands (e.g., TGFβ2, TGFβ1, or TGFβ2 and TGFβ1), one or more type I and/or type II receptors (e.g., TβRII and ALK5), and/or one or more co-receptors (e.g., betaglycan). In some embodiments, a combination of antibodies that comprises a TGFβ3 antibody further comprises a TGFβ1 antibody but does not comprise a TGFβ2 antibody.

In some embodiments, the TGFβ antagonist antibody binds to all three TGFβ isoforms, i.e., TGFβ1, TGFβ2, and TGFβ3. In some embodiments the TGFβ antagonist antibody is fresolimumab.

In certain aspects, a TGFβ antagonist antibody, or combination of antibodies, is an antibody that inhibits at least TβRII. Therefore, in some embodiments, a TGFβ antagonist antibody, or combination of antibodies, binds to at least TβRII. As used herein, a TβRII antibody (anti-TβRII antibody) generally refers to an antibody that binds to TβRII with sufficient affinity such that the antibody is useful as a diagnostic and/or therapeutic agent in targeting TβRII. In certain embodiments, the extent of binding of an anti-TβRII antibody to an unrelated, non-TβRII protein is less than about 10%, 9%, 8%, 7%, 6%, 5%, 4%, 3%, 2%, or less than about 1% of the binding of the antibody to TβRII as measured, for example, by a radioimmunoassay (RIA), Biacore, or other protein-protein interaction or binding affinity assay. In certain embodiments, an anti-TβRII antibody binds to an epitope of TβRII that is conserved among TβRII from different species. In certain preferred embodiments, an anti-TβRII antibody binds to human TβRII. In some embodiments, an anti-TβRII antibody may inhibit one or more ligands [e.g., TGFβ1; TGFβ2; TGFβ3; TGFβ1 and TGFβ3; TGFβ1 and TGFβ2; TGFβ2 and TGFβ3; or TGFβ1, TGFβ2, and TGFβ3] from binding to TβRII. In some embodiments, an anti-TβRII antibody is a multispecific antibody (e.g., bi-specific antibody) that binds to TβRII and one or more ligands [e.g., TGFβ1, TGFβ2, and TGFβ3], type I receptor (e.g., ALK5), and/or co-receptor (e.g., betaglycan). In some embodiments, the disclosure relates to combinations of antibodies, and uses thereof, wherein the combination of antibodies comprises an anti-TβRII antibody and one or more additional antibodies that bind to, for example, one or more ligands [e.g., TGFβ1, TGFβ2, and TGFβ3], type I receptors (e.g., ALK5), and/or co-receptor (e.g., betaglycan).

In certain aspects, a TGFβ antagonist antibody, or combination of antibodies, is an antibody that inhibits at least ALK5. Therefore, in some embodiments, a TGFβ antagonist antibody, or combination of antibodies, binds to at least ALK5. As used herein, an ALK5 antibody (anti-ALK5 antibody) generally refers to an antibody that binds to ALK5 with sufficient affinity such that the antibody is useful as a diagnostic and/or therapeutic agent in targeting ALK5. In certain embodiments, the extent of binding of an anti-ALK5 antibody to an unrelated, non-ALK5 protein is less than about 10%, 9%, 8%, 7%, 6%, 5%, 4%, 3%, 2%, or less than about 1% of the binding of the antibody to ALK5 as measured, for example, by a radioimmunoassay (RIA), Biacore, or other protein-protein interaction or binding affinity assay. In certain embodiments, an anti-ALK5 antibody binds to an epitope of ALK5 that is conserved among ALK5 from different species. In certain preferred embodiments, an anti-ALK5 antibody binds to human ALK5. In some embodiments, an anti-ALK5 antibody may inhibit one or more ligands [e.g., TGFβ1; TGFβ2; TGFβ3; TGFβ1 and TGFβ3; TGFβ1 and TGFβ2; TGFβ2 and TGFβ3; or TGFβ1, TGFβ2, and TGFβ3] from binding to ALK5. In some embodiments, an anti-ALK5 antibody is a multispecific antibody (e.g., bi-specific antibody) that binds to ALK5 and one or more ligands [e.g., TGFβ1, TGFβ2, and TGFβ3], type II receptor (e.g., TβRII), and/or co-receptor (e.g., betaglycan). In some embodiments, the disclosure relates to combinations of antibodies, and uses thereof, wherein the combination of antibodies comprises an anti-ALK5 antibody and one or more additional antibodies that bind to, for example, one or more ligands [e.g., TGFβ1, TGFβ2, and TGFβ3], type II receptors (e.g., TβRII), and/or co-receptor (e.g., betaglycan).

In certain aspects, a TGFβ antagonist antibody, or combination of antibodies, is an antibody that inhibits at least betaglycan. Therefore, in some embodiments, a TGFβ antagonist antibody, or combination of antibodies, binds to at least betaglycan. As used herein, a betaglycan antibody (anti-betaglycan antibody) generally refers to an antibody that binds to betaglycan with sufficient affinity such that the antibody is useful as a diagnostic and/or therapeutic agent in targeting betaglycan. In certain embodiments, the extent of binding of an anti-betaglycan antibody to an unrelated, non-betaglycan protein is less than about 10%, 9%, 8%, 7%, 6%, 5%, 4%, 3%, 2%, or less than about 1% of the binding of the antibody to betaglycan as measured, for example, by a radioimmunoassay (RIA), Biacore, or other protein-protein interaction or binding affinity assay. In certain embodiments, an anti-betaglycan antibody binds to an epitope of betaglycan that is conserved among betaglycan from different species. In certain preferred embodiments, an anti-betaglycan antibody binds to human betaglycan. In some embodiments, an anti-betaglycan antibody may inhibit one or more ligands [e.g., TGFβ1; TGFβ2; TGFβ3; TGFβ1 and TGFβ3; TGFβ1 and TGFβ2; TGFβ2 and TGFβ3; or TGFβ1, TGFβ2, and TGFβ3] from binding to betaglycan. In some embodiments, an anti-betaglycan antibody is a multispecific antibody (e.g., bi-specific antibody) that binds to betaglycan and one or more ligands [e.g., TGFβ1, TGFβ2, and TGFβ3], type I receptor (e.g., ALK5), and/or type II receptors (e.g., TβRII). In some embodiments, the disclosure relates to combinations of antibodies, and uses thereof, wherein the combination of antibodies comprises an anti-betaglycan antibody and one or more additional antibodies that bind to, for example, one or more ligands [e.g., TGFβ1, TGFβ2, and TGFβ3], type I receptors (e.g., ALK5), and/or type II receptors (e.g., TβRII).

The term antibody is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. An antibody fragment refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g., scFv); and multispecific antibodies formed from antibody fragments. See, e.g., Hudson et al. (2003) Nat. Med. 9:129-134; Pluckthun, in The Pharmacology of Monoclonal Antibodies, vol. 113, Rosenburg and Moore eds., (Springer-Verlag, New York), pp. 269-315 (1994); WO 93/16185; and U.S. Pat. Nos. 5,571,894, 5,587,458, and 5,869,046. Antibodies disclosed herein may be polyclonal antibodies or monoclonal antibodies. In certain embodiments, the antibodies of the present disclosure comprise a label attached thereto and able to be detected (e.g., the label can be a radioisotope, fluorescent compound, enzyme, or enzyme co-factor). In preferred embodiments, the antibodies of the present disclosure are isolated antibodies. Diabodies are antibody fragments with two antigen-binding sites that may be bivalent or bispecific. See, e.g., EP 404,097; WO 1993/01161; Hudson et al. (2003) Nat. Med. 9:129-134 (2003); and Hollinger et al. (1993) Proc. Natl. Acad. Sci. USA 90: 6444-6448. Triabodies and tetrabodies are also described in Hudson et al. (2003) Nat. Med. 9:129-134. Single-domain antibodies are antibody fragments comprising all or a portion of the heavy-chain variable domain or all or a portion of the light-chain variable domain of an antibody. In certain embodiments, a single-domain antibody is a human single-domain antibody. See, e.g., U.S. Pat. No. 6,248,516. Antibody fragments can be made by various techniques, including but not limited to proteolytic digestion of an intact antibody as well as production by recombinant host cells (e.g., E. coli or phage), as described herein.

The antibodies herein may be of any class. The class of an antibody refers to the type of constant domain or constant region possessed by its heavy chain. There are five major classes of antibodies: IgA, IgD, IgE, IgG, and IgM, and several of these may be further divided into subclasses (isotypes), for example, IgG$_1$, IgG$_2$, IgG$_3$, IgG$_4$, IgA$_1$, and IgA$_2$. The heavy-chain constant domains that correspond to the different classes of immunoglobulins are called alpha, delta, epsilon, gamma, and mu.

In general, an antibody for use in the methods disclosed herein specifically binds to its target antigen, preferably with high binding affinity. Affinity may be expressed as a $K_D$ value and reflects the intrinsic binding affinity (e.g., with minimized avidity effects). Typically, binding affinity is measured in vitro, whether in a cell-free or cell-associated setting. Any of a number of assays known in the art, including those disclosed herein, can be used to obtain binding affinity measurements including, for example, surface plasmon resonance (Biacore™ assay), radiolabeled antigen binding assay (RIA), and ELISA. In some embodiments, antibodies of the present disclosure bind to their target antigens (e.g. TGFβ1, TGFβ2, TGFβ2, ALK5, betaglycan, and TβRII.) with at least a $K_D$ of $1\times10^{-7}$ or stronger, $1\times10^{-8}$ or stronger, $1\times10^{-9}$ or stronger, $1\times10^{-10}$ or stronger, $1\times10^{-11}$ or stronger, $1\times10^{-12}$ or stronger, $1\times10^{-13}$ or stronger, or $1\times10^{-14}$ or stronger.

In certain embodiments, $K_D$ is measured by RIA performed with the Fab version of an antibody of interest and its target antigen as described by the following assay. Solution binding affinity of Fabs for the antigen is measured by equilibrating Fab with a minimal concentration of radiolabeled antigen (e.g., $^{125}$I-labeled) in the presence of a titration series of unlabeled antigen, then capturing bound antigen with an anti-Fab antibody-coated plate [see, e.g., Chen et al. (1999) J. Mol. Biol. 293:865-881]. To establish conditions for the assay, multi-well plates (e.g., MICROTITER® from Thermo Scientific) are coated (e.g., overnight) with a capturing anti-Fab antibody (e.g., from Cappel Labs) and subsequently blocked with bovine serum albumin, preferably at room temperature (e.g., approximately 23° C.). In a non-adsorbent plate, radiolabeled antigen are mixed with serial dilutions of a Fab of interest [e.g., consistent with assessment of the anti-VEGF antibody, Fab-12, in Presta et al., (1997) Cancer Res. 57:4593-4599]. The Fab of interest is then incubated, preferably overnight but the incubation may continue for a longer period (e.g., about 65 hours) to ensure that equilibrium is reached. Thereafter, the mixtures are transferred to the capture plate for incubation, preferably at room temperature for about one hour. The solution is then removed and the plate is washed times several times, preferably with polysorbate 20 and PBS mixture. When the plates have dried, scintillant (e.g., MICROSCINT® from Packard) is added, and the plates are counted on a gamma counter (e.g., TOPCOUNT® from Packard).

According to another embodiment, $K_D$ is measured using surface plasmon resonance assays using, for example a BIACORE® 2000 or a BIACORE® 3000 (Biacore, Inc., Piscataway, N.J.) with immobilized antigen CM5 chips at about 10 response units (RU). Briefly, carboxymethylated dextran biosensor chips (CM5, Biacore, Inc.) are activated with N-ethyl-N'-(3-dimethylaminopropyl)-carbodiimide hydrochloride (EDC) and N-hydroxysuccinimide (NHS) according to the supplier's instructions. For example, an antigen can be diluted with 10 mM sodium acetate, pH 4.8, to 5 pg/ml (about 0.2 pM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20®) surfactant (PBST) at at a flow rate of approximately 25 µl/min. Association rates ($k_{on}$) and dissociation rates ($k_{off}$) are calculated using, for example, a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$ [see, e.g., Chen et al., (1999) J. Mol. Biol. 293:865-881]. If the on-rate exceeds, for example, $10^6$ M$^{-1}$ s$^{-1}$ by the surface plasmon resonance assay above, then the on-rate can be determined by using a fluorescent quenching technique that measures the increase or decrease in fluorescence emission intensity (e.g., excitation=295 nm; emission=340 nm, 16 nm band-pass) of a 20 nM anti-antigen antibody (Fab form) in PBS in the presence of increasing concentrations of antigen as measured in a spectrometer, such as a stop-flow equipped spectrophotometer (Aviv Instruments) or a 8000-series SLM-AMINCO® spectrophotometer (ThermoSpectronic) with a stirred cuvette.

The nucleic acid and amino acid sequences of TβRII, ALK5, betaglycan, TGFβ1, TGFβ2, and TGFβ3, particularly human sequences, are well known in the art and thus antibody antagonists for use in accordance with this disclosure may be routinely made by the skilled artisan based on the knowledge in the art and teachings provided herein.

In certain embodiments, an antibody provided herein is a chimeric antibody. A chimeric antibody refers to an antibody in which a portion of the heavy and/or light chain is derived from a particular source or species, while the remainder of the heavy and/or light chain is derived from a different source or species. Certain chimeric antibodies are described, for example, in U.S. Pat. No. 4,816,567; and Morrison et al., (1984) Proc. Natl. Acad. Sci. USA, 81:6851-6855. In some embodiments, a chimeric antibody comprises a non-human variable region (e.g., a variable region derived from a mouse, rat, hamster, rabbit, or non-human primate, such as a monkey) and a human constant region. In some embodiments, a chimeric antibody is a "class switched" antibody in which the class or subclass has been changed from that of the parent antibody. In general, chimeric antibodies include antigen-binding fragments thereof.

In certain embodiments, a chimeric antibody provided herein is a humanized antibody. A humanized antibody refers to a chimeric antibody comprising amino acid residues from non-human hypervariable regions (HVRs) and amino acid residues from human framework regions (FRs). In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

Humanized antibodies and methods of making them are reviewed, for example, in Almagro and Fransson (2008) Front. Biosci. 13:1619-1633 and are further described, for example, in Riechmann et al., (1988) Nature 332:323-329; Queen et al. (1989) Proc. Nat'l Acad. Sci. USA 86:10029-10033; U.S. Pat. Nos. 5,821,337, 7,527,791, 6,982,321, and 7,087,409; Kashmiri et al., (2005) Methods 36:25-34 [describing SDR (a-CDR) grafting]; Padlan, Mol. Immunol. (1991) 28:489-498 (describing "resurfacing"); Dall'Acqua et al. (2005) Methods 36:43-60 (describing "FR shuffling"); Osbourn et al. (2005) Methods 36:61-68; and Klimka et al. Br. J. Cancer (2000) 83:252-260 (describing the "guided selection" approach to FR shuffling).

Human framework regions that may be used for humanization include but are not limited to: framework regions selected using the "best-fit" method [see, e.g., Sims et al. (1993) J. Immunol. 151:2296]; framework regions derived from the consensus sequence of human antibodies of a particular subgroup of light-chain or heavy-chain variable regions [see, e.g., Carter et al. (1992) Proc. Natl. Acad. Sci. USA, 89:4285; and Presta et al. (1993) J. Immunol., 151: 2623]; human mature (somatically mutated) framework regions or human germline framework regions [see, e.g., Almagro and Fransson (2008) Front. Biosci. 13:1619-1633]; and framework regions derived from screening FR libraries [see, e.g., Baca et al., (1997) J. Biol. Chem. 272:10678-10684; and Rosok et al., (1996) J. Biol. Chem. 271:22611-22618].

In certain embodiments, an antibody provided herein is a human antibody. Human antibodies can be produced using various techniques known in the art. Human antibodies are described generally in van Dijk and van de Winkel (2001) Curr. Opin. Pharmacol. 5: 368-74 and Lonberg (2008) Curr. Opin. Immunol. 20:450-459.

Human antibodies may be prepared by administering an immunogen (e.g. a TβRII, ALK5, betaglycan, TGFβ1, TGFβ2, or TGFβ3 polypeptide) to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. For a review of methods for obtaining human antibodies from transgenic animals, see, for example, Lonberg (2005) Nat. Biotechnol. 23:1117-1125; U.S. Pat. Nos. 6,075,181 and 6,150,584 (describing XENOMOUSE™ technology); U.S. Pat. No. 5,770,429 (describing HuMab® technology); U.S. Pat. No. 7,041,870 (describing K-M MOUSE® technology); and U.S. Patent Application Publication No. 2007/0061900 (describing VelociMouse® technology). Human variable regions from intact antibodies generated by such animals may be further modified, for example, by combining with a different human constant region.

Human antibodies provided herein can also be made by hybridoma-based methods. Human myeloma and mouse-human heteromyeloma cell lines for the production of human monoclonal antibodies have been described [see, e.g., Kozbor J. Immunol., (1984) 133: 3001; Brodeur et al. (1987) Monoclonal Antibody Production Techniques and Applications, pp. 51-63, Marcel Dekker, Inc., New York; and Boerner et al. (1991) J. Immunol., 147: 86]. Human antibodies generated via human B-cell hybridoma technology are also described in Li et al., (2006) Proc. Natl. Acad. Sci. USA, 103:3557-3562. Additional methods include those described, for example, in U.S. Pat. No. 7,189,826 (describing production of monoclonal human IgM antibodies from hybridoma cell lines) and Ni, Xiandai Mianyixue (2006) 26(4):265-268 (2006) (describing human-human hybridomas). Human hybridoma technology (Trioma technology) is also described in Vollmers and Brandlein (2005) Histol. Histopathol., 20(3):927-937 (2005) and Vollmers and Brandlein (2005) Methods Find Exp. Clin. Pharmacol., 27(3):185-91.

Human antibodies provided herein may also be generated by isolating Fv clone variable-domain sequences selected from human-derived phage display libraries. Such variable-domain sequences may then be combined with a desired human constant domain. Techniques for selecting human antibodies from antibody libraries are described herein.

For example, antibodies of the present disclosure may be isolated by screening combinatorial libraries for antibodies with the desired activity or activities. A variety of methods are known in the art for generating phage-display libraries and screening such libraries for antibodies possessing the desired binding characteristics. Such methods are reviewed, for example, in Hoogenboom et al. (2001) in Methods in Molecular Biology 178:1-37, O'Brien et al., ed., Human Press, Totowa, N.J. and further described, for example, in the McCafferty et al. (1991) Nature 348:552-554; Clackson et al., (1991) Nature 352: 624-628; Marks et al. (1992) J. Mol. Biol. 222:581-597; Marks and Bradbury (2003) in Methods in Molecular Biology 248:161-175, Lo, ed., Human Press, Totowa, N.J.; Sidhu et al. (2004) J. Mol. Biol. 338(2):299-310; Lee et al. (2004) J. Mol. Biol. 340(5):1073-1093; Fellouse (2004) Proc. Natl. Acad. Sci. USA 101(34): 12467-12472; and Lee et al. (2004) J. Immunol. Methods 284(1-2): 119-132.

In certain phage display methods, repertoires of VH and VL genes are separately cloned by polymerase chain reaction (PCR) and recombined randomly in phage libraries, which can then be screened for antigen-binding phage as described in Winter et al. (1994) Ann. Rev. Immunol., 12: 433-455. Phage typically display antibody fragments, either as single-chain Fv (scFv) fragments or as Fab fragments. Libraries from immunized sources provide high-affinity antibodies to the immunogen (e.g., a TβRII, TGFβ1, TGFβ2, or TGFβ3 polypeptide) without the requirement of constructing hybridomas. Alternatively, the naive repertoire can be cloned (e.g., from human) to provide a single source of antibodies directed against a wide range of non-self and also self-antigens without any immunization as described by Griffiths et al. (1993) EMBO J, 12: 725-734. Finally, naive libraries can also be made synthetically by cloning un-rearranged V-gene segments from stem cells and using PCR primers containing random sequence to encode the highly variable CDR3 regions and to accomplish rearrangement in vitro, as described by Hoogenboom and Winter (1992) J. Mol. Biol., 227: 381-388. Patent publications describing human antibody phage libraries include, for example: U.S. Pat. No. 5,750,373, and U.S. Patent Publication Nos. 2005/0079574, 2005/0119455, 2005/0266000, 2007/0117126, 2007/0160598, 2007/0237764, 2007/0292936, and 2009/0002360.

In certain embodiments, an antibody provided herein is a multispecific antibody, for example, a bispecific antibody. Multispecific antibodies (typically monoclonal antibodies) have binding specificities for at least two different epitopes (e.g., two, three, four, five, or six or more) on one or more (e.g., two, three, four, five, six or more) antigens.

Engineered antibodies with three or more functional antigen binding sites, including "octopus antibodies," are also included herein (see, e.g., US 2006/0025576A1).

In certain embodiments, the antibodies disclosed herein are monoclonal antibodies. Monoclonal antibody refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. Thus, the modifier "monoclonal" indicates the character of the antibody as being obtained from a substantially homogeneous population of antibodies and is not to be construed as requiring production of the antibody by any particular method. For example, the monoclonal antibodies to be used in accordance with the present methods may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

For example, by using immunogens derived from TβRII, anti-protein/anti-peptide antisera or monoclonal antibodies can be made by standard protocols [see, e.g., Antibodies: A Laboratory Manual (1988) ed. by Harlow and Lane, Cold Spring Harbor Press]. A mammal, such as a mouse, hamster, or rabbit can be immunized with an immunogenic form of the TβRII polypeptide, an antigenic fragment which is capable of eliciting an antibody response, or a fusion protein. Techniques for conferring immunogenicity on a protein or peptide include conjugation to carriers or other techniques well known in the art. An immunogenic portion of a TβRII polypeptide can be administered in the presence of adjuvant. The progress of immunization can be monitored by detection of antibody titers in plasma or serum. Standard ELISA or other immunoassays can be used with the immunogen as antigen to assess the levels of antibody production and/or level of binding affinity.

Following immunization of an animal with an antigenic preparation of TβRII, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique [see, e.g., Kohler and Milstein (1975) Nature, 256: 495-497], the human B cell hybridoma technique [see, e.g., Kozbar et al. (1983) Immunology Today, 4:72], and the EBV-hybridoma technique to produce human monoclonal antibodies [Cole et al. (1985) Monoclonal Antibodies and Cancer Therapy, Alan R. Liss, Inc. pp. 77-96]. Hybridoma cells can be screened immunochemically for production of antibodies specifically reactive with a TβRII polypeptide, and monoclonal antibodies isolated from a culture comprising such hybridoma cells.

In certain embodiments, one or more amino acid modifications may be introduced into the Fc region of an antibody provided herein thereby generating an Fc-region variant. The Fc-region variant may comprise a human Fc-region sequence (e.g., a human IgG1, IgG2, IgG3 or IgG4 Fc region) comprising an amino acid modification (e.g., a substitution, deletion, and/or addition) at one or more amino acid positions.

For example, the present disclosure contemplates an antibody variant that possesses some but not all effector functions, which make it a desirable candidate for applications in which the half-life of the antibody in vivo is important yet for which certain effector functions [e.g., complement-dependent cytotoxicity (CDC) and antibody-dependent cellular cytotoxicity (ADCC)] are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in, for example, Ravetch and Kinet (1991) Annu. Rev. Immunol. 9:457-492. Non-limiting examples of in vitro assays to assess ADCC activity of a molecule of interest are described in U.S. Pat. No. 5,500,362; Hellstrom, I. et al. (1986) Proc. Nat'l Acad. Sci. USA 83:7059-7063; Hellstrom, I et al. (1985) Proc. Nat'l Acad. Sci. USA 82:1499-1502; U.S. Pat. No. 5,821,337; and Bruggemann, M. et al. (1987) J. Exp. Med. 166:1351-1361. Alternatively, non-radioactive assay methods may be employed (e.g., ACTI™, non-radioactive cytotoxicity assay for flow cytometry; CellTechnology, Inc. Mountain View, Calif.; and CytoTox 96® non-radioactive cytotoxicity assay, Promega, Madison, Wis.). Useful effector cells for such assays include peripheral blood mononuclear cells (PBMC) and natural killer (NK) cells. Alternatively, or additionally, ADCC activity of the molecule of interest may be assessed in vivo, for example, in an animal model such as that disclosed in Clynes et al. (1998) Proc. Nat'l Acad. Sci. USA 95:652-656. C1q binding assays may also be carried out to confirm that the antibody is unable to bind C1q and hence lacks CDC activity [see, e.g., C1q and C3c binding ELISA in WO 2006/029879 and WO 2005/100402]. To assess complement activation, a CDC assay may be performed [see, e.g., Gazzano-Santoro et al. (1996) J. Immunol. Methods 202:163; Cragg, M. S. et al. (2003) Blood 101:1045-1052; and Cragg, M. S, and M. J. Glennie (2004) Blood 103:2738-2743]. FcRn binding and in vivo clearance/half-life determinations can also be performed using methods known in the art [see, e.g., Petkova, S. B. et al. (2006) Int. Immunol. 18(12):1759-1769].

Antibodies of the present disclosure with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In certain embodiments, it may be desirable to create cysteine-engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy-chain Fc region. Cysteine engineered antibodies may be generated as described, for example, in U.S. Pat. No. 7,521,541.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interaction between antibodies and antigens to identify particularly desirable antibodies. Such techniques include ELISAs, surface plasmon resonance binding assays (e.g., the Biacore™ binding assay, Biacore AB, Uppsala, Sweden), sandwich assays (e.g., the paramagnetic bead system of IGEN International, Inc., Gaithersburg, Maryland), western blots, immunoprecipitation assays, and immunohistochemistry.

In certain embodiments, amino acid sequence variants of the antibodies and/or the binding polypeptides provided herein are contemplated. For example, it may be desirable to improve the binding affinity and/or other biological properties of the antibody and/or binding polypeptide. Amino acid sequence variants of an antibody and/or binding polypeptides may be prepared by introducing appropriate modifications into the nucleotide sequence encoding the antibody and/or binding polypeptide, or by peptide synthesis. Such modifications include, for example, deletions from, and/or insertions into, and/or substitutions of residues within, the amino acid sequences of the antibody and/or binding polypeptide. Any combination of deletion, insertion, and substitution can be made to arrive at the final construct, provided that the final construct possesses the desired characteristics, e.g., target-binding (TβRII, ALK5, betaglycan, TGFβ1, TGFβ2, and/or TGFβ3).

Alterations (e.g., substitutions) may be made in HVRs, for example, to improve antibody affinity. Such alterations may be made in HVR "hotspots," i.e., residues encoded by codons that undergo mutation at high frequency during the somatic maturation process (see, e.g., Chowdhury (2008) Methods Mol. Biol. 207:179-196 (2008)), and/or SDRs (a-CDRs), with the resulting variant VH or VL being tested for binding affinity. Affinity maturation by constructing and reselecting from secondary libraries has been described in the art [see, e.g., Hoogenboom et al., in Methods in Molecular Biology 178:1-37, O'Brien et al., ed., Human Press, Totowa, N.J., (2001)]. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind to the antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two, or three amino acid substitutions.

A useful method for identification of residues or regions of the antibody and/or the binding polypeptide that may be targeted for mutagenesis is called "alanine scanning mutagenesis", as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody or binding polypeptide with antigen is affected. Further substitutions may be introduced at the amino acid locations demonstrating functional sensitivity to the initial substitutions. Alternatively, or additionally, a crystal structure of an antigen-antibody complex can be used to identify contact points between the antibody and antigen. Such contact residues and neighboring residues may be targeted or eliminated as candidates for substitution. Variants may be screened to determine whether they contain the desired properties.

Amino-acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include fusion of the N- or C-terminus of the antibody to an enzyme (e.g., for ADEPT) or a polypeptide which increases the serum half-life of the antibody.

In certain embodiments, an antibody and/or binding polypeptide provided herein may be further modified to contain additional non-proteinaceous moieties that are known in the art and readily available. The moieties suitable for derivatization of the antibody and/or binding polypeptide include but are not limited to water-soluble polymers. Non-limiting examples of water-soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody and/or binding polypeptide may vary, and if more than one polymer are attached, they can be the same or different molecules. In general, the number and/or type of polymers used for derivatization can be determined based on considerations including, but not limited to, the particular properties or functions of the antibody and/or binding polypeptide to be improved, whether the antibody derivative and/or binding polypeptide derivative will be used in a therapy under defined conditions.

D. Small Molecules

In certain aspects, a TGFβ antagonist to be used in accordance with the methods and uses disclosed herein is a small molecule (TGFβ antagonist small molecule) or combination of small molecules. A TGFβ antagonist small molecule, or combination of small molecules, may inhibit, for example, one or more ligands (e.g., TGFβ1, TGFβ2, and TGFβ3), TβRII receptor, TβRII-associated type I receptor (e.g., ALK5), TβRII-associated co-receptor (e.g., betaglycan), and/or downstream signaling component (e.g., Smads). In some embodiments, the ability for a TGFβ antagonist small molecule, or combination of small molecules, to inhibit signaling (e.g., Smad signaling) is determined in a cell-based assay including, for example, those described herein. A TGFβ antagonist small molecule, or combination of small molecules, may be used alone or in combination with one or more additional supportive therapies or active agents to treat heterotopic ossification, preferably preventing or reducing the severity or duration of one or more complications of heterotopic ossification.

In certain aspects, a TGFβ antagonist small molecule, or combination of small molecules, inhibits at least TGFβ1 (e.g., inhibition of Smad signaling). Therefore, in some embodiments, a small molecule inhibitor of TGFβ1 binds to TGFβ1. In some embodiments, a small molecule inhibitor of TGFβ1 inhibits expression (e.g., transcription, translation, secretion, or combinations thereof) of TGFβ1. In some embodiments, a small molecule inhibitor of TGFβ1 further inhibits one or more of TGFβ2, TGFβ3, TβRII, ALK5, and betaglycan. In some embodiments, a small molecule inhibitor of TGFβ1 does not inhibit or does not substantially inhibit TGFβ2. In some embodiments, a small molecule inhibitor of TGFβ1 further inhibits TGFβ3 but does not inhibit or does not substantially inhibit TGFβ2. In certain aspects, a TGFβ antagonist small molecule, or combination of small molecules, inhibits at least TGFβ2 (e.g., inhibition of Smad signaling). Therefore, in some embodiments, a small molecule inhibitor of TGFβ2 binds to TGFβ2. In some embodiments, a small molecule inhibitor of TGFβ2 inhibits expression (e.g., transcription, translation, secretion, or combinations thereof) of TGFβ2. In some embodiments, a small molecule inhibitor of TGFβ2 further inhibits one or more of TGFβ3, TGFβ1, TβRII, ALK5, and betaglycan. In certain aspects, a TGFβ antagonist small molecule, or combination of small molecules, inhibits at least TGFβ3 (e.g., inhibition of Smad signaling). Therefore, in some embodiments, a small molecule inhibitor of TGFβ3 binds to TGFβ3. In some embodiments, a small molecule inhibitor of TGFβ3 inhibits expression (e.g., transcription, translation, secretion, or combinations thereof) of TGFβ3. In some embodiments, a small molecule inhibitor of TGFβ3 further inhibits one or more of TGFβ2, TGFβ1, TβRII, ALK5, and betaglycan. In some embodiments, a small molecule inhibitor of TGFβ3 does not inhibit or does not substantially inhibit TGFβ2. In some embodiments, a small molecule inhibitor of TGFβ3 further inhibits TGFβ1 but does not inhibit or does not substantially inhibit TGFβ2. In certain aspects, a TGFβ antagonist small molecule, or combination of small molecules, inhibits at least TβRII (e.g., inhibition of Smad signaling). Therefore, in some embodiments, a small molecule inhibitor of TβRII binds to TβRII. In some embodiments, a small molecule inhibitor of TβRII inhibits expression (e.g., transcription, translation, secretion, or combinations thereof) of TβRII. In some embodiments, a small molecule inhibitor of TβRII further inhibits one or more of TGFβ1, TGFβ2, TGFβ3, ALK5, and betaglycan. In certain aspects, a TGFβ antagonist small molecule, or combination of small molecules, inhibits TGFβ1 from binding to TβRII. In certain aspects, a TGFβ antagonist small molecule, or combination of small molecules, inhibits TGFβ2 from binding to TβRII. In certain aspects, a TGFβ antagonist small molecule, or combination of small molecules, inhibits TGFβ3 from binding to TβRII. In certain aspects, a TGFβ antagonist small molecule, or combination of small molecules, inhibits TGFβ1 and TGFβ3 from binding to TβRII. In certain aspects, a TGFβ antagonist small molecule, or combination of small molecules, inhibits TGFβ1, TGFβ2, and TGFβ3 from binding to TβRII. In certain aspects, a TGFβ antagonist small molecule, or combination of small molecules, inhibits TGFβ1 from binding to TβRII but does not inhibit or does not substantially inhibit TGFβ2 from binding to TβRII. In certain aspects, a TGFβ antagonist small molecule, or combination of small molecules, inhibits TGFβ3 from binding to TβRII but does not inhibit or does not substantially inhibit TGFβ2 from binding to TβRII. In certain aspects, a TGFβ antagonist small molecule, or combination of small molecules, inhibits TGFβ1 and TGFβ3 from binding to TβRII but does not inhibit or does not substantially inhibit TGFβ2 from binding to TβRII. In certain aspects, a Tβ TGFβ RII antagonist small molecule, or combination of small molecules, inhibits at least ALK5 (e.g., inhibition of Smad signaling). Therefore, in some embodiments, a small molecule inhibitor of ALK5 binds to ALK5. In some embodiments, a small molecule inhibitor of ALK5 inhibits expression (e.g., transcription, translation, secretion, or combinations thereof) of ALK5. In some embodiments, a small molecule inhibitor of ALK5 further inhibits one or more of TGFβ1, TGFβ2, TGFβ3, TβRII, and betaglycan. In certain aspects, a TGFβ antagonist small molecule, or combination of small molecules, inhibits TGFβ1 from binding to ALK5. In certain aspects, a TGFβ antagonist small molecule, or combination of small molecules, inhibits TGFβ2 from binding to ALK5. In certain aspects, a TGFβ antagonist small molecule, or combination of small molecules, inhibits TGFβ3 from binding to ALK5. In certain aspects, a TGFβ antagonist small molecule, or combination of small molecules, inhibits TGFβ1 and TGFβ3 from binding to ALK5. In certain aspects, a TGFβ antagonist small molecule, or combination of small molecules, inhibits TGFβ1, TGFβ2, and TGFβ3 from binding to ALK5. In certain aspects, a TGFβ antagonist small molecule, or combination of small molecules, inhibits TGFβ1 from binding to ALK5 but does not inhibit or does not substantially inhibit TGFβ2 from binding to ALK5. In certain aspects, a TGFβ antagonist small molecule, or combination of small molecules, inhibits TGFβ3 from binding to ALK5 but does not inhibit or does not substantially inhibit TGFβ2 from binding to ALK5. In certain aspects, a TGFβ antagonist small molecule, or combination of small molecules, inhibits TGFβ1 and TGFβ3 from binding to ALK5 but does not inhibit or does not substantially inhibit TGFβ2 from binding to ALK5. In certain aspects, a TGFβ antagonist small molecule, or combination of small molecules, inhibits at least betaglycan (e.g., inhibition of Smad signaling). Therefore, in some embodiments, a small molecule inhibitor of betaglycan binds to betaglycan. In some embodiments, a small molecule inhibitor of betaglycan inhibits expression (e.g., transcription, translation, secretion, or combinations thereof) of betaglycan. In some embodiments, a small molecule inhibitor of betaglycan further inhibits one or more of TGFβ1, TGFβ2, TGFβ3, TβRII, and ALK5. In certain aspects, a TGFβ antagonist small molecule, or combination of small molecules, inhibits TGFβ1 from binding to betaglycan. In certain aspects, a TGFβ antagonist small molecule, or combination of small molecules, inhibits TGFβ2 from binding to betaglycan. In certain aspects, a TGFβ antagonist small molecule, or combination of small molecules, inhibits TGFβ3 from binding to betaglycan. In certain aspects, a TGFβ antagonist small molecule, or combination of small molecules, inhibits TGFβ1 and TGFβ3 from binding to betaglycan. In certain aspects, a TGFβ antagonist small molecule, or combination of small molecules, inhibits TGFβ1, TGFβ2, and TGFβ3 from binding to betaglycan. In certain aspects, a TGFβ antagonist small molecule, or combination of small molecules, inhibits TGFβ1 from binding to betaglycan but does not inhibit or does not substantially inhibit TGFβ2 from binding to betaglycan. In certain aspects, a TGFβ antagonist small molecule, or combination of small molecules, inhibits TGFβ3 from binding to betaglycan but does not inhibit or does not substantially inhibit TGFβ2 from binding to betaglycan. In certain aspects, a TGFβ antagonist small molecule, or combination of small molecules, inhibits TGFβ1 and TGFβ3 from binding to betaglycan but does not inhibit or does not substantially inhibit TGFβ2 from binding to betaglycan.

TGFβ antagonist small molecules can be direct or indirect inhibitors. For example, a TGFβ antagonist small molecule, or combination of small molecules, may inhibit the expression (e.g., transcription, translation, cellular secretion, or combinations thereof) of at least one or more of TβRII, ALK5, betaglycan, TGFβ1, TGFβ2, TGFβ3, and/or one or more downstream signaling factors (Smads). Alternatively, a direct TGFβ antagonist small molecule, or combination of small molecules, may directly bind to, for example, one or more of TβRII, ALK5, betaglycan, TGFβ1, TGFβ2, and TGFβ3 or one or more downstream signaling factors. Combinations of one or more indirect and one or more direct TGFβ antagonist small molecule may be used in accordance with the methods disclosed herein.

Binding organic small molecule antagonists of the present disclosure may be identified and chemically synthesized using known methodology (see, e.g., PCT Publication Nos. WO 00/00823 and WO 00/39585). In general, small molecule antagonists of the disclosure are usually less than about 2000 daltons in size, alternatively less than about 1500, 750, 500, 250 or 200 daltons in size, wherein such organic small molecules that are capable of binding, preferably specifically, to a polypeptide as described herein (e.g., TβRII, ALK5, betaglycan, TGFβ1, TGFβ2, and TGFβ3). Such small molecule antagonists may be identified without undue experimentation using well-known techniques. In this regard, it is noted that techniques for screening organic small molecule libraries for molecules that are capable of binding to a polypeptide target are well-known in the art (see, e.g., international patent publication Nos. WO00/00823 and WO00/39585).

Binding organic small molecules of the present disclosure may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, and acid chlorides.

E. Nucleic Acids

In certain aspects, a TGFβ antagonist to be used in accordance with the methods and uses disclosed herein is a polynucleotide (TGFβ antagonist polynucleotide) or combination of polynucleotides. A TGFβ antagonist polynucleotide, or combination of polynucleotides, may inhibit, for example, one or more ligands (e.g., TGFβ1, TGFβ2, and TGFβ3), TβRII receptor, TβRII-associated type I receptor (e.g., ALK5), TβRII-associated co-receptor (e.g., betaglycan), and/or downstream signaling component (e.g., Smads). In some embodiments, the ability for a TGFβ antagonist polynucleotide, or combination of polynucleotides, to inhibit signaling (e.g., Smad signaling) is determined in a cell-based assay including, for example, those described herein. A TGFβ antagonist polynucleotide, or combination of polynucleotide, may be used, alone or in combination with one or more additional supportive therapies or active agents, to treat heterotopic ossification, preferably preventing or reducing the severity or duration of one or more complications of heterotopic ossification.

In certain aspects, a TGFβ antagonist polynucleotide, or combination of polynucleotides, inhibits at least TGFβ1 (e.g., inhibition of Smad signaling). Therefore, in some embodiments, a polynucleotide inhibitor of TGFβ1 binds to TGFβ1. In some embodiments, a polynucleotide inhibitor of TGFβ1 inhibits expression (e.g., transcription, translation, secretion, or combinations thereof) of TGFβ1. In some embodiments, a polynucleotide inhibitor of TGFβ1 further inhibits one or more of TGFβ2, TGFβ3, TβRII, ALK5, and betaglycan. In some embodiments, a polynucleotide inhibitor of TGFβ1 does not inhibit or does not substantially inhibit TGFβ2. In some embodiments, a polynucleotide inhibitor of TGFβ1 further inhibits TGFβ3 but does not inhibit or does not substantially inhibit TGFβ2. In certain aspects, a TGFβ antagonist polynucleotide, or combination of polynucleotides, inhibits at least TGFβ2 (e.g., inhibition of Smad signaling). Therefore, in some embodiments, a polynucleotide inhibitor of TGFβ2 binds to TGFβ2. In some embodiments, a polynucleotide inhibitor of TGFβ2 inhibits expression (e.g., transcription, translation, secretion, or combinations thereof) of TGFβ2. In some embodiments, a polynucleotide inhibitor of TGFβ2 further inhibits one or more of TGFβ3, TGFβ1, TβRII, ALK5, and betaglycan. In certain aspects, a TGFβ antagonist polynucleotide, or combination of polynucleotides, inhibits at least TGFβ3 (e.g., inhibition of Smad signaling). Therefore, in some embodiments, a polynucleotide inhibitor of TGFβ3 binds to TGFβ3. In some embodiments, a polynucleotide inhibitor of TGFβ3 inhibits expression (e.g., transcription, translation, secretion, or combinations thereof) of TGFβ3. In some embodiments, a polynucleotide inhibitor of TGFβ3 further inhibits one or more of TGFβ2, TGFβ1, TβRII, ALK5, and betaglycan. In some embodiments, a polynucleotide inhibitor of TGFβ3 does not inhibit or does not substantially inhibit TGFβ2. In some embodiments, a polynucleotide inhibitor of TGFβ3 further inhibits TGFβ1 but does not inhibit or does not substantially inhibit TGFβ2. In certain aspects, a TGFβ antagonist polynucleotide, or combination of polynucleotides, inhibits at least TβRII (e.g., inhibition of Smad signaling). Therefore, in some embodiments, a polynucleotide inhibitor of TβRII binds to TβRII. In some embodiments, a polynucleotide inhibitor of TβRII inhibits expression (e.g., transcription, translation, secretion, or combinations thereof) of TβRII. In some embodiments, a polynucleotide inhibitor of TβRII further inhibits one or more of TGFβ1, TGFβ2, TGFβ3, ALK5, and betaglycan. In some embodiments, a TGFβ antagonist polynucleotide, or combination of polynucleotides, inhibits TGFβ1 from binding to TβRII. In some embodiments a TGFβ antagonist polynucleotide, or combination of polynucleotides, inhibits TGFβ2 from binding to TβRII. In some embodiments, a TGFβ antagonist polynucleotide, or combination of polynucleotides, inhibits TGFβ3 from binding to TβRII. In some embodiments, a TGFβ antagonist polynucleotide, or combination of polynucleotides, inhibits TGFβ1 and TGFβ3 from binding to TβRII. In some embodiments, a TGFβ antagonist polynucleotide, or combination of polynucleotides, inhibits TGFβ1, TGFβ2, and TGFβ3 from binding to TβRII. In some embodiments, a TGFβ antagonist polynucleotide, or combination of polynucleotides, inhibits TGFβ1 from binding to TβRII but does not inhibit or does not substantially inhibit TGFβ2 from binding to TβRII. In some embodiments, a TGFβ antagonist polynucleotide, or combination of polynucleotides, inhibits TGFβ3 from binding to TβRII but does not inhibit or does not substantially inhibit TGFβ2 from binding to TβRII. In some embodiments, a TGFβ antagonist polynucleotide, or combination of polynucleotides, inhibits TGFβ1 and TGFβ3 from binding to TβRII but does not inhibit or does not substantially inhibit TGFβ2 from binding to TβRII. In certain aspects, a TGFβ antagonist polynucleotide, or combination of polynucleotides, inhibits at least ALK5 (e.g., inhibition of Smad signaling). Therefore, in some embodiments, a polynucleotide inhibitor of ALK5 binds to ALK5. In some embodiments, a polynucleotide inhibitor of ALK5 inhibits expression (e.g., transcription, translation, secretion, or combinations thereof) of ALK5. In some embodiments, a polynucleotide inhibitor of ALK5 further inhibits one or more of TGFβ1, TGFβ2, TGFβ3, TβRII, and betaglycan. In some embodiments, a TGFβ antagonist polynucleotide, or combination of polynucleotides, inhibits TGFβ1 from binding to ALK5. In some embodiments, a TGFβ antagonist polynucleotide, or combination of polynucleotides, inhibits TGFβ2 from binding to ALK5. In some embodiments, a TGFβ antagonist polynucleotide, or combination of polynucleotides, inhibits TGFβ3 from binding to ALK5. In some embodiments, a TGFβ antagonist polynucleotide, or combination of polynucleotides, inhibits TGFβ1 and TGFβ3 from binding to ALK5. In some embodiments, a TGFβ antagonist polynucleotide, or combination of polynucleotides, inhibits TGFβ1, TGFβ2, and TGFβ3 from binding to ALK5. In some embodiments, a TGFβ antagonist polynucleotide, or combination of polynucleotides, inhibits TGFβ1 from binding to ALK5 but does not inhibit or does not substantially inhibit TGFβ2 from binding to ALK5. In some embodiments, a TGFβ antagonist polynucleotide, or combination of polynucleotides, inhibits TGFβ3 from binding to ALK5 but does not inhibit or does not substantially inhibit TGFβ2 from binding to ALK5. In some embodiments, a TGFβ antagonist polynucleotide, or combination of polynucleotides, inhibits TGFβ1 and TGFβ3 from binding to ALK5 but does not inhibit or does not substantially inhibit TGFβ2 from binding to ALK5. In certain aspects, a TGFβ antagonist polynucleotide, or combination of polynucleotides, inhibits at least betaglycan (e.g., inhibition of Smad signaling). Therefore, in some embodiments, a polynucleotide inhibitor of betaglycan binds to betaglycan. In some embodiments, a polynucleotide inhibitor of betaglycan inhibits expression (e.g., transcription, translation, secretion, or combinations thereof) of betaglycan. In some embodiments, a polynucleotide inhibitor of betaglycan further inhibits one or more of TGFβ1, TGFβ2, TGFβ3, TβRII, and ALK5. In some embodiments, a TGFβ antagonist polynucleotide, or combination of polynucleotides, inhibits TGFβ1 from binding to betaglycan. In some embodiments, a TGFβ antagonist polynucleotide, or combination of polynucleotides, inhibits TGFβ2 from binding to betaglycan. In some embodiments, a TGFβ antagonist polynucleotide, or combination of polynucleotides, inhibits TGFβ3 from binding to betaglycan. In some embodiments, a TGFβ antagonist polynucleotide, or combination of polynucleotides, inhibits TGFβ1 and TGFβ3 from binding to betaglycan. In some embodiments, a TGFβ antagonist polynucleotide, or combination of polynucleotides, inhibits TGFβ1, TGFβ2, and TGFβ3 from binding to betaglycan. In some embodiments, a TGFβ antagonist polynucleotide, or combination of polynucleotides, inhibits TGFβ1 from binding to betaglycan but does not inhibit or does not substantially inhibit TGFβ2 from binding to betaglycan. In some embodiments, a TGFβ antagonist polynucleotide, or combination of polynucleotides, inhibits TGFβ3 from binding to betaglycan but does not inhibit or does not substantially inhibit TGFβ2 from binding to betaglycan. In some embodiments, a TGFβ antagonist polynucleotide, or combination of polynucleotides, inhibits TGFβ1 and TGFβ3 from binding to betaglycan but does not inhibit or does not substantially inhibit TGFβ2 from binding to betaglycan.

The polynucleotide antagonists of the present disclosure may be an antisense nucleic acid, an RNAi molecule [e.g., small interfering RNA (siRNA), small-hairpin RNA (shRNA), microRNA (miRNA)], an aptamer and/or a ribozyme. The nucleic acid and amino acid sequences of human TβRII, ALK5, betaglycan, TGFβ1, TGFβ2, and TGFβ3 are known in the art and thus polynucleotide antagonists for use in accordance with methods of the present disclosure may be routinely made by the skilled artisan based on the knowledge in the art and teachings provided herein.

For example, antisense technology can be used to control gene expression through antisense DNA or RNA, or through triple-helix formation. Antisense techniques are discussed, for example, in Okano (1991) J. Neurochem. 56:560; Oligodeoxynucleotides as Antisense Inhibitors of Gene Expression, CRC Press, Boca Raton, Fla. (1988). Triple helix formation is discussed in, for instance, Cooney et al. (1988) Science 241:456; and Dervan et al., (1991)Science 251: 1300. The methods are based on binding of a polynucleotide to a complementary DNA or RNA. In some embodiments, the antisense nucleic acids comprise a single-stranded RNA or DNA sequence that is complementary to at least a portion of an RNA transcript of a desired gene. However, absolute complementarity, although preferred, is not required.

A sequence "complementary to at least a portion of an RNA," referred to herein, means a sequence having sufficient complementarity to be able to hybridize with the RNA, forming a stable duplex; in the case of double-stranded antisense nucleic acids of a gene disclosed herein, a single strand of the duplex DNA may thus be tested, or triplex formation may be assayed. The ability to hybridize will depend on both the degree of complementarity and the length of the antisense nucleic acid. Generally, the larger the hybridizing nucleic acid, the more base mismatches with an RNA it may contain and still form a stable duplex (or triplex as the case may be). One skilled in the art can ascertain a tolerable degree of mismatch by use of standard procedures to determine the melting point of the hybridized complex.

Polynucleotides that are complementary to the 5' end of the message, for example, the 5'-untranslated sequence up to and including the AUG initiation codon, should work most efficiently at inhibiting translation. However, sequences complementary to the 3'-untranslated sequences of mRNAs have been shown to be effective at inhibiting translation of mRNAs as well [see, e.g., Wagner, R., (1994) Nature 372:333-335]. Thus, oligonucleotides complementary to either the 5'- or 3'-untranslated, noncoding regions of a gene of the disclosure, could be used in an antisense approach to inhibit translation of an endogenous mRNA. Polynucleotides complementary to the 5'-untranslated region of the mRNA should include the complement of the AUG start codon. Antisense polynucleotides complementary to mRNA coding regions are less efficient inhibitors of translation but could be used in accordance with the methods of the present disclosure. Whether designed to hybridize to the 5'-untranslated, 3'-untranslated, or coding regions of an mRNA of the disclosure, antisense nucleic acids should be at least six nucleotides in length, and are preferably oligonucleotides ranging from 6 to about 50 nucleotides in length. In specific aspects, the oligonucleotide is at least 10 nucleotides, at least 17 nucleotides, at least 25 nucleotides, or at least 50 nucleotides.

In one embodiment, the antisense nucleic acid of the present disclosure is produced intracellularly by transcription from an exogenous sequence. For example, a vector or a portion thereof, is transcribed, producing an antisense nucleic acid (RNA) of a gene of the disclosure. Such a vector would contain a sequence encoding the desired antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding desired genes of the instant disclosure, or fragments thereof, can be by any promoter known in the art to act in vertebrate, preferably human cells. Such promoters can be inducible or constitutive. Such promoters include, but are not limited to, the SV40 early promoter region [see, e.g., Benoist and Chambon (1981) Nature 29:304-310], the promoter contained in the 3' long terminal repeat of Rous sarcoma virus [see, e.g., Yamamoto et al. (1980) Cell 22:787-797], the herpes thymidine promoter [see, e.g., Wagner et al. (1981) Proc. Natl. Acad. Sci. U.S.A. 78:1441-1445], and the regulatory sequences of the metallothionein gene [see, e.g., Brinster, et al. (1982) Nature 296:39-42].

In some embodiments, the polynucleotide antagonists are interfering RNA or RNAi molecules that target the expression of one or more genes. RNAi refers to the expression of an RNA which interferes with the expression of the targeted mRNA. Specifically, RNAi silences a targeted gene via interacting with the specific mRNA through a siRNA (small interfering RNA). The ds RNA complex is then targeted for degradation by the cell. An siRNA molecule is a double-stranded RNA duplex of 10 to 50 nucleotides in length, which interferes with the expression of a target gene which is sufficiently complementary (e.g. at least 80% identity to the gene). In some embodiments, the siRNA molecule comprises a nucleotide sequence that is at least 85, 90, 95, 96, 97, 98, 99, or 100% identical to the nucleotide sequence of the target gene.

Additional RNAi molecules include short-hairpin RNA (shRNA); also short-interfering hairpin and microRNA (miRNA). The shRNA molecule contains sense and antisense sequences from a target gene connected by a loop. The shRNA is transported from the nucleus into the cytoplasm, and it is degraded along with the mRNA. Pol III or U6 promoters can be used to express RNAs for RNAi. Paddison et al. [Genes & Dev. (2002) 16:948-958, 2002] have used small RNA molecules folded into hairpins as a means to effect RNAi. Accordingly, such short hairpin RNA (shRNA) molecules are also advantageously used in the methods described herein. The length of the stem and loop of functional shRNAs varies; stem lengths can range anywhere from about 25 to about 30 nt, and loop size can range between 4 to about 25 nt without affecting silencing activity. While not wishing to be bound by any particular theory, it is believed that these shRNAs resemble the double-stranded RNA (dsRNA) products of the DICER RNase and, in any event, have the same capacity for inhibiting expression of a specific gene. The shRNA can be expressed from a lentiviral vector. An miRNA is a single-stranded RNA of about 10 to 70 nucleotides in length that are initially transcribed as pre-miRNA characterized by a "stem-loop" structure and which are subsequently processed into mature miRNA after further processing through the RISC.

Molecules that mediate RNAi, including without limitation siRNA, can be produced in vitro by chemical synthesis (Hohjoh, FEBS Lett 521:195-199, 2002), hydrolysis of dsRNA (Yang et al., Proc Natl Acad Sci USA 99:9942-9947, 2002), by in vitro transcription with T7 RNA polymerase (Donzeet et al., Nucleic Acids Res 30:e46, 2002; Yu et al., Proc Natl Acad Sci USA 99:6047-6052, 2002), and by hydrolysis of double-stranded RNA using a nuclease such as E. coli RNase III (Yang et al., Proc Natl Acad Sci USA 99:9942-9947, 2002).

According to another aspect, the disclosure provides polynucleotide antagonists including but not limited to, a decoy DNA, a double-stranded DNA, a single-stranded DNA, a complexed DNA, an encapsulated DNA, a viral DNA, a plasmid DNA, a naked RNA, an encapsulated RNA, a viral RNA, a double-stranded RNA, a molecule capable of generating RNA interference, or combinations thereof.

In some embodiments, the polynucleotide antagonists of the disclosure are aptamers. Aptamers are nucleic acid molecules, including double-stranded DNA and single-stranded RNA molecules, which bind to and form tertiary structures that specifically bind to a target molecule, such as a TβRII, TGFβ1, TGFβ2, and TGFβ3 polypeptide. The generation and therapeutic use of aptamers are well established in the art. See, e.g., U.S. Pat. No. 5,475,096. Additional information on aptamers can be found in U.S. Patent Application Publication No. 20060148748. Nucleic acid aptamers are selected using methods known in the art, for example via the Systematic Evolution of Ligands by Exponential Enrichment (SELEX) process. SELEX is a method for the in vitro evolution of nucleic acid molecules with highly specific binding to target molecules as described in, e.g., U.S. Pat. Nos. 5,475,096, 5,580,737, 5,567,588, 5,707,796, 5,763,177, 6,011,577, and 6,699,843. Another screening method to identify aptamers is described in U.S. Pat. No. 5,270,163. The SELEX process is based on the capacity of nucleic acids for forming a variety of two- and three-dimensional structures, as well as the chemical versatility available within the nucleotide monomers to act as ligands (form specific binding pairs) with virtually any chemical compound, whether monomeric or polymeric, including other nucleic acid molecules and polypeptides. Molecules of any size or composition can serve as targets. The SELEX method involves selection from a mixture of candidate oligonucleotides and step-wise iterations of binding, partitioning and amplification, using the same general selection scheme, to achieve desired binding affinity and selectivity. Starting from a mixture of nucleic acids, which can comprise a segment of randomized sequence, the SELEX method includes steps of contacting the mixture with the target under conditions favorable for binding; partitioning unbound nucleic acids from those nucleic acids which have bound specifically to target molecules; dissociating the nucleic acid-target complexes; amplifying the nucleic acids dissociated from the nucleic acid-target complexes to yield a ligand enriched mixture of nucleic acids. The steps of binding, partitioning, dissociating and amplifying are repeated through as many cycles as desired to yield highly specific high affinity nucleic acid ligands to the target molecule.

Typically, such binding molecules are separately administered to the animal [see, e.g., O'Connor (1991) J. Neurochem. 56:560], but such binding molecules can also be expressed in vivo from polynucleotides taken up by a host cell and expressed in vivo [see, e.g., Oligodeoxynucleotides as Antisense Inhibitors of Gene Expression, CRC Press, Boca Raton, Fla. (1988)].

3. Screening Assays

In certain aspects, the present invention relates to the use of TβRII polypeptides (e.g., soluble TβRII polypeptides) to identify compounds (agents) which are agonist or antagonists of the TGFβ1, TGFβ3 and TβRII signaling pathway. Compounds identified through this screening can be tested to assess their ability to modulate TGFβ1 and TGFβ3 signaling activity in vitro. Optionally, these compounds can further be tested in animal models to assess their ability to modulate tissue growth in vivo.

There are numerous approaches to screening for therapeutic agents for modulating tissue growth by targeting TGFβ1, TGFβ3 and TβRII polypeptides. In certain embodiments, high-throughput screening of compounds can be carried out to identify agents that perturb TGFβ1, TGFβ3 or TβRII-mediated cell signaling. In certain embodiments, the assay is carried out to screen and identify compounds that specifically inhibit or reduce binding of a TβRII polypeptide to TGFβ1 or TGFβ3. Alternatively, the assay can be used to identify compounds that enhance binding of a TβRII polypeptide to TGFβ1 or TGFβ3. In a further embodiment, the compounds can be identified by their ability to interact with a TGFβ1, TGFβ3 or TβRII polypeptide.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In a specific embodiment, the test agent is a small organic molecule having a molecular weight of less than about 2,000 daltons.

The test compounds of the invention can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase (GST), photoactivatible crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between a TβRII polypeptide and TGFβ1 or TGFβ3.

Merely to illustrate, in an exemplary screening assay of the present invention, the compound of interest is contacted with an isolated and purified TβRII polypeptide which is ordinarily capable of binding to TGFβ1 or TGFβ3. To the mixture of the compound and TβRII polypeptide is then added a composition containing a TβRII ligand. Detection and quantification of TβRII/TGFβ1 or TβRII/TGFβ3 complexes provides a means for determining the compound's efficacy at inhibiting (or potentiating) complex formation between the TβRII polypeptide and TGFβ1 or TGFβ3. The efficacy of the compound can be assessed by generating dose response curves from data obtained using various concentrations of the test compound. Moreover, a control assay can also be performed to provide a baseline for comparison. For example, in a control assay, isolated and a purified TGFβ1 or TGFβ3 is added to a composition containing the TβRII polypeptide, and the formation of TβRII/TGFβ1 or TβRII/TGFβ3 complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between the TβRII polypeptide and TGFβ1 or TGFβ3 may be detected by a variety of techniques. For instance, modulation of the formation of complexes can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled TβRII polypeptide or TGFβ1 or TGFβ3, by immunoassay, or by chromatographic detection.

In certain embodiments, the present invention contemplates the use of fluorescence polarization assays and fluorescence resonance energy transfer (FRET) assays in measuring, either directly or indirectly, the degree of interaction between a TβRII polypeptide and its binding protein. Further, other modes of detection, such as those based on optical waveguides (PCT Publication WO 96/26432 and U.S. Pat. No. 5,677,196), surface plasmon resonance (SPR), surface charge sensors, and surface force sensors, are compatible with many embodiments of the invention.

Moreover, the present invention contemplates the use of an interaction trap assay, also known as the "two hybrid assay," for identifying agents that disrupt or potentiate interaction between a TβRII polypeptide and its binding protein. See for example, U.S. Pat. No. 5,283,317; Zervos et al. (1993) Cell 72:223-232; Madura et al. (1993) J Biol Chem 268:12046-12054; Bartel et al. (1993) Biotechniques 14:920-924; and Iwabuchi et al. (1993) Oncogene 8:1693-1696). In a specific embodiment, the present invention contemplates the use of reverse two hybrid systems to identify compounds (e.g., small molecules or peptides) that dissociate interactions between a TβRII polypeptide and its binding protein. See for example, Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368.

In certain embodiments, the subject compounds are identified by their ability to interact with a TβRII or TGFβ1 or TGFβ3 polypeptide of the invention. The interaction between the compound and the TβRII or TGFβ1 or TGFβ3 polypeptide may be covalent or non-covalent. For example, such interaction can be identified at the protein level using in vitro biochemical methods, including photo-crosslinking, radiolabeled ligand binding, and affinity chromatography (Jakoby W B et al., 1974, Methods in Enzymology 46: 1). In certain cases, the compounds may be screened in a mechanism based assay, such as an assay to detect compounds which bind to a TGFβ1 or TGFβ3 or TβRII polypeptide. This may include a solid-phase or fluid-phase binding event. Alternatively, the gene encoding a TGFβ1 or TGFβ3 or TβRII polypeptide can be transfected with a reporter system (e.g., 0-galactosidase, luciferase, or green fluorescent protein) into a cell and screened against the library preferably by a high-throughput screening or with individual members of the library. Other mechanism-based binding assays may be used, for example, binding assays which detect changes in free energy. Binding assays can be performed with the target fixed to a well, bead or chip or captured by an immobilized antibody or resolved by capillary electrophoresis. The bound compounds may be detected usually using colorimetric or fluorescence or surface plasmon resonance.

In certain aspects, the present invention provides methods and agents for modulating (stimulating or inhibiting) TGFβ1- or TGFβ3-mediated cell signaling. Therefore, any compound identified can be tested in whole cells or tissues, in vitro or in vivo, to confirm their ability to modulate TGFβ1 or TGFβ3 signaling. Various methods known in the art can be utilized for this purpose.

4. Exemplary Therapeutic Uses

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The terms "treatment", "treating", "alleviation" and the like are used herein to generally mean obtaining a desired pharmacologic and/or physiologic effect, and may also be used to refer to improving, alleviating, and/or decreasing the severity of one or more symptoms of a condition being treated. The effect may be prophylactic in terms of completely or partially delaying the onset or recurrence of a disease, condition, or symptoms thereof, and/or may be therapeutic in terms of a partial or complete cure for a disease or condition and/or adverse effect attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition (e.g., arresting its development); or (c) relieving the disease or condition (e.g., causing regression of the disease or condition, providing improvement in one or more symptoms).

The terms "patient", "subject", or "individual" are used interchangeably herein and refer to either a human or a non-human animal. These terms include mammals, such as humans, non-human primates, laboratory animals, livestock animals (including bovines, porcines, camels, etc.), companion animals (e.g., canines, felines, other domesticated animals, etc.) and rodents (e.g., mice and rats). In particular embodiments, the patient, subject or individual is a human.

As used herein, "combination", "in combination with", "conjoint administration" and the like refers to any form of administration such that the second therapy is still effective in the body (e.g., the two compounds are simultaneously effective in the patient, which may include synergistic effects of the two compounds). Effectiveness may not correlate to measurable concentration of the agent in blood, serum, or plasma. For example, the different therapeutic compounds can be administered either in the same formulation or in separate formulations, either concomitantly or sequentially, and on different schedules. Thus, an individual who receives such treatment can benefit from a combined effect of different therapies. One or more TGFβ antagonists of the disclosure can be administered concurrently with, prior to, or subsequent to, one or more other additional agents or supportive therapies. In general, each therapeutic agent will be administered at a dose and/or on a time schedule determined for that particular agent. The particular combination to employ in a regimen will take into account compatibility of the antagonist of the present disclosure with the therapy and/or the desired therapeutic effect to be achieved.

In part, the disclosure provides methods of treating heterotopic ossification by administering to a patient in need thereof an effective amount of a TGFβ antagonists. In some embodiments, the methods relate to preventing or reducing the severity and/or duration of heterotopic ossification in a patient in need thereof an effective amount of a TGFβ antagonists. In some embodiments, the disclosure provides methods of treating a disease or condition associated with heterotopic ossification by administering to a patient in need thereof an effective amount of a TGFβ antagonists. In some embodiments, the methods relate to preventing or reducing the severity and/or duration of a disease or condition associated heterotopic ossification in a patient in need thereof an effective amount of a TGFβ antagonists. Optionally, such methods further include administering the TGFβ antagonists in combination with one or more additional active agents or supportive therapies for treating heterotopic ossification.

In general, heterotopic ossification (HO) result from osteoid formation of mature lamellar bone in soft tissue sites outside the skeletal periosteum (skeletal system). Often, there is an inciting event prior to onset of HO, usually an episode of trauma which may result in hematoma. In general, HO progression requires a supply of pluripotent (multipotent) mesenchymal cells, which can differentiate into osteoblasts or chondroblasts. However, the mechanism of action behind HO development otherwise is largely unknown. Osteoid formation often is associated with an inflammatory phase characterized by local swelling, pain, erythema and sometimes fever. This pathological process may occur in sites such as the skin, subcutaneous tissue, skeletal muscle, and fibrous tissue adjacent to joints. Bone may also form in walls of blood vessels as well as in ligaments. Lesions range from small clinically insignificant foci to massive deposits throughout the body. HO may result in joint contracture and ankylosis, pain, spasticity, swelling fever, neurovascular compression, pressure ulcers, and significant disability. In some embodiments, the disclosure relates to methods of treating one or more complication associated with heterotopic ossification (e.g., osseous deposition, marrow space formation, joint contracture, ankylosis, pain, spasticity, swelling, fever, neurovascular compression, and pressure ulcers) by administering to a subject in need thereof an effective amount of a TGFβ antagonists, optionally in combination with one or more additional active agents or supportive therapies for treating heterotopic ossification.

HO is most commonly it is associated with spinal cord injury, trauma, brain injuries, burns, fractures, muscle contusion, and joint arthroplasty. In some embodiments, the disclosure relates to methods of treating heterotopic ossification associated with one or more disorders or conditions selected from the group consisting of: spinal cord injury, trauma, brain injuries, burns, fractures, muscle contusion, and joint arthroplasty by administering to a subject in need thereof an effective amount of a TGFβ antagonists, optionally in combination with one or more additional active agents or supportive therapies for treating heterotopic ossification.

HO is a severe complication of hip, acetabular, and elbow fracture surgery. About every third patient who has total hip arthroplasty (joint replacement) or a severe fracture of the long bones of the lower leg will develop HO, but is uncommonly symptomatic. Between 50% and 90% of patients who developed HO following a previous hip arthroplasty will develop additional heterotopic ossification. In some embodiments, the disclosure relates to methods of treating heterotopic ossification associated with one or more of joint, hip, acetabular, and elbow fracture surgery (e.g., replacement surgery) by administering to a subject in need thereof an effective amount of a TGFβ antagonists, optionally in combination with one or more additional active agents or supportive therapies for treating heterotopic ossification.

HO often develops in patients with traumatic injury. In particular, HO is associated with brain or spinal cord injuries, which may account for the clinical observation that traumatic brain injuries cause accelerated fracture healing. Morley et al. (2005) Injury 36(3): 363. HO is also associated with severe burns, combat-related trauma, and amputation. In traumatic heterotopic ossification, the patient may complain of a warm, tender, firm swelling in a muscle and decreased range of motion in the joint served by the muscle involved. There is often a history of a blow or other trauma to the area a few weeks to a few months earlier. Patients with traumatic neurological injuries, severe neurologic disorders or severe burns who develop heterotopic ossification experience limitation of motion in the areas affected. In some embodiments, the disclosure relates to methods of treating heterotopic ossification associated with one or more of traumatic injury, brain or spinal cord injuries, burns, combat-related trauma, and amputation by administering to a subject in need thereof an effective amount of a TGFβ antagonists, optionally in combination with one or more additional active agents or supportive therapies for treating heterotopic ossification.

There are also rare genetic disorders causing heterotopic ossification such as fibrodysplasia ossificans progressiva (FOP). FOP is an extremely rare connective tissue disease. The disease is caused by a mutation of the body's repair mechanism, which causes fibrous tissue (including muscle, tendon, and ligament) to be ossified spontaneously or when damaged. In many cases, injuries can cause joints to become permanently frozen in place. For unknown reasons, children born with FOP have deformed big toes, possibly missing a joint or simply presenting with a notable lump at the minor joint. The first "flare-up" that leads to the formation of FOP bones usually occurs before the age of 10. The bone growth progresses from the top downward, just as bones grow in fetuses. A child with FOP will typically develop bones starting at the neck, then on the shoulders, arms, chest area and finally on the feet. Specifically, ossification is typically first seen in the dorsal, axial, cranial and proximal regions of the body. Later the disease progresses in the ventral, appendicular, caudal and distal regions of the body. However, it does not necessarily occur in this order due to injury-caused flare-ups. Often, the tumor-like lumps that characterize the disease appear suddenly. This condition causes loss of mobility to affected joints, including inability to fully open the mouth limiting speech and eating. Extra bone formation around the rib cage restricts the expansion of lungs and diaphragm causing breathing complications. Since the disease is so rare, the symptoms are often misdiagnosed as cancer or fibrosis. This leads physicians to order biopsies, which can exacerbate the growth of these lumps. The median age of survival is 40 years with proper management. However, delayed diagnosis, trauma and infections can decrease life expectancy. In general, FOP is caused by an autosomal dominant allele on chromosome 2q23-24. The allele has variable expressivity, but complete penetrance. Most cases are caused by spontaneous mutation in the gametes. A similar but less catastrophic disease is fibrous dysplasia, which is caused by a post-zygotic mutation. A mutation in the gene ACVR1 (also known as activin-like kinase 2 (ALK2)) is responsible for the disease. ACVR1 encodes activin receptor type-1, a BMP type-1 receptor. The mutation causes substitution of codon 206 from arginine to histidine in the ACVR1 protein. This substitution causes abnormal activation of ACVR1, leading to the transformation of connective tissue and muscle tissue into a secondary skeleton. This causes endothelial cells to transform to mesenchymal stem cells and then to bone. In some embodiments, the disclosure relates to methods of treating heterotopic ossification associated with fibrodysplasia ossificans progressiva by administering to a subject in need thereof an effective amount of a TGFβ antagonists, optionally in combination with one or more additional active agents or supportive therapies for treating heterotopic ossification and/or fibrodysplasia ossificans progressiva. In some embodiments, the disclosure relates to methods of treating heterotopic ossification associated with fibrous dysplasia by administering to a subject in need thereof an effective amount of a TGFβ antagonists, optionally in combination with one or more additional active agents or supportive therapies for treating heterotopic ossification and/or fibrous dysplasia.

There is no cure or approved treatment for FOP. Attempts to surgically remove the bone result in explosive bone growth. Clinical trials of isotretinoin, etidronate with oral corticosteroids, and perhexiline maleate have failed to demonstrate effectiveness, though the variable course of the disease and small prevalence induces uncertainty. A handful of pharmaceutical companies focused on rare disease are currently in varying stages of investigation into different therapeutic approaches for FOP. In August 2015, U.S. Food and Drug Administration Office of Orphan Products Development granted La Jolla Pharmaceuticals orphan drug designation for two novel compounds for FOP. The compounds are small-molecule kinase inhibitors designed to selectively block ACVR1 (ALK2). In August 2015, Clementia Pharmaceuticals also began the enrollment of children into its Phase II clinical trial investigating palovarotene for the treatment of FOP. Preclinical studies demonstrated that palovarotene, a retinoic acid receptor gamma agonist, blocked abnormal bone formation in animal models via inhibition of secondary messenger systems in the BMP pathway. In September 2015, Regeneron announced new insight into the mechanism of disease involving the activation of the ACVR1 receptor by activin A. In 2016, the company initiated a phase 1 study of REGN 2477 (an activin A antibody) in healthy volunteers. Another potential therapeutic approach involves allele-specific RNA interference that targets mutated mRNA for degradation while preserving normal ACVR1 gene expression. J. W. Lowery et al. (2012) Gene Therapy 19(701-702): 701-702. A mouse model of FOP expressing a strong constitutively active ALK2 R206H mutant, was found to be useful in identifying a selective agonist to nuclear retinoic acid receptor-α (RAR-α) in mesenchymal cells. RAR-α agonists were found to partly inhibit HO, while an agonist to RAR-γ was found to be a potent inhibitor of intramuscular and subcutaneous HO in FOP models. Shimono et al., 2011, Nature Medicine 17:454-60). In some embodiments, the disclosure relates to methods of treating heterotopic ossification associated with FOP by administering to a subject in need thereof an effective amount of a TGFβ antagonists in combination with one or more additional active agents or supportive therapies for treating FOP, wherein the additional active agent or supportive therapy is selected from the group consisting of: isotretinoin, etidronate with oral corticosteroids, perhexiline maleate, ALK2 small-molecule inhibitors, palovarotene, retinoic acid receptor gamma agonists, retinoic acid receptor alpha agonists, activin antibodies (e.g., activin A antibodies such as REGN 2477, and allele-specific RNA interference of ALK2.

Another rare genetic disorder causing heterotopic ossification is progressive osseous heteroplasia (POH), which is a condition characterized by cutaneous or subcutaneous ossification. POH is associated with inactivating mutation in the GNAS gene, which encodes Gas, the alpha subunit of the stimulatory guanine nucleotide binding protein that acts downstream of many G protein-coupled receptors in activating adenylyl cyclase. Kaplan, et al. 1994, J Bone Joint Surg Am 76, 425-436; Shore, et al., 2002, N Engl J Med 346, 99-106; and Eddy, et al., 2000, J Bone Miner Res 15, 2074-2083. Clinically, POH presents during infancy with dermal and subcutaneous ossifications that progress during childhood into skeletal muscle and deep connective tissues (e.g., tendon, ligaments, fascia). Over time these ossifications lead to joint stiffness, bone and joint fusions and growth retardation of the affected limbs. Currently, patients with POH undergo aggressive surgical resection of ectopic bone to abrogate spreading of the lesion. This often results in partial or full amputation of limbs and lesions frequently return (Kaplan, et al., 2000, J Bone Miner Res 15, 2084-94; and Shehab, et al., 2003, J Nucl Med 43, 346-353), which underscores the importance of developing improved therapeutic interventions. Observations made in patients with POH suggest that mesenchymal stem cells present in soft tissues inappropriately differentiate into osteoblasts and begin to deposit bone. Due to a lack of both in vitro and in vivo animal models, the pathogenesis of POH remains unknown and, like all forms of HO, lacks adequate treatments. In some embodiments, the disclosure relates to methods of treating heterotopic ossification associated with progressive osseous heteroplasia by administering to a subject in need thereof an effective amount of a TGFβ antagonists, optionally in combination with one or more additional active agents or supportive therapies for treating heterotopic ossification and/or progressive osseous heteroplasia.

HO also may occur in patients who are on neuromuscular blockade to manage adult respiratory distress syndrome and in patients with nontraumatic myelopathies. In some embodiments, the disclosure relates to methods of treating heterotopic ossification associated with neuromuscular blockade used manage adult respiratory distress syndrome by administering to a subject in need thereof an effective amount of a TGFβ antagonists, optionally in combination with one or more additional active agents or supportive therapies for treating heterotopic ossification. In some embodiments, the disclosure relates to methods of treating heterotopic ossification associated with nontraumatic myelopathies by administering to a subject in need thereof an effective amount of a TGFβ antagonists, optionally in combination with one or more additional active agents or supportive therapies for treating heterotopic ossification.

There is no clear form of treatment for HO. Originally, bisphosphonates were expected to be of value after hip surgery but there has been no convincing evidence of benefit, despite having been used prophylactically. Prophylactic radiation therapy for the prevention of heterotopic ossification has been employed since the 1970s. A variety of doses and techniques have been used. Generally, radiation therapy should be delivered as close as practical to the time of surgery. A dose of 7-8 Gray in a single fraction within 24-48 hours of surgery has been used successfully. Treatment volumes include the peri-articular region, and can be used for hip, knee, elbow, shoulder, jaw or in patients after spinal cord trauma. Single dose radiation therapy has been found to be well tolerated and is cost effective, without an increase in bleeding, infection or wound healing disturbances. Certain anti-inflammatory agents, such as indomethacin, ibuprofen and aspirin, have shown some effect in preventing recurrence of heterotopic ossification after total hip replacement. Conservative treatments such as passive range of motion exercises or other mobilization techniques provided by physical therapists or occupational therapists may also assist in preventing HO. In some embodiments, the disclosure relates to methods of treating heterotopic ossification by administering to a subject in need thereof an effective amount of a TGFβ antagonists in combination with one or more additional active agents or supportive therapies for treating heterotopic ossification, wherein the one or more additional active agents or supportive therapies is selected from the group consisting of: bisphosphonates, radiation therapy anti-inflammatory agents (e.g., indomethacin, ibuprofen and aspirin), and conservative treatments such as passive range of motion exercises or other mobilization techniques.

5. Pharmaceutical Compositions

The therapeutic agents described herein (e.g., TβRII fusion polypeptides) may be formulated into pharmaceutical compositions. Pharmaceutical compositions for use in accordance with the present disclosure may be formulated in conventional manner using one or more physiologically acceptable carriers or excipients. Such formulations will generally be substantially pyrogen-free, in compliance with most regulatory requirements.

In certain embodiments, the therapeutic method of the disclosure includes administering the composition systemically, or locally as an implant or device. When administered, the therapeutic composition for use in this disclosure is in a pyrogen-free, physiologically acceptable form. Therapeutically useful agents other than the TGFβ signaling antagonist which may also optionally be included in the composition as described above, may be administered simultaneously or sequentially with the subject compounds (e.g., TβRII polypeptides) in the methods disclosed herein.

Typically, protein therapeutic agents disclosed herein will be administered parentally, and particularly intravenously or subcutaneously. Pharmaceutical compositions suitable for parenteral administration may comprise one or more TGFβ antagonists in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The compositions and formulations may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration Further, the composition may be encapsulated or injected in a form for delivery to a target tissue site. In certain embodiments, compositions of the present invention may include a matrix capable of delivering one or more therapeutic compounds (e.g., TGFβ antagonists) to a target tissue site, providing a structure for the developing tissue and optimally capable of being resorbed into the body. For example, the matrix may provide slow release of the TGFβ antagonists. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalcium phosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability.

In certain embodiments, methods of the invention can be administered for orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the subject compounds of the invention (e.g., TGFβ antagonists). The various factors include, but are not limited to, the patient's age, sex, and diet, the severity disease, time of administration, and other clinical factors. Optionally, the dosage may vary with the type of matrix used in the reconstitution and the types of compounds in the composition. The addition of other known growth factors to the final composition, may also affect the dosage. Progress can be monitored by periodic assessment of bone growth and/or repair, for example, X-rays (including DEXA), histomorphometric determinations, and tetracycline labeling.

In certain embodiments, the present invention also provides gene therapy for the in vivo production of TGFβ antagonists. Such therapy would achieve its therapeutic effect by introduction of the TGFβ antagonist polynucleotide sequences into cells or tissues having the disorders as listed above. Delivery of TGFβ antagonist polynucleotide sequences can be achieved using a recombinant expression vector such as a chimeric virus or a colloidal dispersion system. Preferred for therapeutic delivery of TGFβ antagonist polynucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the TGFβ antagonist polynucleotide. In a preferred embodiment, the vector is targeted to bone or cartilage.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for TGFβ antagonist polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

The disclosure provides formulations that may be varied to include acids and bases to adjust the pH; and buffering agents to keep the pH within a narrow range.

EXEMPLIFICATION

The invention now being generally described, it will be more readily understood by reference to the following examples, which are included merely for purposes of illustration of certain embodiments of the present invention, and are not intended to limit the invention.

Example 1. Generation of Receptor Fusion Protein Variants

TβRII ECD Variants

TβRII fusion proteins comprising a soluble extracellular portion of human TβRII and a human Fc portion were generated. For each fusion protein, a TβRII amino acid sequence having the amino acid sequence of SEQ ID NO: 18 was fused to an IgG Fc portion having the amino acid sequence of SEQ ID NO: 49 by means of one of several different linkers. Each of the fusion proteins also included a TPA leader sequence having the amino acid sequence of SEQ ID NO: 23 (below).

```
                                    (SEQ ID NO: 23)
Tissue plasminogen activator (TPA):
MDAMKRGLCCVLLLCGAVFVSP
```

An illustration summary of several of the constructs designed is provided as FIG. 3. A table detailing the sequences for the different constructs tested in the Exemplification section is provided below:

| Construct Name | Construct Amino Acid Sequence | Linker Sequence |
|---|---|---|
| hTβRII-hFc | SEQ ID NO: 9 | TGGG (SEQ ID NO: 3) |
| hTβRII (G4S)2-hFc | SEQ ID NO: 15 | TGGGGSGGGGS (SEQ ID NO: 4) |
| hTβRII (G4S)3-hFc | SEQ ID NO: 11 | TGGGGSGGGGSGGGGS (SEQ ID NO: 5) |
| hTβRII (G4S)4-hFc | SEQ ID NO: 13 | TGGGGSGGGGSGGGGSGGGGS (SEQ ID NO: 6) |
| hTβRII extended hinge-hFc | SEQ ID NO: 17 | TGGGPKSCDK (SEQ ID NO: 7) |
| hTpRII (G4S)5-hFc | SEQ ID NO: 44 | TGGGGSGGGGSGGGGSGGGGSGGGGS (SEQ ID NO: 25) |
| hTβRII (G4S)6-hFc | SEQ ID NO: 45 | TGGGGSGGGGSGGGGSGGGGSGGGGSGGGGS (SEQ ID NO: 26) |

The amino acid sequences for the construct components and each of the constructs, along with the nucleic acid sequence used to express these constructs, are provided below.

```
TβRII Portion: Amino Acid Sequence
                                        (SEQ ID NO: 18)
   1 TIPPHVQKSD VEMEAQKDEI ICPSCNRTAH
     PLRHINNDMI VTDNNGAVKF
  51 PQLCKFCDVR FSTCDNQKSC MSNCSITSIC
     EKPQEVCVAV WRKNDENITL
 101 ETVCHDPKLP YHDFILEDAA SPKCIMKEKK
     KPGETFFMCS CSSDECNDNI
 151 IFSEEYNTSN PD Fc Portion: Amino Acid Sequence
                                        (SEQ ID NO: 49)
   1 THTCPPCPAP ELLGGPSVFL FPPKPKDTLM
     ISRTPEVTCV VVDVSHEDPE
  51 VKFNWYVDGV EVHNAKTKPR EEQYNSTYRV
     VSVLTVLHQD WLNGKEYKCK
 101 VSNKALPAPI EKTISKAKGQ PREPQVYTLP
     PSREEMTKNQ VSLTCLVKGF
 151 YPSDIAVEWE SNGQPENNYK TTPPVLDSDG
     SFFLYSKLTV DKSRWQQGNV
 201 FSCSVMHEAL HNHYTQKSLS LSPGK
``` hTβRII-hFc: Nucleic Acid Sequence

-continued
(SEQ ID NO: 8)

```
  1 ATGGATGCAA TGAAGAGAGG GCTCTGCTGT
    GTGCTGCTGC TGTGTGGAGC
 51 AGTCTTCGTT TCGCCCGGCG CCACGATCCC
    ACCGCACGTT CAGAAGTCGG
101 ATGTGGAAAT GGAGGCCCAG AAAGATGAAA
    TCATCTGCCC CAGCTGTAAT
151 AGGACTGCCC ATCCACTGAG ACATATTAAT
    AACGACATGA TAGTCACTGA
201 CAACAACGGT GCAGTCAAGT TTCCACAACT
    GTGTAAATTT TGTGATGTGA
251 GATTTTCCAC CTGTGACAAC CAGAAATCCT
    GCATGAGCAA CTGCAGCATC
301 ACCTCCATCT GTGAGAAGCC ACAGGAAGTC
    TGTGTGGCTG TATGGAGAAA
351 GAATGACGAG AACATAACAC TAGAGACAGT
    TTGCCATGAC CCCAAGCTCC
401 CCTACCATGA CTTTATTCTG GAAGATGCTG
    CTTCTCCAAA GTGCATTATG
451 AAGGAAAAAA AAAAGCCTGG TGAGACTTTC
    TTCATGTGTT CCTGTAGCTC
501 TGATGAGTGC AATGACAACA TCATCTTCTC
    AGAAGAATAT AACACCAGCA
551 ATCCTGACAC CGGTGGTGGA ACTCACACAT
    GCCCACCGTG CCCAGCACCT
601 GAACTCCTGG GGGGACCGTC AGTCTTCCTC
    TTCCCCCCAA AACCCAAGGA
651 CACCCTCATG ATCTCCCGGA CCCCTGAGGT
    CACATGCGTG GTGGTGGACG
701 TGAGCCACGA AGACCCTGAG GTCAAGTTCA
    ACTGGTACGT GGACGGCGTG
751 GAGGTGCATA ATGCCAAGAC AAAGCCGCGG
    GAGGAGCAGT ACAACAGCAC
801 GTACCGTGTG GTCAGCGTCC TCACCGTCCT
    GCACCAGGAC TGGCTGAATG
851 GCAAGGAGTA CAAGTGCAAG GTCTCCAACA
    AAGCCCTCCC AGCCCCCATC
901 GAGAAAACCA TCTCCAAAGC CAAAGGGCAG
    CCCCGAGAAC CACAGGTGTA
951 CACCCTGCCC CCATCCCGGG AGGAGATGAC
    CAAGAACCAG GTCAGCCTGA
1001 CCTGCCTGGT CAAAGGCTTC TATCCCAGCG
     ACATCGCCGT GGAGTGGGAG
1051 AGCAATGGGC AGCCGGAGAA CAACTACAAG
     ACCACGCCTC CCGTGCTGGA
1101 CTCCGACGGC TCCTTCTTCC TCTATAGCAA
     GCTCACCGTG GACAAGAGCA
1151 GGTGGCAGCA GGGGAACGTC TTCTCATGCT
     CCGTGATGCA TGAGGCTCTG
1201 CACAACCACT ACACGCAGAA GAGCCTCTCC
     CTGTCTCCGG GTAAATGA
``` hTβRII-hFc: Amino Acid Sequence
(SEQ ID NO: 9)

```
  1 MDAMKRGLCC VLLLCGAVFV SPGATIPPHV
    QKSDVEMEAQ KDEIICPSCN
 51 RTAHPLRHIN NDMIVTDNNG AVKFPQLCKF
    CDVRFSTCDN QKSCMSNCSI
101 TSICEKPQEV CVAVWRKNDE NITLETVCHD
    PKLPYHDFIL EDAASPKCIM
151 KEKKKPGETF FMCSCSSDEC NDNIIFSEEY
    NTSNPDTGGG THTCPPCPAP
201 ELLGGPSVFL FPPKPKDTLM ISRTPEVTCV
    VVDVSHEDPE VKFNWYVDGV
251 EVHNAKTKPR EEQYNSTYRV VSVLTVLHQD
    WLNGKEYKCK VSNKALPAPI
301 EKTISKAKGQ PREPQVYTLP PSREEMTKNQ
    VSLTCLVKGF YPSDIAVEWE
351 SNGQPENNYK TTPPVLDSDG SFFLYSKLTV
    DKSRWQQGNV FSCSVMHEAL
401 HNHYTQKSLS LSPGK
```

For the animal experiments described below, a mouse version of SEQ ID NO: 9 was generated by fusing the mouse extracellular domain of TβRII, which corresponds to isoform A of the human TβRII, to mouse G1Fc via a linker domain (TGGG). This fusion protein is designated herein as mTβRII-mFc.

hTβRII (G4S)3-hFc: Nucleic Acid Sequence
(SEQ ID NO: 10)

```
  1 ATGGATGCAA TGAAGAGAGG GCTCTGCTGT GTGCTGCTGC TGTGTGGAGC
 51 AGTCTTCGTT TCGCCCGGCG CCACGATCCC ACCGCACGTT CAGAAGTCGG
```

```
 101 ATGTGGAAAT GGAGGCCCAG AAAGATGAAA TCATCTGCCC CAGCTGTAAT

151 AGGACTGCCC ATCCACTGAG ACATATTAAT AACGACATGA TAGTCACTGA

201 CAACAACGGT GCAGTCAAGT TTCCACAACT GTGTAAATTT TGTGATGTGA

251 GATTTTCCAC CTGTGACAAC CAGAAATCCT GCATGAGCAA CTGCAGCATC

301 ACCTCCATCT GTGAGAAGCC ACAGGAAGTC TGTGTGGCTG TATGGAGAAA

351 GAATGACGAG AACATAACAC TAGAGACAGT TTGCCATGAC CCCAAGCTCC

401 CCTACCATGA CTTTATTCTG GAAGATGCTG CTTCTCCAAA GTGCATTATG

451 AAGGAAAAAA AAAAGCCTGG TGAGACTTTC TTCATGTGTT CCTGTAGCTC

501 TGATGAGTGC AATGACAACA TCATCTTCTC AGAAGAATAT AACACCAGCA

551 ATCCTGACAC CGGTGGTGGA GGAAGTGGTG GAGGTGGTTC TGGAGGTGGT

601 GGAAGTACTC ACACATGCCC ACCGTGCCCA GCACCTGAAC TCCTGGGGGG

651 ACCGTCAGTC TTCCTCTTCC CCCCAAAACC CAAGGACACC CTCATGATCT

701 CCCGGACCCC TGAGGTCACA TGCGTGGTGG TGGACGTGAG CCACGAAGAC

751 CCTGAGGTCA AGTTCAACTG GTACGTGGAC GGCGTGGAGG TGCATAATGC

801 CAAGACAAAG CCGCGGGAGG AGCAGTACAA CAGCACGTAC CGTGTGGTCA

851 GCGTCCTCAC CGTCCTGCAC CAGGACTGGC TGAATGGCAA GGAGTACAAG

901 TGCAAGGTCT CCAACAAAGC CCTCCCAGCC CCCATCGAGA AAACCATCTC

951 CAAAGCCAAA GGGCAGCCCC GAGAACCACA GGTGTACACC CTGCCCCCAT

1001 CCCGGGAGGA GATGACCAAG AACCAGGTCA GCCTGACCTG CCTGGTCAAA

1051 GGCTTCTATC CCAGCGACAT CGCCGTGGAG TGGGAGAGCA ATGGGCAGCC

1101 GGAGAACAAC TACAAGACCA CGCCTCCCGT GCTGGACTCC GACGGCTCCT

1151 TCTTCCTCTA TAGCAAGCTC ACCGTGGACA AGAGCAGGTG GCAGCAGGGG

1201 AACGTCTTCT CATGCTCCGT GATGCATGAG GCTCTGCACA ACCACTACAC

1251 GCAGAAGAGC CTCTCCCTGT CTCCGGGTAA ATGA
``` hTβRII (G4S)3-hFc: Amino Acid Sequence (SEQ ID NO: 11)

```
  1 MDAMKRGLCC VLLLCGAVFV SPGATIPPHV QKSDVEMEAQ KDEIICPSCN

51 RTAHPLRHIN NDMIVTDNNG AVKFPQLCKF CDVRFSTCDN QKSCMSNCSI

101 TSICEKPQEV CVAVWRKNDE NITLETVCHD PKLPYHDFIL EDAASPKCIM

151 KEKKKPGETF FMCSCSSDEC NDNIIFSEEY NTSNPDTGGG GSGGGGSGGG

201 GSTHTCPPCP APELLGGPSV FLFPPKPKDT LMISRTPEVT CVVVDVSHED

251 PEVKFNWYVD GVEVHNAKTK PREEQYNSTY RVVSVLTVLH QDWLNGKEYK

301 CKVSNKALPA PIEKTISKAK GQPREPQVYT LPPSREEMTK NQVSLTCLVK

351 GFYPSDIAVE WESNGQPENN YKTTPPVLDS DGSFFLYSKL TVDKSRWQQG

401 NVFSCSVMHE ALHNHYTQKS LSLSPGK
``` hTβRII (G4S)4-hFc: Nucleic Acid Sequence (SEQ ID NO: 12)

```
  1 ATGGATGCAA TGAAGAGAGG GCTCTGCTGT GTGCTGCTGC TGTGTGGAGC

51 AGTCTTCGTT TCGCCCGGCG CCACGATCCC ACCGCACGTT CAGAAGTCGG

101 ATGTGGAAAT GGAGGCCCAG AAAGATGAAA TCATCTGCCC CAGCTGTAAT

151 AGGACTGCCC ATCCACTGAG ACATATTAAT AACGACATGA TAGTCACTGA

201 CAACAACGGT GCAGTCAAGT TTCCACAACT GTGTAAATTT TGTGATGTGA
```

```
 251 GATTTTCCAC CTGTGACAAC CAGAAATCCT GCATGAGCAA CTGCAGCATC

301 ACCTCCATCT GTGAGAAGCC ACAGGAAGTC TGTGTGGCTG TATGGAGAAA

351 GAATGACGAG AACATAACAC TAGAGACAGT TTGCCATGAC CCCAAGCTCC

401 CCTACCATGA CTTTATTCTG GAAGATGCTG CTTCTCCAAA GTGCATTATG

451 AAGGAAAAAA AAAAGCCTGG TGAGACTTTC TTCATGTGTT CCTGTAGCTC

501 TGATGAGTGC AATGACAACA TCATCTTCTC AGAAGAATAT AACACCAGCA

551 ATCCTGACAC CGGTGGTGGA GGTTCTGGAG GTGGAGGAAG TGGTGGAGGT

601 GGTTCTGGAG GTGGTGGAAG TACTCACACA TGCCCACCGT GCCCAGCACC

651 TGAACTCCTG GGGGGACCGT CAGTCTTCCT CTTCCCCCCA AAACCCAAGG

701 ACACCCTCAT GATCTCCCGG ACCCCTGAGG TCACATGCGT GGTGGTGGAC

751 GTGAGCCACG AAGACCCTGA GGTCAAGTTC AACTGGTACG TGGACGGCGT

801 GGAGGTGCAT AATGCCAAGA CAAAGCCGCG GGAGGAGCAG TACAACAGCA

851 CGTACCGTGT GGTCAGCGTC CTCACCGTCC TGCACCAGGA CTGGCTGAAT

901 GGCAAGGAGT ACAAGTGCAA GGTCTCCAAC AAAGCCCTCC CAGCCCCCAT

951 CGAGAAAACC ATCTCCAAAG CCAAAGGGCA GCCCCGAGAA CCACAGGTGT

1001 ACACCCTGCC CCCATCCCGG GAGGAGATGA CCAAGAACCA GGTCAGCCTG

1051 ACCTGCCTGG TCAAAGGCTT CTATCCCAGC GACATCGCCG TGGAGTGGGA

1101 GAGCAATGGG CAGCCGGAGA ACAACTACAA GACCACGCCT CCCGTGCTGG

1151 ACTCCGACGG CTCCTTCTTC CTCTATAGCA AGCTCACCGT GGACAAGAGC

1201 AGGTGGCAGC AGGGGAACGT CTTCTCATGC TCCGTGATGC ATGAGGCTCT

1251 GCACAACCAC TACACGCAGA AGAGCCTCTC CCTGTCTCCG GGTAAATGA
``` hTβRII (G4S)4-hFc: Amino Acid Sequence
(SEQ ID NO: 13)
```
  1 MDAMKRGLCC VLLLCGAVFV SPGATIPPHV QKSDVEMEAQ KDEIICPSCN

51 RTAHPLRHIN NDMIVTDNNG AVKFPQLCKF CDVRFSTCDN QKSCMSNCSI

101 TSICEKPQEV CVAVWRKNDE NITLETVCHD PKLPYHDFIL EDAASPKCIM

151 KEKKKPGETF FMCSCSSDEC NDNIIFSEEY NTSNPDTGGG GSGGGGSGGG

201 GSGGGGSTHT CPPCPAPELL GGPSVFLFPP KPKDTLMISR TPEVTCVVVD

251 VSHEDPEVKF NWYVDGVEVH NAKTKPREEQ YNSTYRVVSV LTVLHQDWLN

301 GKEYKCKVSN KALPAPIEKT ISKAKGQPRE PQVYTLPPSR EEMTKNQVSL

351 TCLVKGFYPS DIAVEWESNG QPENNYKTTP PVLDSDGSFF LYSKLTVDKS

401 RWQQGNVFSC SVMHEALHNH YTQKSLSLSP GK
``` hTβRII (G4S)4-hFc: Amino Acid Sequence lacking leader sequence
(SEQ ID NO: 63)
```
  1 GATIPPHVQK SDVEMEAQKD EIICPSCNRT AHPLRHINND MIVTDNNGAV

51 KFPQLCKFCD VRFSTCDNQK SCMSNCSITS ICEKPQEVCV AVWRKNDENI

101 TLETVCHDPK LPYHDFILED AASPKCIMKE KKKPGETFFM CSCSSDECND

151 NIIFSEEYNT SNPDTGGGGS GGGGSGGGGS GGGGSTHTCP PCPAPELLGG

201 PSVFLFPPKP KDTLMISRTP EVTCVVVDVS HEDPEVKFNW YVDGVEVHNA

251 KTKPREEQYN STYRVVSVLT VLHQDWLNGK EYKCKVSNKA LPAPIEKTIS

301 KAKGQPREPQ VYTLPPSREE MTKNQVSLTC LVKGFYPSDI AVEWESNGQP

351 ENNYKTTPPV LDSDGSFFLY SKLTVDKSRW QQGNVFSCSV MHEALHNHYT

401 QKSLSLSPGK
``` hTβRII (G45)4-hFc: Amino Acid Sequence lacking leader sequence
and lacking glycine prior to h7-81311 portion
(SEQ ID NO: 64)

```
  1 ATIPPHVQKS DVEMEAQKDE IICPSCNRTA HPLRHINNDM IVTDNNGAVK

51 FPQLCKFCDV RFSTCDNQKS CMSNCSITSI CEKPQEVCVA VWRKNDENIT

101 LETVCHDPKL PYHDFILEDA ASPKCIMKEK KKPGETFFMC SCSSDECNDN

151 IIFSEEYNTS NPDTGGGGSG GGGSGGGGSG GGGSTHTCPP CPAPELLGGP

201 SVFLFPPKPK DTLMISRTPE VTCVVVDVSH EDPEVKFNWY VDGVEVHNAK

251 TKPREEQYNS TYRVVSVLTV LHQDWLNGKE YKCKVSNKAL PAPIEKTISK

301 AKGQPREPQV YTLPPSREEM TKNQVSLTCL VKGFYPSDIA VEWESNGQPE

351 NNYKTTPPVL DSDGSFFLYS KLTVDKSRWQ QGNVFSCSVM HEALHNHYTQ

401 KSLSLSPGK
``` hTβRII (G45)4-hFc: Amino Acid Sequence lacking leader sequence
and lacking glycine, alanine, and threonine prior to h7-81311
portion
(SEQ ID NO: 65)

```
  1 IPPHVQKSDV EMEAQKDEII CPSCNRTAHP LRHINNDMIV TDNNGAVKFP

51 QLCKFCDVRF STCDNQKSCM SNCSITSICE KPQEVCVAVW RKNDENITLE

101 TVCHDPKLPY HDFILEDAAS PKCIMKEKKK PGETFFMCSC SSDECNDNII

151 FSEEYNTSNP DTGGGGSGGG GSGGGGSGGG GSTHTCPPCP APELLGGPSV

201 FLFPPKPKDT LMISRTPEVT CVVVDVSHED PEVKFNWYVD GVEVHNAKTK

251 PREEQYNSTY RVVSVLTVLH QDWLNGKEYK CKVSNKALPA PIEKTISKAK

301 GQPREPQVYT LPPSREEMTK NQVSLTCLVK GFYPSDIAVE WESNGQPENN

351 YKTTPPVLDS DGSFFLYSKL TVDKSRWQQG NVFSCSVMHE ALHNHYTQKS

401 LSLSPGK
``` hTβRII (G45)4-hFc: Amino Acid Sequence lacking leader sequence
and lacking glycine, alanine, threonine, and isoleucine prior
to h7-81311 portion
(SEQ ID NO: 66)

```
  1 PPHVQKSDVE MEAQKDEIIC PSCNRTAHPL RHINNDMIVT DNNGAVKFPQ

51 LCKFCDVRFS TCDNQKSCMS NCSITSICEK PQEVCVAVWR KNDENITLET

101 VCHDPKLPYH DFILEDAASP KCIMKEKKKP GETFFMCSCS SDECNDNIIF

151 SEEYNTSNPD TGGGGSGGGG SGGGGSGGGG STHTCPPCPA PELLGGPSVF

201 LFPPKPKDTL MISRTPEVTC VVVDVSHEDP EVKFNWYVDG VEVHNAKTKP

251 REEQYNSTYR VVSVLTVLHQ DWLNGKEYKC KVSNKALPAP IEKTISKAKG

301 QPREPQVYTL PPSREEMTKN QVSLTCLVKG FYPSDIAVEW ESNGQPENNY

351 KTTPPVLDSD GSFFLYSKLT VDKSRWQQGN VFSCSVMHEA LHNHYTQKSL

401 SLSPGK
``` hTβRII (G4S)4-hFc: Amino Acid Sequence lacking leader sequence
and lacking glycine, alanine, threonine, isoleucine, and proline
prior to hTβRII portion
(SEQ ID NO: 67)

```
  1 PHVQKSDVEM EAQKDEITCP SCNRTAHPLR HINNDMIVTD NNGAVKFPQL

51 CKFCDVRFST CDNQKSCMSN CSITSICEKP QEVCVAVWRK NDENITLETV

101 CHDPKLPYHD FILEDAASPK CIMKEKKKPG ETFFMCSCSS DECNDNIIFS

151 EEYNTSNPDT GGGGSGGGGS GGGGSGGGGS THTCPPCPAP ELLGGPSVFL

201 FPPKPKDTLM ISRTPEVTCV VVDVSHEDPE VKFNWYVDGV EVHNAKTKPR

251 EEQYNSTYRV VSVLTVLHQD WLNGKEYKCK VSNKALPAPI EKTISKAKGQ
```

```
301 PREPQVYTLP PSREEMTKNQ VSLTCLVKGF YPSDIAVEWE SNGQPENNYK

351 TTPPVLDSDG SFFLYSKLTV DKSRWQQGNV FSCSVMHEAL HNHYTQKSLS

401 LSPGK
``` hTβRII (G45)4-hFc: Amino Acid Sequence lacking leader sequence
and lacking glycine, alanine, threonine, isoleucine, proline,
and proline prior to hTβRII portion (SEQ ID NO: 68)

```
  1 HVQKSDVEME AQKDEITCPS CNRTAHPLRH INNDMIVTDN NGAVKFPQLC

51 KFCDVRFSTC DNQKSCMSNC SITSICEKPQ EVCVAVWRKN DENITLETVC

101 HDPKLPYHDF ILEDAASPKC IMKEKKKPGE TFFMCSCSSD ECNDNIIFSE

151 EYNTSNPDTG GGGSGGGGSG GGGSGGGGST HTCPPCPAPE LLGGPSVFLF

201 PPKPKDTLMI SRTPEVTCVV VDVSHEDPEV KFNWYVDGVE VHNAKTKPRE

251 EQYNSTYRVV SVLTVLHQDW LNGKEYKCKV SNKALPAPIE KTISKAKGQP

301 REPQVYTLPP SREEMTKNQV SLTCLVKGFY PSDIAVEWES NGQPENNYKT

351 TPPVLDSDGS FFLYSKLTVD KSRWQQGNVF SCSVMHEALH NHYTQKSLSL

401 SPGK
``` hTβRII (G45)2-hFc: Nucleic Acid Sequence (SEQ ID NO: 14)

```
   1 ATGGATGCAA TGAAGAGAGG GCTCTGCTGT GTGCTGCTGC TGTGTGGAGC

51 AGTCTTCGTT TCGCCCGGCG CCACGATCCC ACCGCACGTT CAGAAGTCGG

101 ATGTGGAAAT GGAGGCCCAG AAAGATGAAA TCATCTGCCC CAGCTGTAAT

151 AGGACTGCCC ATCCACTGAG ACATATTAAT AACGACATGA TAGTCACTGA

201 CAACAACGGT GCAGTCAAGT TCCCACAACT GTGTAAATTT TGTGATGTGA

251 GATTTTCCAC CTGTGACAAC CAGAAATCCT GCATGAGCAA CTGCAGCATC

301 ACCTCCATCT GTGAGAAGCC ACAGGAAGTC TGTGTGGCTG TATGGAGAAA

351 GAATGACGAG AACATAACAC TAGAGACAGT TTGCCATGAC CCCAAGCTCC

401 CCTACCATGA CTTTATTCTG GAAGATGCTG CTTCTCCAAA GTGCATTATG

451 AAGGAAAAAA AAAAGCCTGG TGAGACTTTC TTCATGTGTT CCTGTAGCTC

501 TGATGAGTGC AATGACAACA TCATCTTCTC AGAAGAATAT AACACCAGCA

551 ATCCTGACAC CGGTGGAGGT GGTTCTGGAG GTGGTGGAAG TACTCACACA

601 TGCCCACCGT GCCCAGCACC TGAACTCCTG GGGGGACCGT CAGTCTTCCT

651 CTTCCCCCCA AAACCCAAGG ACACCCTCAT GATCTCCCGG ACCCCTGAGG

701 TCACATGCGT GGTGGTGGAC GTGAGCCACG AAGACCCTGA GGTCAAGTTC

751 AACTGGTACG TGGACGGCGT GGAGGTGCAT AATGCCAAGA CAAAGCCGCG

801 GGAGGAGCAG TACAACAGCA CGTACCGTGT GGTCAGCGTC CTCACCGTCC

851 TGCACCAGGA CTGGCTGAAT GGCAAGGAGT ACAAGTGCAA GGTCTCCAAC

901 AAAGCCCTCC CAGCCCCCAT CGAGAAAACC ATCTCCAAAG CCAAGGGCA

951 GCCCCGAGAA CCACAGGTGT ACACCCTGCC CCCATCCCGG GAGGAGATGA

1001 CCAAGAACCA GGTCAGCCTG ACCTGCCTGG TCAAAGGCTT CTATCCCAGC

1051 GACATCGCCG TGGAGTGGGA GAGCAATGGG CAGCCGGAGA ACAACTACAA

1101 GACCACGCCT CCCGTGCTGG ACTCCGACGG CTCCTTCTTC CTCTATAGCA
```

-continued

```
1151 AGCTCACCGT GGACAAGAGC AGGTGGCAGC AGGGGAACGT CTTCTCATGC

1201 TCCGTGATGC ATGAGGCTCT GCACAACCAC TACACGCAGA AGAGCCTCTC

1251 CCTGTCTCCG GGTAAATGA
``` hTβRII (G4S)2-hFc: Amino Acid Sequence (SEQ ID NO: 15)

```
  1 MDAMKRGLCC VLLLCGAVFV SPGATIPPHV QKSDVEMEAQ KDEIICPSCN

51 RTAHPLRHIN NDMIVTDNNG AVKFPQLCKF CDVRFSTCDN QKSCMSNCSI

101 TSICEKPQEV CVAVWRKNDE NITLETVCHD PKLPYHDFIL EDAASPKCIM

151 KEKKKPGETF FMCSCSSDEC NDNIIFSEEY NTSNPDTGGG GSGGGGSTHT

201 CPPCPAPELL GGPSVFLFPP KPKDTLMISR TPEVTCVVVD VSHEDPEVKF

251 NWYVDGVEVH NAKTKPREEQ YNSTYRVVSV LTVLHQDWLN GKEYKCKVSN

301 KALPAPIEKT ISKAKGQPRE PQVYTLPPSR EEMTKNQVSL TCLVKGFYPS

351 DIAVEWESNG QPENNYKTTP PVLDSDGSFF LYSKLTVDKS RWQQGNVFSC

401 SVMHEALHNH YTQKSLSLSP GK
``` hTβRII extended hinge-hFc: Nucleic Acid Sequence (SEQ ID NO: 16)

```
  1 ATGGATGCAA TGAAGAGAGG GCTCTGCTGT GTGCTGCTGC TGTGTGGAGC

51 AGTCTTCGTT TCGCCCGGCG CCACGATCCC ACCGCACGTT CAGAAGTCGG

101 ATGTGGAAAT GGAGGCCCAG AAAGATGAAA TCATCTGCCC CAGCTGTAAT

151 AGGACTGCCC ATCCACTGAG ACATATTAAT AACGACATGA TAGTCACTGA

201 CAACAACGGT GCAGTCAAGT TTCCACAACT GTGTAAATTT TGTGATGTGA

251 GATTTTCCAC CTGTGACAAC CAGAAATCCT GCATGAGCAA CTGCAGCATC

301 ACCTCCATCT GTGAGAAGCC ACAGGAAGTC TGTGTGGCTG TATGGAGAAA

351 GAATGACGAG AACATAACAC TAGAGACAGT TTGCCATGAC CCCAAGCTCC

401 CCTACCATGA CTTTATTCTG GAAGATGCTG CTTCTCCAAA GTGCATTATG

451 AAGGAAAAAA AAAAGCCTGG TGAGACTTTC TTCATGTGTT CCTGTAGCTC

501 TGATGAGTGC AATGACAACA TCATCTTCTC AGAAGAATAT AACACCAGCA

551 ATCCTGACAC CGGTGGTGGA CCCAAATCTT GTGACAAAAC TCACACATGC

601 CCACCGTGCC CAGCACCTGA ACTCCTGGGG GGACCGTCAG TCTTCCTCTT

651 CCCCCCAAAA CCCAAGGACA CCCTCATGAT CTCCCGGACC CCTGAGGTCA

701 CATGCGTGGT GGTGGACGTG AGCCACGAAG ACCCTGAGGT CAAGTTCAAC

751 TGGTACGTGG ACGGCGTGGA GGTGCATAAT GCCAAGACAA AGCCGCGGGA

801 GGAGCAGTAC AACAGCACGT ACCGTGTGGT CAGCGTCCTC ACCGTCCTGC

851 ACCAGGACTG GCTGAATGGC AAGGAGTACA AGTGCAAGGT CTCCAACAAA

901 GCCCTCCCAG CCCCCATCGA GAAAACCATC TCCAAAGCCA AAGGGCAGCC

951 CCGAGAACCA CAGGTGTACA CCCTGCCCCC ATCCCGGGAG GAGATGACCA

1001 AGAACCAGGT CAGCCTGACC TGCCTGGTCA AAGGCTTCTA TCCCAGCGAC

1051 ATCGCCGTGG AGTGGGAGAG CAATGGGCAG CCGGAGAACA ACTACAAGAC

1101 CACGCCTCCC GTGCTGGACT CCGACGGCTC CTTCTTCCTC TATAGCAAGC
```

```
1151 TCACCGTGGA CAAGAGCAGG TGGCAGCAGG GGAACGTCTT CTCATGCTCC

1201 GTGATGCATG AGGCTCTGCA CAACCACTAC ACGCAGAAGA GCCTCTCCCT

1251 GTCCCCGGGT AAATGA
``` hTβRII extended hinge-hFc: Amino Acid Sequence (SEQ ID NO: 17)

```
  1 MDAMKRGLCC VLLLCGAVFV SPGATIPPHV QKSDVEMEAQ KDEIICPSCN

51 RTAHPLRHIN NDMIVTDNNG AVKFPQLCKF CDVRFSTCDN QKSCMSNCSI

101 TSICEKPQEV CVAVWRKNDE NITLETVCHD PKLPYHDFIL EDAASPKCIM

151 KEKKKPGETF FMCSCSSDEC NDNIIFSEEY NTSNPDTGGG PKSCDKTHTC

201 PPCPAPELLG GPSVFLFPPK PKDTLMISRT PEVTCVVVDV SHEDPEVKFN

251 WYVDGVEVHN AKTKPREEQY NSTYRVVSVL TVLHQDWLNG KEYKCKVSNK

301 ALPAPIEKTI SKAKGQPREP QVYTLPPSRE EMTKNQVSLT CLVKGFYPSD

351 IAVEWESNGQ PENNYKTTPP VLDSDGSFFL YSKLTVDKSR WQQGNVFSCS

401 VMHEALHNHY TQKSLSLSPG K
``` hTβRII (G4S)5-hFc: Amino Acid Sequence (SEQ ID NO: 44)

```
  1 MDAMKRGLCC VLLLCGAVFV SPGATIPPHV QKSDVEMEAQ KDEIICPSCN

51 RTAHPLRHIN NDMIVTDNNG AVKFPQLCKF CDVRFSTCDN QKSCMSNCSI

101 TSICEKPQEV CVAVWRKNDE NITLETVCHD PKLPYHDFIL EDAASPKCIM

151 KEKKKPGETF FMCSCSSDEC NDNIIFSEEY NTSNPDTGGG GSGGGGSGGG

201 GSGGGGSGGG GSTHTCPPCP APELLGGPSV FLFPPKPKDT LMISRTPEVT

251 CVVVDVSHED PEVKFNWYVD GVEVHNAKTK PREEQYNSTY RVVSVLTVLH

301 QDWLNGKEYK CKVSNKALPA PIEKTISKAK GQPREPQVYT LPPSREEMTK

351 NQVSLTCLVK GFYPSDIAVE WESNGQPENN YKTTPPVLDS DGSFFLYSKL

401 TVDKSRWQQG NVFSCSVMHE ALHNHYTQKS LSLSPGK
``` hTβRII (G4S)6-hFc: Amino Acid Sequence (SEQ ID NO: 45)

```
  1 MDAMKRGLCC VLLLCGAVFV SPGATIPPHV QKSDVEMEAQ KDEIICPSCN

51 RTAHPLRHIN NDMIVTDNNG AVKFPQLCKF CDVRFSTCDN QKSCMSNCSI

101 TSICEKPQEV CVAVWRKNDE NITLETVCHD PKLPYHDFIL EDAASPKCIM

151 KEKKKPGETF FMCSCSSDEC NDNIIFSEEY NTSNPDTGGG GSGGGGSGGG

201 GSGGGGSGGG GSGGGGSTHT CPPCPAPELL GGPSVFLFPP KPKDTLMISR

251 TPEVTCVVVD VSHEDPEVKF NWYVDGVEVH NAKTKPREEQ YNSTYRVVSV

301 LTVLHQDWLN GKEYKCKVSN KALPAPIEKT ISKAKGQPRE PQVYTLPPSR

351 EEMTKNQVSL TCLVKGFYPS DIAVEWESNG QPENNYKTTP PVLDSDGSFF

401 LYSKLTVDKS RWQQGNVFSC SVMHEALHNH YTQKSLSLSP GK
``` hTβRII (G4S)5-hFc: Nucleotide Sequence (SEQ ID NO: 46)

```
  1 ATGGATGCAA TGAAGAGAGG GCTCTGCTGT GTGCTGCTGC TGTGTGGAGC

51 AGTCTTCGTT TCGCCCGGCG CCACGATCCC ACCGCACGTT CAGAAGTCGG

101 ATGTGGAAAT GGAGGCCCAG AAAGATGAAA TCATCTGCCC CAGCTGTAAT

151 AGGACTGCCC ATCCACTGAG ACATATTAAT AACGACATGA TAGTCACTGA

201 CAACAACGGT GCAGTCAAGT TTCCACAACT GTGTAAATTT TGTGATGTGA

251 GATTTTCCAC CTGTGACAAC CAGAAATCCT GCATGAGCAA CTGCAGCATC

301 ACCTCCATCT GTGAGAAGCC ACAGGAAGTC TGTGTGGCTG TATGGAGAAA
```

-continued

```
 351 GAATGACGAG AACATAACAC TAGAGACAGT TTGCCATGAC CCCAAGCTCC
 401 CCTACCATGA CTTTATTCTG GAAGATGCTG CTTCTCCAAA GTGCATTATG
 451 AAGGAAAAAA AAAAGCCTGG TGAGACTTTC TTCATGTGTT CCTGTAGCTC
 501 TGATGAGTGC AATGACAACA TCATCTTCTC AGAAGAATAT AACACCAGCA
 551 ATCCTGACAC CGGTGGAGGA GGTTCTGGTG GTGGAGGTTC TGGAGGTGGA
 601 GGAAGTGGTG GAGGTGGTTC TGGAGGTGGT GGAAGTACTC ACACATGCCC
 651 ACCGTGCCCA GCACCTGAAC TCCTGGGGGG ACCGTCAGTC TTCCTCTTCC
 701 CCCCAAAACC CAAGGACACC CTCATGATCT CCCGGACCCC TGAGGTCACA
 751 TGCGTGGTGG TGGACGTGAG CCACGAAGAC CCTGAGGTCA AGTTCAACTG
 801 GTACGTGGAC GGCGTGGAGG TGCATAATGC CAAGACAAAG CCGCGGGAGG
 851 AGCAGTACAA CAGCACGTAC CGTGTGGTCA GCGTCCTCAC CGTCCTGCAC
 901 CAGGACTGGC TGAATGGCAA GGAGTACAAG TGCAAGGTCT CCAACAAAGC
 951 CCTCCCAGCC CCCATCGAGA AAACCATCTC AAAGCCAAA GGGCAGCCCC
1001 GAGAACCACA GGTGTACACC CTGCCCCCAT CCCGGGAGGA GATGACCAAG
1051 AACCAGGTCA GCCTGACCTG CCTGGTCAAA GGCTTCTATC CCAGCGACAT
1101 CGCCGTGGAG TGGGAGAGCA ATGGGCAGCC GGAGAACAAC TACAAGACCA
1151 CGCCTCCCGT GCTGGACTCC GACGGCTCCT TCTTCCTCTA TAGCAAGCTC
1201 ACCGTGGACA AGAGCAGGTG GCAGCAGGGG AACGTCTTCT CATGCTCCGT
1251 GATGCATGAG GCTCTGCACA ACCACTACAC GCAGAAGAGC CTCTCCCTGT
1301 CTCCGGGTAA ATGA
``` hTβRII (G45)6-hFc: Nucleotide Sequence (SEQ ID NO: 47)

```
   1 ATGGATGCAA TGAAGAGAGG GCTCTGCTGT GTGCTGCTGC TGTGTGGAGC
  51 AGTCTTCGTT TCGCCCGGCG CCACGATCCC ACCGCACGTT CAGAAGTCGG
 101 ATGTGGAAAT GGAGGCCCAG AAAGATGAAA TCATCTGCCC CAGCTGTAAT
 151 AGGACTGCCC ATCCACTGAG ACATATTAAT AACGACATGA TAGTCACTGA
 201 CAACAACGGT GCAGTCAAGT TTCCACAACT GTGTAAATTT TGTGATGTGA
 251 GATTTTCCAC CTGTGACAAC CAGAAATCCT GCATGAGCAA CTGCAGCATC
 301 ACCTCCATCT GTGAGAAGCC ACAGGAAGTC TGTGTGGCTG TATGGAGAAA
 351 GAATGACGAG AACATAACAC TAGAGACAGT TTGCCATGAC CCCAAGCTCC
 401 CCTACCATGA CTTTATTCTG GAAGATGCTG CTTCTCCAAA GTGCATTATG
 451 AAGGAAAAAA AAAAGCCTGG TGAGACTTTC TTCATGTGTT CCTGTAGCTC
 501 TGATGAGTGC AATGACAACA TCATCTTCTC AGAAGAATAT AACACCAGCA
 551 ATCCTGACAC CGGTGGAGGT GGAAGTGGTG GAGGAGGTTC TGGTGGTGGA
 601 GGTTCTGGAG GTGGAGGAAG TGGTGGAGGT GGTTCTGGAG GTGGTGGAAG
 651 TACTCACACA TGCCCACCGT GCCCAGCACC TGAACTCCTG GGGGGACCGT
 701 CAGTCTTCCT CTTCCCCCCA AAACCCAAGG ACACCCTCAT GATCTCCCGG
 751 ACCCCTGAGG TCACATGCGT GGTGGTGGAC GTGAGCCACG AAGACCCTGA
 801 GGTCAAGTTC AACTGGTACG TGGACGGCGT GGAGGTGCAT AATGCCAAGA
 851 CAAAGCCGCG GGAGGAGCAG TACAACAGCA CGTACCGTGT GGTCAGCGTC
 901 CTCACCGTCC TGCACCAGGA CTGGCTGAAT GGCAAGGAGT ACAAGTGCAA
```

```
 951 GGTCTCCAAC AAAGCCCTCC CAGCCCCCAT CGAGAAAACC ATCTCCAAAG

1001 CCAAAGGGCA GCCCCGAGAA CCACAGGTGT ACACCCTGCC CCCATCCCGG

1051 GAGGAGATGA CCAAGAACCA GGTCAGCCTG ACCTGCCTGG TCAAAGGCTT

1101 CTATCCCAGC GACATCGCCG TGGAGTGGGA GAGCAATGGG CAGCCGGAGA

1151 ACAACTACAA GACCACGCCT CCCGTGCTGG ACTCCGACGG CTCCTTCTTC

1201 CTCTATAGCA AGCTCACCGT GGACAAGAGC AGGTGGCAGC AGGGGAACGT

1251 CTTCTCATGC TCCGTGATGC ATGAGGCTCT GCACAACCAC TACACGCAGA

1301 AGAGCCTCTC CCTGTCTCCG GGTAAATGA
```

The various constructs were successfully expressed in CHO cells and were purified to a high degree of purity as determined by analytical size-exclusion chromatography and SDS-PAGE. The hTβRII (G4S)2-hFc, hTβRII (G4S)3-hFc, hTβRII (G4S)4-hFc, hTβRII (G4S)5-hFc and hTβRII (G4S)6-hFc proteins displayed similarly strong stability as determined by SDS-PAGE analysis when maintained in PBS for 13 days at 37° C. The hTβRII (G4S)2-hFc, hTβRII (G4S)3-hFc, hTβRII (G4S)4-hFc proteins were also maintained in rat, mouse or human serum and displayed similarly strong stability.

TβRII ECD Variants

In addition to the TβRII domains included in the fusion proteins described above (e.g., SEQ ID NO: 18), the disclosure also contemplates fusion proteins comprising alternative TβRII domains. For example, the fusion protein may comprise the wild-type hTβRII$_{short}$(23-159) sequence shown below (SEQ ID NO: 27) or any of the other TβRII polypeptides disclosed below:

```
                              (SEQ ID NO: 27)
  1 TIPPHVQKSV NNDMIVTDNN GAVKFPQLCK

FCDVRFSTCD NQKSCMSNCS

51 ITSICEKPQE VCVAVWRKND ENITLETVCH

DPKLPYHDFI LEDAASPKCI

101 MKEKKKPGET FFMCSCSSDE CNDNIIFSEE

YNTSNPD
```

(1) The hTβRII$_{short}$(23-159/D110K) amino acid sequence shown below (SEQ ID NO: 36), in which the substituted residue is underlined.

```
                              (SEQ ID NO: 36)
  1 TIPPHVQKSV NNDMIVTDNN GAVKFPQLCK

FCDVRFSTCD NQKSCMSNCS

51 ITSICEKPQE VCVAVWRKND ENITLETVCH

DPKLPYHKFI LEDAASPKCI
              ‾
101 MKEKKKPGET FFMCSCSSDE CNDNIIFSEE

YNTSNPD
```

(2) The N-terminally truncated hTβRII$_{short}$(29-159) amino acid sequence shown below (SEQ ID NO: 28).

```
                              (SEQ ID NO: 28)
  1 QKSVNNDMIV TDNNGAVKFP QLCKFCDVRF

STCDNQKSCM SNCSITSICE

51 KPQEVCVAVW RKNDENITLE TVCHDPKLPY

HDFILEDAAS PKCIMKEKKK

101 PGETFFMCSC SSDECNDNII FSEEYNTSNP

D
```

(3) The N-terminally truncated hTβRII$_{short}$(35-159) amino acid sequence shown below (SEQ ID NO: 29).

```
                              (SEQ ID NO: 29)
  1 DMIVTDNNGA VKFPQLCKFC DVRFSTCDNQ

KSCMSNCSIT SICEKPQEVC

51 VAVWRKNDEN ITLETVCHDP KLPYHDFILE

DAASPKCIMK EKKKPGETFF

101 MCSCSSDECN DNIIFSEEYN TSNPD
```

(4) The C-terminally truncated hTβRII$_{short}$(23-153) amino acid sequence shown below (SEQ ID NO: 30).

```
                                                          (SEQ ID NO: 30)
  1 TIPPHVQKSV NNDMIVTDNN GAVKFPQLCK FCDVRFSTCD NQKSCMSNCS

51 ITSICEKPQE VCVAVWRKND ENITLETVCH DPKLPYHDFI LEDAASPKCI

101 MKEKKKPGET FFMCSCSSDE CNDNIIFSEE Y
```

(5) The C-terminally truncated hTβRII$_{short}$(23-153/N70D) amino acid sequence shown below (SEQ ID NO: 38), in which the substituted residue is underlined.

```
                                              (SEQ ID NO: 38)
  1 TIPPHVQKSV NNDMIVTDNN GAVKFPQLCK FCDVRFSTCD NQKSCMSDCS

51 ITSICEKPQE VCVAVWRKND ENITLETVCH DPKLPYHDFI LEDAASPKCI

101 MKEKKKPGET FFMCSCSSDE CNDNIIFSEE Y
```

Applicants also envision five corresponding variants (SEQ ID NOs: 37, 33, 34, 39) based on the wild-type hTβRII$_{long}$(23-184) sequence shown above and below (SEQ ID NO: 20), in which the 25 amino-acid insertion is underlined. Note that splicing results in a conservative amino acid substitution (Val→Ile) at the flanking position C-terminal to the insertion.

```
                                              (SEQ ID NO: 20)
  1 TIPPHVQKSD VEMEAQKDEI ICPSCNRTAH PLRHINNDMI VTDNNGAVKF

51 PQLCKFCDVR FSTCDNQKSC MSNCSITSIC EKPQEVCVAV WRKNDENITL

101 ETVCHDPKLP YHDFILEDAA SPKCIMKEKK KPGETFFMCS CSSDECNDNI

151 IFSEEYNTSN PD
```

(1) The hTβRII$_{long}$(23-184/D135K) amino acid sequence shown below (SEQ ID NO: 37), in which the substituted residue is double underlined.

```
                                              (SEQ ID NO: 37)
  1 TIPPHVQKSD VEMEAQKDEI ICPSCNRTAH PLRHINNDMI VTDNNGAVKF

51 PQLCKFCDVR FSTCDNQKSC MSNCSITSIC EKPQEVCVAV WRKNDENITL

101 ETVCHDPKLP YHKFILEDAA SPKCIMKEKK KPGETFFMCS CSSDECNDNI

151 IFSEEYNTSN PD
```

(2) The N-terminally truncated hTβRII$_{long}$(29-184) amino acid sequence shown below (SEQ ID NO: 33).

```
                                              (SEQ ID NO: 33)
  1 QKSDVEMEAQ KDEIICPSCN RTAHPLRHIN NDMIVTDNNG AVKFPQLCKF

51 CDVRFSTCDN QKSCMSNCSI TSICEKPQEV CVAVWRKNDE NITLETVCHD

101 PKLPYHDFIL EDAASPKCIM KEKKKPGETF FMCSCSSDEC NDNIIFSEEY

151 NTSNPD
```

(3) The N-terminally truncated hTβRII$_{long}$(60-184) amino acid sequence shown below (same as SEQ ID NO: 29).

```
                                           (same as SEQ ID NO: 29)
  1 DMIVTDNNGA VKFPQLCKFC DVRFSTCDNQ KSCMSNCSIT SICEKPQEVC

51 VAVWRKNDEN ITLETVCHDP KLPYHDFILE DAASPKCIMK EKKKPGETFF

101 MCSCSSDECN DNIIFSEEYN TSNPD
```

(4) The C-terminally truncated hTβRII$_{long}$(23-178) amino acid sequence shown below (SEQ ID NO: 34).

```
                                            (SEQ ID NO: 34)
  1 TIPPHVQKSD VEMEAQKDEI ICPSCNRTAH PLRHINNDMI VTDNNGAVKF

51 PQLCKFCDVR FSTCDNQKSC MSNCSITSIC EKPQEVCVAV WRKNDENITL

101 ETVCHDPKLP YHDFILEDAA SPKCIMKEKK KPGETFFMCS CSSDECNDNI

151 IFSEEY
```

(5) The C-terminally truncated hTβRII$_{long}$(23-178/N95D) amino acid sequence shown below (SEQ ID NO: 39), in which the substituted residue is double underlined.

```
                                            (SEQ ID NO: 39)
  1 TIPPHVQKSD VEMEAQKDEI ICPSCNRTAH PLRHINNDMI VTDNNGAVKF

51 PQLCKFCDVR FSTCDNQKSC MSDCSITSIC EKPQEVCVAV WRKNDENITL

101 ETVCHDPKLP YHDFILEDAA SPKCIMKEKK KPGETFFMCS CSSDECNDNI

151 IFSEEY
```

Additional TβRII ECD variants include:
(A) The N- and C-terminally truncated hTβRII$_{short}$(35-153) or hTβRII$_{long}$(60-178) amino acid sequence shown below (SEQ ID NO: 32).

```
                                            (SEQ ID NO: 32)
  1 DMIVTDNNGA VKFPQLCKFC DVRFSTCDNQ KSCMSNCSIT SICEKPQEVC

51 VAVWRKNDEN ITLETVCHDP KLPYHDFILE DAASPKCIMK EKKKPGETFF

101 MCSCSSDECN DNIIFSEEY
```

(B) The N- and C-terminally truncated hTβRII$_{short}$(29-153) amino acid sequence shown below (SEQ ID NO: 31).

```
                                            (SEQ ID NO: 31)
  1 QKSVNNDMIV TDNNGAVKFP QLCKFCDVRF STCDNQKSCM SNCSITSICE

51 KPQEVCVAVW RKNDENITLE TVCHDPKLPY HDFILEDAAS PKCIMKEKKK

101 PGETFFMCSC SSDECNDNII FSEEY
```

(C) The N- and C-terminally truncated hTβRII$_{long}$(29-178) amino acid sequence shown below (SEQ ID NO: 35).

```
                                            (SEQ ID NO: 35)
  1 QKSDVEMEAQ KDEIICPSCN RTAHPLRHIN NDMIVTDNNG AVKFPQLCKF

51 CDVRFSTCDN QKSCMSNCSI TSICEKPQEV CVAVWRKNDE NITLETVCHD

101 PKLPYHDFIL EDAASPKCIM KEKKKPGETF FMCSCSSDEC NDNIIFSEEY
```

Any of the above variants (SEQ ID NO: 36, 28, 29, 30, 38, 37, 33, 34, 39, 32, 31, and 35) could incorporate an insertion of 36 amino acids (SEQ ID NO: 41) between the pair of glutamate residues (positions 151 and 152 of SEQ ID NO: 1, or positions 176 and 177 of SEQ ID NO: 2) located near the C-terminus of the hTβRII ECD, as occurs naturally in the hTβRII isoform C (Konrad et al., BMC Genomics 8:318, 2007).

```
                                   (SEQ ID NO: 41)
GRCKIRHIGS NNRLQRSTCQ NTGWESAHVM KTPGFR
```

As an example, the paired glutamate residues flanking the optional insertion site are denoted below (underlined) for the hTβRII$_{short}$(29-159) variant (SEQ ID NO: 28).

```
                                          (SEQ ID NO: 28)
  1 QKSVNNDMIV TDNNGAVKFP QLCKFCDVRF STCDNQKSCM SNCSITSICE

51 KPQEVCVAVW RKNDENITLE TVCHDPKLPY HDFILEDAAS PKCIMKEKKK

101 PGETFFMCSC SSDECNDNII FSEEYNTSNP D
```

Fc Domain Variants

While the constructs described above were generated with an Fe domain having the amino acid sequence of SEQ ID NO: 49, the disclosure contemplates hTβRII-hFc fusion proteins comprising alternative Fc domains, including a human IgG2 Fc domain (SEQ ID NO: 42, below) or full-length human IgG1 Fc (hG1Fc) (SEQ ID NO: 43, below). Optionally, a polypeptide unrelated to an Fc domain could be attached in place of the Fc domain.

```
                                          (SEQ ID NO: 42)
  1 VECPPCPAPP VAGPSVFLFP PKPKDTLMIS RTPEVTCVVV DVSHEDPEVQ

51 FNWYVDGVEV HNAKTKPREE QFNSTFRVVS VLTVVHQDWL NGKEYKCKVS

101 NKGLPAPIEK TISKTKGQPR EPQVYTLPPS REEMTKNQVS LTCLVKGFYP

151 SDIAVEWESN GQPENNYKTT PPMLDSDGSF FLYSKLTVDK SRWQQGNVFS

201 CSVMHEALHN HYTQKSLSLS PGK (SEQ ID NO: 43)
  1 GGPKSCDKTH TCPPCPAPEL LGGPSVFLFP PKPKDTLMIS RTPEVTCVVV

51 DVSHEDPEVK FNWYVDGVEV HNAKTKPREE QYNSTYRVVS VLTVLHQDWL

101 NGKEYKCKVS NKALPAPIEK TISKAKGQPR EPQVYTLPPS REEMTKNQVS

151 LTCLVKGFYP SDIAVEWESN GQPENNYKTT PPVLDSDGSF FLYSKLTVDK

201 SRWQQGNVFS CSVMHEALHN HYTQKSLSLS PGK
```

Leader Sequence Variants

While the generated constructs described above included the TPA leader sequence, alternative leader sequences may be used, such as the native leader sequence (SEQ ID NO: 22—below) or the honey bee melittin (SEQ ID NO: 24—below) leader sequences.

```
Native:
MGRGLLRGLWPLHIVLWTRIAS     (SEQ ID NO: 22)

Honey bee melittin (HBML):
MKFLVNVALVFMVVYISYIYA      (SEQ ID NO: 24)
```

Example 2. Differential Ligand Inhibition by Receptor Fusion Protein Variants in Cell-Based Assay Affinities of TGFβ1, TGFβ2 and TGFβ3 for hTβRII (G4S)2-hFc; hTβRII (G4S)3-hFc; hTβRII (G4S)4-hFc; hTβRII-hFc; and hTβRII extended hinge-hFc proteins were evaluated in vitro with a Biacore™ instrument, and the results are summarized in FIGS. 4A and 4B. Each of the fusion proteins was capable of binding TGFβ1 and TGFβ3 with high affinity, but the constructs having linker lengths longer than or equal to (G4S)4 were surprisingly capable of binding to both TGFβ1 and TGFβ3 with higher affinity than constructs having linker lengths shorter than (G4S)4. Binding between TGFβ2 and any of the constructs was low or transient. Deglycosylation of the constructs did not change binding.

A reporter gene assay in A549 cells was used to determine the ability of hTβRII-hFc variants to inhibit activity of TGFβ1, TGFβ2 and TGFβ3. This assay is based on a human lung carcinoma cell line transfected with a pGL3(CAGA)12 reporter plasmid (Dennler et al, 1998, EMBO 17: 3091-3100) as well as a *Renilla* reporter plasmid (pRLCMV) to control for transfection efficiency. The CAGA motif is present in the promoters of TGFβ-responsive genes (for example, PAI-1), so this vector is of general use for factors signaling through SMAD2 and SMAD3.

On the first day of the assay, A549 cells (ATCC®: CCL-185™) were distributed in 48-well plates. On the second day, a solution containing pGL3(CAGA)12, pRLCMV, X-tremeGENE 9 (Roche Applied Science), and OptiMEM (Invitrogen) was preincubated, then added to Eagle's minimum essential medium (EMEM, ATCC®) supplemented with 0.1% BSA, which was applied to the plated cells for incubation overnight at 37° C., 5% $CO_2$. On the third day, medium was removed, and cells were incubated overnight at 37° C., 5% $CO_2$ with a mixture of ligands and inhibitors prepared as described below.

Serial dilutions of test articles were made in a 48-well plate in assay buffer (EMEM+0.1% BSA). An equal volume of assay buffer containing the test ligand was added to obtain a final ligand concentration equal to the EC50 determined previously. Human TGFβ1, human TGFβ2, and human TGFβ3 were obtained from PeproTech. Test solutions were incubated at 37° C. for 30 minutes, then a portion of the mixture was added to all wells. After incubation with test solutions overnight, cells were rinsed with phosphate-buffered saline, then lysed with passive lysis buffer (Promega E1941) and stored overnight at −70° C. On the fourth and final day, plates were warmed to room temperature with gentle shaking. Cell lysates were transferred in duplicate to a chemiluminescence plate (96-well) and analyzed in a luminometer with reagents from a Dual-Luciferase Reporter Assay system (Promega E1980) to determine normalized luciferase activity.

Figure 5A:
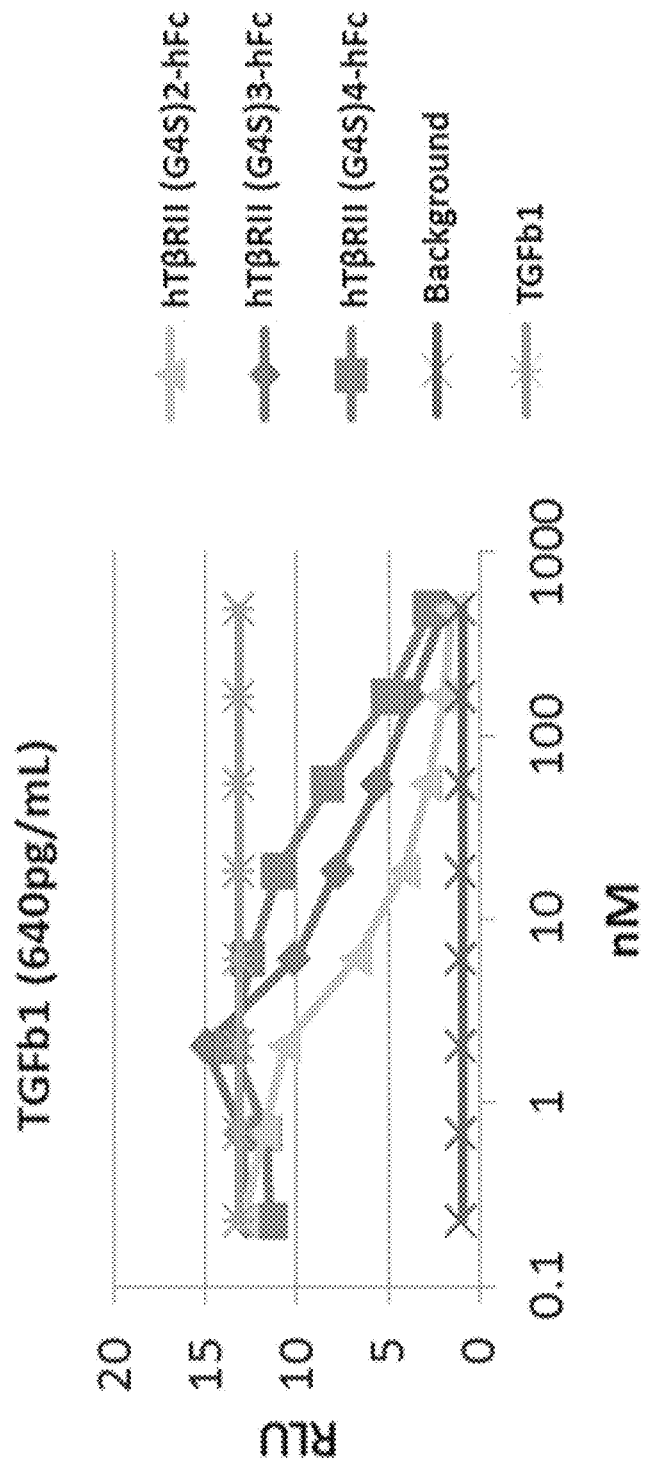
FIGS. 5A and 5C graph the results from reporter gene assays testing the affinity of TGFβ1 for one of several different TβRII-Fc fusion protein constructs.
Figure 5B:
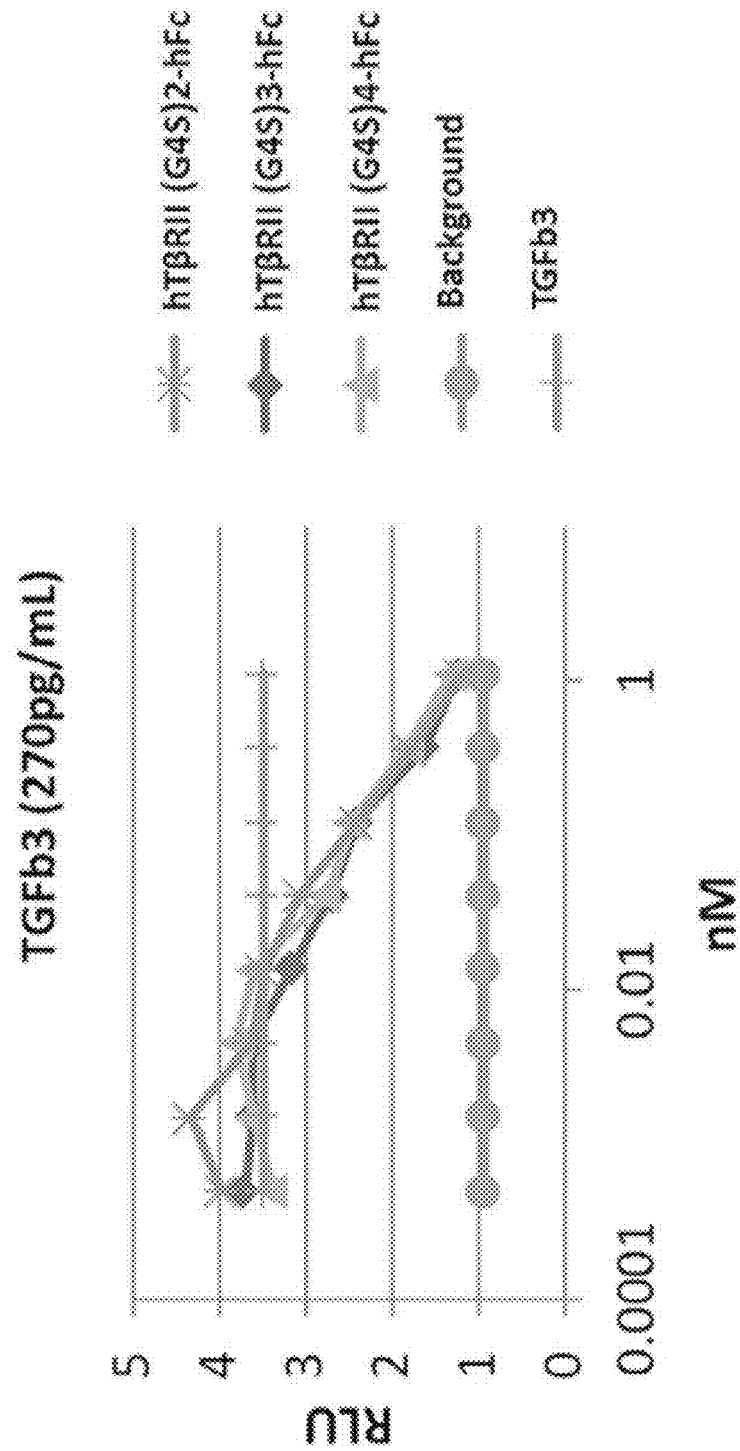
FIGS. 5B and 5D graph the results from reporter gene assays testing the affinity of the TGFβ3 for one of several different TβRII-Fc fusion protein constructs.
Figure 5C:
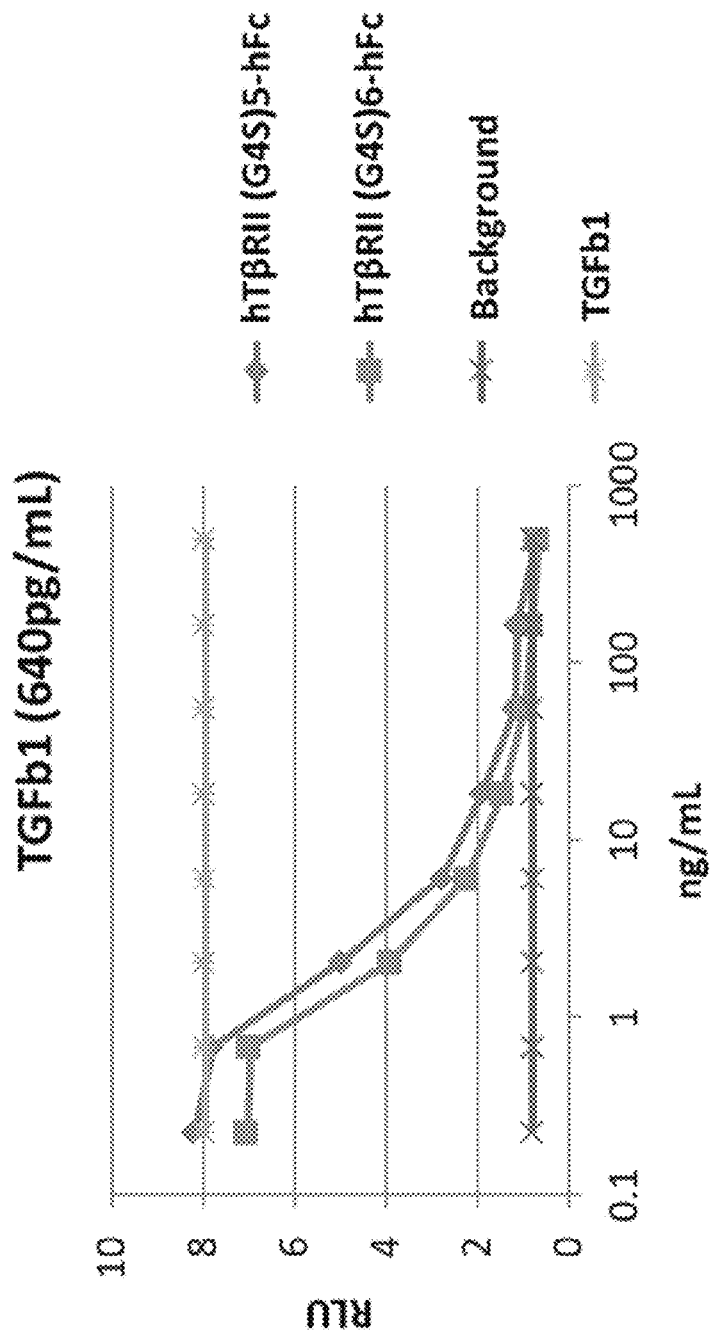
Figure 5D:
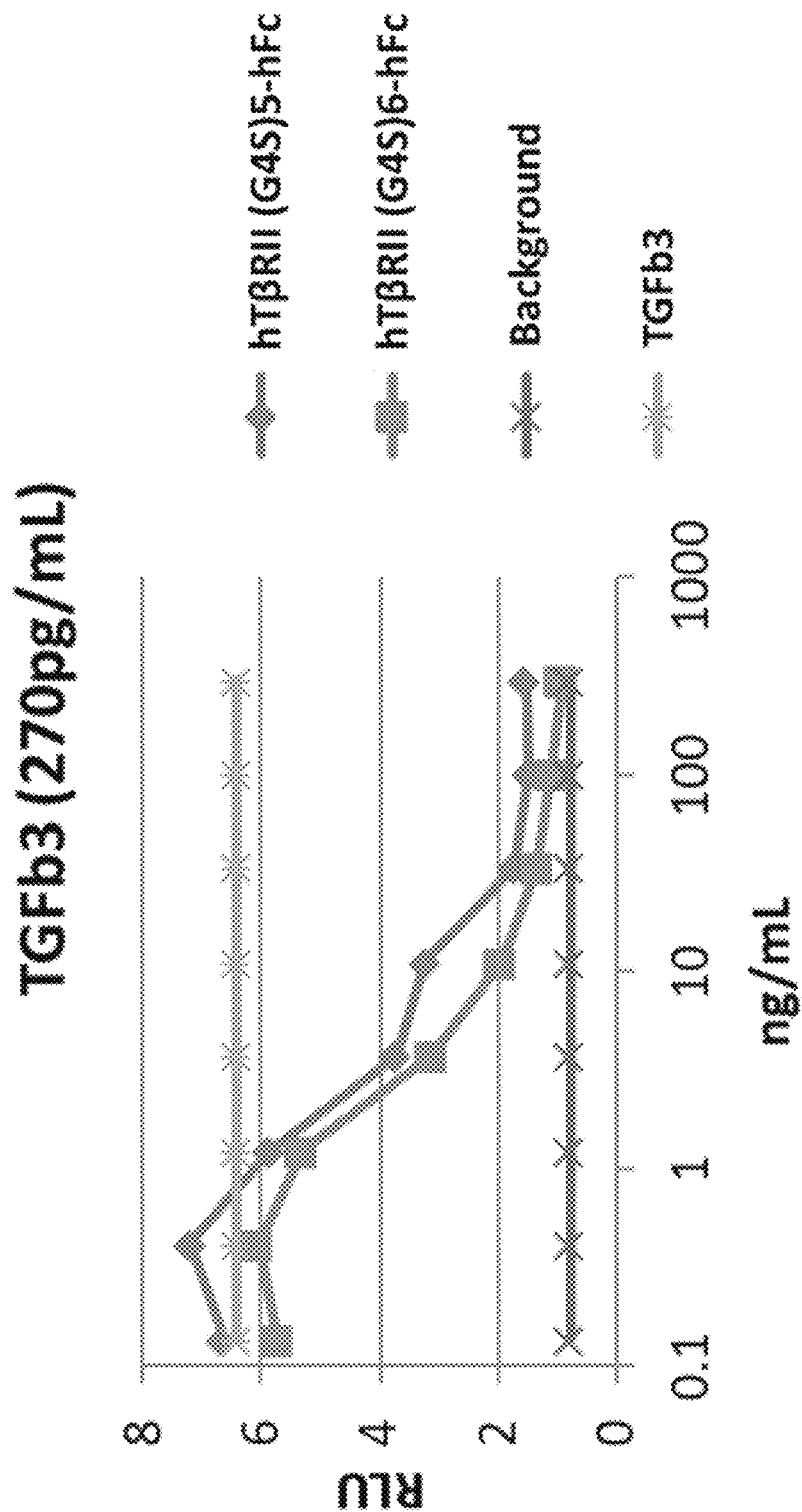

As illustrated in FIGS. 5A-5F, the hTβRII (G4S)2-hFc; hTβRII (G4S)3-hFc; hTβRII (G4S)4-hFc; hTβRII (G4S)5-hFc; hTβRII (G4S)6-hFc; hTβRII-hFc; and hTβRII extended hinge-hFc proteins all were capable of inhibiting both TGFβ1 and TGFβ3. Interestingly, while there was a correlation between improved TGFβ1 and TGFβ3 inhibition and linker length for the hTβRII (G4S)2-hFc; hTβRII (G4S)3-hFc and hTβRII (G4S)4-hFc constructs (FIG. 5E), this improvement trend appeared to have plateaued for hTβRII (G4S)5-hFc and hTβRII (G4S)6-hFc constructs (FIG. 5F).

Example 3. Effects of TβRII-Fc in a Heterotopic Ossification Animal Model

Heterotopic ossification (HO) can commonly occur after severe trauma, burn injuries, and is a debilitating consequence of the congenital disease fibrodysplasia ossificans progressiva (FOP). The etiology remains poorly understood, however, it is presumed that inflammation plays a critical role with several inflammatory cell types being recruited to the site of HO development. The effects of mTβRII-mFc, as described above, on the progression of HO were investigated using a HO animal model.

Recruited macrophages are a known source of cytokines that influence the inflammatory microenvironment. Therefore, the secretion of TGFβ1 in cultured macrophages was initially assessed. Bone marrow derived macrophages were isolated and polarized into M2 phenotype in-vitro. Secreted TGFβ was measured in conditioned media using ELISA. Interestingly, it was observed that, while M0 macrophages secrete only minimal TGFβ1, the regenerative M2 macrophages, which are known to be recruited to inflammatory sites such as those occurring at sites of osseous deposition in HO, had a 500-fold increase in TGFβ1 secretion. Furthermore, the increase in TGFβ1 secretion was completely abrogated when the mTβRII-mFc (5.44 pg/ml) was present in the culture media (FIG. 6A).

Next, the effect of systemically administered mTβRII-mFc were observed in a model of traumatic heterotopic ossification involving a 30% dorsal burn and Achilles tenotomy. Agarwal et al. (2016) Proc Natl Acad Sci USA 113(3): E338-347. Six-week old male C57BL/6 mice were induced for HO and then randomized into one of two treatment groups: 1) treatment with the mTβRII-mFc (10 mg/kg) (n=10) or 2) PBS control (n=10). This was administered subcutaneously twice weekly for 3 weeks. At 3 weeks, histology samples were collected, decalcified and stained with Safranin O to assess formation of HO anlagen. Volume of mature formed HO was quantified using micro CT analysis and imaging reconstruction at 9 weeks. Following treatment for 3 weeks, a substantially attenuated development of HO anlagen in mice treated with mTβRII-mFc was observed upon histologic examination along with decreased osseous deposition and marrow space formation (FIG. 6B). Furthermore, the volume of mature HO was significantly decreased in the mTβRII-mFc treatment group (FIG. 6C).

In this study, it was demonstrated that TGFβ1 signaling plays a critical role in HO formation and treatment with mTβRII-mFc is effective in attenuating ectopic bone deposition, thus resulting in decreased HO volume. Therefore, these data suggest that TβRII polypeptides, as well as other TGFβ antagonist, may be used to treat HO, revealing a new avenue for the treatment of this condition in human patients.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

We claim:

1. A method for treating heterotopic ossification (HO) in a patient in need thereof, comprising administering to the patient an effective amount of a Transforming Growth Factor-β (TGFβ) antagonist, wherein the TGFB antagonist is a fusion polypeptide comprising:
   a Transforming Growth Factor-β Receptor II (TβRII) polypeptide comprising an amino acid sequence that is at least 90% identical to SEQ ID NO: 18;
   a linker domain comprising (GGGGS) n (SEQ ID NO: 19), wherein n≠>5; and
   an Fc domain comprising an amino acid sequence that is at least 90% identical to SEQ ID NO: 49,
   wherein the linker domain connects the TBRII polypeptide and Fc domain; and
   wherein the TβRII polypeptide (1) binds to TGFβ1 and/or TGFβ3, and (2) inhibits TGFβ1 and/or TGFβ3 signaling.

2. The method of claim 1, wherein the TβRII polypeptide comprises an amino acid sequence that is at least 95% identical to SEQ ID NO: 18.

3. The method of claim 1, wherein the TβRII polypeptide comprises the amino acid sequence of SEQ ID NO: 18.

4. The method of claim 1, wherein the Fc domain comprises the amino acid sequence of SEQ ID NO: 49.

5. The method of claim 1, wherein the linker is between 10 and 25 amino acids in length.

6. The method of claim 1, wherein the linker domain comprises an amino acid sequence of (GGGGS)n (SEQ ID NO: 19), wherein n≥2.

7. The method of claim 1, wherein the linker domain comprises an amino acid sequence of (GGGGS)n (SEQ ID NO: 19), wherein n≥3.

8. The method of claim 1, wherein the linker domain comprises an amino acid sequence of (GGGGS)n (SEQ ID NO: 19), wherein n≥4.

9. The method of claim 1, wherein the linker domain comprises an amino acid sequence of (GGGGS)n (SEQ ID NO: 19), wherein n=2-4.

10. The method of claim 1, wherein the linker domain comprises the amino acid sequence of any one of SEQ ID NOs: 4-6, 21 and 25.

11. The method of claim 1, wherein the fusion polypeptide comprises:
    a TβRII polypeptide comprising the amino acid sequence of SEQ ID NO: 18;
    a linker portion comprising the amino acid sequence of SEQ ID NO: 6; and
    an Fc domain comprising the amino acid sequence of SEQ ID NO: 49.

12. The method of claim 1, wherein the fusion polypeptide consists of:
    a TβRII polypeptide comprising an amino acid sequence that is at least 90% identical to the amino acid sequence of SEQ ID NO: 18 and no more than 10, 9, 8, 7, 6, 5, 4, 3, 2 or 1 additional amino acids;
    a linker domain comprising (GGGGS) n (SEQ ID NO: 19), wherein n≠>5, and no more than 5, 4, 3, 2 or 1 additional amino acids; and
    an Fc domain comprising an amino acid sequence that is at least 90% identical to the amino acid sequence of SEQ ID NO: 49 and no more than 25, 20, 15, 10, 5, 4, 3, 2 or 1 additional amino acids.

13. The method of claim 1, wherein the fusion polypeptide comprises an amino acid sequence that is at least 90% identical to the amino acid sequence of SEQ ID NO: 11, 13, 15, 65 or 68.

14. The method of claim 1, wherein the fusion polypeptide comprises the amino acid sequence of SEQ ID NO: 48.

15. The method of claim 1, wherein the fusion polypeptide includes one or more modified amino acid residues selected from: a glycosylated amino acid, a PEGylated amino acid, a farnesylated amino acid, an acetylated amino acid, a biotinylated amino acid, and an amino acid conjugated to a lipid moiety.

16. The method of claim 1, wherein the fusion polypeptide is a homodimer.

17. The method of claim 1, wherein the heterotopic ossification is associated with one or more disorders or conditions selected from the group consisting of: spinal cord injury, trauma, brain injuries, burns, fractures, muscle contusion, joint arthroplasty/replacement, hip surgery/replacement, acetabular surgery/replacement, elbow fracture, fracture of the long bones of the lower leg, combat-related trauma, amputation, neuromuscular blockade used to manage adult respiratory distress syndrome, and non-traumatic myelopathies.

18. The method of claim 1, wherein the heterotopic ossification occurs in one or more tissues selected from the group consisting of: bone, skin, subcutaneous tissue, skeletal muscle, fibrosis tissue adjacent to joints, walls of blood vessels, and ligaments.

19. The method of claim 1, wherein the fusion polypeptide prevents or reduces the severity or duration of heterotopic ossification in the patient, or prevents or reduces one or more complications of heterotopic ossification selected from the group consisting of: joint contracture, ankylosis, pain, spasticity, swelling fever, neurovascular compression, and pressure ulcers.

20. The method of claim 1, wherein the fusion polypeptide is administered in combination with an additional active agent or supportive therapy for treating heterotopic ossification, fibrodysplasia ossificans progressiva (FOP), progressive osseous heteroplasia (POH), or fibrous dysplasia,
    said additional active agent or supportive therapy being selected from the group consisting of: isotretinoin, etidronate with oral corticosteroids, perhexiline maleate, ALK2 small molecule inhibitors, palovarotene, retinoic acid receptor gamma agonists, retinoic acid receptor alpha agonists, activin antibodies, ALK2 allele-specific RNA interference, bisphosphonates, radiation therapy, anti-inflammatory agents, conservative treatments, passive range of motion exercises, and mobilization techniques.

* * * * *